(12) United States Patent
Kawakami et al.

(10) Patent No.: US 12,089,491 B2
(45) Date of Patent: Sep. 10, 2024

(54) LIGHT-EMITTING ELEMENT, LIGHT-EMITTING DEVICE, ELECTRONIC DEVICE, AND LIGHTING DEVICE

(71) Applicant: SEMICONDUCTOR ENERGY LABORATORY CO., LTD., Atsugi (JP)

(72) Inventors: Sachiko Kawakami, Kanagawa (JP); Tsunenori Suzuki, Kanagawa (JP); Yusuke Takita, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 0 days.

(21) Appl. No.: 17/401,948

(22) Filed: Aug. 13, 2021

(65) Prior Publication Data
US 2021/0384440 A1 Dec. 9, 2021

Related U.S. Application Data

(63) Continuation of application No. 16/533,881, filed on Aug. 7, 2019, now Pat. No. 11,101,432, which is a
(Continued)

(30) Foreign Application Priority Data

Jan. 29, 2016 (JP) .................. 2016-016262

(51) Int. Cl.
*H01L 51/50* (2006.01)
*C07D 307/77* (2006.01)
(Continued)

(52) U.S. Cl.
CPC ......... *H10K 85/636* (2023.02); *C07D 307/77* (2013.01); *C09K 11/06* (2013.01);
(Continued)

(58) Field of Classification Search
None
See application file for complete search history.

(56) References Cited

U.S. PATENT DOCUMENTS

| 7,771,843 | B2 | 8/2010 | Suh et al. |
| 8,703,304 | B2 | 4/2014 | Yabunouchi |
| | | (Continued) | |

FOREIGN PATENT DOCUMENTS

| CN | 001575070 A | 2/2005 |
| CN | 102214795 A | 10/2011 |
| | (Continued) | |

OTHER PUBLICATIONS

Chinese Office Action (Application No. 201911346522.6) Dated Nov. 18, 2021.
(Continued)

*Primary Examiner* — Gregory D Clark
(74) *Attorney, Agent, or Firm* — Fish & Richardson P.C.

(57) ABSTRACT

A novel light-emitting element is provided. A light-emitting element with a long lifetime is provided. A light-emitting element with high emission efficiency is provided. A novel organic compound is provided. A novel organic compound having a hole-transport property is provided. A novel hole-transport material is provided. A hole-transport material including an organic compound having a substituted or unsubstituted benzonaphthofuran skeleton and a substituted or unsubstituted amine skeleton is provided. A light-emitting element using the hole-transport material is provided. An organic compound in which an amine skeleton including two aromatic hydrocarbon groups having 6 to 60 carbon atoms is bonded to the 6- or 8-position of the benzonaphthofuran skeleton is provided.

21 Claims, 46 Drawing Sheets

Related U.S. Application Data continuation of application No. 15/416,348, filed on Jan. 26, 2017, now Pat. No. 10,411,193.

(51) Int. Cl.

| | | |
|---|---|---|
| *C09K 11/06* | (2006.01) | |
| *H10K 85/60* | (2023.01) | |
| *H10K 50/11* | (2023.01) | |
| *H10K 50/15* | (2023.01) | |
| *H10K 59/121* | (2023.01) | |
| *H10K 101/30* | (2023.01) | |
| *H10K 101/40* | (2023.01) | |

(52) U.S. Cl.
CPC ....... *H10K 85/633* (2023.02); *H10K 85/6572* (2023.02); *H10K 85/6574* (2023.02); *C09K 2211/1007* (2013.01); *C09K 2211/1011* (2013.01); *C09K 2211/1014* (2013.01); *H10K 50/11* (2023.02); *H10K 50/15* (2023.02); *H10K 50/156* (2023.02); *H10K 59/1213* (2023.02); *H10K 85/622* (2023.02); *H10K 85/626* (2023.02); *H10K 2101/30* (2023.02); *H10K 2101/40* (2023.02)

(56) References Cited

U.S. PATENT DOCUMENTS

| | | | |
|---|---|---|---|
| 8,822,434 | B2 | 9/2014 | Liang et al. |
| 9,028,977 | B2 | 5/2015 | Bae et al. |
| 9,087,997 | B2 | 7/2015 | Yabunouchi |
| 9,093,649 | B2 | 7/2015 | Kawakami et al. |
| 9,260,390 | B2 | 2/2016 | Kato |
| 9,303,053 | B2 | 4/2016 | Liang et al. |
| 9,526,739 | B2 | 12/2016 | Liang et al. |
| 9,548,468 | B2 | 1/2017 | Seo et al. |
| 9,586,924 | B2 | 3/2017 | Kawakami et al. |
| 9,614,160 | B2 | 4/2017 | Kato |
| 9,876,056 | B2 | 1/2018 | Seo et al. |
| 9,899,603 | B2 | 2/2018 | Kawakami et al. |
| 9,978,971 | B2 | 5/2018 | Seo et al. |
| 10,305,043 | B2 | 5/2019 | Yun et al. |
| 10,355,218 | B2 | 7/2019 | Kato |
| 10,411,193 | B2 | 9/2019 | Kawakami et al. |
| 10,468,619 | B2 | 11/2019 | Seo et al. |
| 10,556,864 | B2 | 2/2020 | Nomura et al. |
| 10,600,969 | B2 | 3/2020 | Mun et al. |
| 10,658,597 | B2 | 5/2020 | Park et al. |
| 10,686,152 | B2 | 6/2020 | Seo et al. |
| 10,854,682 | B2 | 12/2020 | Seo et al. |
| 11,271,175 | B2 | 3/2022 | Park et al. |
| 11,335,858 | B2 | 5/2022 | Kato |
| 11,673,875 | B2 | 6/2023 | Jung et al. |
| 2004/0021136 | A1 | 2/2004 | Matsuo et al. |
| 2004/0265630 | A1 | 12/2004 | Suh et al. |
| 2007/0037011 | A1 | 2/2007 | Nakashima et al. |
| 2007/0096639 | A1 | 5/2007 | Nakashima et al. |
| 2007/0149784 | A1 | 6/2007 | Murata et al. |
| 2007/0215867 | A1 | 9/2007 | Kawakami et al. |
| 2007/0215889 | A1 | 9/2007 | Kawakami et al. |
| 2008/0206598 | A1 | 8/2008 | Ohsawa et al. |
| 2009/0160323 | A1 | 6/2009 | Nomura et al. |
| 2009/0284140 | A1 | 11/2009 | Osaka et al. |
| 2010/0001636 | A1 | 1/2010 | Yabunouchi |
| 2010/0245217 | A1 | 9/2010 | Nomura et al. |
| 2010/0301744 | A1 | 12/2010 | Osaka et al. |
| 2011/0168992 | A1 | 7/2011 | Bae et al. |
| 2011/0240969 | A1 | 10/2011 | Kim et al. |
| 2012/0305898 | A1 | 12/2012 | Okamoto |
| 2014/0183500 | A1 | 7/2014 | Ikeda et al. |
| 2015/0031900 | A1 | 1/2015 | Kawakami et al. |
| 2015/0060813 | A1 | 3/2015 | Kawakami et al. |
| 2015/0318495 | A1 | 11/2015 | Kawakami et al. |
| 2015/0329514 | A1 | 11/2015 | Kawakami et al. |
| 2016/0079314 | A1 | 3/2016 | Seo et al. |
| 2016/0163994 | A1 | 6/2016 | Park et al. |
| 2017/0040535 | A1* | 2/2017 | Ogita ............... H10K 85/636 |
| 2017/0084843 | A1 | 3/2017 | Yun et al. |
| 2017/0125689 | A1 | 5/2017 | Lee et al. |
| 2018/0009751 | A1 | 1/2018 | Nomura et al. |
| 2018/0186764 | A1* | 7/2018 | Jung ............... H10K 85/6574 |
| 2019/0229273 | A1 | 7/2019 | Yun et al. |
| 2020/0148640 | A1 | 5/2020 | Nomura et al. |
| 2020/0411788 | A1 | 12/2020 | Seo et al. |
| 2021/0104580 | A1 | 4/2021 | Seo et al. |
| 2022/0255005 | A1 | 8/2022 | Kato |
| 2022/0388958 | A1 | 12/2022 | Nomura et al. |

FOREIGN PATENT DOCUMENTS

| | | | | |
|---|---|---|---|---|
| CN | 102224148 | A | 10/2011 | |
| CN | 102482215 | A | 5/2012 | |
| CN | 104761535 | A * | 7/2015 | ............. H01L 51/50 |
| CN | 104884444 | A | 9/2015 | |
| CN | 105683173 | A | 6/2016 | |
| CN | 106432157 | A | 2/2017 | |
| CN | 106575713 | A | 4/2017 | |
| CN | 107849000 | A | 3/2018 | |
| CN | 109467543 | * | 3/2019 | ............. H01L 51/50 |
| DE | 112014003458 | | 4/2016 | |
| DE | 102016214546 | | 2/2017 | |
| EP | 2295421 | A | 3/2011 | |
| EP | 2332931 | A | 6/2011 | |
| EP | 2372807 | A | 10/2011 | |
| EP | 2468725 | A | 6/2012 | |
| EP | 2757094 | A | 7/2014 | |
| JP | 2012-503027 | | 2/2012 | |
| JP | 2015-042636 | A | 3/2015 | |
| JP | 2015-181169 | A | 10/2015 | |
| JP | 2017-036267 | A | 2/2017 | |
| JP | 6317846 | | 4/2018 | |
| KR | 2015-0016896 | A | 2/2015 | |
| KR | 2015-0089427 | A | 8/2015 | |
| KR | 2015-0098631 | A | 8/2015 | |
| KR | 10-1579490 | | 12/2015 | |
| KR | 2015-0145033 | A | 12/2015 | |
| KR | 2016-0034937 | A | 3/2016 | |
| KR | 2017-0017761 | A | 2/2017 | |
| TW | 200946501 | | 11/2009 | |
| TW | 201002678 | | 1/2010 | |
| TW | 201509937 | | 3/2015 | |
| TW | 201538498 | | 10/2015 | |
| WO | WO-2009/072587 | | 6/2009 | |
| WO | WO-2009/145016 | | 12/2009 | |
| WO | WO-2010/036027 | | 4/2010 | |
| WO | WO-2011/021520 | | 2/2011 | |
| WO | WO-2011/065136 | | 6/2011 | |
| WO | WO-2011/103552 | | 8/2011 | |
| WO | WO-2014/104144 | | 7/2014 | |
| WO | WO-2015/011614 | | 1/2015 | |
| WO | WO-2015/115756 | | 8/2015 | |
| WO | WO-2015/178585 | | 11/2015 | |
| WO | WO-2015/181667 | | 12/2015 | |
| WO | WO-2015/194791 | | 12/2015 | |
| WO | WO-2016/020801 | | 2/2016 | |
| WO | WO-2017/130079 | | 8/2017 | |

OTHER PUBLICATIONS

International Search Report (Application No. PCT/IB2017/050250) Dated May 9, 2017.

Written Opinion (Application No. PCT/IB2017/050250) Dated May 9, 2017.

Chinese Office Action (Application No. 201780008471.9) Dated Jan. 16, 2020.

Taiwanese Office Action (Application No. 106102671) Dated Jul. 14, 2020.

Chinese Office Action (Application No. 201910507175.4) Dated Nov. 9, 2022.

Third party observation on counterpart TW application 110133965, filed with TIPO on Jun. 28, 2023.

(56) References Cited

OTHER PUBLICATIONS

Chinese Office Action (Application No. 201910507175.4) Dated Sep. 1, 2023.
German Office Action (Application No. 112017000558.2) Dated May 3, 2024.

* cited by examiner

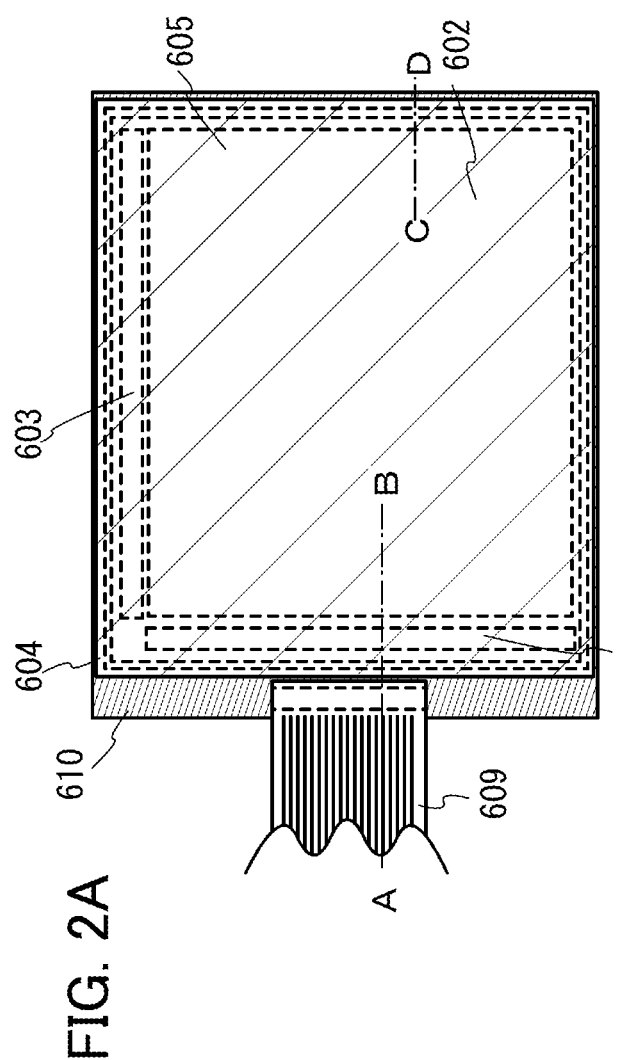
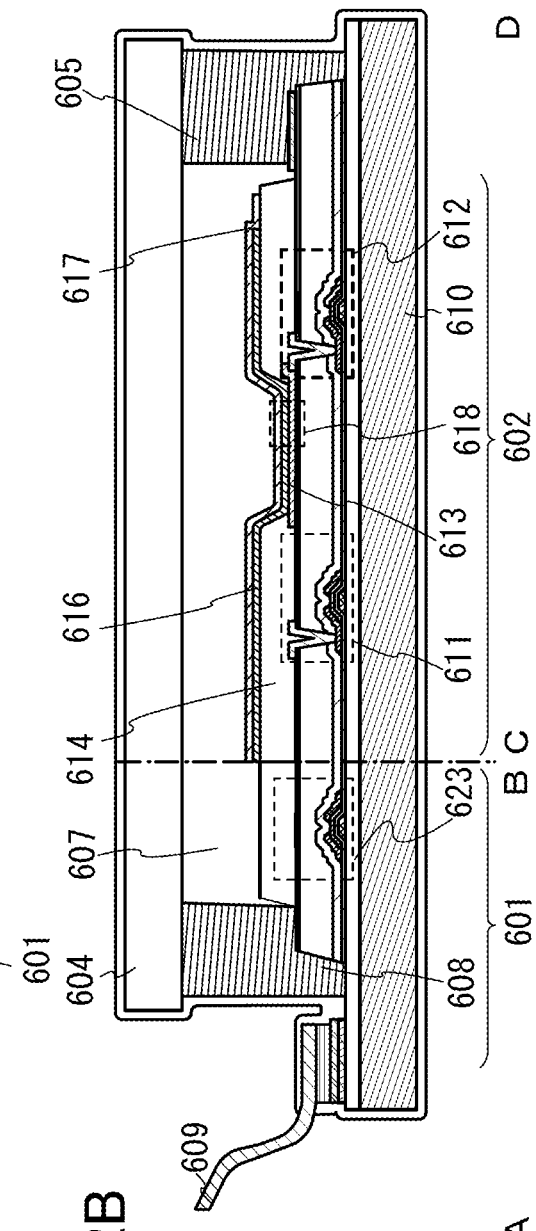
FIG. 2A
FIG. 2B

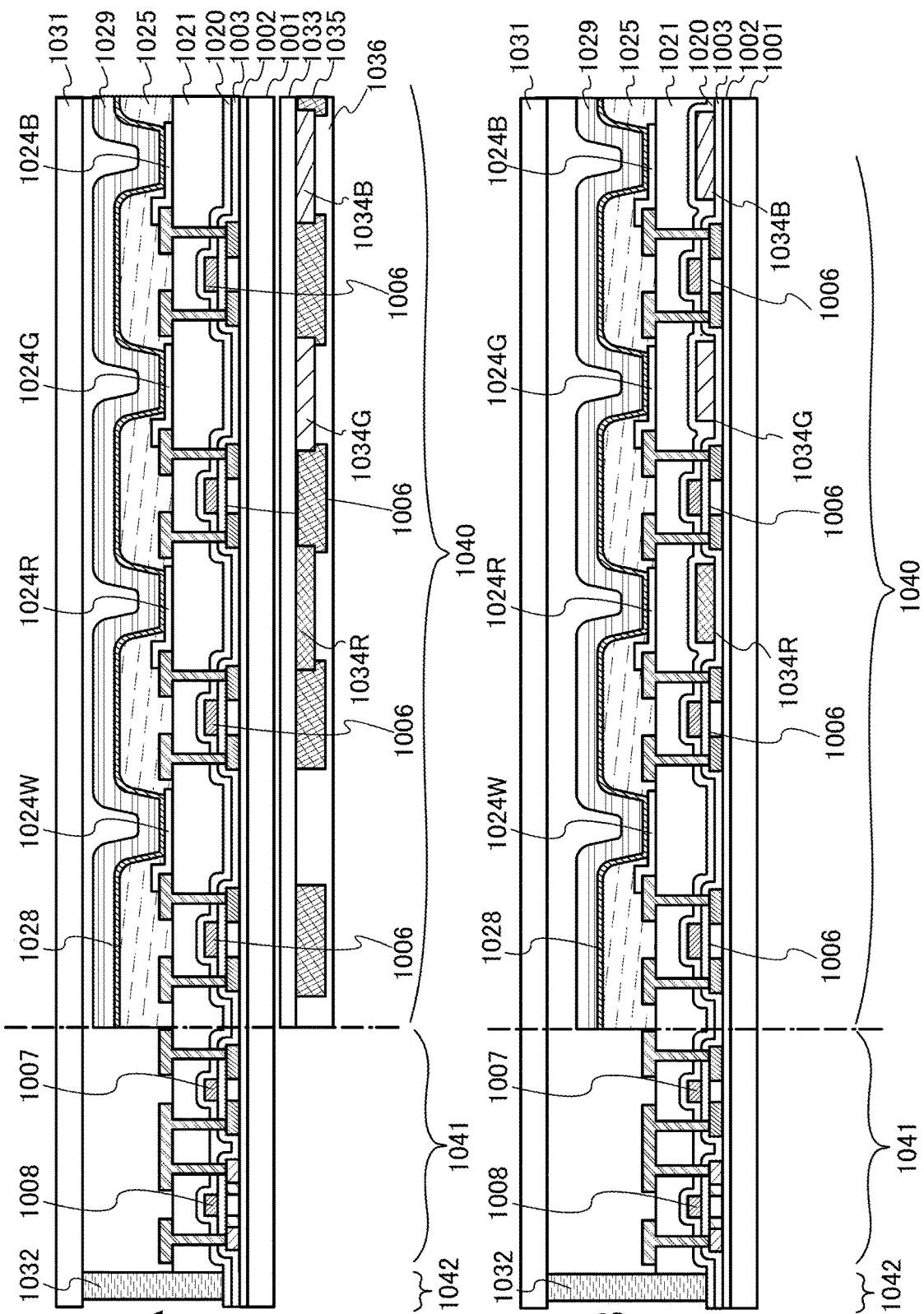

FIG. 7A
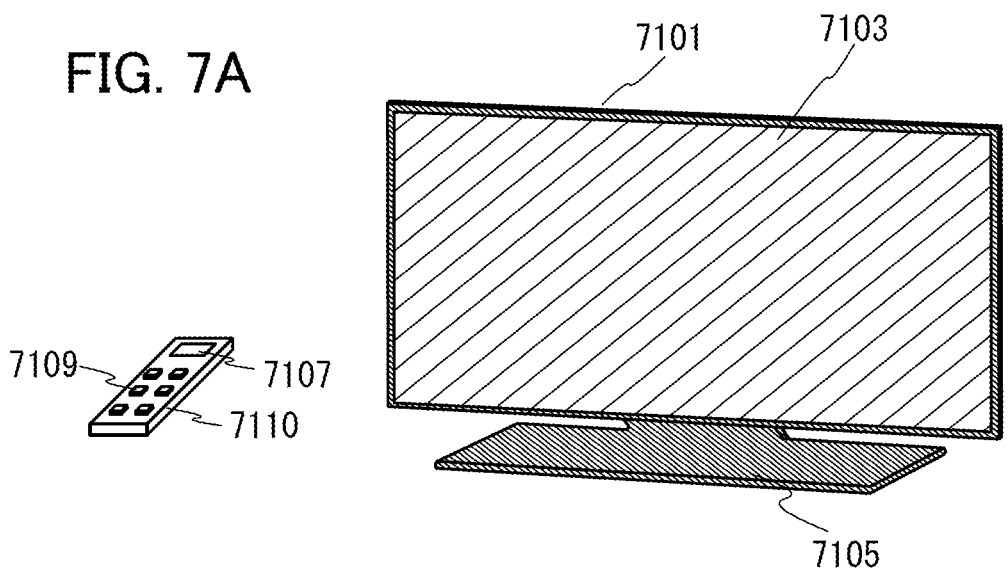
FIG. 7B1
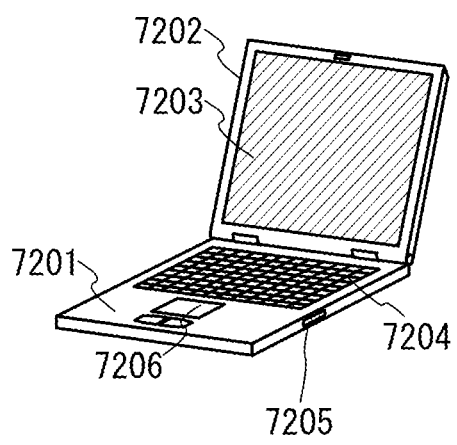
FIG. 7B2
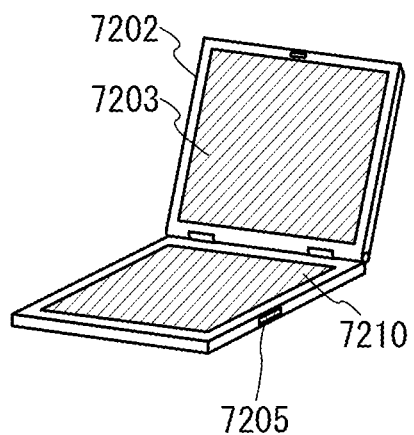
FIG. 7C
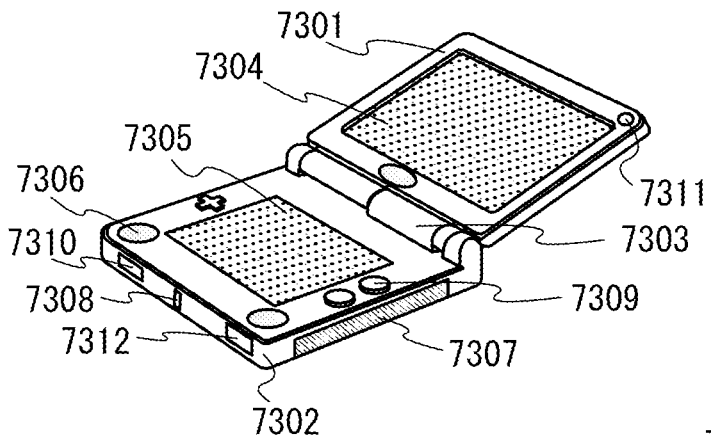
FIG. 7D
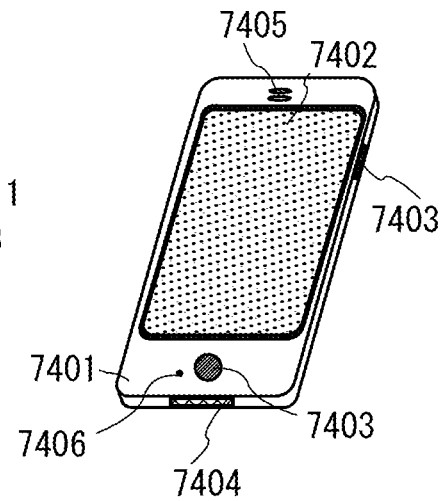

LIGHT-EMITTING ELEMENT, LIGHT-EMITTING DEVICE, ELECTRONIC DEVICE, AND LIGHTING DEVICE

CROSS-REFERENCE TO RELATED APPLICATIONS

This application is a continuation of U.S. application Ser. No. 16/533,881, filed Aug. 7, 2019, now allowed, which is a continuation of U.S. application Ser. No. 15/416,348, filed Jan. 26, 2017, now U.S. Pat. No. 10,411,193, which claims the benefit of a foreign priority application filed in Japan as Serial No. 2016-016262 on Jan. 29, 2016, all of which are incorporated by reference.

TECHNICAL FIELD

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. Furthermore, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, an imaging device, a method for driving any of them, and a method for manufacturing any of them.

BACKGROUND ART

Light-emitting elements (organic EL elements) including organic compounds and utilizing electroluminescence (EL) have been put to more practical use. In the basic structure of such a light-emitting element, an organic compound layer containing a light-emitting material (an EL layer) is provided between a pair of electrodes. Carriers are injected by application of voltage to the element, and light emission can be obtained from the light-emitting material by using the recombination energy of the carriers.

The light-emitting elements are self-luminous elements and thus have advantages over liquid crystal displays, such as high visibility and no need for backlight when used as pixels of a display, and are suitable as flat panel display elements. In addition, it is also a great advantage that a display including such light-emitting elements can be manufactured as a thin and lightweight display. Furthermore, an extremely high response speed is also a feature thereof.

In such light-emitting elements, light-emitting layers can be successively formed two-dimensionally, so that planar light emission can be obtained. This feature is difficult to realize with point light sources typified by incandescent lamps and LEDs or linear light sources typified by fluorescent lamps. Thus, light-emitting elements also have great potential as planar light sources applied to lighting devices and the like.

Displays or lighting devices including light-emitting elements can be suitably used for a variety of electronic devices as described above, and research and development of light-emitting elements have progressed for higher efficiency or longer lifetime.

An organic compound having an acceptor property is a material for a hole-injection layer that is used to facilitate the injection of carriers, particularly holes, into an EL layer. The organic compound having an acceptor property can be easily deposited by evaporation and thus is suitable for mass production and has become widely used. However, the injection of holes into an EL layer is difficult when the LUMO level of the organic compound having an acceptor property is distanced from the HOMO level of an organic compound included in a hole-transport layer. In contrast, when the HOMO level of the organic compound included in the hole-transport layer is raised so as to be closer to the LUMO level of the organic compound having an acceptor property, the difference between the HOMO level of the light-emitting layer and the HOMO level of the organic compound included in the hole-transport layer is large, causing difficulty in hole injection from the hole-transport layer into a host material in the light-emitting layer even when holes can be injected into the EL layer.

In a structure disclosed in Patent Document 1, a hole-transport material whose HOMO level is between the HOMO level of a first hole-injection layer and the HOMO level of a host material is provided between a light-emitting layer and a first hole-transport layer in contact with the hole-injection layer.

Although the characteristics of light-emitting elements have been improved remarkably, advanced requirements for various characteristics including efficiency and durability are not yet satisfied.

REFERENCE

Patent Document

[Patent Document 1] PCT International Publication No. WO2011/065136

DISCLOSURE OF INVENTION

In view of the above, an object of one embodiment of the present invention is to provide a novel light-emitting element. Another object of one embodiment of the present invention is to provide a light-emitting element with a long lifetime. Another object of one embodiment of the present invention is to provide a light-emitting element with high emission efficiency. Another object of one embodiment of the present invention is to provide a novel organic compound. Another object of one embodiment of the present invention is to provide a novel organic compound having a hole-transport property. Another object of one embodiment of the present invention is to provide a novel hole-transport material.

Another object of one embodiment of the present invention is to provide a highly reliable light-emitting device, electronic device, and display device. Another object of one embodiment of the present invention is to provide a low-power-consumption light-emitting device, electronic device, and display device.

It is only necessary that at least one of the above-described objects be achieved in the present invention.

One embodiment of the present invention is a hole-transport material including an organic compound having a substituted or unsubstituted benzonaphthofuran skeleton and a substituted or unsubstituted amine skeleton.

Another embodiment of the present invention is a hole-transport material including an organic compound having a substituted or unsubstituted benzonaphthofuran skeleton and one substituted or unsubstituted amine skeleton.

Another embodiment of the present invention is the hole-transport material with either of the above structures, in which the amine skeleton is bonded to the 6- or 8-position of the benzonaphthofuran skeleton.

Another embodiment of the present invention is the hole-transport material with any of the above structures, in which the benzonaphthofuran skeleton is directly bonded to a nitrogen atom of the amine skeleton.

Another embodiment of the present invention is a light-emitting element including an anode, a cathode, and an EL layer. The EL layer includes a light-emitting layer and is positioned between the anode and the cathode. The EL layer includes the hole-transport material according to any one of the above.

Another embodiment of the present invention is a light-emitting element including an anode, a cathode, and an EL layer. The EL layer is positioned between the anode and the cathode, and includes a light-emitting layer and a hole-transport layer. The hole-transport layer is positioned between the light-emitting layer and the anode, and includes the hole-transport material according to any one of the above.

Another embodiment of the present invention is the light-emitting element with any of the above structures, in which the light-emitting layer includes a light-emitting material and the hole-transport material.

Another embodiment of the present invention is the light-emitting element with any of the above structures, in which the light-emitting layer further includes an electron-transport material.

Another embodiment of the present invention is an organic compound represented by General Formula (G1).

[Chemical formula 1]

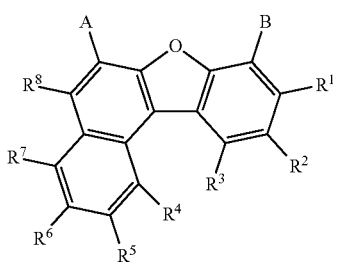

(G1)

Note that in General Formula (G1), $R^1$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. One of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms.

[Chemical Formula 2]

(g1)

Note that in General Formula (g1), $Ar^1$ and $Ar^2$ independently represent any one of a substituted or unsubstituted aromatic hydrocarbon group having 6 to 60 carbon atoms and a group represented by General Formula (g2). In the case where $Ar^1$ and $Ar^2$ are each an aromatic hydrocarbon group having 6 to 60 carbon atoms and include a substituent, the substituent includes a benzonaphthofuranyl group and a dinaphthofuranyl group.

[Chemical Formula 3]

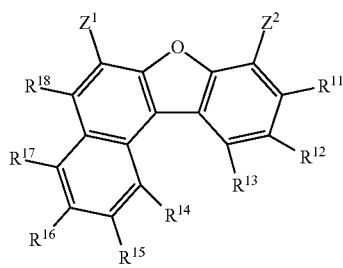

(g2)

Note that in General Formula (g2), $R^{11}$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. One of $Z^1$ and $Z^2$ is bonded to a nitrogen atom in General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms.

Another embodiment of the present invention is the organic compound with any of the above structures, in which the group represented by General Formula (g1) is a group represented by General Formula (g3).

[Chemical Formula 4]

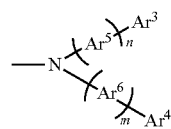

(g3)

Note that in General Formula (g3), $Ar^3$ and $Ar^4$ independently represent any one of a substituted or unsubstituted aromatic hydrocarbon group having 6 to 60 carbon atoms, a substituted or unsubstituted benzonaphthofuranyl group, and a substituted or unsubstituted dinaphthofuranyl group. $Ar^5$ and $Ar^6$ independently represent a substituted or unsubstituted divalent aromatic hydrocarbon group having 6 to 54 carbon atoms, and n and m independently represent 0 to 2. Note that the sum of carbon atoms of $Ar^3$ and $Ar^5$ is less than or equal to 60, and the sum of carbon atoms of $Ar^4$ and $Ar^6$ is less than or equal to 60.

Another embodiment of the present invention is the organic compound with any of the above structures, in which $Ar^3$ and $Ar^4$ independently represent any one of a substituted or unsubstituted phenyl group, a substituted or unsubstituted naphthyl group, a substituted or unsubstituted anthracenyl group, and a substituted or unsubstituted pyrenyl group.

Another embodiment of the present invention is the organic compound with any of the above structures, in which $Ar^5$ and $Ar^6$ independently represent any one of a substituted or unsubstituted phenylene group, a substituted or unsubstituted naphthylene group, a substituted or unsubstituted anthracenylene group, and a substituted or unsubstituted pyrenylene group.

Another embodiment of the present invention is the organic compound with any of the above structures, in which $Ar^3$ and $Ar^4$ are each a phenyl group.

Another embodiment of the present invention is the organic compound with any of the above structures, in which $Ar^5$ and $Ar^6$ are each a phenylene group.

Another embodiment of the present invention is the organic compound with any of the above structures, in which one of n and m is 1 and the other is 0.

Another embodiment of the present invention is a light-emitting element including an anode, a cathode, and an EL layer. The EL layer is positioned between the anode and the cathode. The EL layer includes the organic compound with any of the above structures.

Another embodiment of the present invention is a light-emitting element including an anode, a cathode, and an EL layer. The EL layer is positioned between the anode and the cathode, and includes a light-emitting layer. The light-emitting layer includes the organic compound with any of the above structures.

Another embodiment of the present invention is the light-emitting element with any of the above structures, in which the light-emitting layer further includes a light-emitting material.

Another embodiment of the present invention is the light-emitting element with any of the above structures, in which the light-emitting layer further includes a material having an electron-transport property.

Another embodiment of the present invention is a light-emitting element including an anode, a cathode, and an EL layer. The EL layer is positioned between the anode and the cathode. The EL layer includes a light-emitting layer and a hole-transport layer. The hole-transport layer is positioned between the light-emitting layer and the anode. The hole-transport layer includes the organic compound with any of the above structures.

Another embodiment of the present invention is the light-emitting element with any of the above structures, in which the EL layer further includes a hole-injection layer, the hole-injection layer is in contact with the anode and the hole-transport layer, and the hole-injection layer includes an organic compound having an acceptor property.

Another embodiment of the present invention is the light-emitting element with any of the above structures, in which the organic compound having an acceptor property is 2,3,6,7,10,11-hexacyano-1,4,5,8,9,12-hexaazatriphenylene.

Another embodiment of the present invention is the light-emitting element with any of the above structures, in which the hole-transport layer includes a first layer, a second layer, and a third layer, the first layer is positioned between the hole-injection layer and the second layer, the third layer is positioned between the second layer and the light-emitting layer, the first layer is in contact with the hole-injection layer, the third layer is in contact with the light-emitting layer, the first layer includes a first hole-transport material, the second layer includes the organic compound, the third layer includes a third hole-transport material, the light-emitting layer includes a host material and a light-emitting material, the HOMO level of the organic compound is deeper than the HOMO level of the first hole-transport material, the HOMO level of the host material is deeper than the HOMO level of the organic compound, and the difference between the HOMO level of the organic compound and the HOMO level of the third hole-transport material is less than or equal to 0.3 eV.

Another embodiment of the present invention is the light-emitting element with any of the above structures, in which the HOMO level of the first hole-transport material is greater than or equal to −5.4 eV.

Another embodiment of the present invention is the light-emitting element with any of the above structures, in which the difference between the HOMO level of the first hole-transport material and the HOMO level of the organic compound is less than or equal to 0.3 eV.

Another embodiment of the present invention is the light-emitting element with any of the above structures, in which the difference between the HOMO level of the organic compound and the HOMO level of the third hole-transport material is less than or equal to 0.2 eV.

Another embodiment of the present invention is the light-emitting element with any of the above structures, in which the difference between the HOMO level of the first hole-transport material and the HOMO level of the organic compound is less than or equal to 0.2 eV.

Another embodiment of the present invention is the light-emitting element with any of the above structures, in which the HOMO level of the light-emitting material is higher than the HOMO level of the host material.

Another embodiment of the present invention is the light-emitting element with any of the above structures, in which the HOMO level of the third hole-transport material is deeper than or equal to the HOMO level of the host material.

Another embodiment of the present invention is the light-emitting element with any of the above structures, in which the light-emitting material is a fluorescent substance.

Another embodiment of the present invention is the light-emitting element with any of the above structures, in which the light-emitting material emits blue fluorescence.

Another embodiment of the present invention is the light-emitting element with any of the above structures, in which the light-emitting material is a condensed aromatic diamine compound.

Another embodiment of the present invention is the light-emitting element with any of the above structures, in which the light-emitting material is a diaminopyrene compound.

Another embodiment of the present invention is a light-emitting device including the light-emitting element with any of the above structures, and a transistor or a substrate.

Another embodiment of the present invention is an electronic device including the above light-emitting device, and a sensor, an operation button, a speaker, or a microphone.

Another embodiment of the present invention is a lighting device including the above light-emitting device and a housing.

Note that the light-emitting device in this specification includes an image display device using a light-emitting element. The light-emitting device may include a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may also be included in lighting equipment and the like.

According to one embodiment of the present invention, a novel light-emitting element can be provided. A light-emitting element with a long lifetime can be provided. A light-emitting element with high emission efficiency can be provided. A novel organic compound can be provided. A novel organic compound having a hole-transport property can be provided. A novel hole-transport material can be provided.

According to another embodiment of the present invention, a highly reliable light-emitting device, electronic device, and display device can be provided. A low-power-consumption light-emitting device, electronic device, and display device can be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF DRAWINGS

FIGS. 2A and 2B are conceptual diagrams of an active matrix light-emitting device.

FIGS. 3A and 3B are conceptual diagrams of an active matrix light-emitting device.

FIGS. 7A to 7D illustrate electronic devices.

BEST MODE FOR CARRYING OUT THE INVENTION

Embodiments of the present invention will be described below in detail with reference to the drawings. Note that the present invention is not limited to the following description, and it will be readily appreciated by those skilled in the art that the modes and details can be changed in various different ways without departing from the spirit and the scope of the present invention. Accordingly, the present invention should not be interpreted as being limited to the content of the embodiments below.

Embodiment 1

The lifetime of a light-emitting element including an organic material is particularly affected by the properties of a hole-transport material in some cases. Above all, the transporting properties of the hole-transport material have considerable influence on the lifetime, which differs significantly according to the type of hole-transport material.

The present inventors have found that a hole-transport material including an organic compound having a substituted or unsubstituted benzonaphthofuran skeleton and a substituted or unsubstituted amine skeleton has a suitable transporting property and contributes to an increase in the lifetime of a light-emitting element including the hole-transport material.

In particular, the hole-transport material preferably includes an organic compound having a substituted or unsubstituted benzonaphthofuran skeleton and one substituted or unsubstituted amine skeleton. Further preferably, the benzonaphthofuran skeleton of the organic compound in the hole-transport material is a benzo[b]naphtho[1,2-d]furan skeleton, in which case a highly reliable element can be provided. Still further preferably, the hole-transport material includes the organic compound in which the amine skeleton is bonded to the 6- or 8-position of the benzo[b]naphtho[1,2-d]furan skeleton.

The hole-transport material preferably includes an organic compound in which a nitrogen atom of an amine skeleton is directly bonded to the benzonaphthofuran skeleton without a substituent, in which case a highly reliable light-emitting element can be provided and the hole-transport material has a suitable HOMO level. This hole-transport material, which includes the organic compound in which a nitrogen atom of an amine skeleton is directly bonded to the benzonaphthofuran skeleton without a substituent, is preferable because it exhibits a high hole-transport property and a light-emitting element with a low driving voltage can be provided.

A light-emitting element using the hole-transport material for an EL layer can have a long lifetime.

Figure 1A:
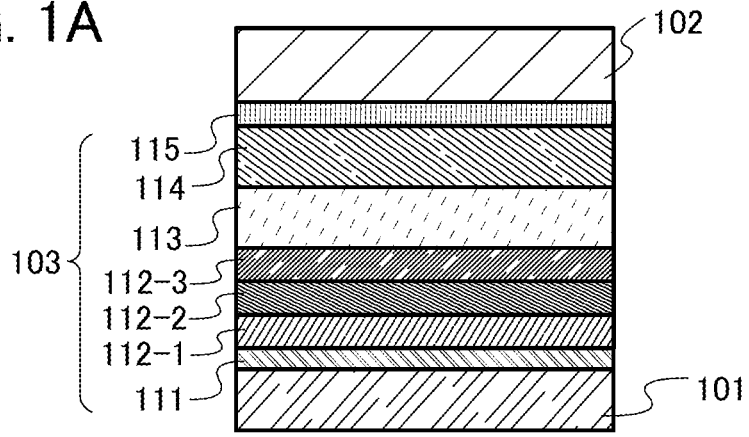
FIGS. 1A to 1C are schematic diagrams of light-emitting elements.
Figure 1B:
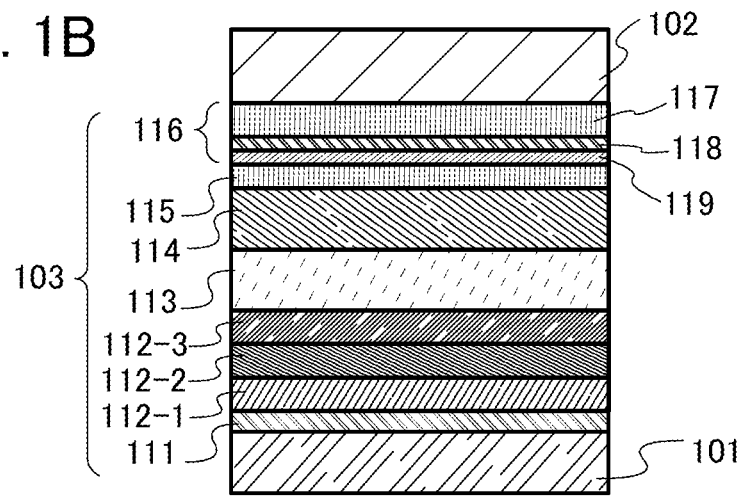
Figure 1C:
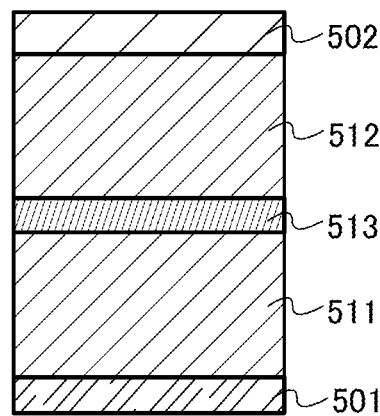

FIGS. 1A to 1C illustrate light-emitting elements of one embodiment of the present invention. The light-emitting elements of one embodiment of the present invention each include an anode 101, a cathode 102, and an EL layer 103 using the aforementioned hole-transport material including the organic compound.

The EL layer 103 includes a light-emitting layer 113 and may also include a hole-transport layer 112. The light-emitting layer 113 includes a light-emitting material and a host material, and light is emitted from the light-emitting material in the light-emitting element of one embodiment of the present invention. The hole-transport material of one embodiment of the present invention may be included in one or both of the light-emitting layer 113 and the hole-transport layer 112.

Note that FIGS. 1A to 1C additionally illustrate a hole-injection layer 111, an electron-transport layer 114, and an electron-injection layer 115; however, the structure of the light-emitting element is not limited thereto.

The hole-transport material can also be used as a host material. Furthermore, the hole-transport material and an electron-transport material may be deposited by co-evaporation so that an exciplex is formed of the electron-transport material and the hole-transport material. The exciplex having an appropriate emission wavelength allows efficient energy transfer to the light-emitting material, achieving a light-emitting element with a high efficiency and a long lifetime.

The above hole-transport material exhibits a good hole-transport property and therefore is suitable for the hole-transport layer 112. In particular, the hole-transport material is preferably used in the case where the hole-injection layer 111 is provided between the hole-transport layer 112 and the anode 101 and includes an organic compound having an acceptor property, which facilitates the injection of holes from the electrode.

In the case where the injection of holes is performed using the organic compound having an acceptor property, a compound included in the hole-transport layer 112 in contact with the hole-injection layer 111 is preferably a hole-transport material with a relatively shallow HOMO level in order to facilitate the extraction of electrons by the organic compound having an acceptor property. However, holes cannot be easily injected into the light-emitting layer 113 from the hole-transport material with a relatively shallow HOMO level, and when the light-emitting layer 113 is formed in contact with the hole-transport layer 112 made of the hole-transport material with a relatively shallow HOMO level, carriers are accumulated at their interface, causing a decrease in the lifetime and efficiency of the light-emitting element. Thus, a layer containing the organic compound of one embodiment of the present invention is provided between the light-emitting layer 113 and the hole-transport material with a relatively shallow HOMO level, in which case holes can be easily injected into the light-emitting layer and the lifetime and efficiency of the light-emitting element can be improved.

That is, the hole-transport layer 112 includes a first hole-transport layer 112-1 and a second hole-transport layer 112-2 from the side of the hole-injection layer 111, and the first hole-transport layer 112-1 contains a first hole-transport material whereas the second hole-transport layer 112-2 contains the hole-transport material of one embodiment of the present invention. The HOMO level of the hole-transport material of one embodiment of the present invention is deeper than the HOMO level of the first hole-transport material, achieving a light-emitting element with a long lifetime and a high efficiency. Note that the HOMO level of the first hole-transport material is preferably greater than or equal to −5.4 eV, in which case electrons can be easily extracted from the organic compound having an acceptor property.

Preferably, the difference between the HOMO level of the first hole-transport material and the HOMO level of the hole-transport material of the present invention is less than or equal to 0.3 eV, more preferably less than or equal to 0.2 eV, in which case holes can be easily injected from the first hole-transport layer 112-1 to the second hole-transport layer 112-2.

The hole-transport layer 112 may further include a third hole-transport layer 112-3 between the second hole-transport layer 112-2 and the light-emitting layer, and the third hole-transport layer 112-3 may contain a third hole-transport material. In that case, the HOMO level of the third hole-transport material is preferably deeper than the HOMO level of the hole-transport material of one embodiment of the present invention included in the second hole-transport layer 112-2, and the difference in the HOMO level is preferably less than or equal to 0.3 eV, more preferably less than or equal to 0.2 eV.

The HOMO level of the third hole-transport material is preferably deeper than or equal to the HOMO level of the host material, in which case holes are suitably transported to the light-emitting layer to increase the lifetime and efficiency.

Note that in the case where the HOMO level of the light-emitting material is shallower (higher) than the HOMO level of the host material, the proportion of holes injected into the light-emitting material increases according to the position of the HOMO level of the hole-transport layer, and furthermore, the holes are trapped in the light-emitting material, which might cause a decreased lifetime due to the light-emitting region unevenly placed. The structure of the light-emitting element of the present invention is preferably applied to such a case, for example, to a blue fluorescence element. In particular, the structure of the present invention can be preferably used for an aromatic diamine compound that emits excellent blue fluorescence, more particularly a pyrenediamine compound and the like, achieving a light-emitting element with excellent lifetime, efficiency, and chromaticity.

Next, examples of specific structures and materials of the aforementioned light-emitting element will be described. As described above, the light-emitting element of one embodiment of the present invention includes the EL layer 103 that is positioned between the pair of electrodes (the anode 101 and the cathode 102) and has a plurality of layers. In the EL layer 103, at least the hole-injection layer 111, the hole-transport layer 112, and the light-emitting layer 113 are provided from the anode 101 side.

There is no particular limitation on the other layers included in the EL layer 103, and various layers such as a hole-injection layer, a hole-transport layer, an electron-transport layer, an electron-injection layer, a carrier-blocking layer, an exciton-blocking layer, and a charge-generation layer can be employed.

The anode 101 is preferably formed using any of metals, alloys, conductive compounds with a high work function (specifically, a work function of 4.0 eV or more), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer in contact with the anode 101 in the EL layer 103, an electrode material can be selected regardless of its work function.

Two kinds of stacked layer structure of the EL layer 103 are described: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. The structure of one embodiment of the present invention is preferably used in the case where an organic compound having an acceptor property is used. As the organic compound having acceptor property, a compound including an electron-withdrawing group (a halogen group or a cyano group), e.g., 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, or 2,3,6,7,10,11-hexacyano-1,4,5,8,9,12-hexaazatriphenylene (abbreviation: HAT-CN), can be used. The organic compound having an acceptor property is preferably a compound in which electron-withdrawing groups are bonded to a condensed aromatic ring having a plurality of hetero atoms, like HAT-CN, because it is thermally stable. The organic compound having an acceptor property can extract electrons from an adjacent hole-transport layer (or hole-transport material) by the application of an electric field.

In the case where the organic compound having an acceptor property is not used for the hole-injection layer 111, molybdenum oxide, vanadium oxide, ruthenium oxide, tungsten oxide, manganese oxide, or the like can be used as the substance having an acceptor property. Alternatively, the hole-injection layer 111 can be formed using a phthalocyanine-based compound such as phthalocyanine (abbreviation: $H_2Pc$) or copper phthalocyanine (CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

Alternatively, a composite material in which a substance having a hole-transport property contains an acceptor substance can be used for the hole-injection layer 111. By using a composite material in which a substance having a hole-transport property contains an acceptor substance, a material used to form an electrode can be selected regardless of its work function. In other words, besides a material having a high work function, a material having a low work function can also be used for the anode 101. Examples of the acceptor substance include an organic compound having an acceptor property, such as 7,7,8,8-tetracyano-2,3,5,6-tetrafluoroquinodimethane (abbreviation: F4-TCNQ), chloranil, or 1,3,4,5,7,8-hexafluorotetracyano-naphthoquinodimethane (abbreviation: F6-TCNNQ), and a transition metal oxide. Alternatively, an oxide of a metal belonging to Group 4 to Group 8 in the periodic table can be used. As the oxide of a metal belonging to Group 4 to Group 8 in the periodic table, vanadium oxide, niobium oxide, tantalum oxide, chromium oxide, molybdenum oxide, tungsten oxide, manganese oxide, rhenium oxide, or the like is preferably used because their electron-accepting property is high. Among these, molybdenum oxide is especially preferable since it is stable in the air and its hygroscopic property is low and is easily treated.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance having a hole-transport property which is used for the composite material is preferably a substance having a hole mobility of $10^{-6}$ cm$^2$/Vs or more. The organic compounds that can be used as the substance having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene.
Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can be used. The aromatic hydrocarbon may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used. In that case, F6-TCNNQ is preferably used as the acceptor substance.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing a hole-injection layer, a high hole-injection property can be achieved to allow a light-emitting element to be driven at a low voltage.

Note that the hole-injection layer may be formed of the above-described acceptor material either alone or in combination with another material. In this case, the acceptor material extracts electrons from the hole-transport layer, so that holes can be injected into the hole-transport layer. The acceptor material transfers the extracted electrons to the anode.

By providing the hole-injection layer 111, a high hole-injection property can be achieved to allow a light-emitting element to be driven at a low voltage. In addition, the organic compound having an acceptor property is easy to use because it is easily deposited by vapor deposition.

The hole-transport layer 112 contains a hole-transport material. The hole-transport material preferably has a hole mobility of $1 \times 10^{-6}$ cm$^2$/Vs or more. The hole-transport layer 112 preferably includes the hole-transport material of one embodiment of the present invention, in which case a light-emitting element with a long lifetime and a high efficiency can be provided.

Particularly when the organic compound having an acceptor property is used for the hole-injection layer 111, at least the hole-injection layer 111 consists of two layers of a first and a second hole-transport layer, a first hole-transport material with a relatively shallow HOMO level is used for the first hole-injection layer, and the hole-transport material of one embodiment of the present invention is used for the second hole-transport layer; as a result, a light-emitting element with a long lifetime and a high efficiency can be provided.

Although the difference between the LUMO level of the organic compound having an acceptor property and the HOMO level of the first hole-transport material is not particularly limited because it depends on the strength of the acceptor property of the organic compound having an acceptor property, holes can be injected when the difference between the levels is less than or equal to approximately 1 eV. Since the LUMO level of HAT-CN is estimated to be −4.41 eV by cyclic voltammetry measurement, in the case where HAT-CN is used as the organic compound having an acceptor property, the HOMO level of the first hole-transport material is preferably greater than or equal to −5.4 eV. Note that if the HOMO level of the first hole-transport material is too high, the hole-injection property for the second hole-transport material deteriorates. In addition, since the work function of an anode such as ITO is approximately −5 eV, the use of a material whose HOMO level is higher than −5 eV as the first hole-transport material brings a disadvantage. Therefore, the HOMO level of the first hole-transport material is preferably less than or equal to −5.0 eV.

A third hole-transport layer may be formed between the second hole-transport layer and the light-emitting layer. The third hole-transport layer includes a third hole-transport material.

The first to third hole-transport layers are described above and not repeatedly described. Note that the hole-transport material included in each hole-transport layer may be selected from the aforementioned materials having hole-transport properties or other various materials having hole-transport properties so that the layers have an appropriate relationship.

The light-emitting layer 113 includes the host material and the light-emitting material. As the light-emitting material, fluorescent materials, phosphorescent materials, substances exhibiting thermally activated delayed fluorescence (TADF), or other light-emitting materials may be used. Furthermore, the light-emitting layer 113 may be a single layer or include a plurality of layers containing different light-emitting materials. Note that one embodiment of the present invention is more preferably used in the case where the light-emitting layer 113 emits fluorescence, specifically, blue fluorescence.

Examples of the material that can be used as a fluorescent substance in the light-emitting layer 113 are described below. Fluorescent substances other than those given below can also be used.

Examples of the fluorescent substance include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N'-diphenyl-N,N'-(1,6-pyrene-diyl)bis[(6-phenylbenzo[b]naphtho[1,2-d]furan)-8-amine] (abbreviation: 1,6BnfAPrn-03). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability.

Examples of the material that can be used as a phosphorescent substance in the light-emitting layer 113 are as follows.

The examples include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato) iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato] iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[(1-2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-J]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl] pyridinato-N,$C^{2'}$}iridium(III) picolinate (abbreviation: [Ir(CF$_3$ppy)$_2$(pic)]), and bis[2-(4',6'-difluorophenyl) pyridinato-N,$C^{2'}$]iridium(III) acetylacetonate (abbreviation: FIracac). These are compounds emitting blue phosphorescence and have an emission peak at 440 nm to 520 nm.

Other examples include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium (III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato) bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and rare earth metal complexes such as tris(acetylacetonato)(monophenanthroline)terbium(III) (abbreviation: [Tb(acac)$_3$(Phen)]). These are mainly compounds emitting green phosphorescence and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), bis[4,6-di(naphthalen-1-yl)pyrimidinato](dipivaloylmethanato)iridium(III) (abbreviation: [Ir(dlnpm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These are compounds emitting red phosphorescence and have an emission peak at 600 nm to 700 nm. Furthermore, organometallic iridium complexes having pyrazine skeletons can provide red light emission with favorable chromaticity.

Besides the above phosphorescent compounds, known phosphorescent materials may be selected and used.

Examples of the TADF material include a fullerene, a derivative thereof, acridine, a derivative thereof, an eosin derivative, and a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are represented by the following structural formulae.

[Chemical Formula 5]

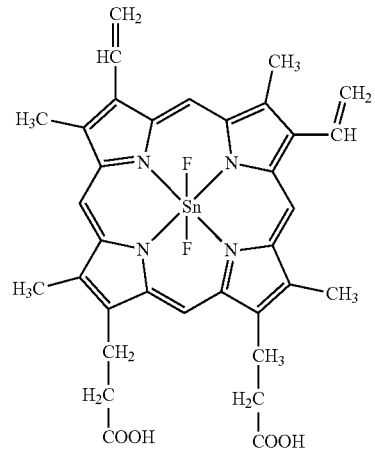

SnF$_2$(Proto IX)

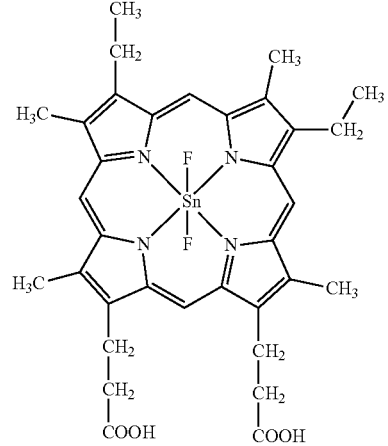

SnF$_2$(Meso IX)

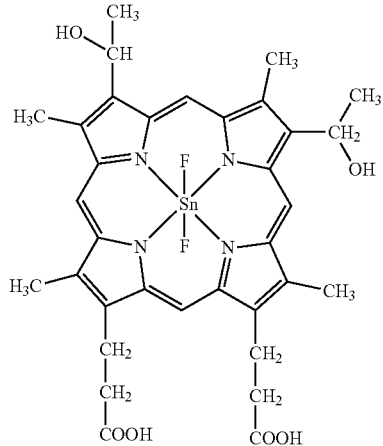

SnF$_2$(Hemato IX)

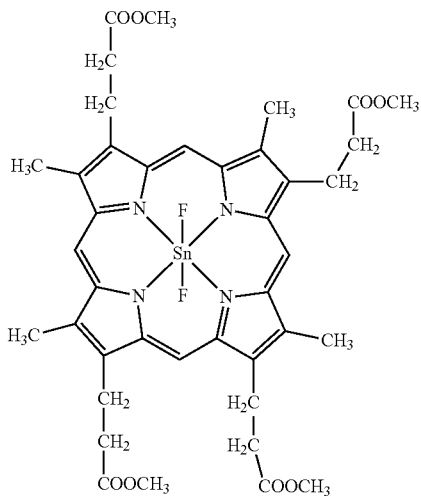

SnF2(Copro III-4Me)

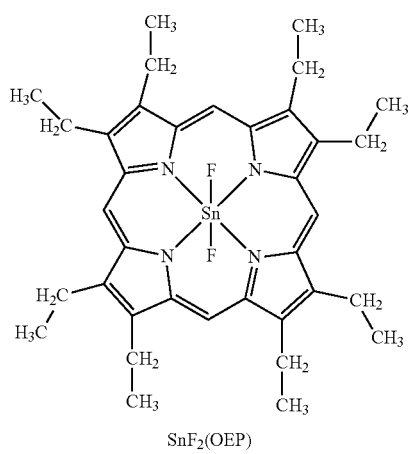

SnF2(OEP)

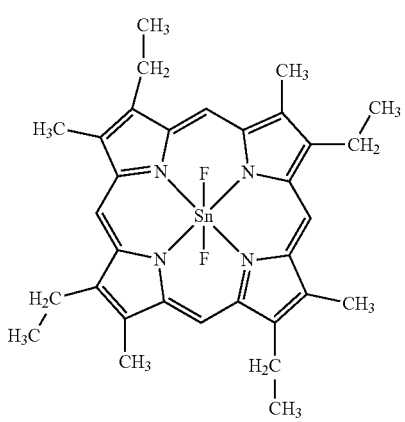

SnF2(Etio 1)

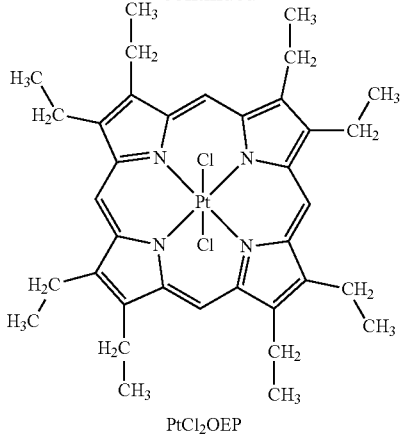

PtCl2OEP

Alternatively, a heterocyclic compound having both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 9-[4-(4,6-diphenyl-1,3,5-triazin-2-yl)phenyl]-9'-phenyl-9H,9'H-3,3'-bicarbazole (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased, the energy difference between the $S_1$ level and the $T_1$ level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring.

[Chemical Formula 6]
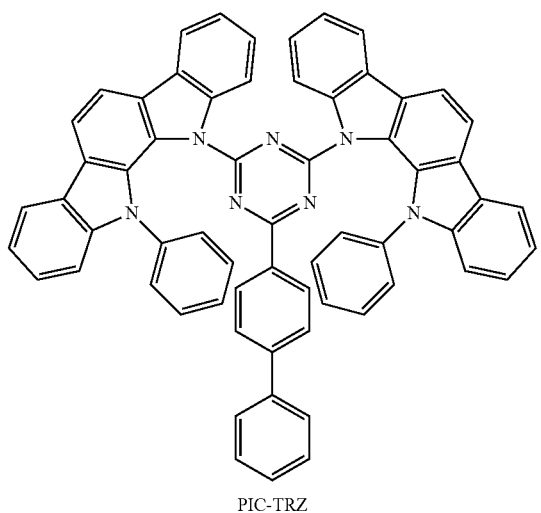
PIC-TRZ
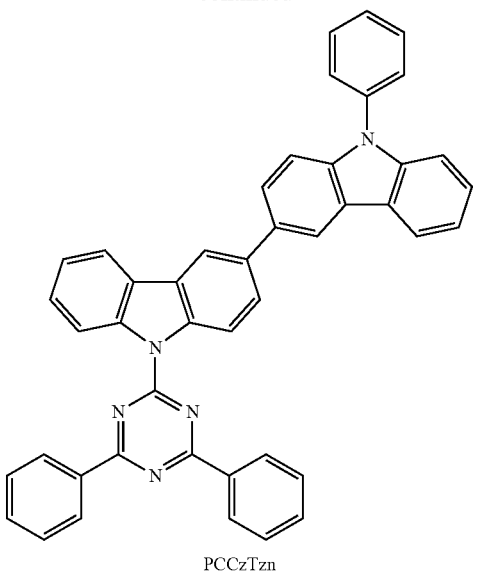
PCCzTzn
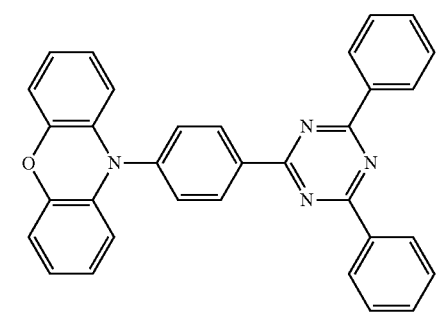
PXZ-TRZ
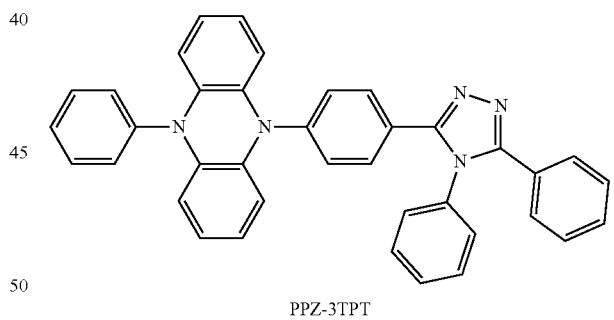
PPZ-3TPT
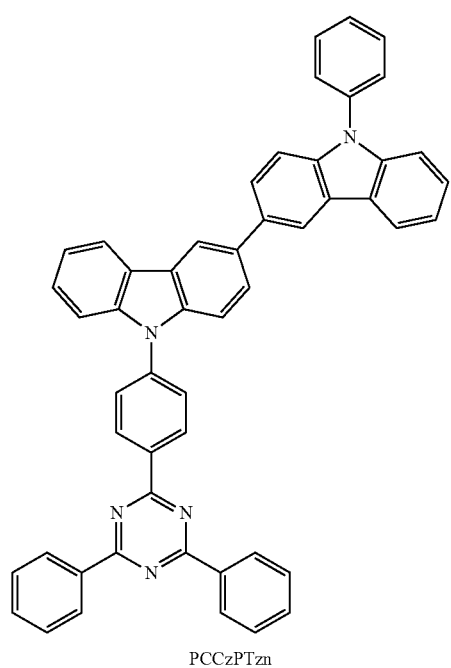
PCCzPTzn
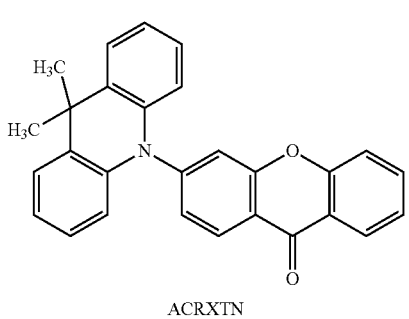
ACRXTN

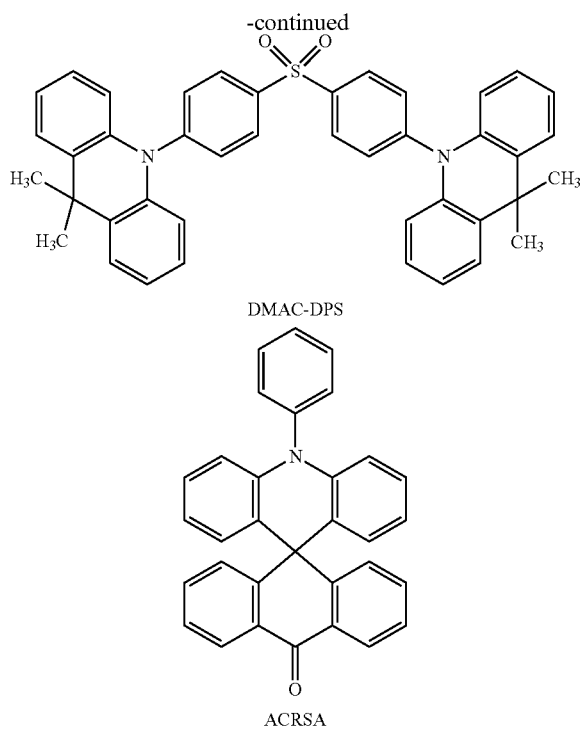

DMAC-DPS

ACRSA

As the host material in the light-emitting layer, various carrier-transport materials such as materials with an electron-transport property and materials with a hole-transport property can be used.

The following are examples of the materials having a hole-transport property: compounds having aromatic amine skeletons, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable, have a high hole-transport property, and contribute to a reduction in drive voltage.

The following are examples of materials having an electron-transport property: metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons and the heterocyclic compounds having pyridine skeletons are highly reliable and preferred. In particular, the heterocyclic compounds having diazine (pyrimidine or pyrazine) skeletons have a high electron-transport property and contribute to a decrease in drive voltage.

In the case where a fluorescent substance is used as the light-emitting material, a material having an anthracene skeleton is preferably used as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, such a material can be preferably used in one embodiment of the present invention. Among the substances having an anthracene skeleton, a substance with a diphenylanthracene skeleton, in particular, a substance with a 9,10-diphenylanthracene skeleton, is chemically stable and thus is preferably used as the host material. The host material preferably has a carbazole skeleton because the hole-injection and hole-transport properties are increased; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably includes a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN) 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). In particular, CzPA, cgDBCzPA, 2mBnfPPA, and PCzPA are preferable choices because of their excellent characteristics.

Note that the light-emitting element of one embodiment of the present invention is particularly preferably applied to a light-emitting element that emits blue fluorescence.

Note that the host material may be a mixture of plural kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed by these mixed materials. It is preferable that the combination of these materials be selected so as to form an exciplex that emits light with a wavelength overlapping with that of the lowest energy absorption band of the light-emitting material, in which case energy is transferred smoothly, light emission can be obtained efficiently, and the drive voltage is reduced.

The electron-transport layer 114 is a layer containing a substance with an electron-transport property. As the substance having an electron-transport property, it is possible to use any of the above-listed substances having electron-transport properties that can be used as the host material.

A layer containing an alkali metal, an alkaline earth metal, or a compound thereof such as lithium fluoride (LiF), cesium fluoride (CsF), or calcium fluoride (CaF$_2$) may be provided as the electron-injection layer 115 between the electron-transport layer 114 and the cathode 102. For example, an electride or a layer that is formed using a substance having an electron-transport property and that contains an alkali metal, an alkaline earth metal, or a compound thereof can be used as the electron-injection layer 115. Examples of the electride include a substance in which electrons are added at high concentration to calcium oxide-aluminum oxide.

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the cathode 102 serving as a cathode; thus, the light-emitting element operates.

Note that the charge-generation layer 116 preferably includes one or both of an electron-relay layer 118 and an electron-injection buffer layer 119 in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used.

For the cathode 102, any of metals, alloys, electrically conductive compounds, and mixtures thereof which have a low work function (specifically, a work function of 3.8 eV or less) can be used, for example. Specific examples of such a cathode material are elements belonging to Group 1 or 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), and alloys thereof. However, when the electron-injection layer is provided between the cathode 102 and the electron-transport layer, for the cathode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the films may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, or a spin coating method may be used.

The electrodes or the layers described above may be formed by different methods.

The structure of the layers provided between the anode 101 and the cathode 102 is not limited to the above-described structure. Preferably, a light-emitting region where holes and electrons recombine is positioned away from the anode 101 and the cathode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a material having a wider band gap than the light-emitting material of the light-emitting layer or the light-emitting material included in the light-emitting layer.

Next, an embodiment of a light-emitting element with a structure in which a plurality of light-emitting units are stacked (this type of light-emitting element is also referred to as a stacked element or a tandem element) is described with reference to FIG. 1C. In this light-emitting element, a plurality of light-emitting units are provided between an anode and a cathode. One light-emitting unit has substantially the same structure as the EL layer 103 illustrated in FIG. 1A. In other words, the light-emitting element illustrated in FIG. 1C is a light-emitting element including a plurality of light-emitting units; each of the light-emitting elements illustrated in FIGS. 1A and 1B is a light-emitting element including a single light-emitting unit.

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the anode 101 and the cathode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. Since the composite material of an organic compound and a metal oxide is superior in carrier-injection property and carrier-transport property, low-voltage driving or low-current driving can be achieved. Note that when a surface of a light-emitting unit on the anode side is in contact with the charge-generation layer 513, the charge-generation layer 513 can also serve as a hole-injection layer in the light-emitting unit and a hole-injection layer is not necessarily formed in the light-emitting unit.

In the case where the electron-injection buffer layer 119 is provided, the electron-injection buffer layer 119 serves as the electron-injection layer in the light-emitting unit on the anode side and thus the light-emitting unit on the anode side does not necessarily need an electron-injection layer.

The light-emitting element having two light-emitting units is described with reference to FIG. 1C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide a long-life element which can emit high luminance light with the current density kept low. Moreover, a low-power-consumption light-emitting device driven at a low voltage can be manufactured.

Furthermore, when emission colors of light-emitting units are made different, light emission of a desired color can be provided from the light-emitting element as a whole. For example, in a light-emitting element having two light-emitting units, the emission colors of the first light-emitting unit may be red and green and the emission color of the second light-emitting unit may be blue, so that the light-emitting element can emit white light as the whole element.

The above-described electrodes and layers such as the EL layer 103, the first light-emitting unit 511, the second light-emitting unit 512, and the charge-generation layer can be deposited by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Here, a method for forming an EL layer 786 by a droplet discharge method is described with reference to FIGS. 34A to 34D. FIGS. 34A to 34D are cross-sectional views illustrating the method for forming the EL layer 786.

Figure 34A:
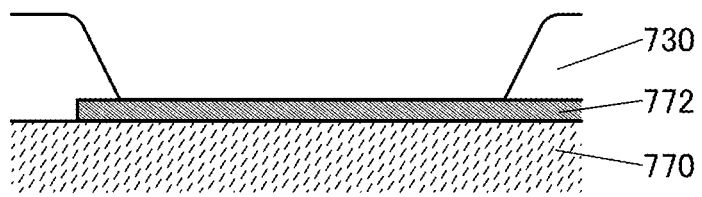
FIGS. 34A to 34D are cross-sectional views illustrating a method for manufacturing an EL layer.
Figure 34B:
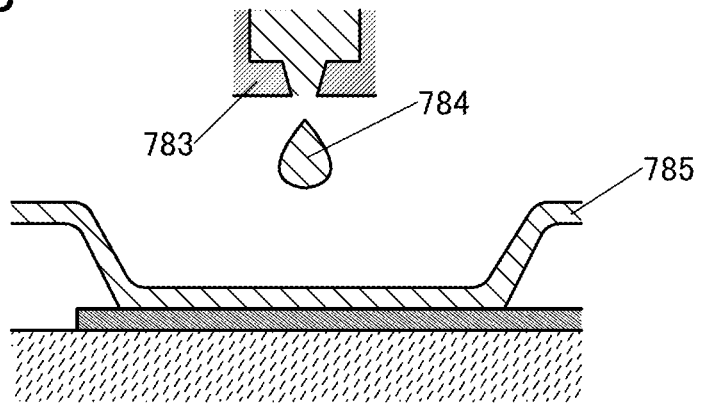

First, a conductive film 772 is formed over a planarization insulating film 770, and an insulating film 730 is formed to cover part of the conductive film 772 (see FIG. 34A).

Then, a droplet 784 is discharged from a droplet discharge apparatus 783 to an exposed portion of the conductive film 772, which is an opening of the insulating film 730, so that a layer 785 containing a composition is formed. The droplet 784 is a composition containing a solvent and is attached to the conductive film 772 (see FIG. 34B).

Note that the step of discharging the droplet 784 may be performed under reduced pressure.

Figure 34C:
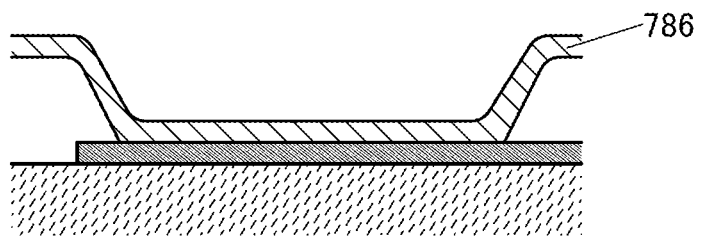

Next, the solvent is removed from the layer 785 containing the composition, and the resulting layer is solidified to form the EL layer 786 (see FIG. 34C).

The solvent may be removed by drying or heating.

Figure 34D:
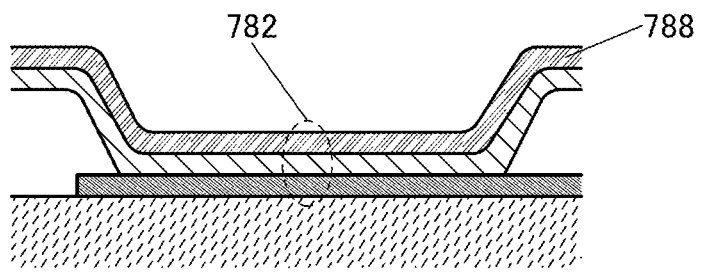

Next, a conductive film 788 is formed over the EL layer 786; thus, a light-emitting element 782 is formed (see FIG. 34D).

When the EL layer 786 is formed by a droplet discharge method as described above, the composition can be selectively discharged; accordingly, waste of material can be reduced. Furthermore, a lithography process or the like for shaping is not needed, simplifying the process and reducing costs.

The droplet discharge method described above is a general term for a means to discharge droplets, such as a nozzle with a composition discharge opening, or a head with one or a plurality of nozzles.

Figure 35:
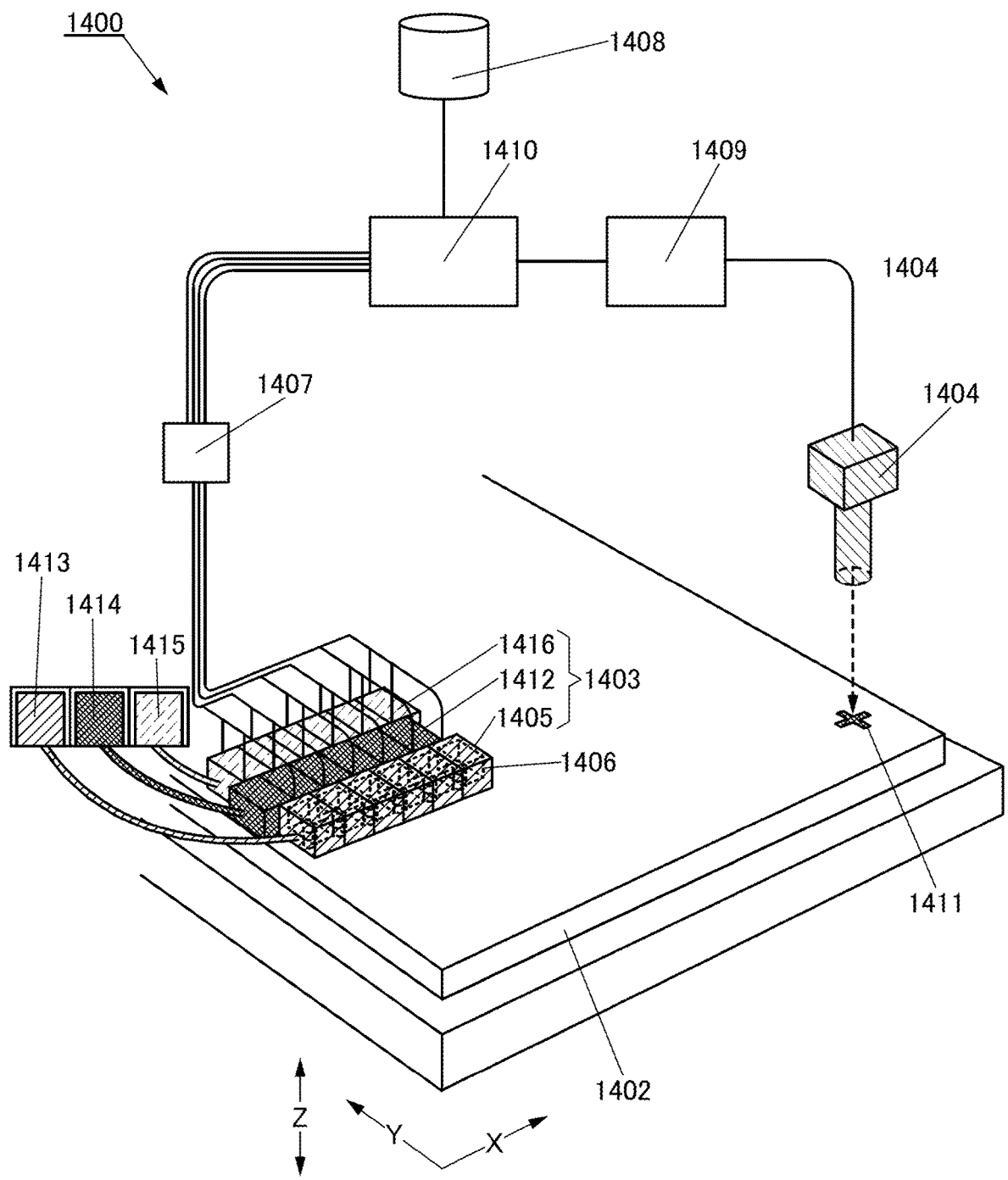
FIG. 35 is a conceptual diagram illustrating a droplet discharge apparatus.

Next, a droplet discharge apparatus used for the droplet discharge method is described with reference to FIG. 35. FIG. 35 is a conceptual diagram illustrating a droplet discharge apparatus 1400.

The droplet discharge apparatus 1400 includes a droplet discharge means 1403. In addition, the droplet discharge means 1403 is equipped with a head 1405, a head 1412, and a head 1416.

The heads 1405, 1412, and 1416 are connected to a control means 1407 that is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The digital signal is recognized by the computer 1410, and then, a control signal is generated and transmitted to the control means 1407.

An image sensor or the like using a charge coupled device (CCD) or a complementary metal oxide semiconductor (CMOS) can be used as the imaging means 1404. Note that information about a pattern to be formed over the substrate 1402 is stored in a storage medium 1408, and a control signal is transmitted to the control means 1407 based on the information, so that each of the heads 1405, 1412, and 1416 of the droplet discharge means 1403 can be individually controlled. A material to be discharged is supplied to the heads 1405, 1412, and 1416 from material supply sources 1413, 1414, and 1415, respectively, through pipes.

Inside the head 1405, a space as indicated by a dotted line 1406 to be filled with a liquid material and a nozzle which is a discharge outlet are provided. Although it is not shown, the inside structures of the heads 1412 and 1416 are similar to the inside structure of the head 1405. When the heads 1405 and 1412 have different nozzle sizes, different materials with different widths can be discharged simultaneously. Each head can discharge and draw a plurality of light-emitting materials. In the case of drawing over a large area, the same material can be simultaneously discharged to be drawn from a plurality of nozzles in order to improve throughput. When a large substrate is used, the heads 1405, 1412, and 1416 can freely scan the substrate in directions indicated by arrows X, Y, and Z in FIG. 35, and a region in which a pattern is drawn can be freely set. Thus, a plurality of the same patterns can be drawn over one substrate.

The step of discharging the composition may be performed under reduced pressure. Also, a substrate may be heated when the composition is discharged. After discharging the composition, one or both of drying and baking are performed. Both the drying and baking are heat treatments but different in purpose, temperature, and time period. The steps of drying and baking are performed under normal or reduced pressure by laser irradiation, rapid thermal annealing, heating using a heating furnace, or the like. Note that the timing of the heat treatment and the number of times of the heat treatment are not particularly limited. The temperature for adequately performing the steps of drying and baking depends on the materials of the substrate and the properties of the composition.

In the above manner, the EL layer 786 can be formed with the droplet discharge apparatus.

In the case where the EL layer 786 is formed with the droplet discharge apparatus, a hole-transport layer can be formed by a wet method using a composition in which the hole-transport material of the present invention is dissolved in a solvent. In that case, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, cyclohexane, and the like. In particular, less polar benzene derivatives such as benzene, toluene, xylene, and mesitylene are preferable because a solution with a suitable concentration can be obtained and the hole-transport material of the present invention contained in ink can be prevented from deteriorating due to oxidation or the like. Furthermore, to achieve a uniform film or a film with a uniform thickness, a solvent with a boiling point of 100° C. or higher is preferably used, and more preferably, toluene, xylene, or mesitylene is used.

Note that the above structure can be combined with any of the structures in this embodiment and the other embodiments as appropriate.

Embodiment 2

In this embodiment, an organic compound of one embodiment of the present invention will be described.

Some of the organic compounds described in Embodiment 1, which can be used as the second hole-transport material, are novel compounds and therefore are embodiments of the present invention. The organic compound of one embodiment of the present invention will be described below.

The organic compound of one embodiment of the present invention is represented by General Formula (G1).

[Chemical Formula 7]

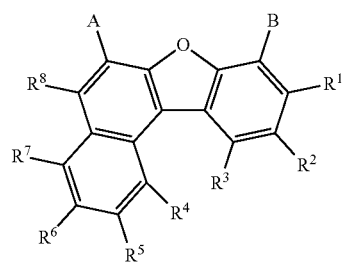

(G1)

Note that in General Formula (G1), $R^1$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

Specific examples of $R^1$ to $R^8$ in General Formula (G1) are represented by Formulae (1-1) to (1-40). In the case where $R^1$ to $R^8$ are each a substituted or unsubstituted aromatic hydrocarbon group having 6 to 60 carbon atoms, aromatic hydrocarbon in a skeleton of a substituent are represented by Formulae (2-1) to (2-13). Note that there is no limitation on the site of substitution of the aromatic hydrocarbon represented by Formulae (2-1) to (2-13), and a plurality of aromatic hydrocarbon groups may be connected to form a skeleton.

[Chemical Formula 8]

(1-1)

(1-2)

(1-3)
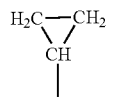

(1-4)
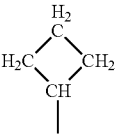

(1-5)
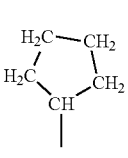

(1-6)
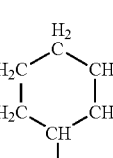

(1-7)
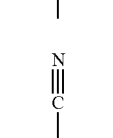

(1-8)

(1-9)

(1-10)

(1-11)
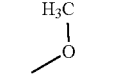

-continued (1-12)
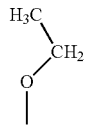

(1-13)
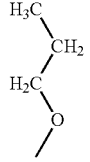

(1-14)
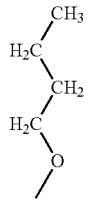

(1-15)
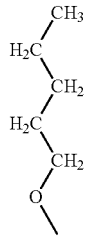

(1-16)
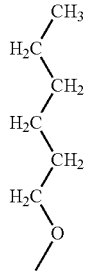

(1-17)
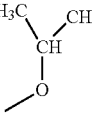

(1-18)
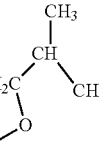

(1-19)
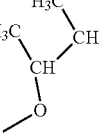

(1-20)

-continued
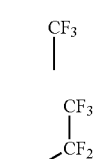 (1-21)
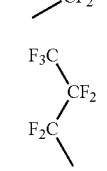 (1-22)
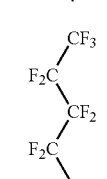 (1-23)
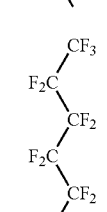 (1-24)
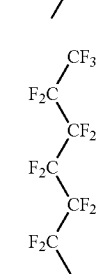 (1-25)
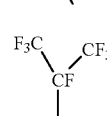 (1-26)
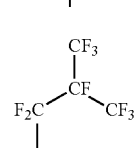 (1-27)
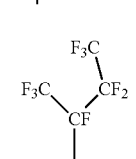 (1-28)
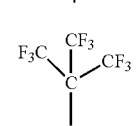 (1-29)
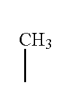 (1-30)
 (1-31)
-continued
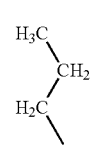 (1-32)
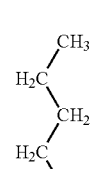 (1-33)
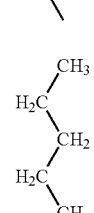 (1-34)
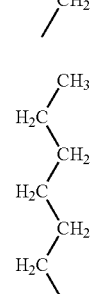 (1-35)
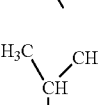 (1-36)
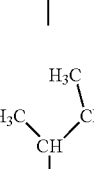 (1-37)
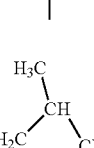 (1-38)
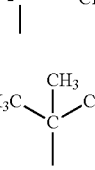 (1-39)
 (1-40)
[Chemical Formula 9]
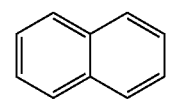 (2-1)
(2-2)

(2-3)
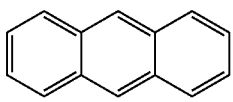

(2-4)
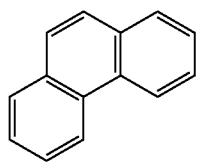

(2-5)
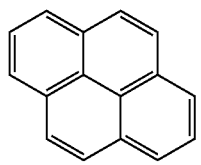

(2-6)
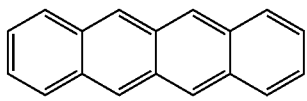

(2-7)
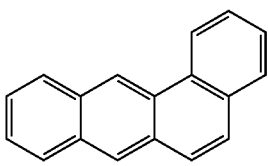

(2-8)
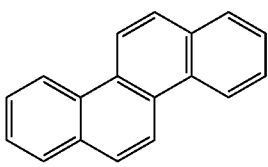

(2-9)
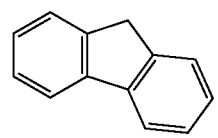

(2-10)
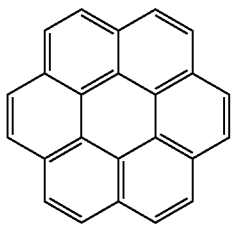

(2-11)
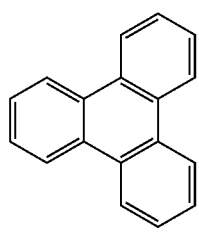

(2-12)
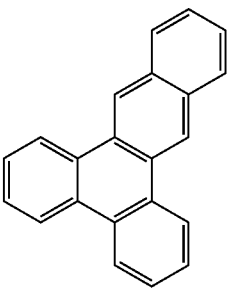

(2-13)
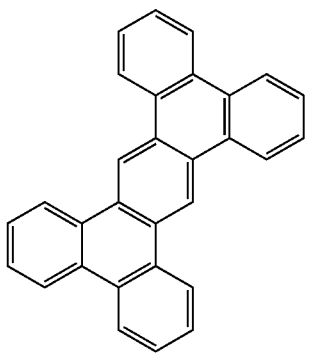

Note that in the case where $R^1$ to $R^8$ are each an aromatic hydrocarbon group including a substituent, the substituent can be any of a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, a substituted or unsubstituted aromatic hydrocarbon group having 6 to 60 carbon atoms, a dibenzofuranyl group, a dibenzothiophenyl group, a benzonaphthofuranyl group, and a benzonaphthothiophenyl group. In the case where $R^1$ to $R^8$ are each an aromatic hydrocarbon group including a substituent and the substituent is any of a hydrocarbon group having 1 to 6 carbon atoms, a cyclic hydrocarbon group having 3 to 6 carbon atoms, an alkoxy group having 1 to 6 carbon atoms, a cyano group, halogen, and a haloalkyl group having 1 to 6 carbon atoms, specific structure examples of $R^1$ to $R^8$ are the same as the structures represented by Formulae (1-1) to (1-40), which are shown above as specific examples of $R^1$ to $R^8$.

In the case where $R^1$ to $R^8$ are each an aromatic hydrocarbon group including a substituent and the substituent is any of a substituted or unsubstituted aromatic hydrocarbon group having 6 to 60 carbon atoms, a dibenzofuranyl group, a dibenzothiophenyl group, a benzonaphthofuranyl group, and a benzonaphthothiophenyl group, specific examples of $R^1$ to $R^8$ are represented by Formulae (1-41) to (1-81). In all the substituents represented by Formulae (1-41) to (1-81), there is no limitation on the site of substitution.

[Chemical Formula 10]

(1-41)
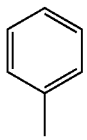

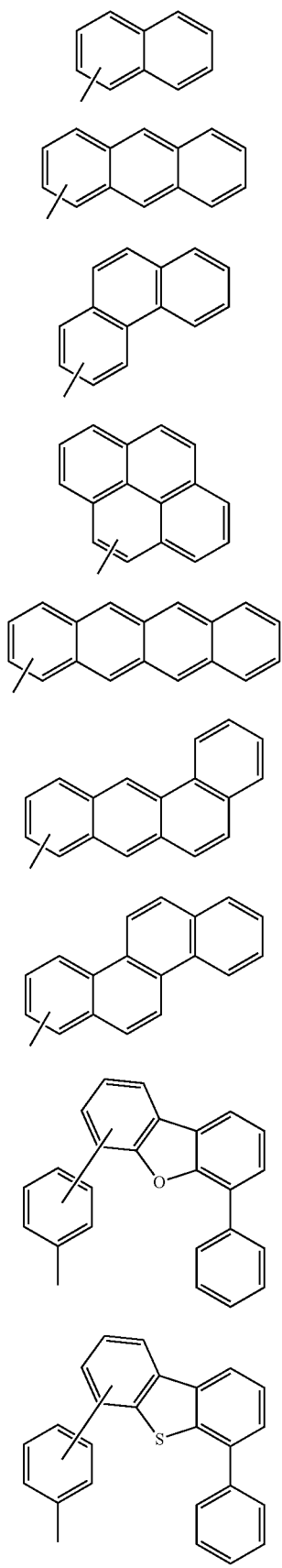
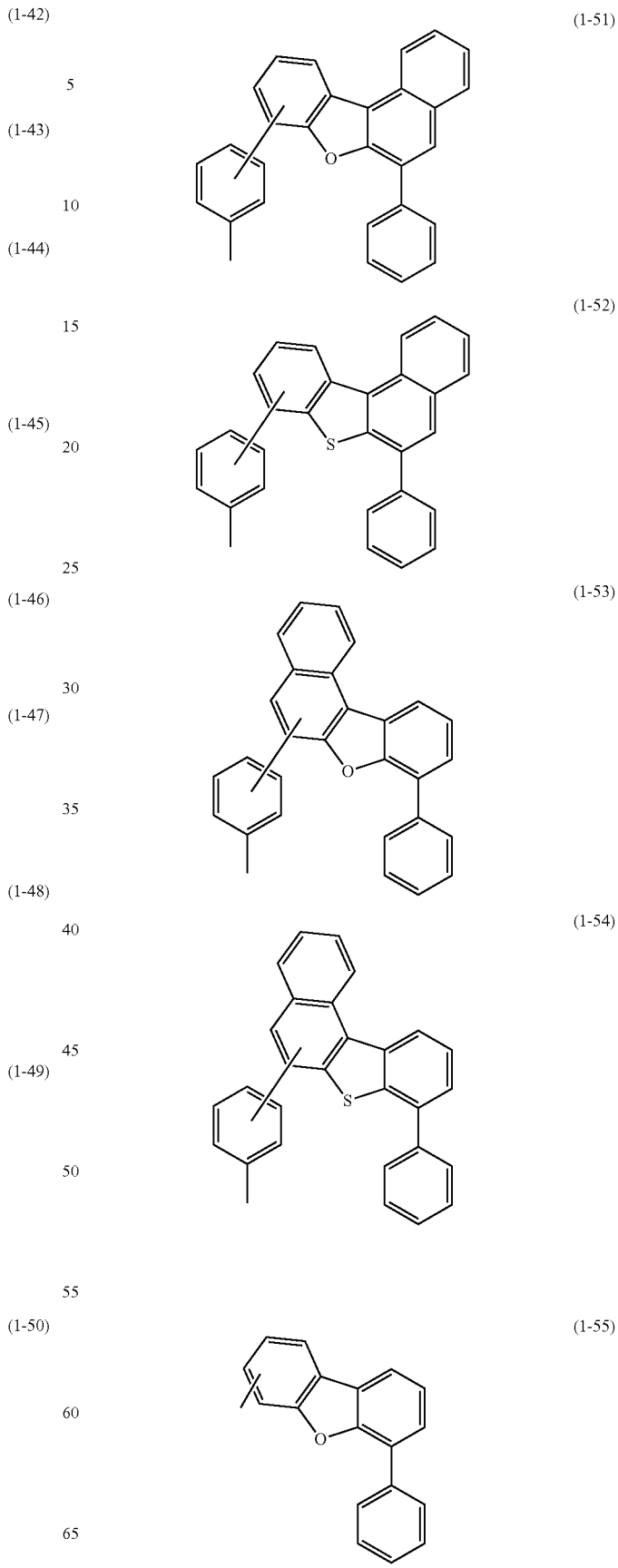

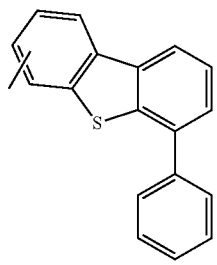
(1-56)
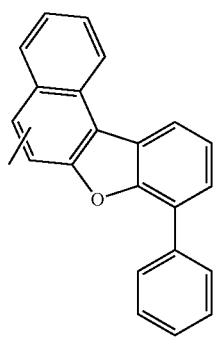
(1-57)
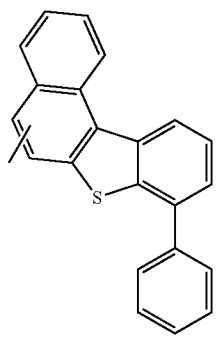
(1-58)
[Chemical Formula 11]
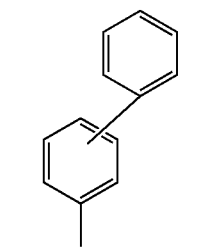
(1-59)
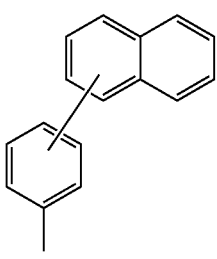
(1-60)
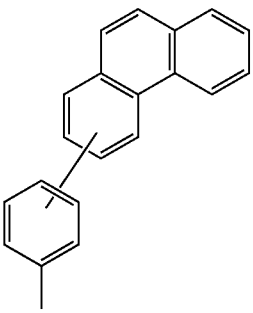
(1-61)
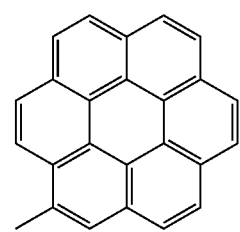
(1-62)
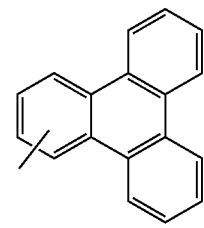
(1-63)
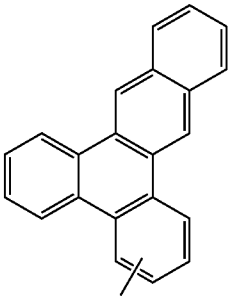
(1-64)
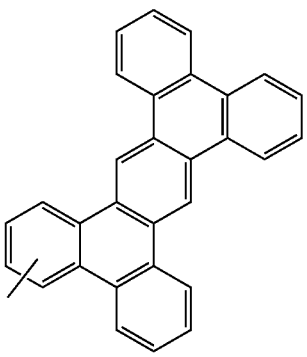
(1-65)
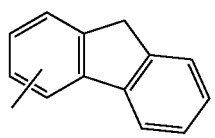
(1-66)

(1-67) 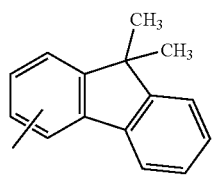
(1-68) 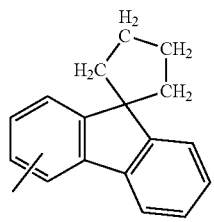
(1-69) 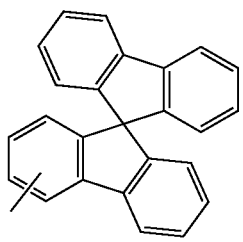
(1-70) 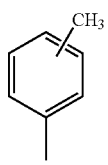
(1-71) 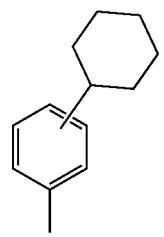
(1-72) 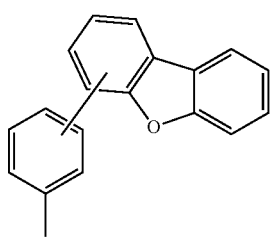
(1-73) 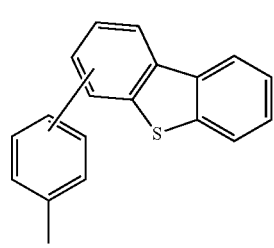
(1-74) 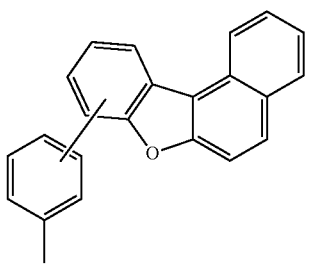
(1-75) 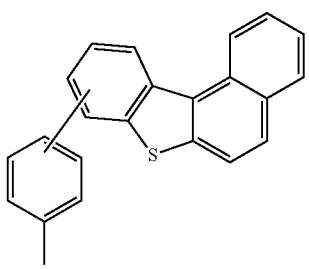
(1-76) 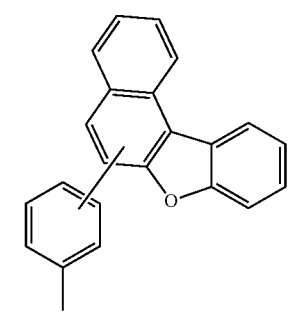
(1-77) 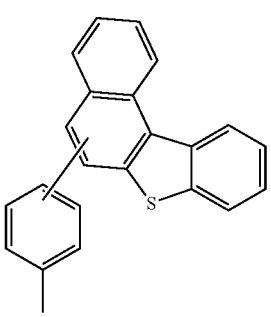
(1-78) 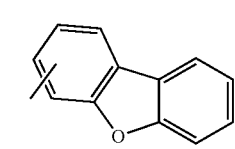
(1-79) 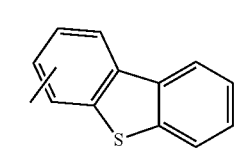

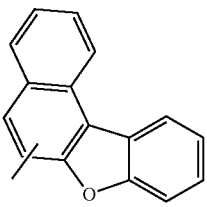
(1-80)

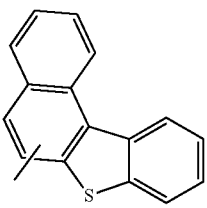
(1-81)

One of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms. Specific examples are the same as those of the substituents $R^1$ to $R^8$.

[Chemical Formula 12]

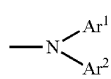
(g1)

Note that in General Formula (g1), $Ar^1$ and $Ar^2$ independently represent any one of a substituted or unsubstituted aromatic hydrocarbon group having 6 to 60 carbon atoms and a group represented by General Formula (g2). In the case where $Ar^1$ and $Ar^2$ are each an aromatic hydrocarbon group having 6 to 60 carbon atoms and include a substituent, the substituent includes a benzonaphthofuranyl group and a dinaphthofuranyl group.

[Chemical Formula 13]

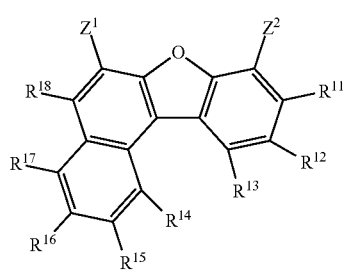
(g2)

Note that in General Formula (g2), $R^{11}$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. One of $Z^1$ and $Z^2$ is bonded to a nitrogen atom in General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms. Note that specific examples of $R^{11}$ to $R^{18}$ in the group represented by General Formula (g2) are the same as those of $R^1$ to $R^8$ in the organic compound represented by General Formula (G1). Further, specific examples of one of $Z^1$ and $Z^2$ that is not bonded to a nitrogen atom in the group represented by General Formula (g1) are the same as those of one of A and B in the organic compound represented by General Formula (G1) that is not represented by General Formula (g1). That is, one of $Z^1$ and $Z^2$ that is not bonded to a nitrogen atom in the group represented by General Formula (g1) represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms. Note that specific examples thereof are the same as those of the above substituents $R^1$ to $R^8$.

Specific skeleton examples of the aromatic hydrocarbon group having 6 to 60 carbon atoms, which can be used as $Ar^1$ and $Ar^2$ in General Formula (g1), are skeletons represented by Structural Formulae (2-1) to (2-13). Note that there is no limitation on the site of substitution and each group may consist of a plurality of skeletons.

[Chemical Formula 14]

(2-1)

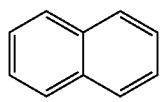
(2-2)

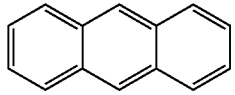
(2-3)

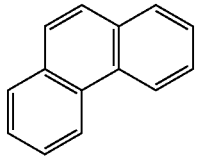
(2-4)

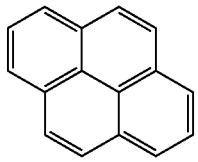
(2-5)

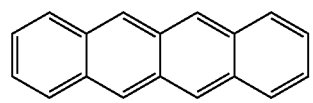
(2-6)

(2-7)
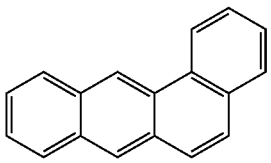

(2-8)
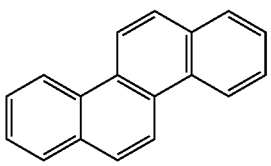

(2-9)
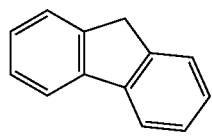

(2-10)
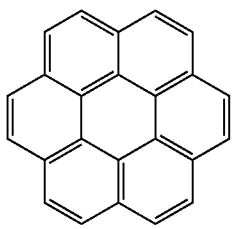

(2-11)
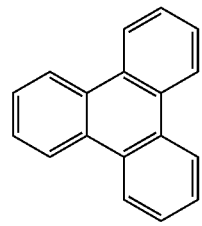

(2-12)
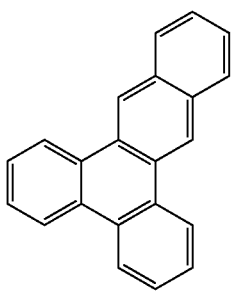

(2-13)
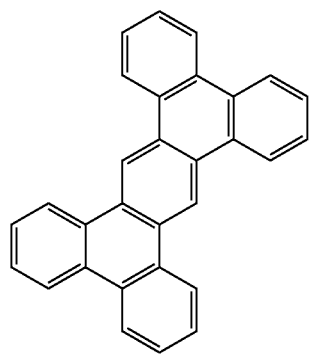

Note that in the case where $Ar^1$ and $Ar^2$ in General Formula (g1) are each an aromatic hydrocarbon group including a substituent, the substituent can be any of a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, a substituted or unsubstituted aromatic hydrocarbon group having 6 to 60 carbon atoms, a dibenzofuranyl group, a dibenzothiophenyl group, a benzonaphthofuranyl group, and a benzonaphthothiophenyl group. In the case where $Ar^1$ and $Ar^2$ are each an aromatic hydrocarbon group including a substituent and the substituent is any of a hydrocarbon group having 1 to 6 carbon atoms, a cyclic hydrocarbon group having 3 to 6 carbon atoms, an alkoxy group having 1 to 6 carbon atoms, a cyano group, halogen, and a haloalkyl group having 1 to 6 carbon atoms, specific structure examples of $Ar^1$ and $Ar^2$ are the same as the structures represented by Formulae (1-1) to (1-40), which are shown above as specific examples of $R^1$ to $R^8$ in General Formula (G1).

In the case where $Ar^1$ and $Ar^2$ in General Formula (g1) are each an aromatic hydrocarbon group including a substituent and the substituent is any of a substituted or unsubstituted aromatic hydrocarbon group having 6 to 60 carbon atoms, a dibenzofuranyl group, a dibenzothiophenyl group, a benzonaphthofuranyl group, and a benzonaphthothiophenyl group, specific examples of $Ar^1$ and $Ar^2$ are represented by Formulae (1-41) to (1-135). In all the substituents represented by Formulae (1-41) to (1-135), there is no limitation on the site of substitution.

[Chemical Formula 15]

(1-41)
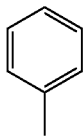

(1-42)
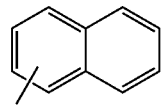

(1-43)
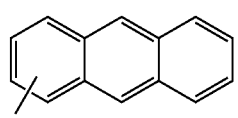

(1-44)
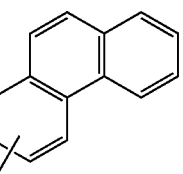

(1-45)
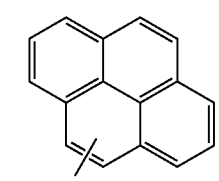

(1-46)
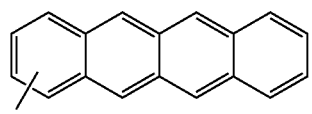
(1-47)
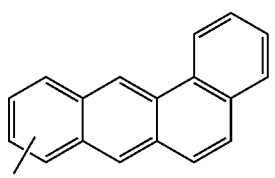
(1-48)
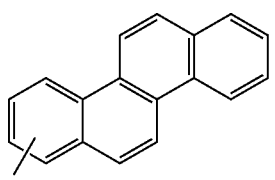
(1-49)
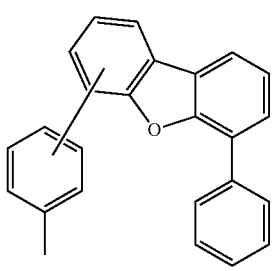
(1-50)
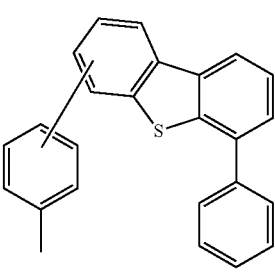
(1-51)
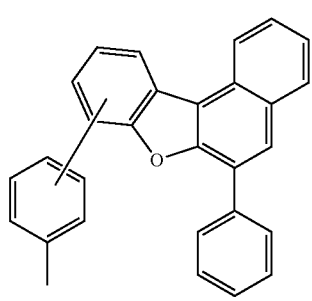
(1-52)
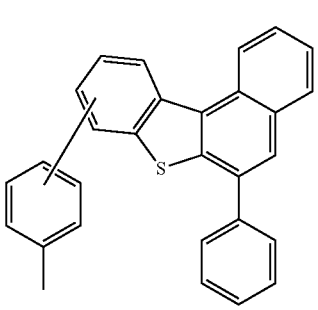
(1-53)
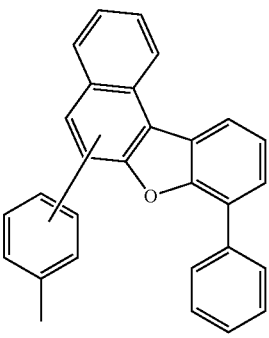
(1-54)
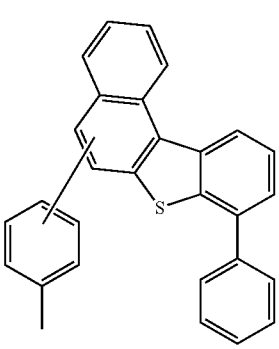
(1-55)
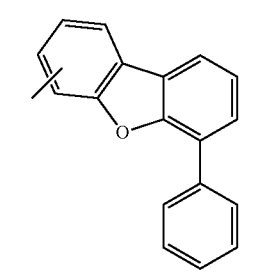
(1-56)
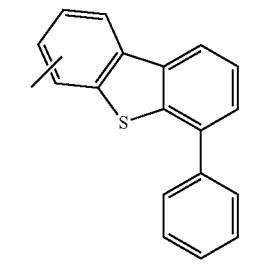
(1-57)
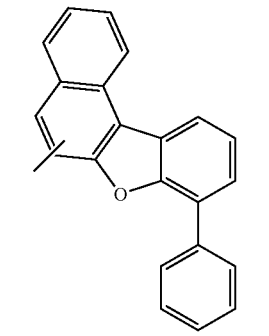

(1-58)
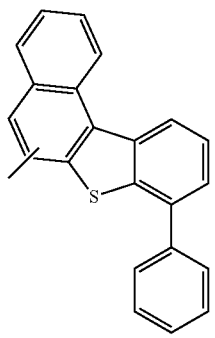
[Chemical Formula 16]
(1-59)
(1-60)
(1-61)
(1-62)
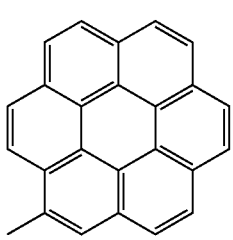
(1-63)
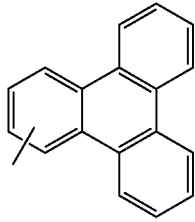
(1-64)
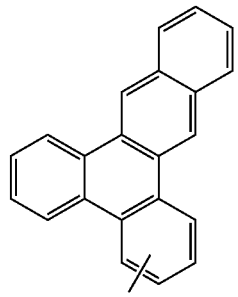
(1-65)
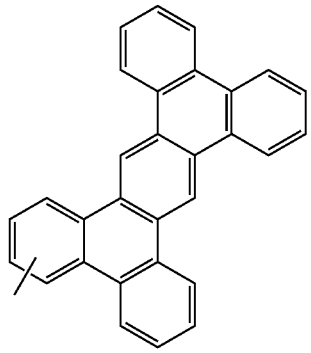
(1-66)
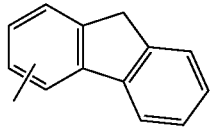
(1-67)
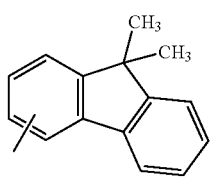
(1-68)
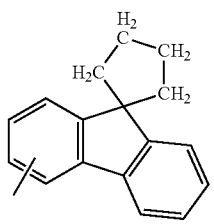

(1-69)
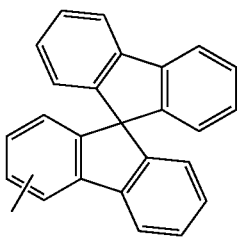
(1-70)
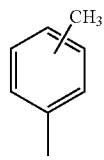
(1-71)
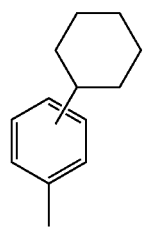
(1-72)
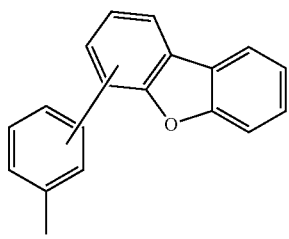
(1-73)
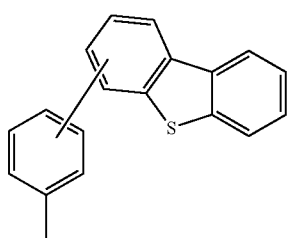
(1-74)
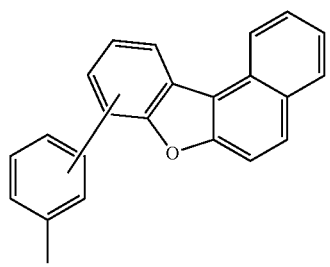
(1-75)
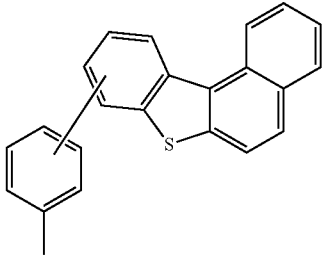
(1-76)
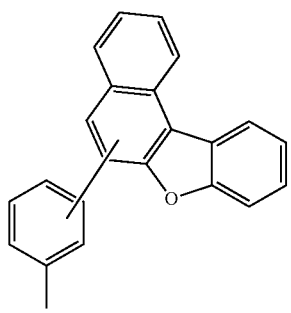
(1-77)
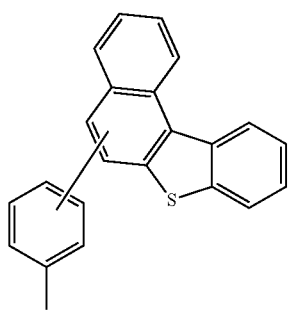
(1-78)
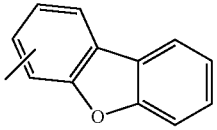
(1-79)
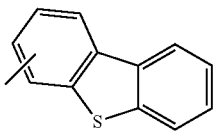
(1-80)
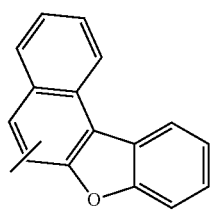
(1-81)
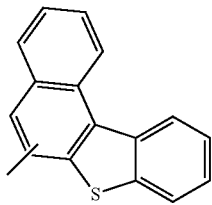

[Chemical Formula 17]
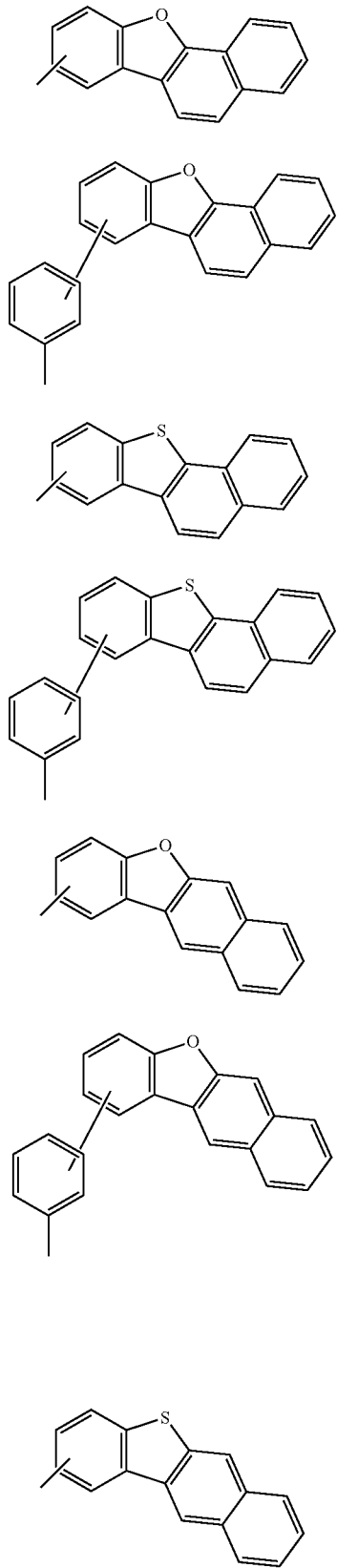
(1-82)
(1-83)
(1-84)
(1-85)
(1-86)
(1-87)
(1-88)
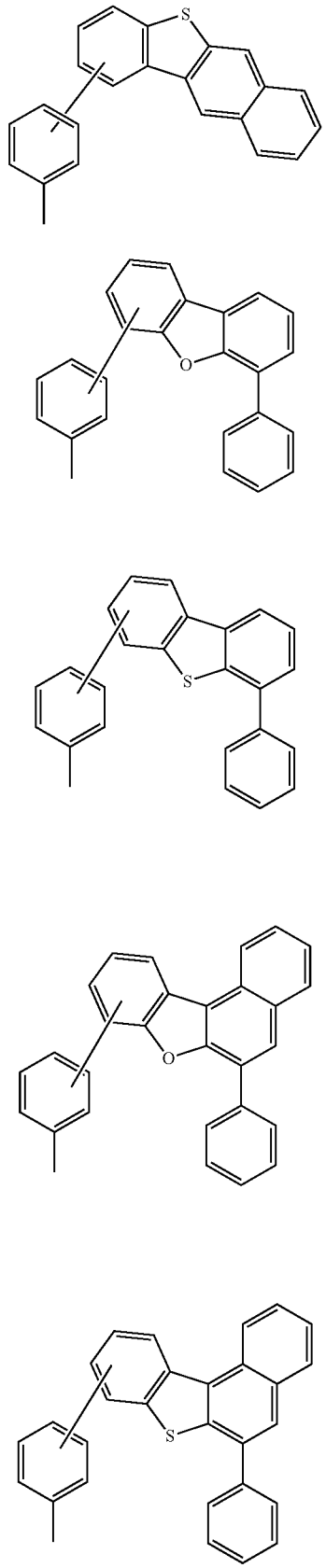
(1-89)
(1-90)
(1-91)
(1-92)
(1-93)

(1-94) 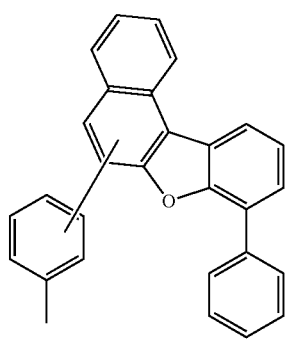
(1-95) 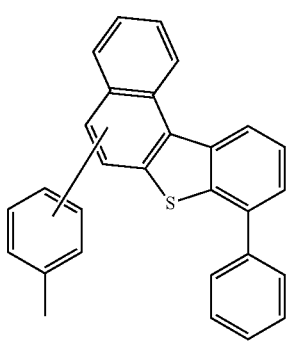
(1-96) 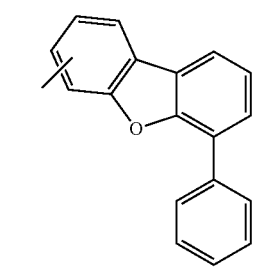
(1-97) 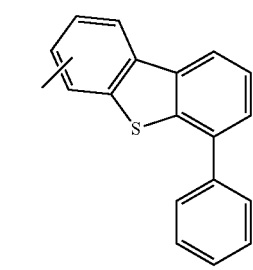
(1-98) 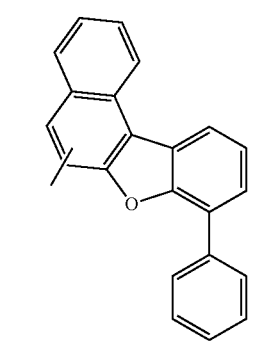
(1-99) 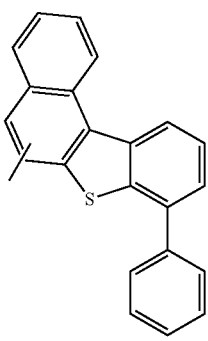
[Chemical Formula 18]
(1-100) 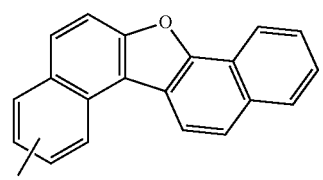
(1-101) 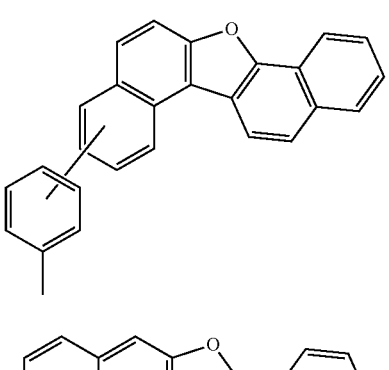
(1-102) 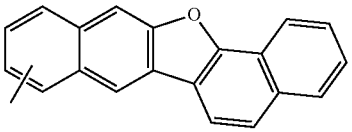
(1-103) 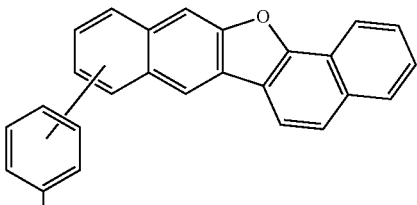
(1-104) 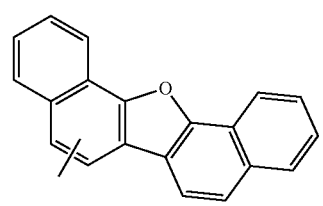

(1-105)
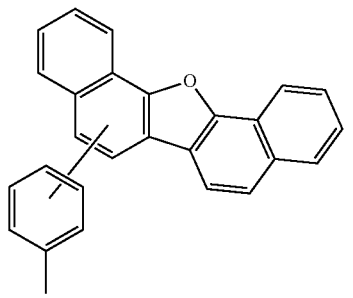
(1-106)
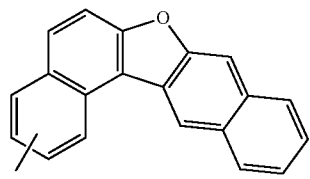
(1-107)
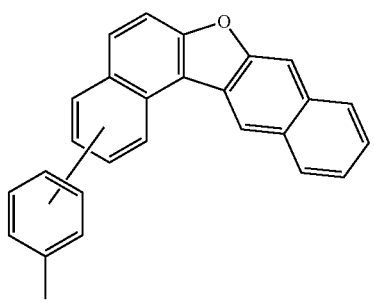
(1-108)
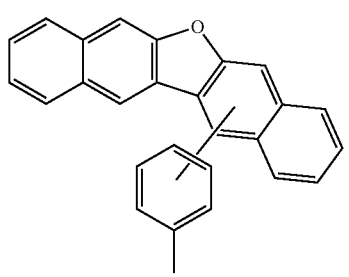
(1-109)
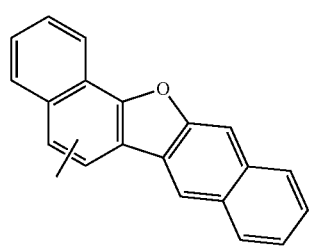
(1-110)
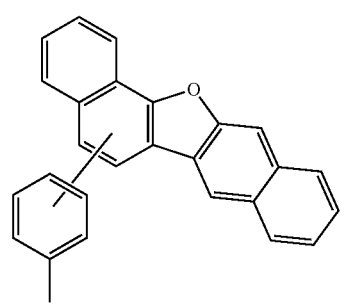
(1-111)
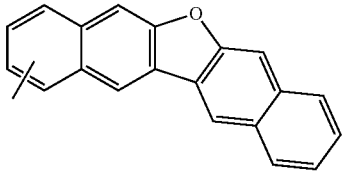
(1-112)
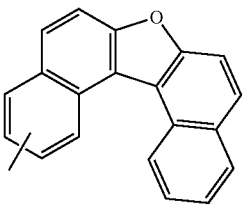
(1-113)
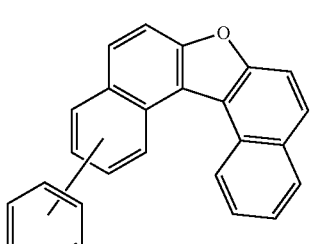
(1-114)
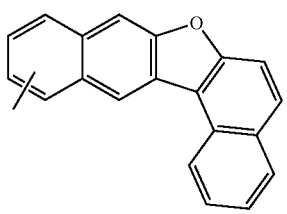
(1-115)
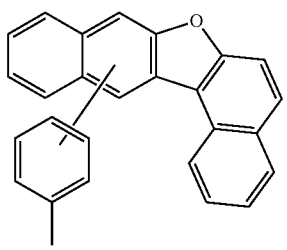
(1-116)
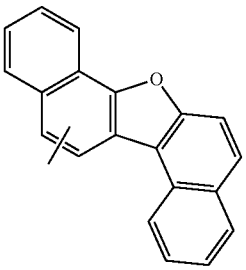

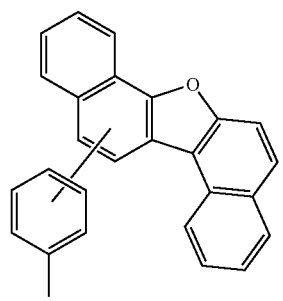 (1-117)
[Chemical Formula 19]
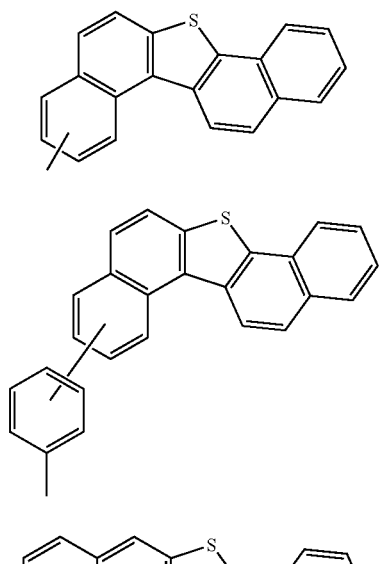 (1-118)
(1-119)
(1-120)
(1-121)
(1-122)
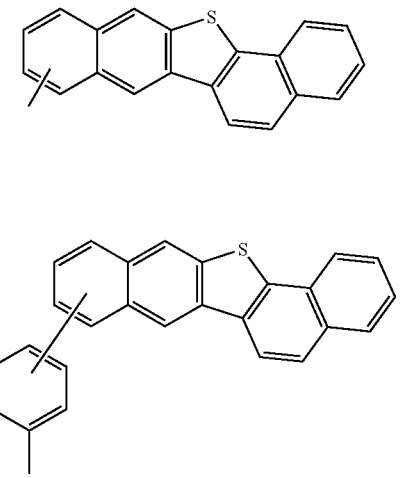 (-123)
(1-124)
(1-125)
(1-126)
(1-127)
(1-128)

(1-129)
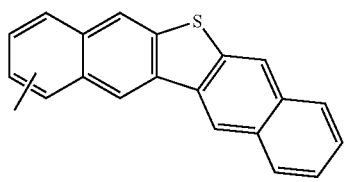
(1-130)
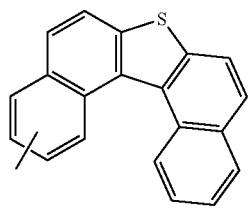
(1-131)
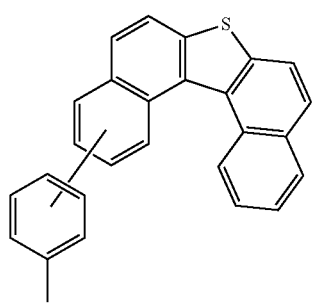
(1-132)
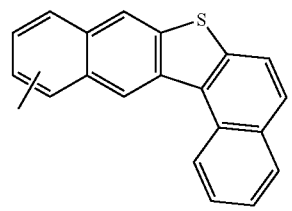
(1-133)
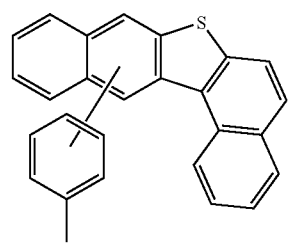
(1-134)
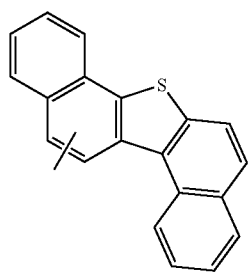
(1-135)
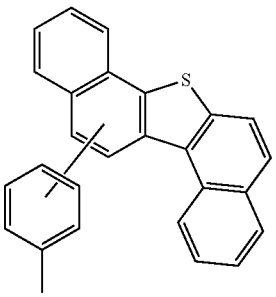
Specific examples of the substituents represented by Formula (g2) are as follows.
[Chemical Formula 20]
(3-1)
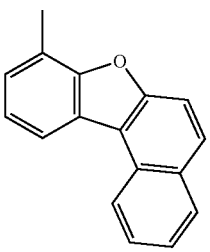
(3-2)
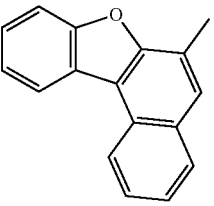
(3-5)
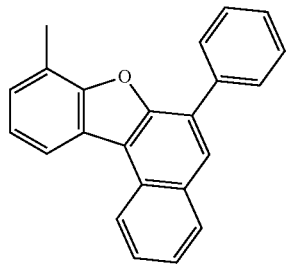
(3-7)
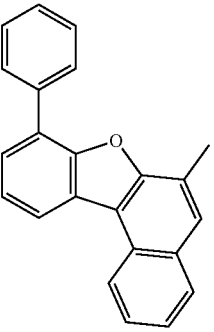

(3-11)
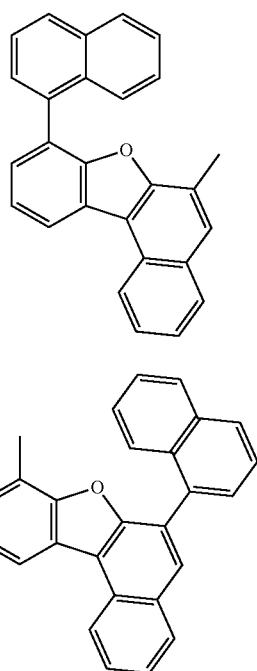
[Chemical Formula 21]
(3-9)
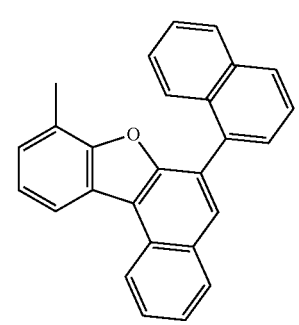
(3-13)
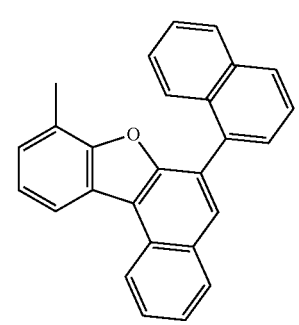
(3-15)
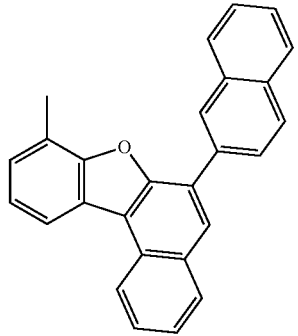
(3-17)
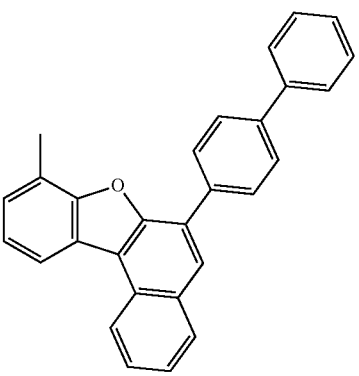
(3-19)
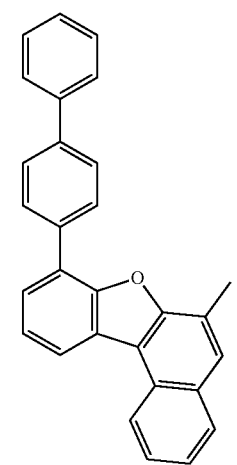
(3-21)
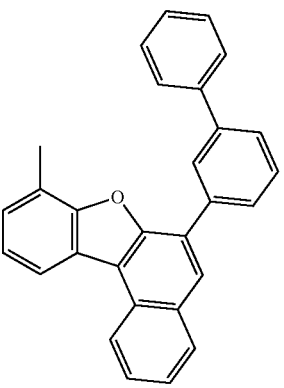
(3-23)
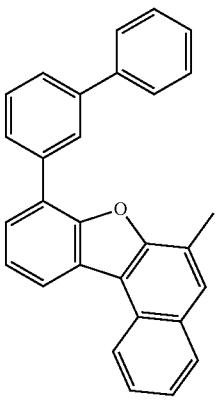

(3-25)
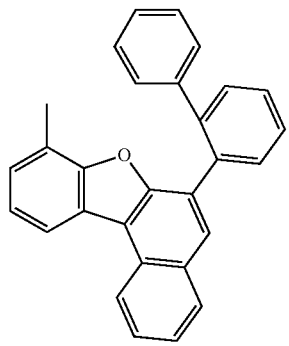
(3-27)
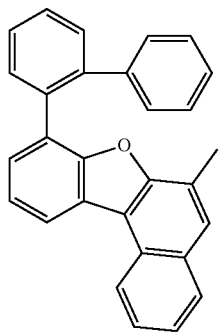
[Chemical Formula 22]
(3-29)
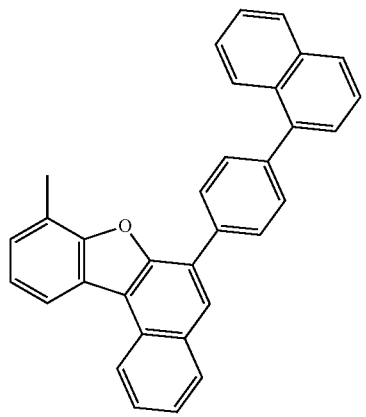
(3-31)
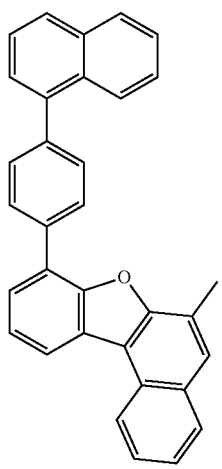
(3-33)
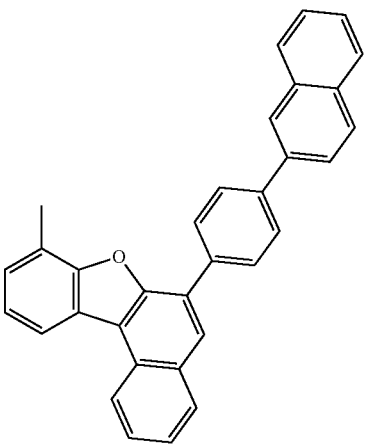
(3-35)
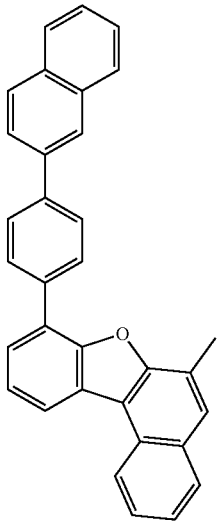
(3-37)
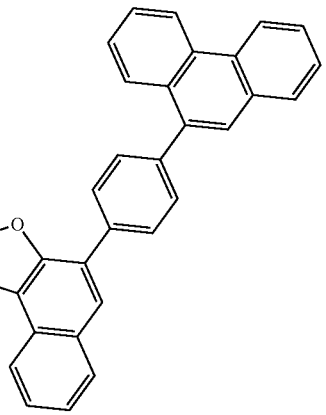

-continued (3-39)

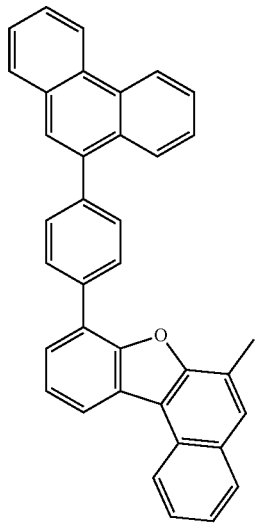

Another embodiment of the present invention is the organic compound in which the group represented by General Formula (g1) is a group represented by General Formula (g3).

[Chemical Formula 23]

(g3)

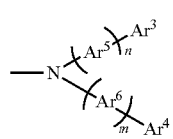

Note that in General Formula (g3), $Ar^3$ and $Ar^4$ independently represent any one of a substituted or unsubstituted aromatic hydrocarbon group having 6 to 60 carbon atoms, a substituted or unsubstituted benzonaphthofuranyl group, and a substituted or unsubstituted dinaphthofuranyl group. $Ar^3$ and $Ar^4$ are the same as Art and $Ar^2$ in General Formula (g1). Note that the sum of carbon atoms of $Ar^3$ and $Ar^5$ is less than or equal to 60, and the sum of carbon atoms of $Ar^4$ and Ar is less than or equal to 60.

$Ar^5$ and $Ar^6$ independently represent a substituted or unsubstituted divalent aromatic hydrocarbon group having 6 to 54 carbon atoms, and n and m independently represent 0 to 2. Note that the sum of carbon atoms of $Ar^3$ and $Ar^5$ is less than or equal to 60, and the sum of carbon atoms of $Ar^4$ and $Ar^6$ is less than or equal to 60. Specific examples of $Ar^5$ and $Ar^6$ are divalent groups having skeletons represented by Structural Formulae (2-1) to (2-13).

[Chemical Formula 24]

(2-1)

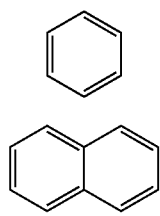

(2-2)

(2-3)

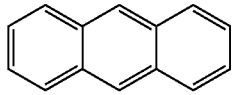

(2-4)

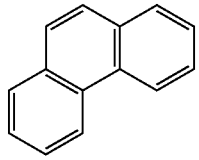

(2-5)

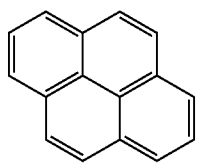

(2-6)

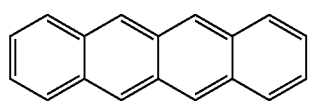

(2-7)

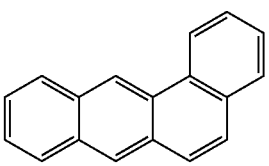

(2-8)

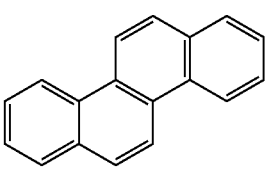

(2-9)

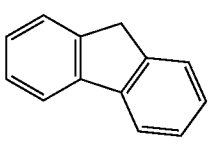

(2-10)

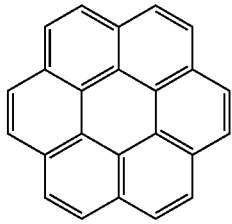

(2-11)

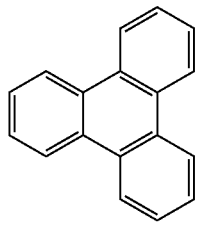

-continued (2-12)
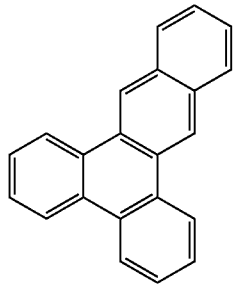

(2-13)
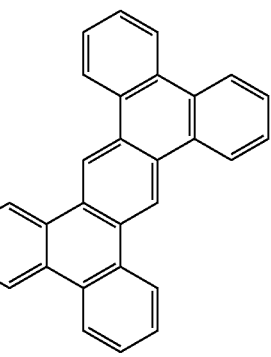

In the organic compound having the above structure, preferably, Ar³ and Ar⁴ each represent any one of a substituted or unsubstituted phenyl group, a substituted or unsubstituted naphthyl group, a substituted or unsubstituted anthracenyl group, and a substituted or unsubstituted pyrenyl group, which allows the transport layer to have high heat resistance, good film quality, and favorable hole-transport properties. In particular, each of Ar³ and Ar⁴ preferably represents a phenyl group because the layer with favorable hole-transport properties can be deposited efficiently.

In the organic compound having the above structure, preferably, Ar⁵ and Ar⁶ each represent any one of a substituted or unsubstituted phenylene group, a substituted or unsubstituted naphthylene group, a substituted or unsubstituted anthracenylene group, and a substituted or unsubstituted pyrenylene group, which allows the transport layer to have high heat resistance, good film quality, and favorable hole-transport properties. In particular, each of Ar⁵ and Ar⁶ preferably represents a phenylene group because the layer with favorable hole-transport properties can be deposited efficiently.

In the organic compound having the above structure, particularly preferably, one of n and m is 1 and the other is 0, in which case a high quality film with favorable hole-transport properties is achieved.

Specific examples of the organic compound with the above structure are shown below.

[Chemical Formula 25]

(100)
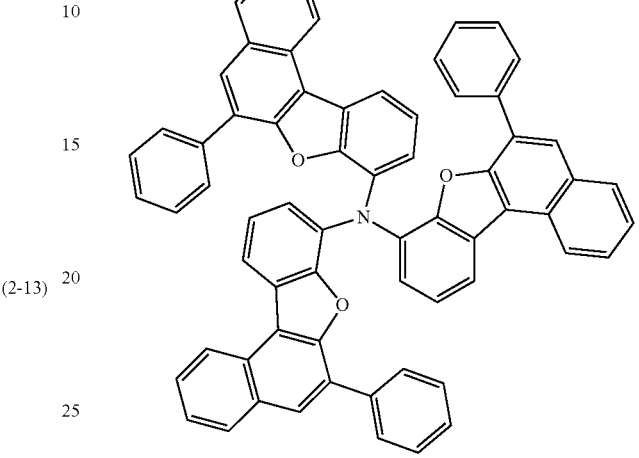

(101)
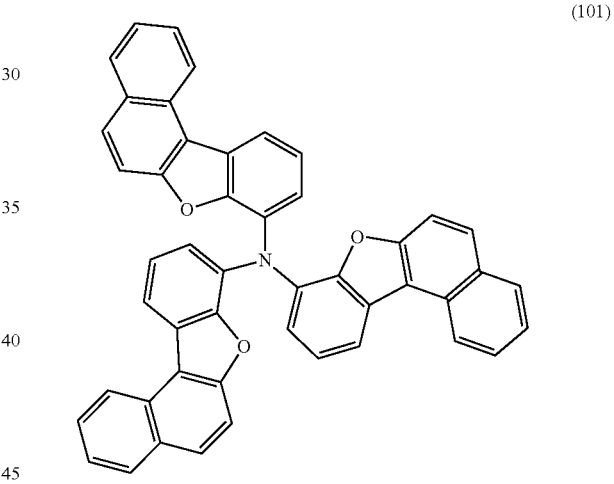

(102)
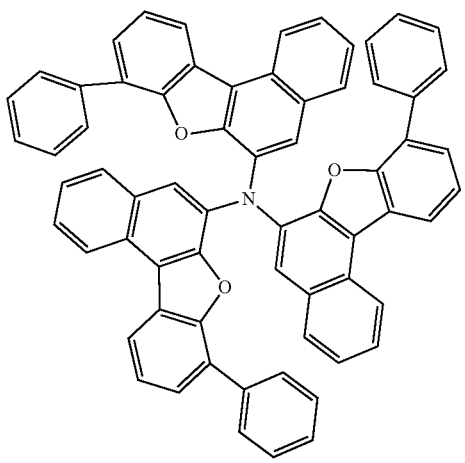

(103)
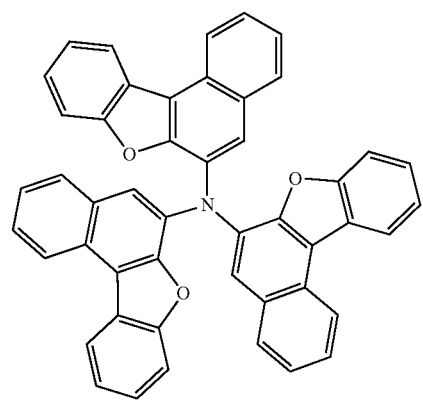
(104)
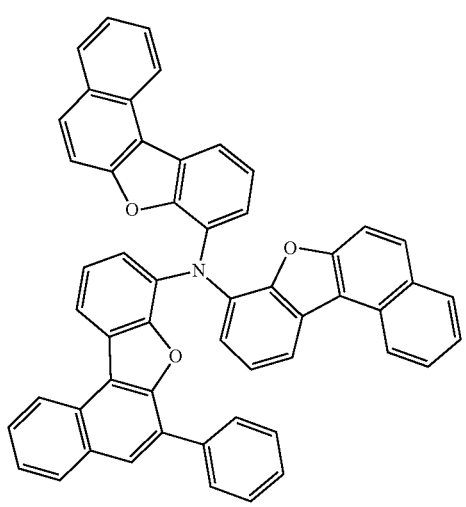
(105)
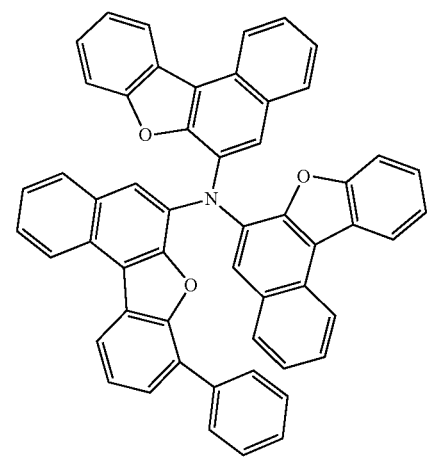
(106)
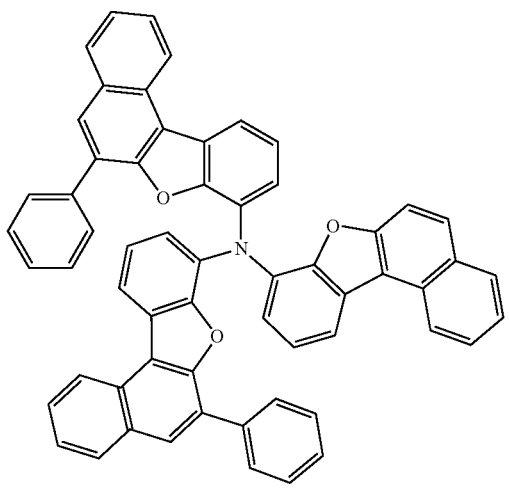
(107)
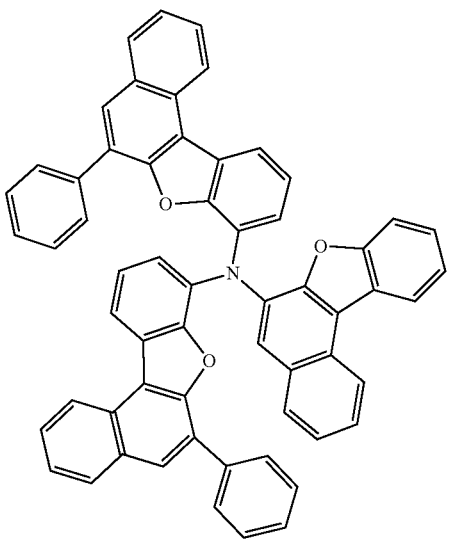
[Chemical Formula 26]
(108)
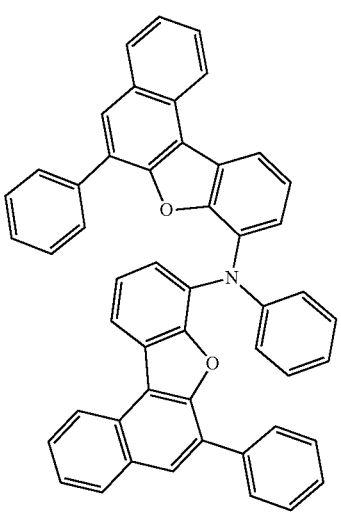

(109)
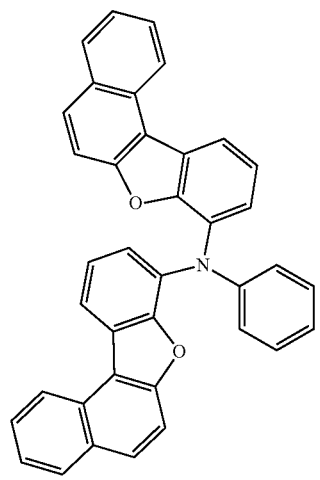
(110)
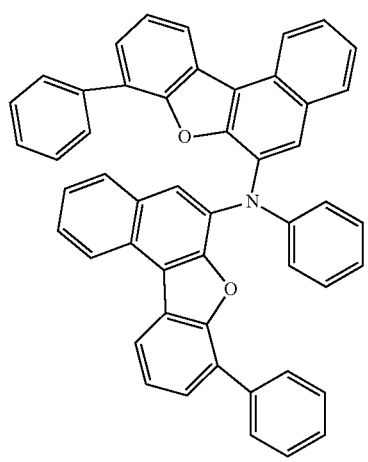
(111)
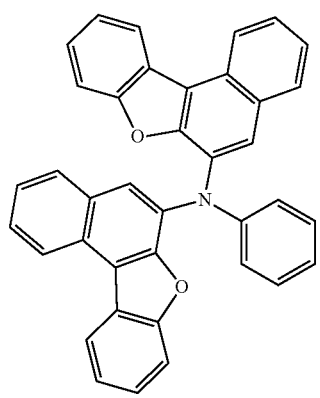
(112)
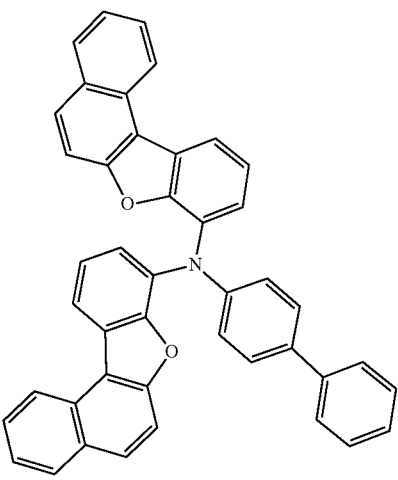
(113)
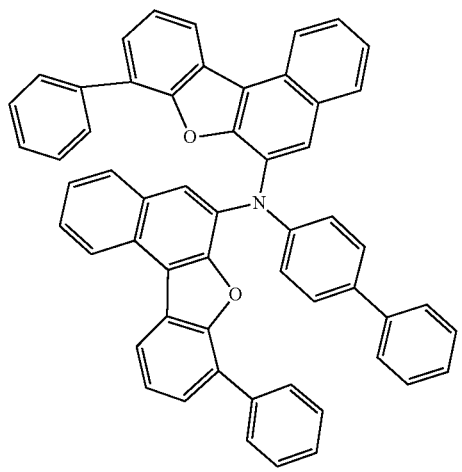
(114)
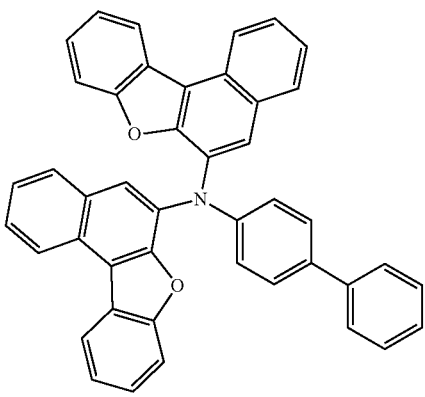

(115)
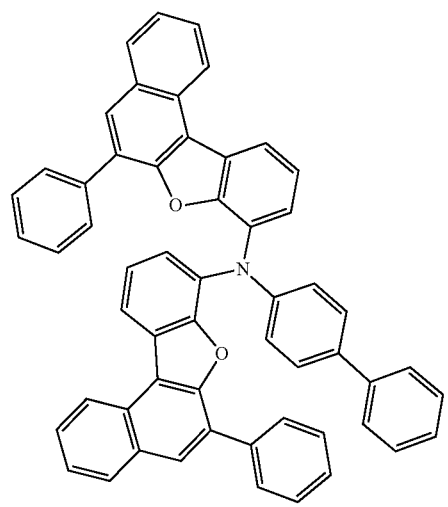
[Chemical Formula 27]
(116)
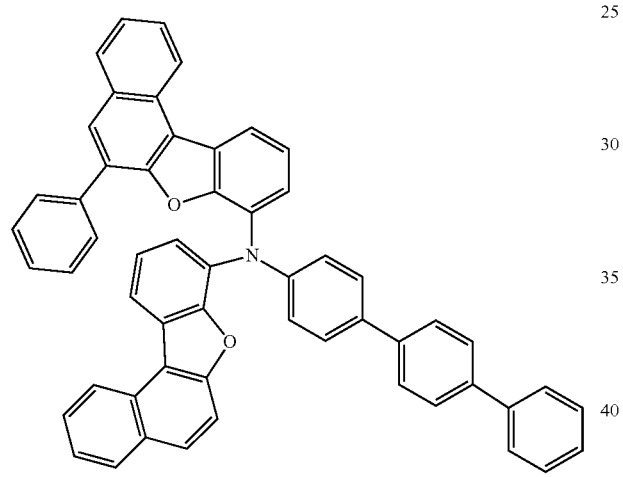
(117)
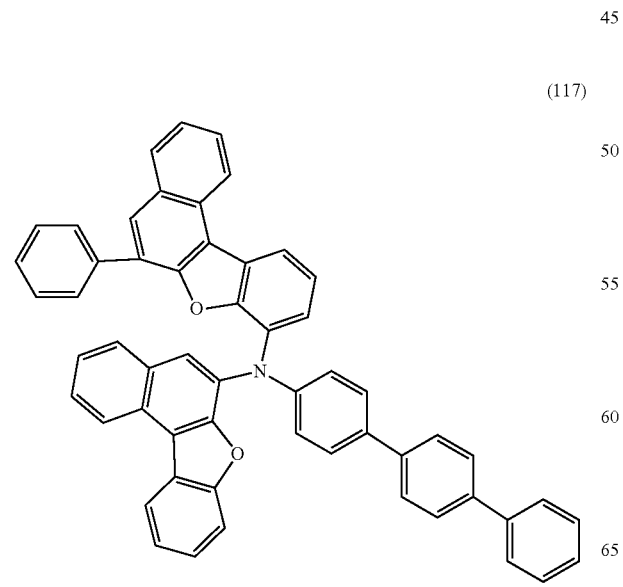
(118)
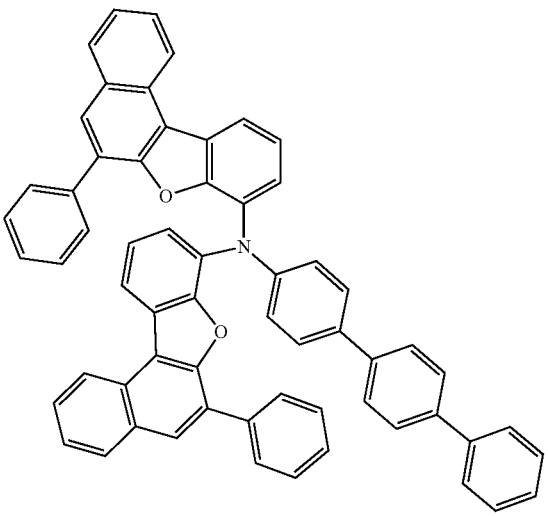
(119)
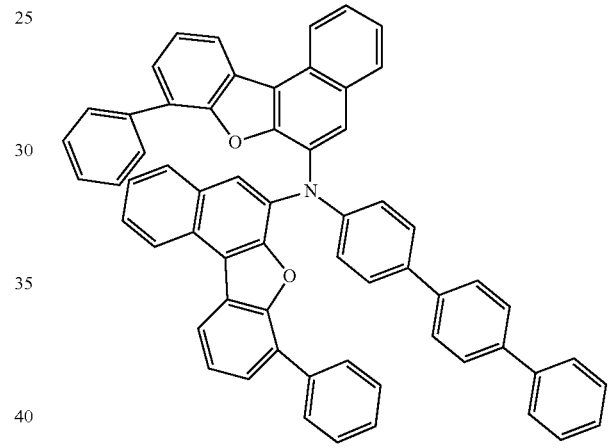
(120)
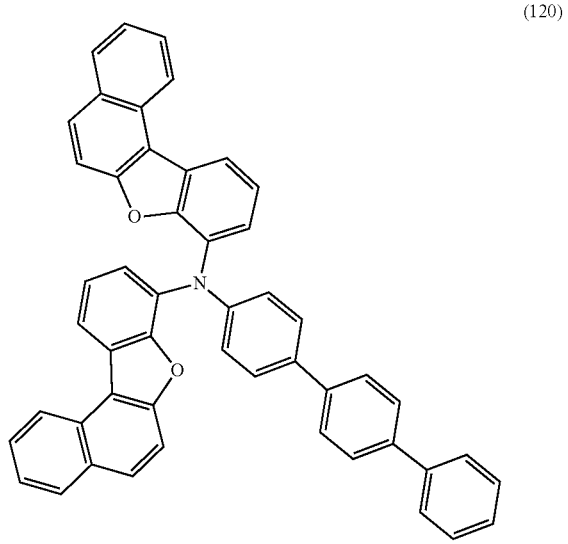

(121)
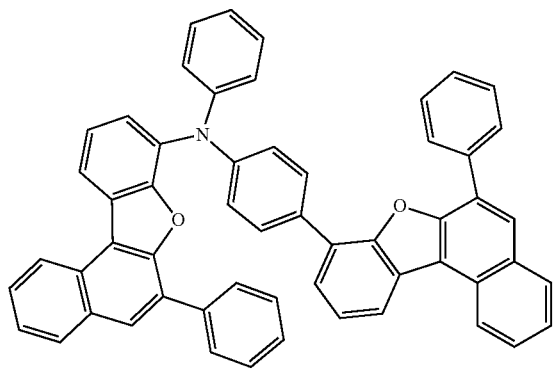
(122)
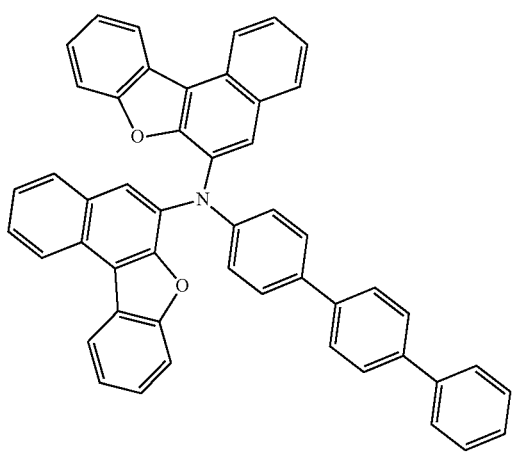
(123)
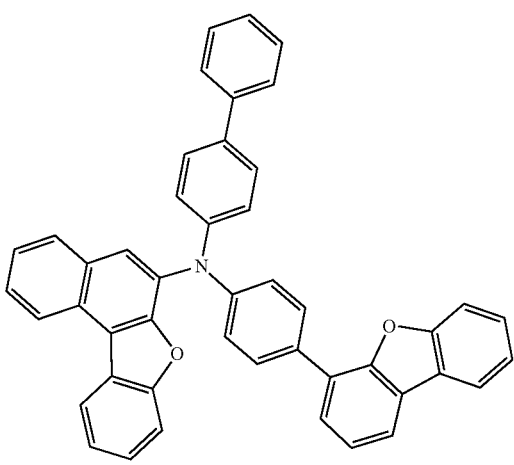
(124)
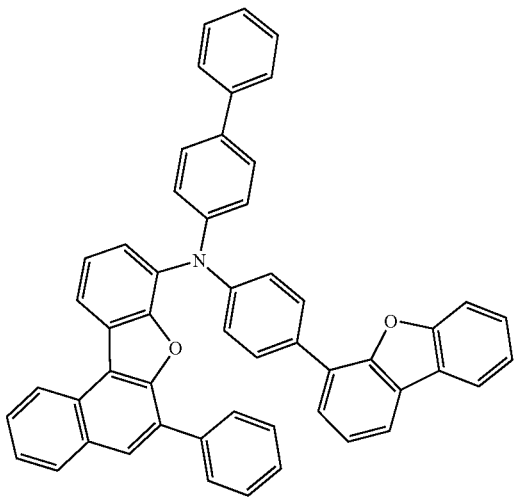
[Chemical Formula 28]
(116)
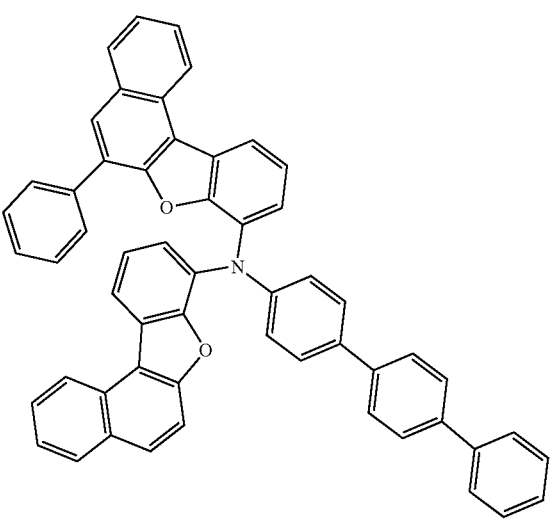
(117)
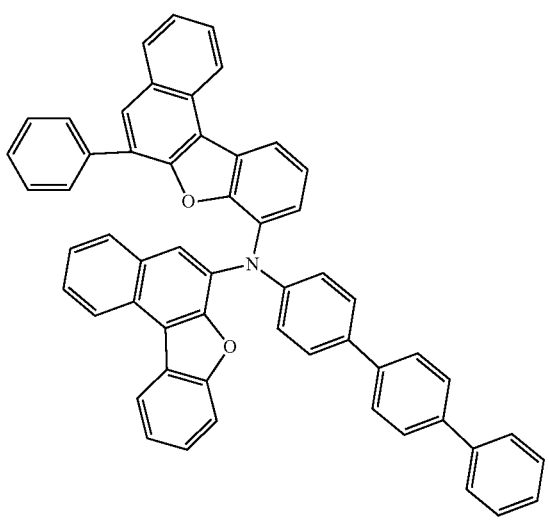

(118)
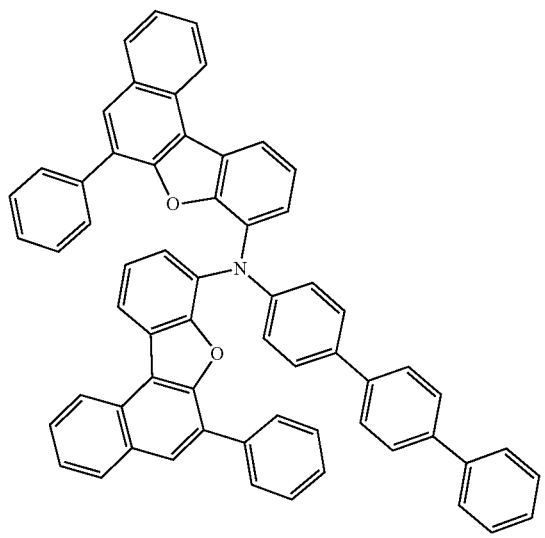
(119)
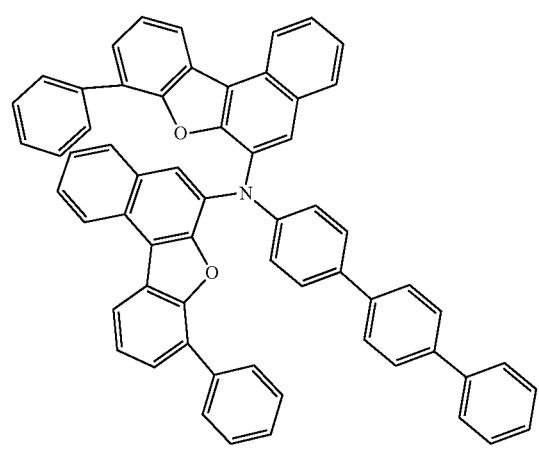
(120)
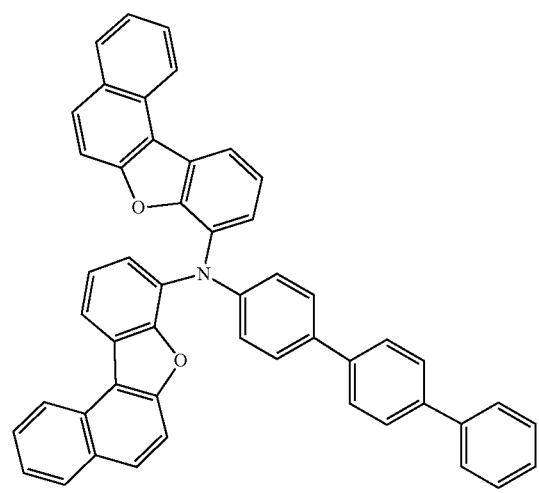
(121)
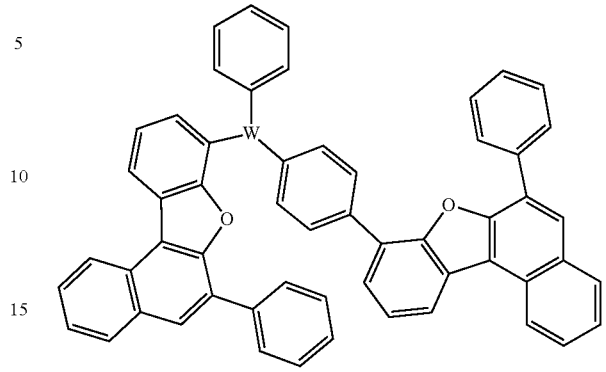
(122)
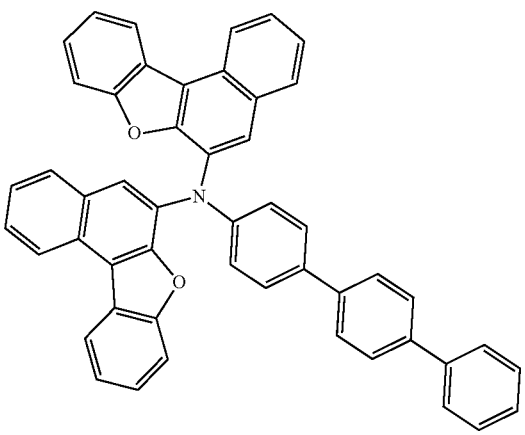
(123)
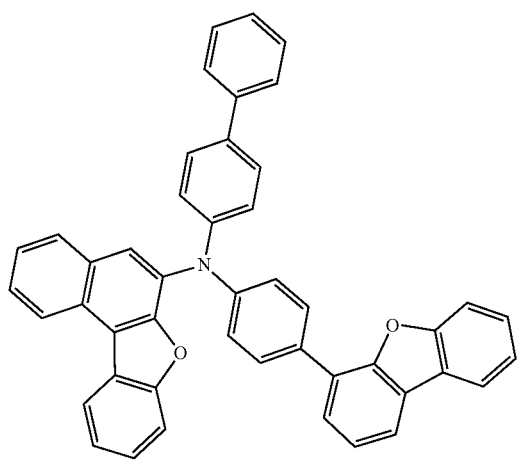

(124)
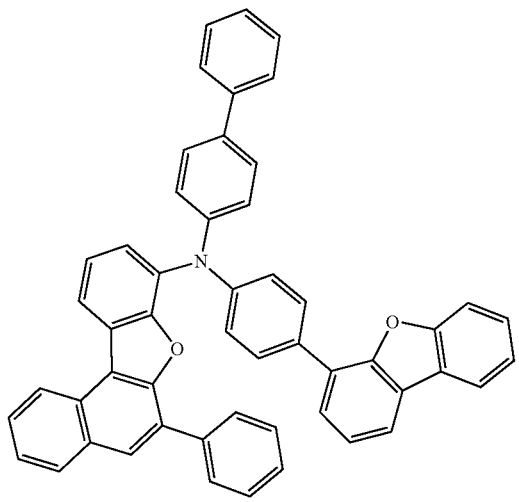
[Chemical Formula 29]
(133)
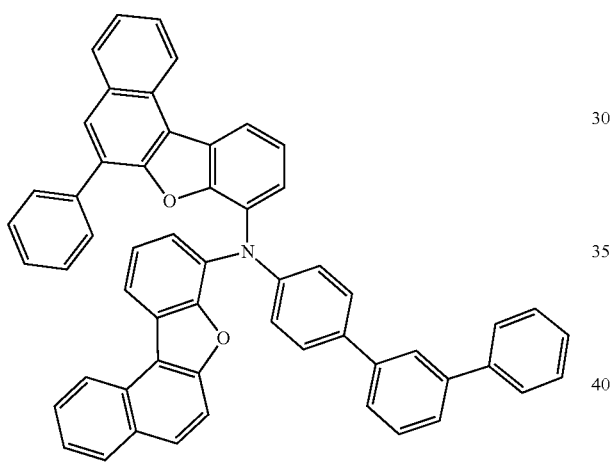
(134)
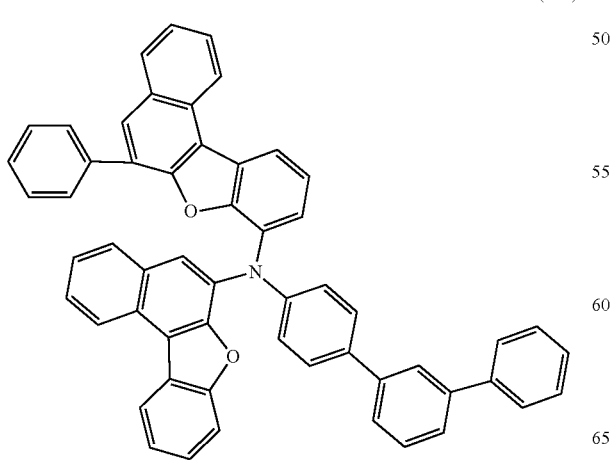
(135)
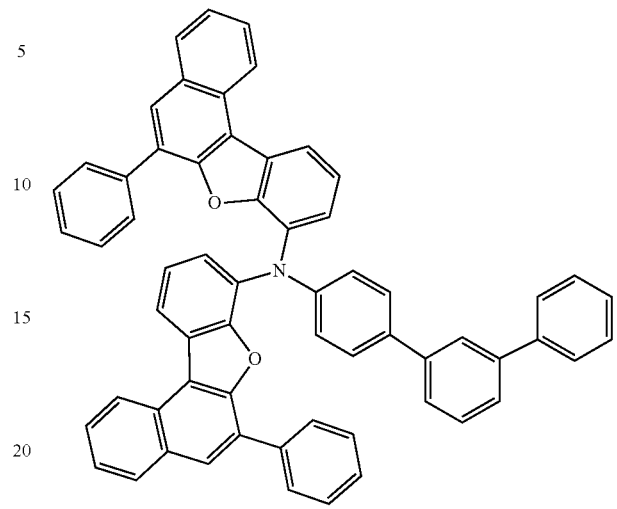
(136)
(137)
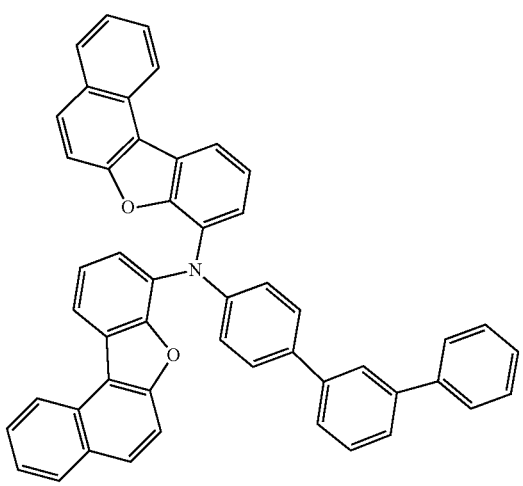

(138)
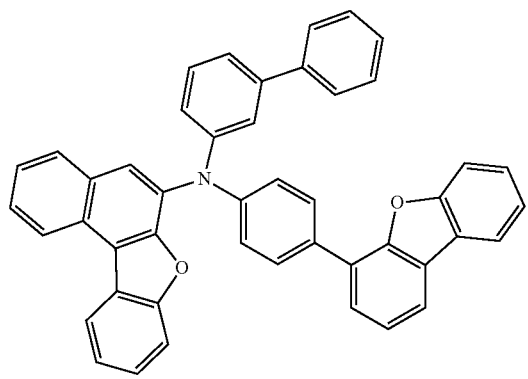
(139)
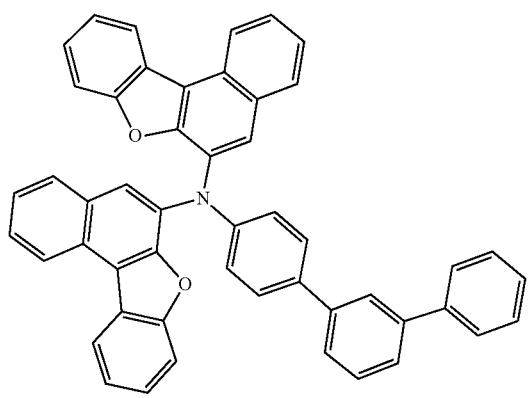
(140)
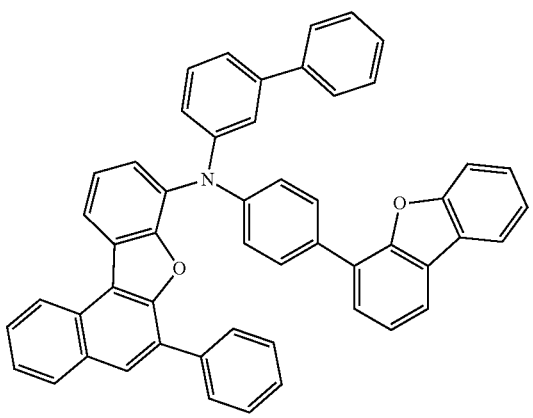
[Chemical Formula 30]
(141)
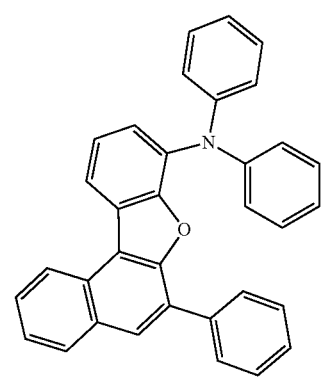
(142)
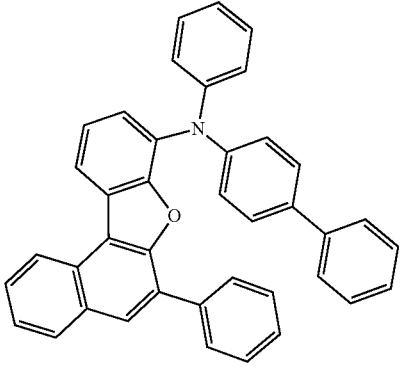
(143)
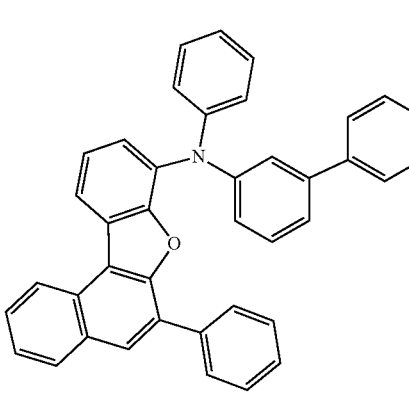
(144)
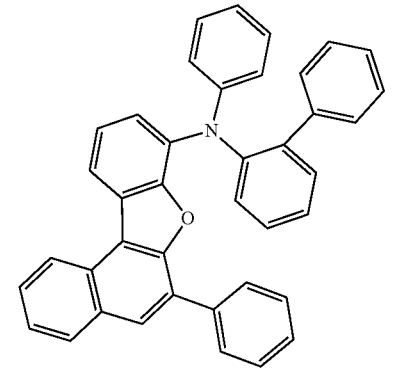
(145)
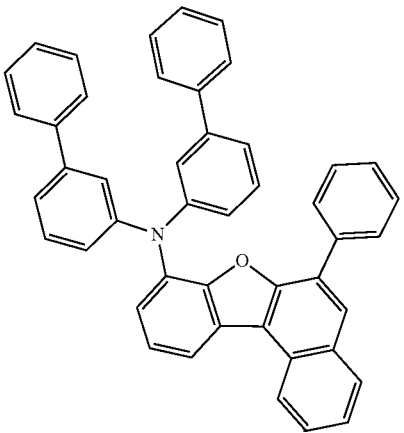

(146)
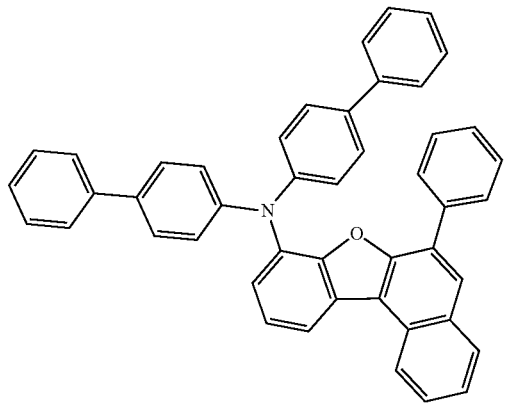
(147)
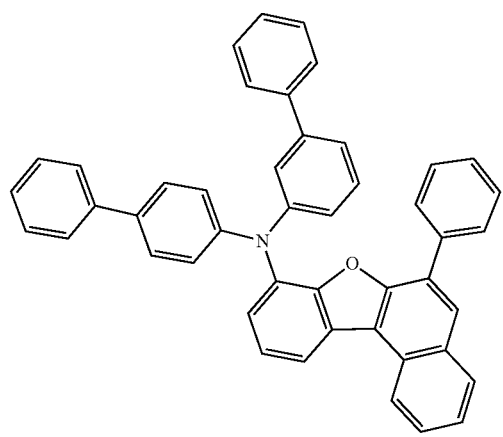
(148)
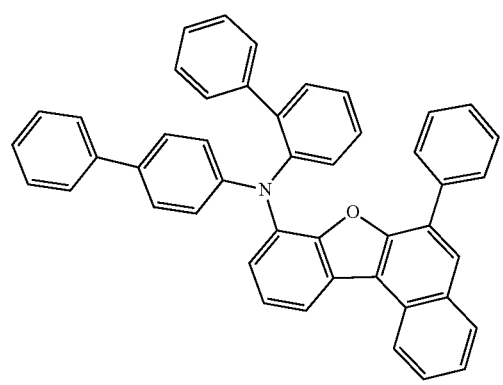
(149)
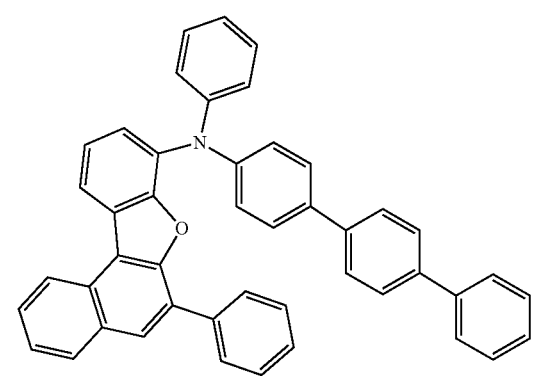
(150)
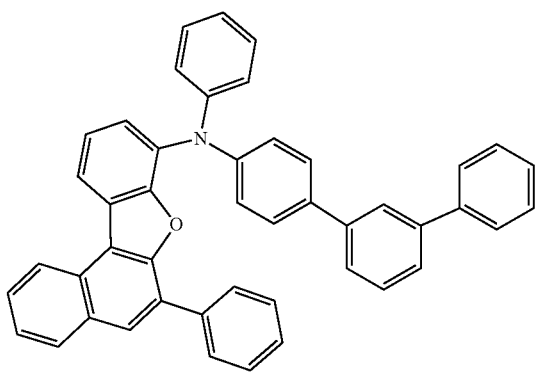
[Chemical Formula 31]
(151)
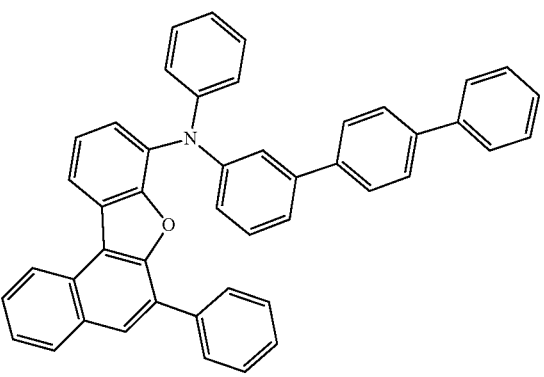
(152)
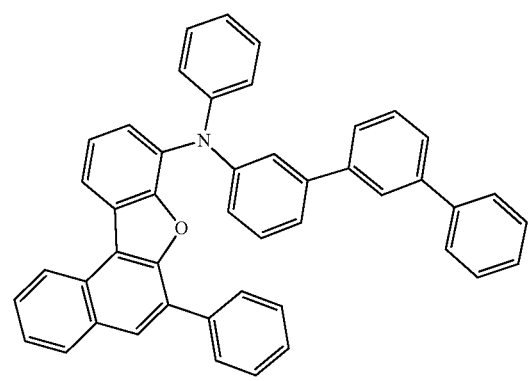

(153)
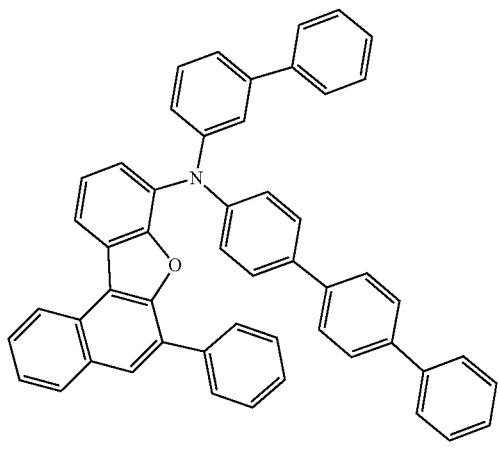
(156)
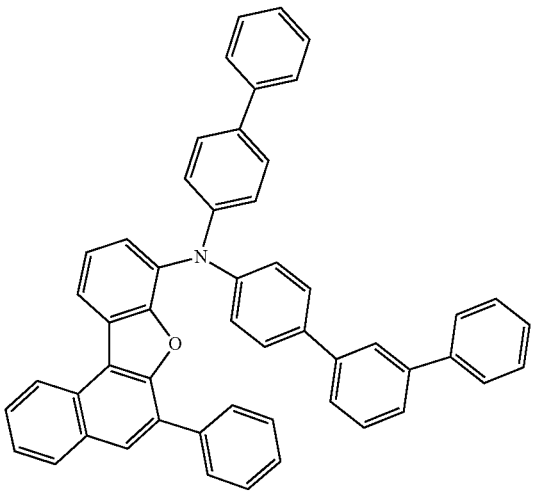
(154)
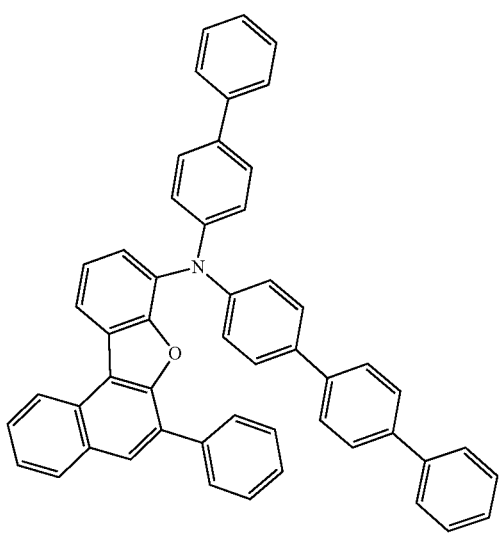
(157)
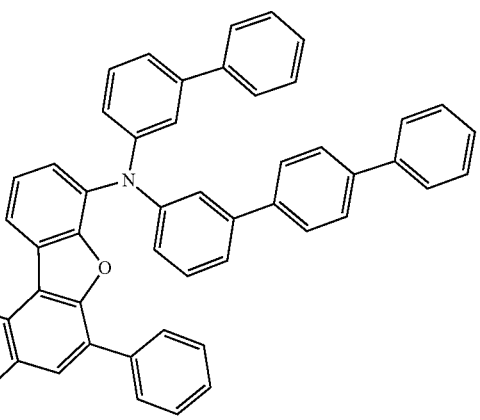
(155)
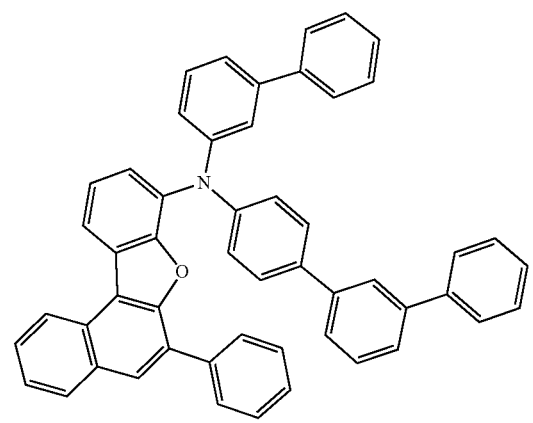
(158)
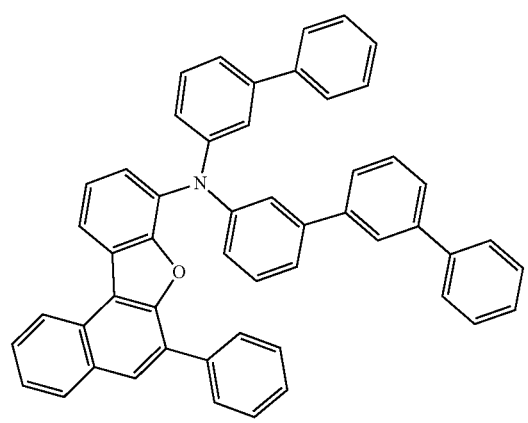

[Chemical Formula 32]
(159)
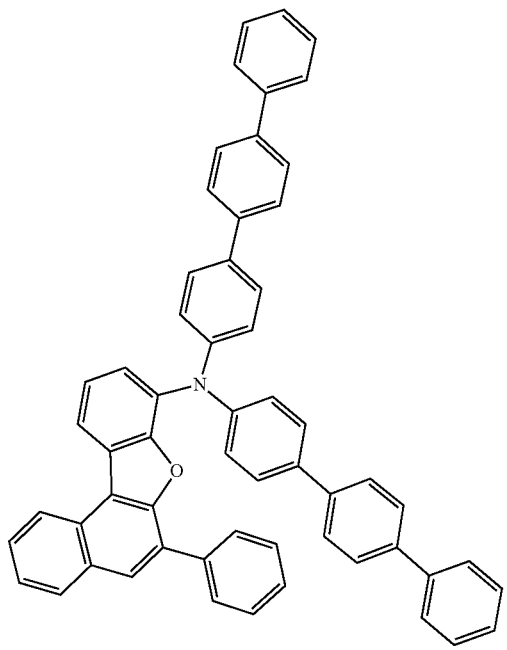
(160)
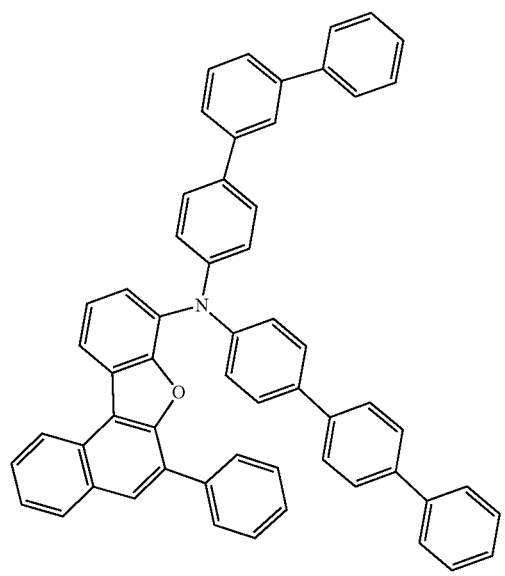
(161)
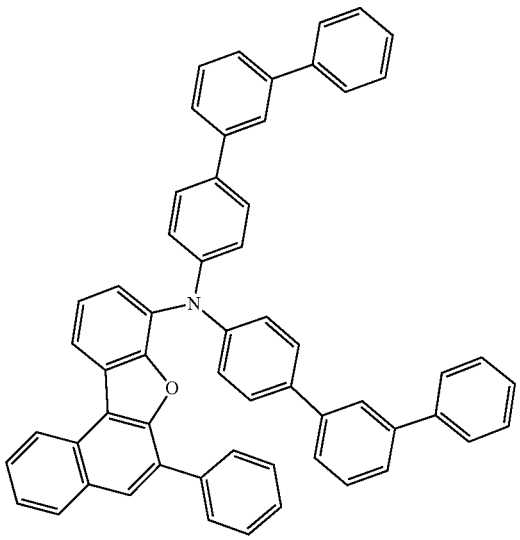
(162)
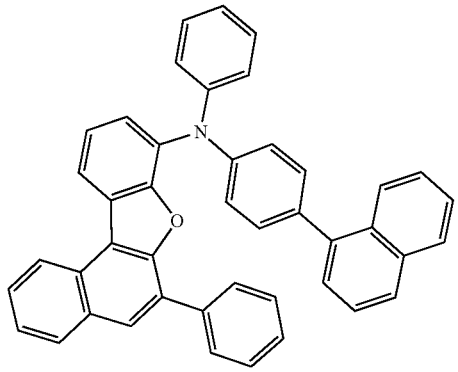
(163)
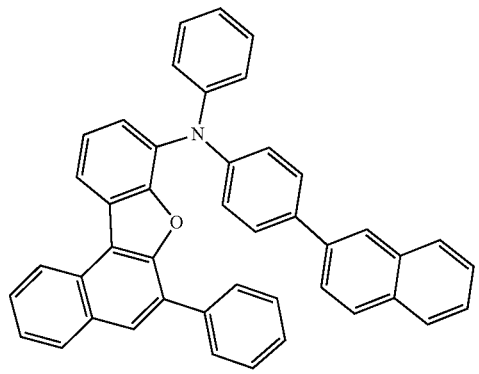

[Chemical Formula 33]
(164)
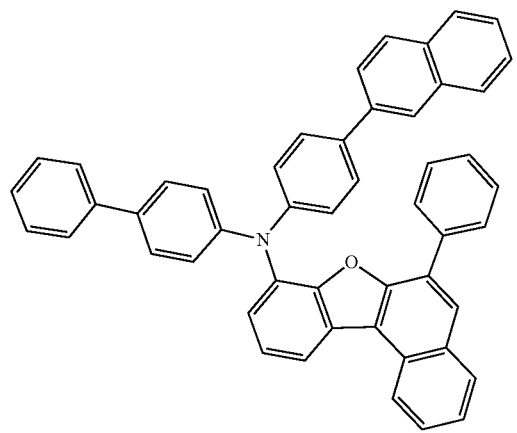
(165)
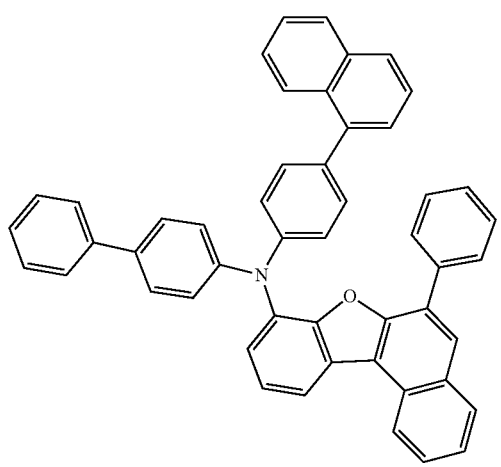
(166)
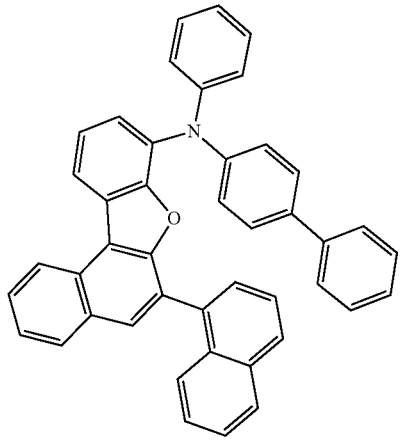
(167)
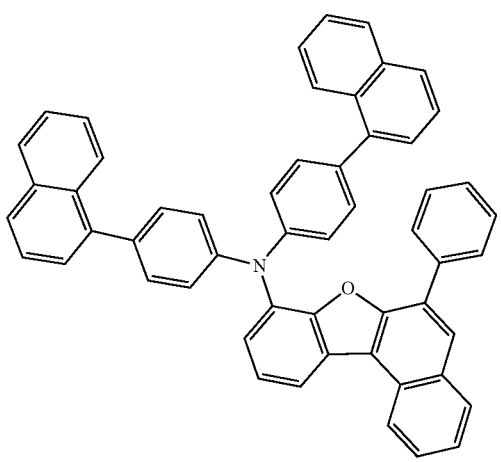
(168)
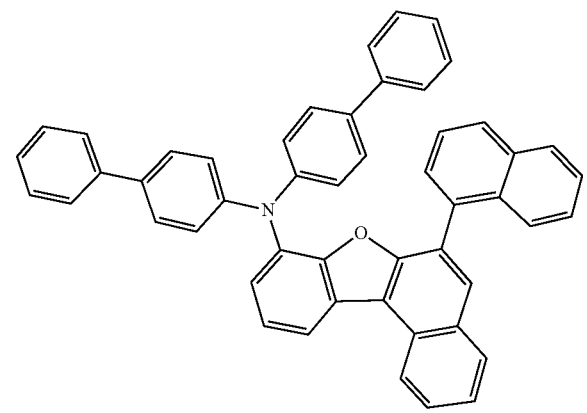
(169)

(170)
(171)
(172)
(173)
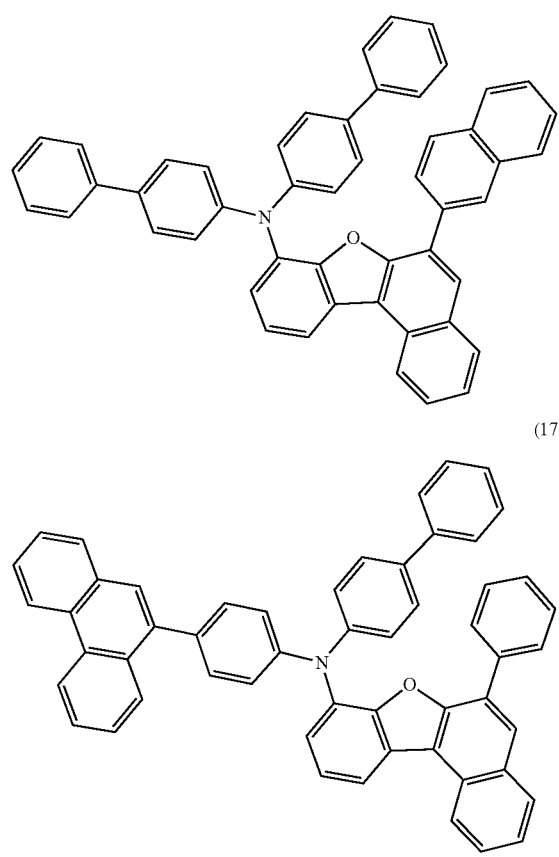
(174)
(175)
[Chemical Formula 34]
(176)
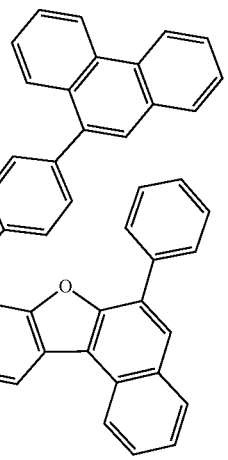
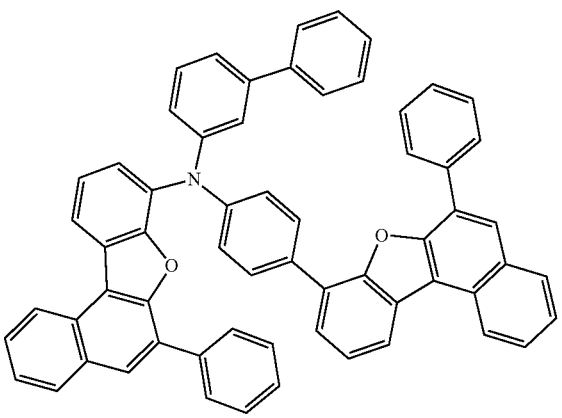

(177)
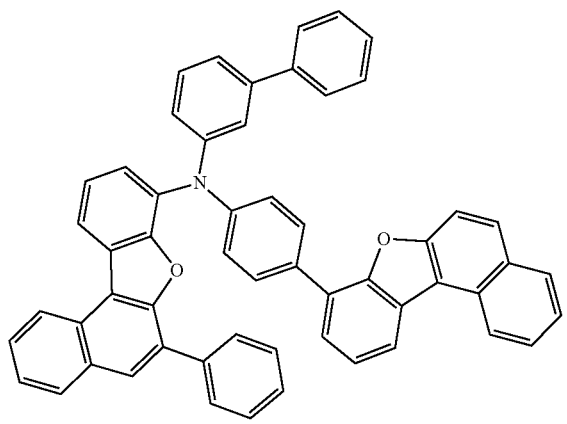
(178)
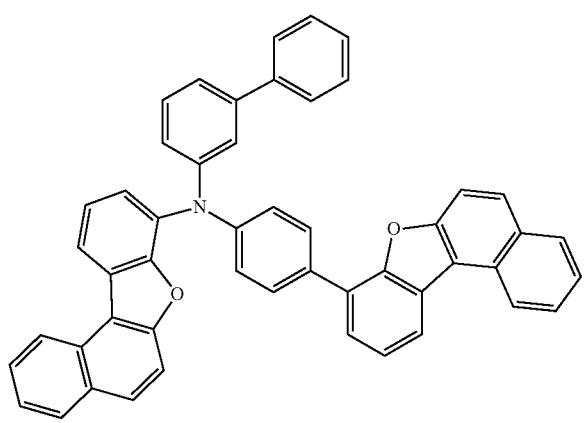
(179)
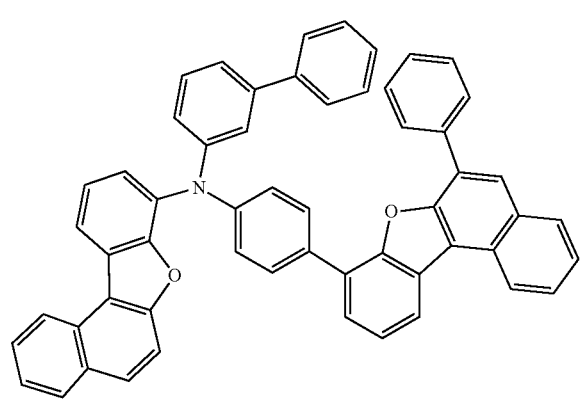
(180)
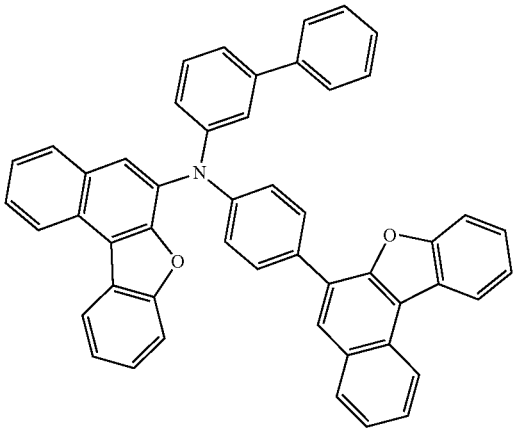
(181)
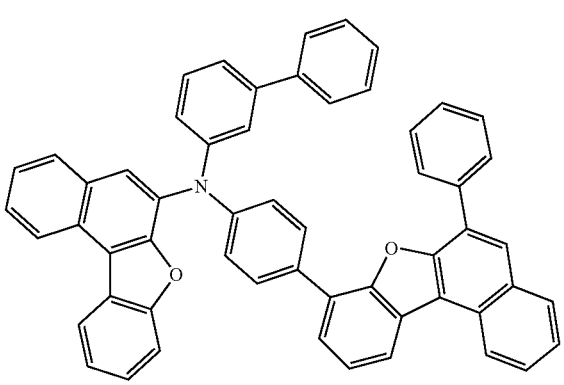
(182)
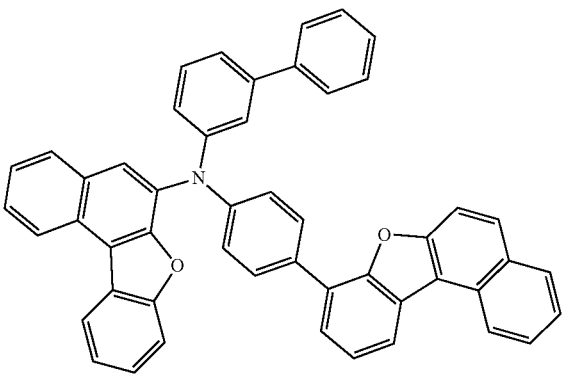
(183)
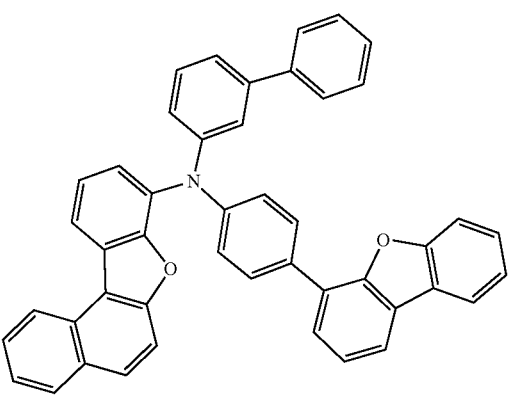

[Chemical Formula 35]
(184) 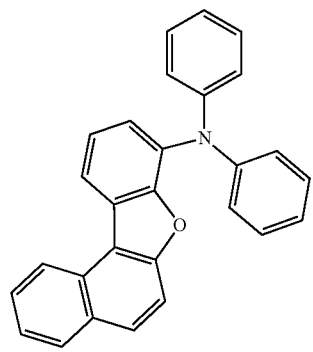
(185) 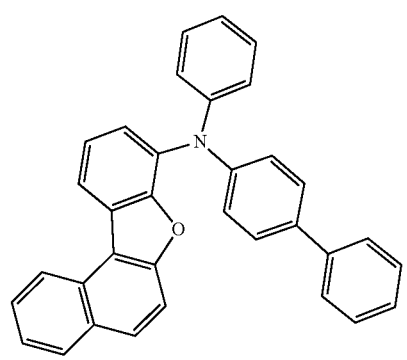
(186) 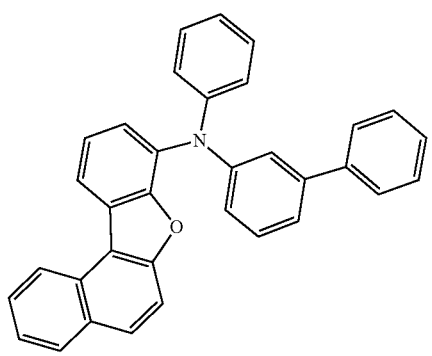
(187) 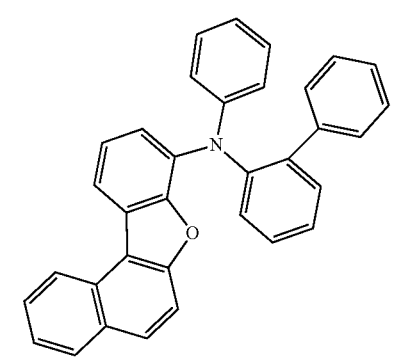
(188) 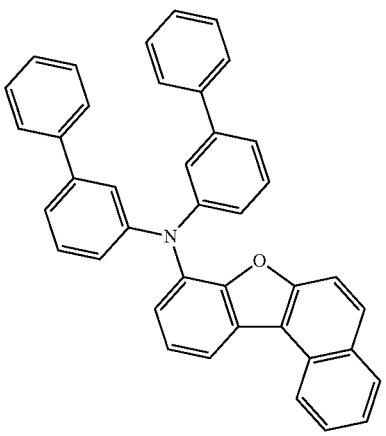
(189) 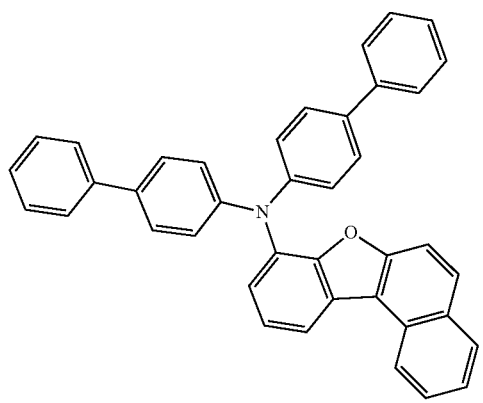
(190) 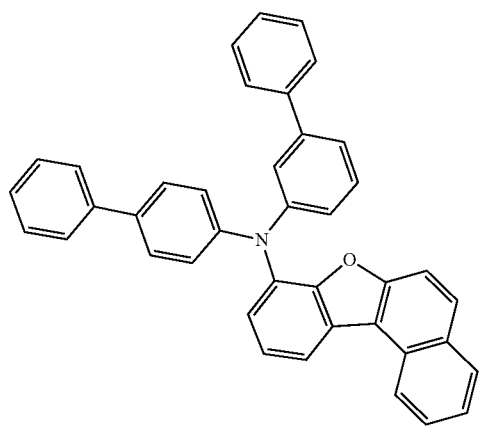
(191) 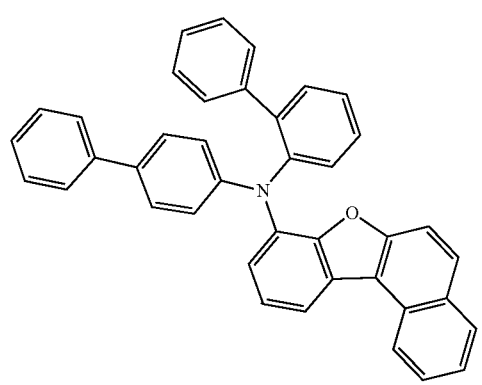

(192)
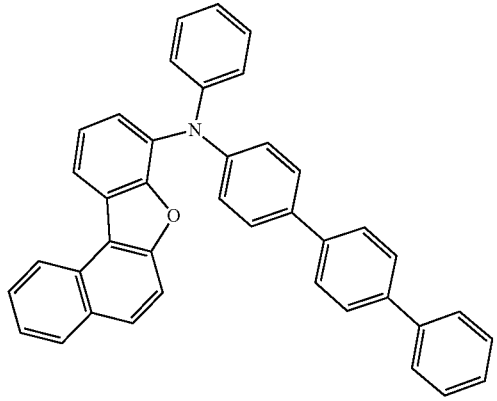
(193)
(194)
[Chemical Formula 36]
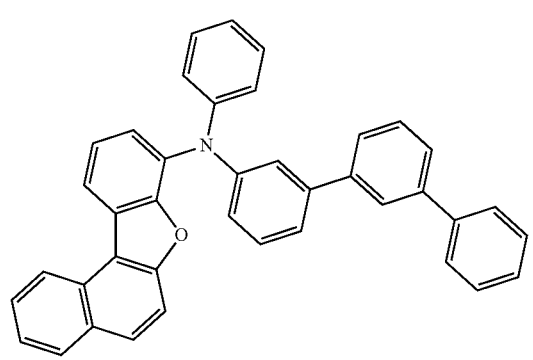
(195)
(196)
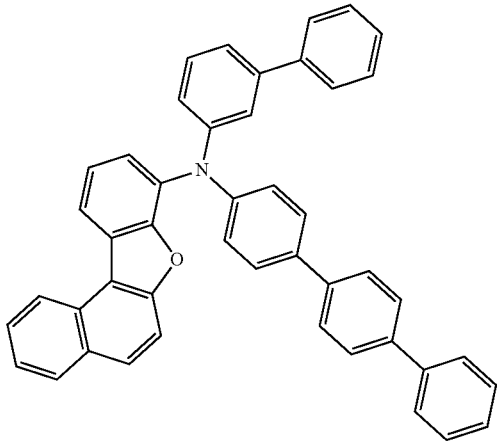
(197)
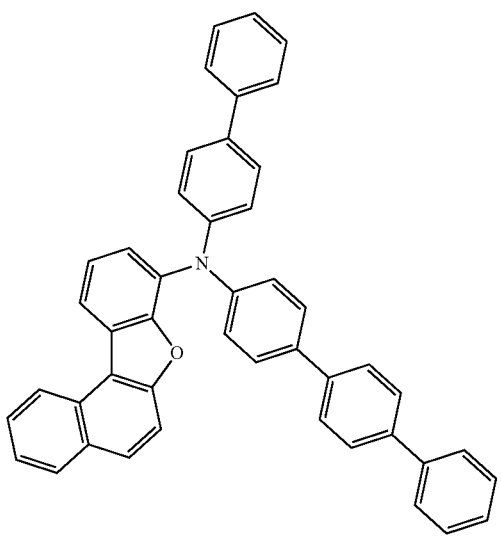
(198)
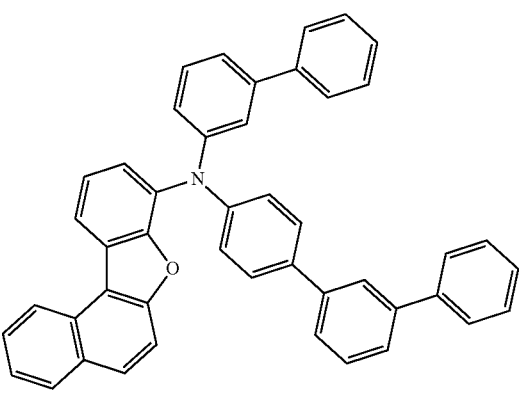

-continued
(199)
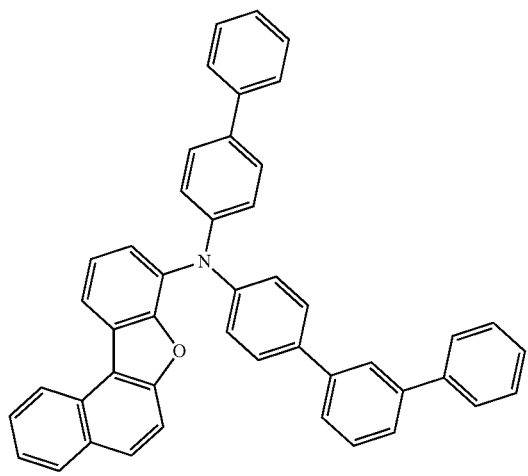
(200)
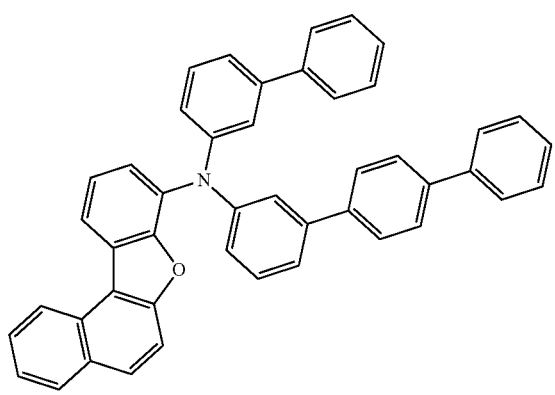
(201)
[Chemical Formula 37]
(202)
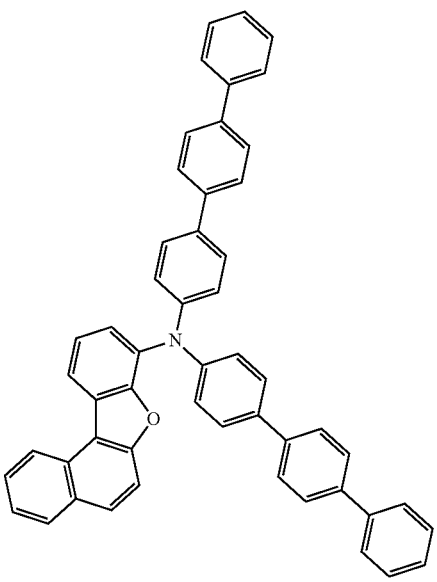
(203)
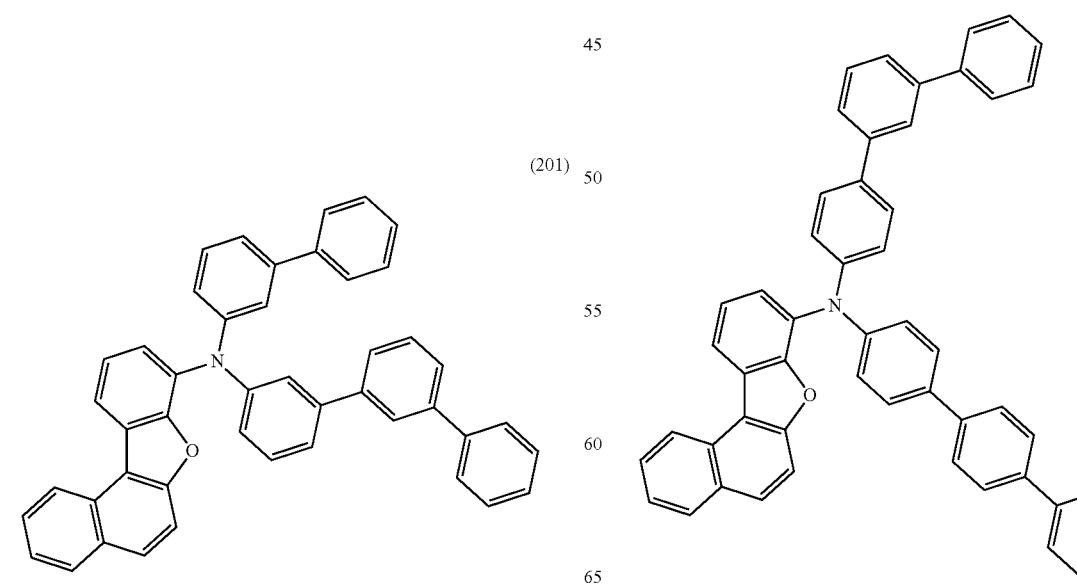

(204)
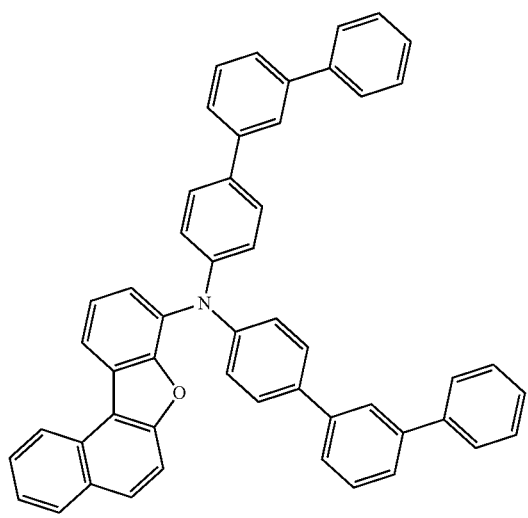
(205)
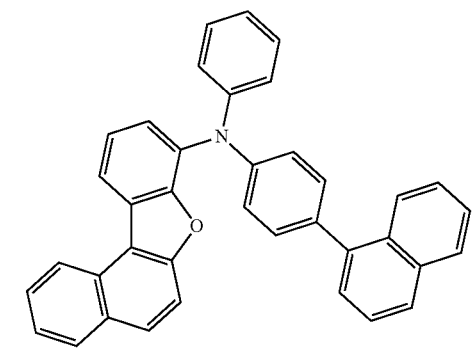
(206)
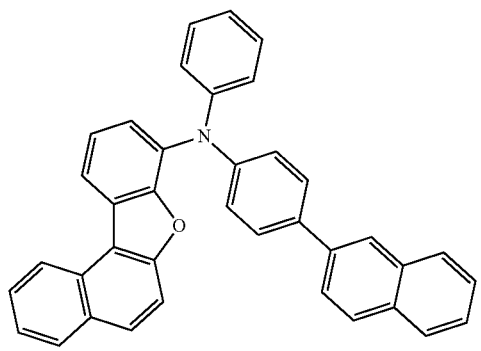
(207)
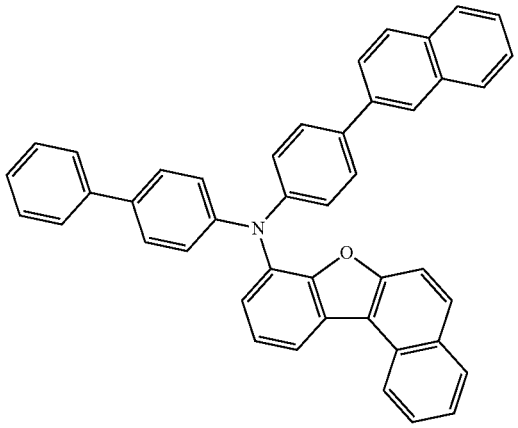
(208)
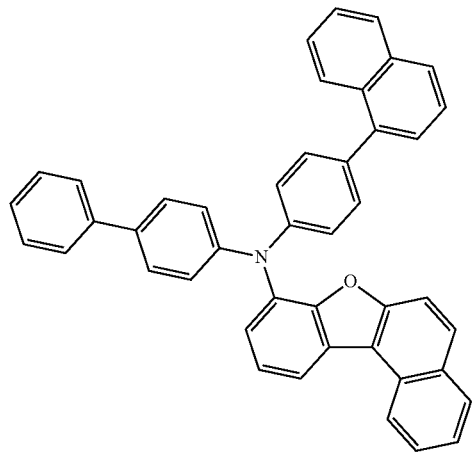
(209)
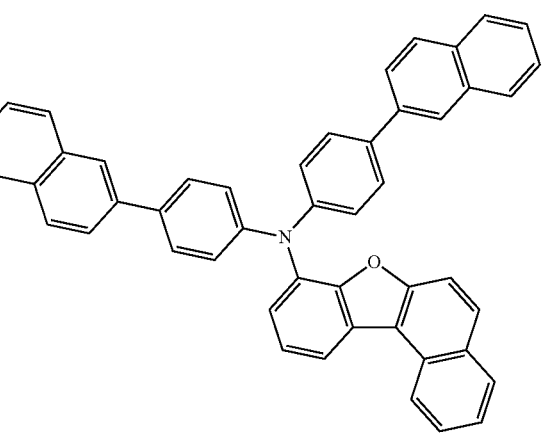

[Chemical Formula 38]
(210)
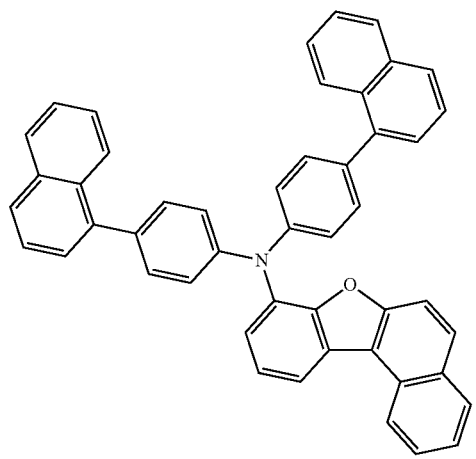
(211)
(212)
(213)
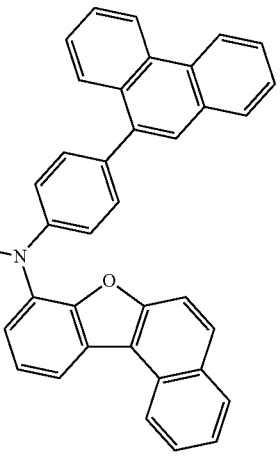
(214)
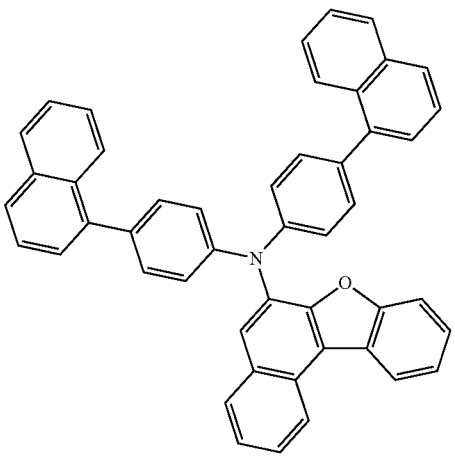
(215)
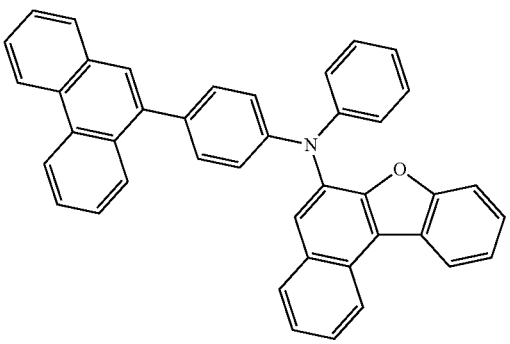

(216) 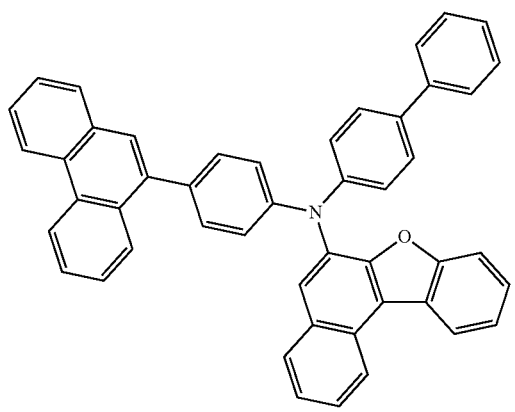
(217) 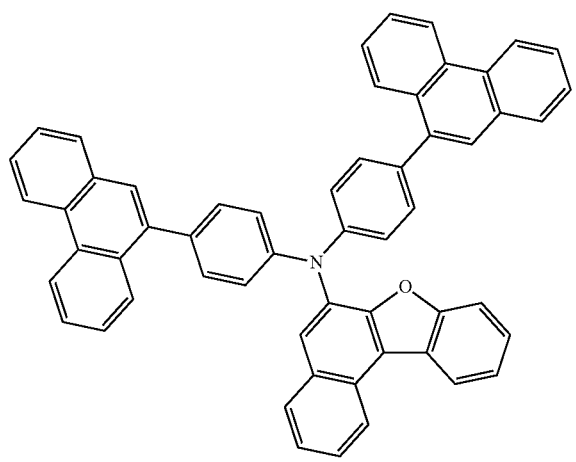
[Chemical Formula 39]
(218) 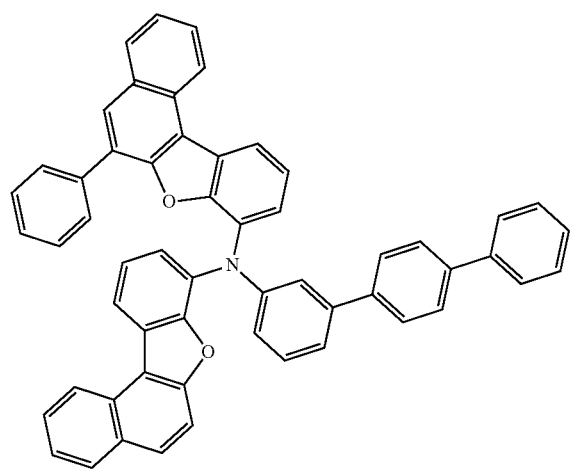
(219) 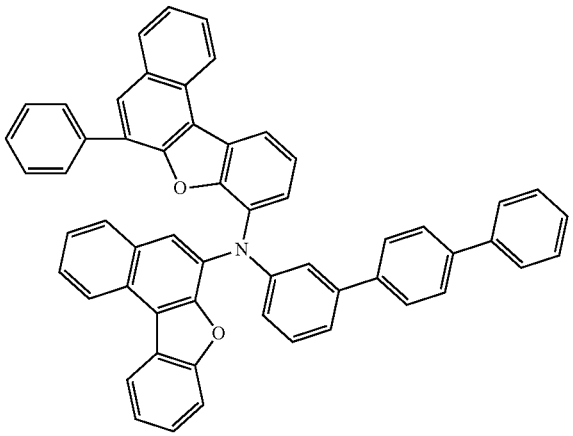
(220) 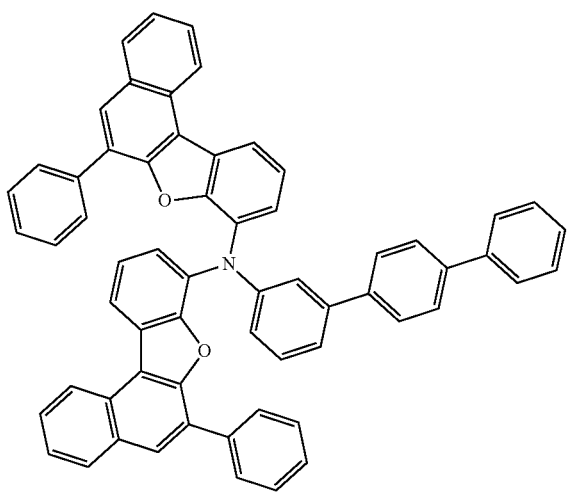
(221) 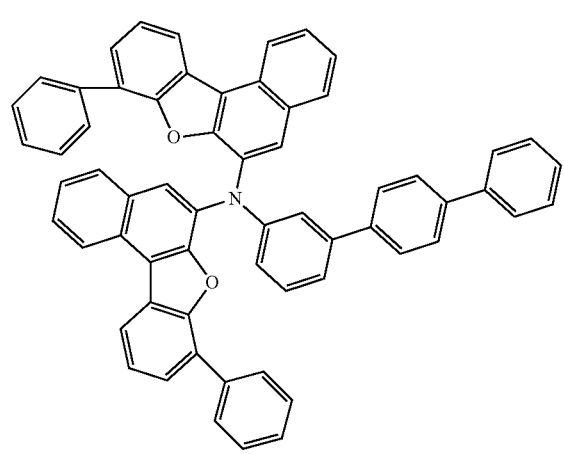

(222)
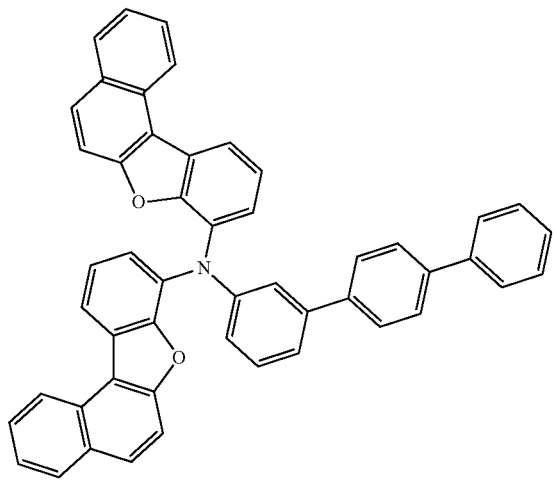
(223)
(224)
(225)
(226)
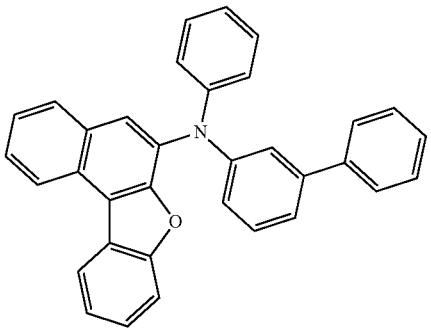
(227)
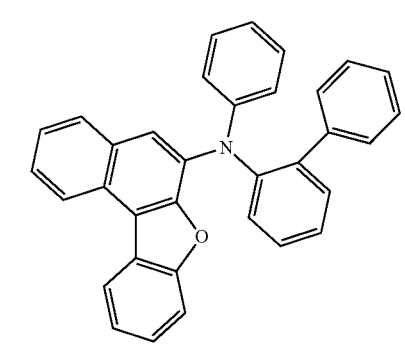
(228)
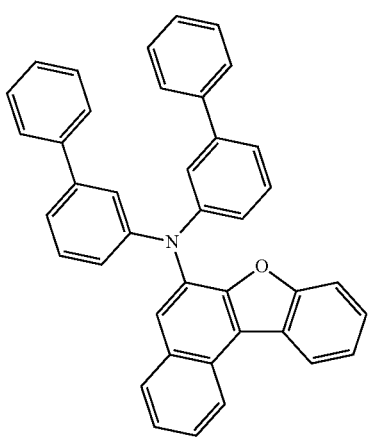
(229)
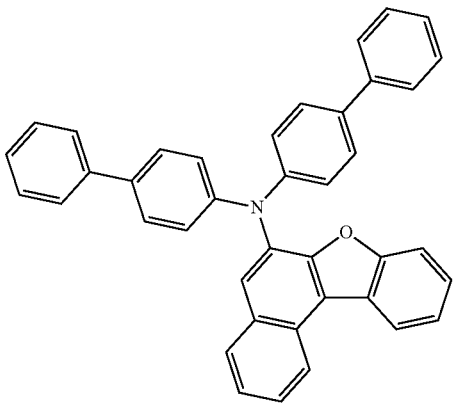
[Chemical Formula 40]

[Chemical Formula 41]
(230) 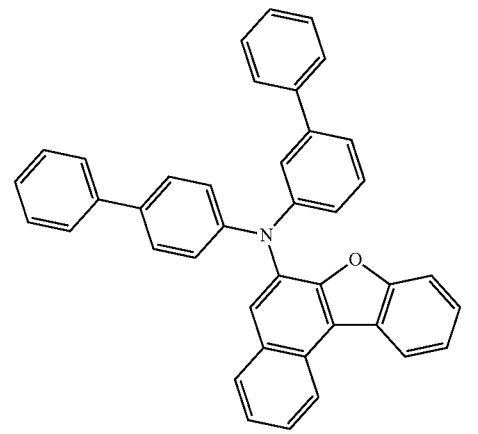
(231) 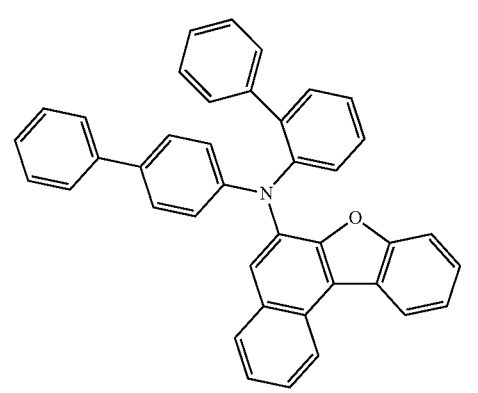
(232) 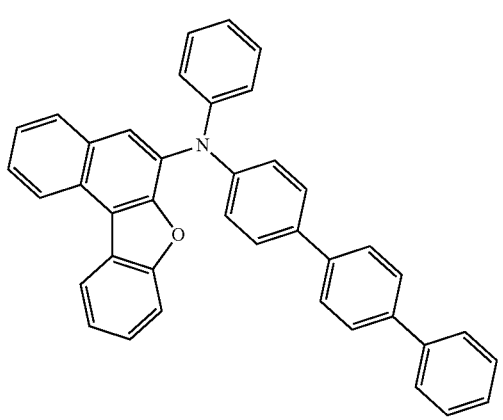
(233) 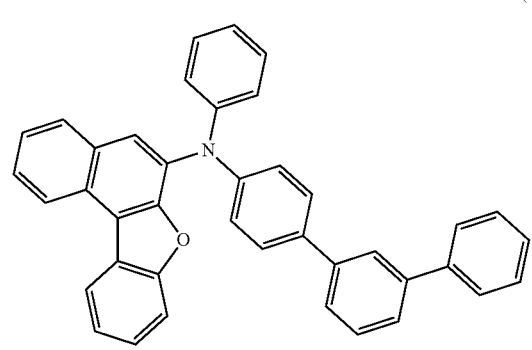
(234) 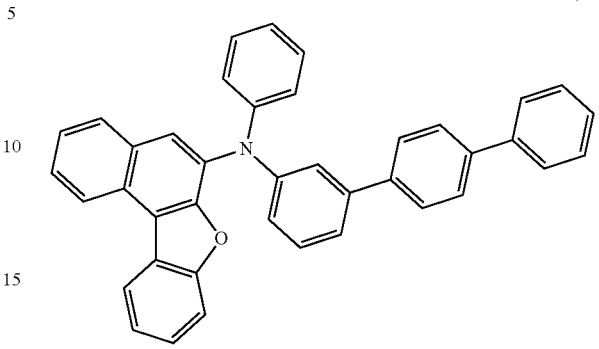
(235) 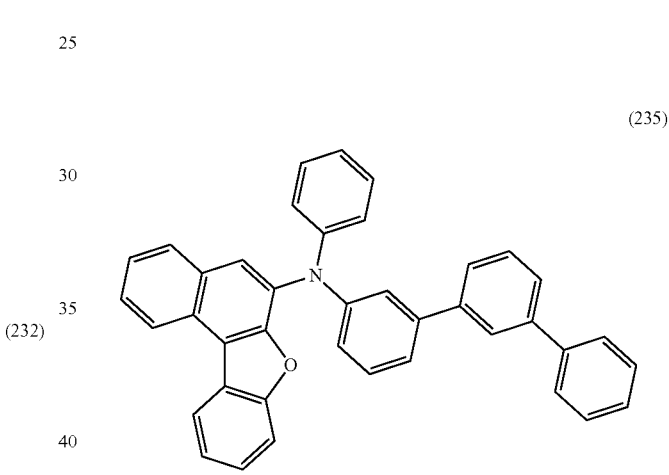
(236) 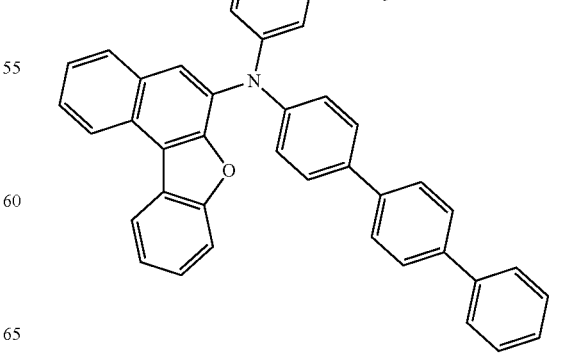
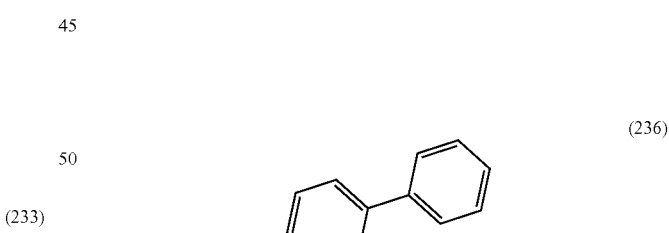

(237)
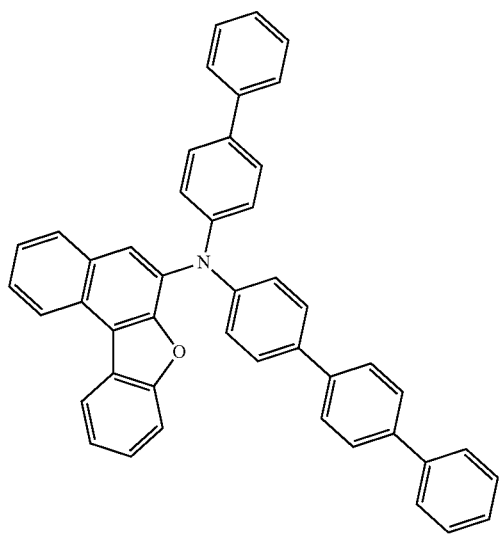
(238)
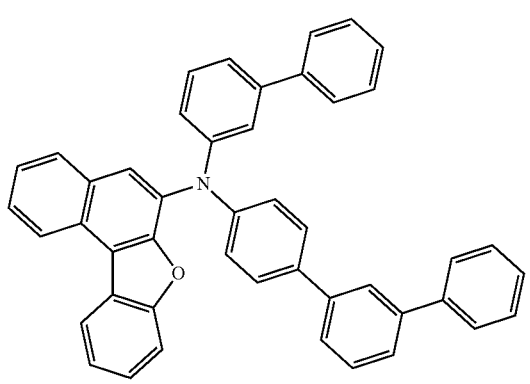
(239)
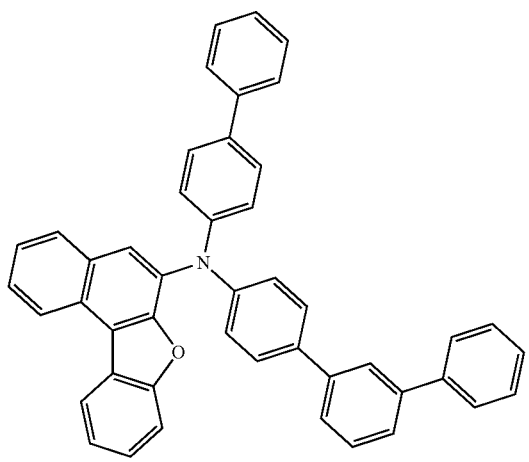
(240)
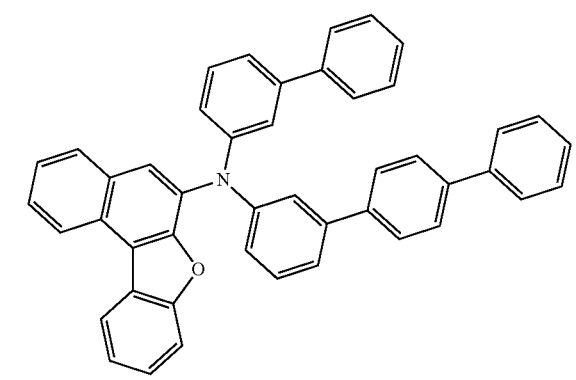
(241)
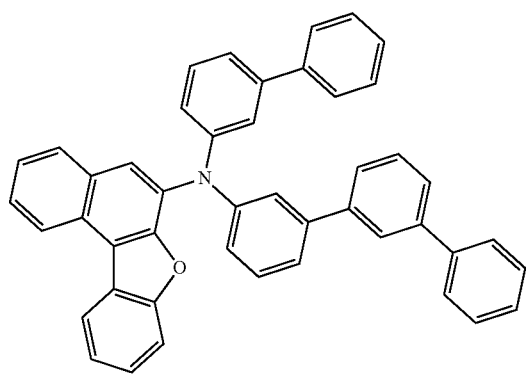
[Chemical Formula 42]
(242)
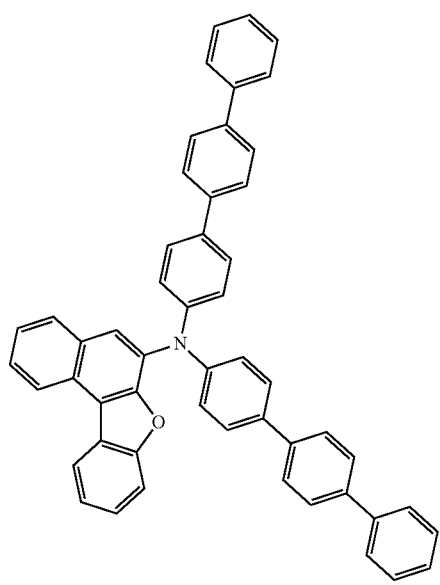

(243)
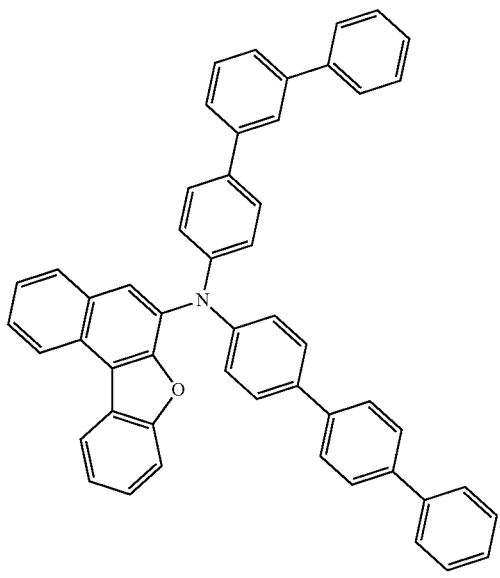
(244)
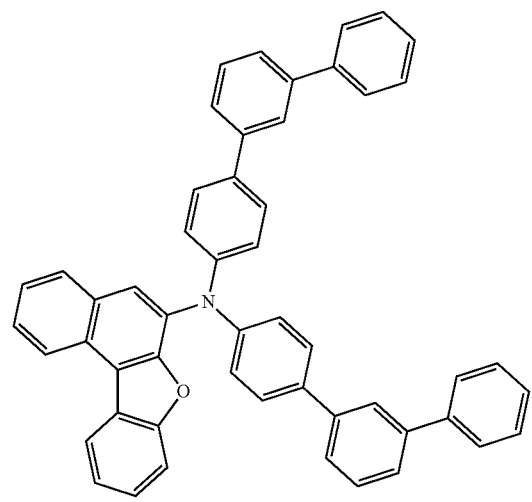
(245)
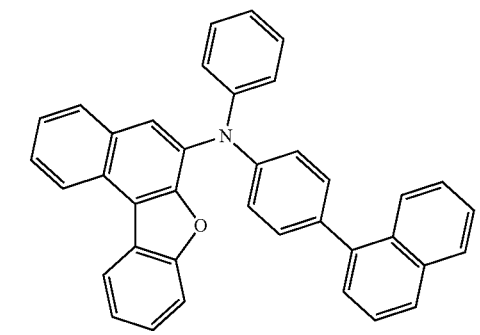
(246)
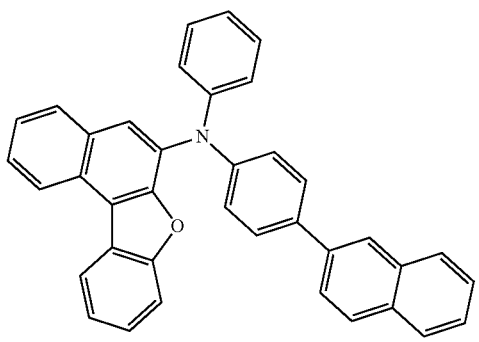
(247)
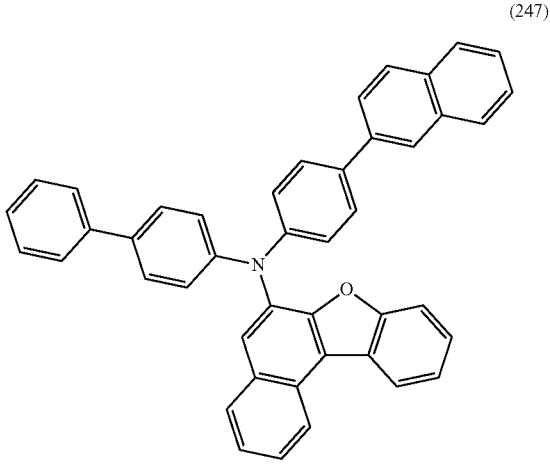
(248)
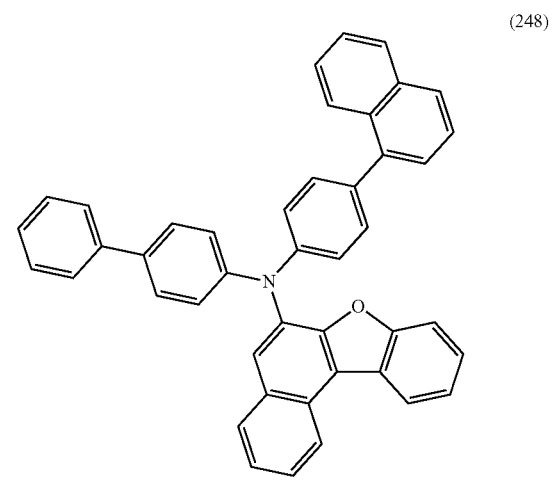

-continued
(249)
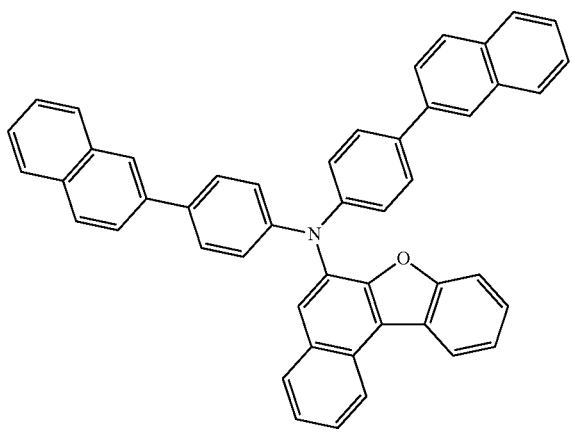
[Chemical Formula 43]
(250)
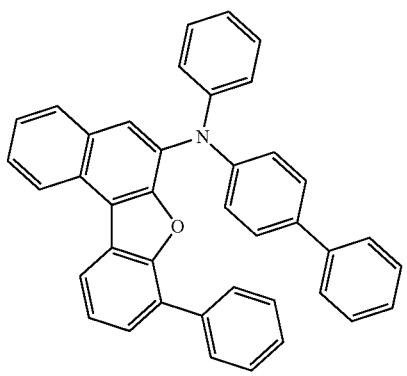
(251)
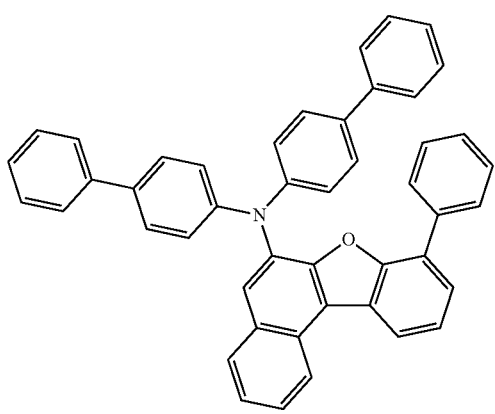
-continued
(252)
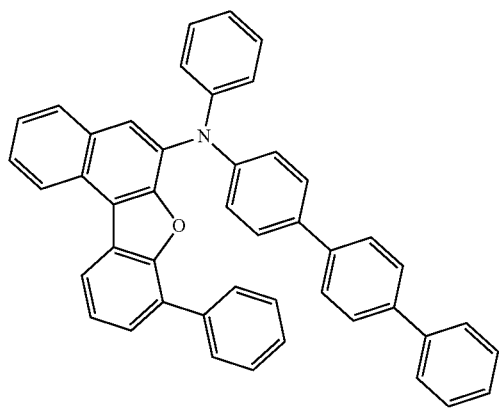
(253)
(254)
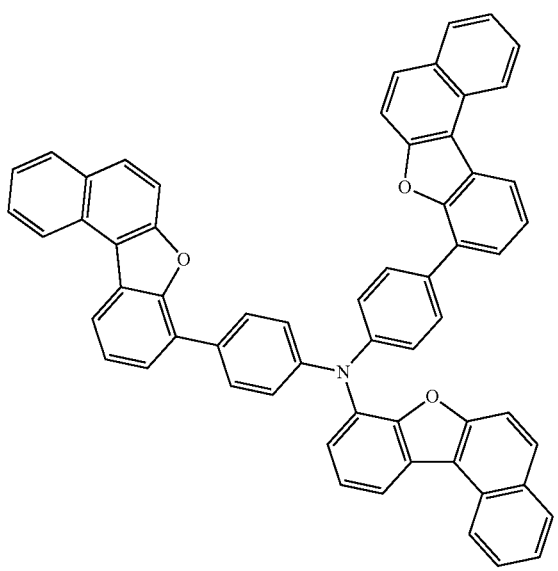
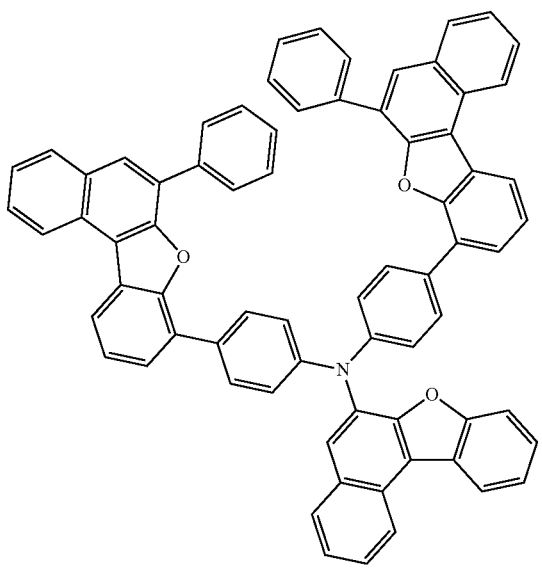

(255)
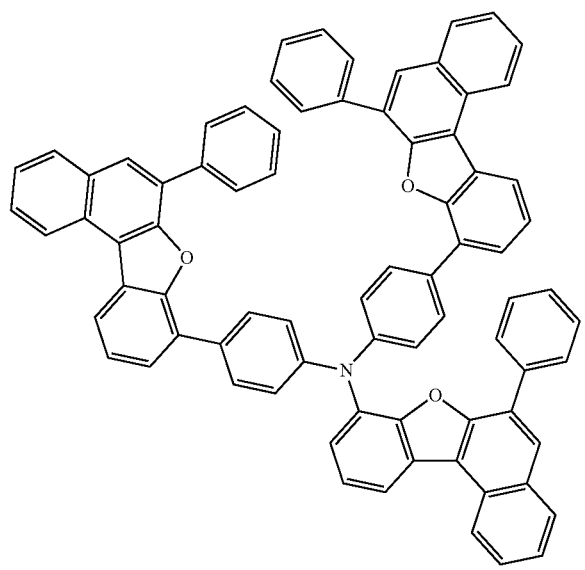
(256)
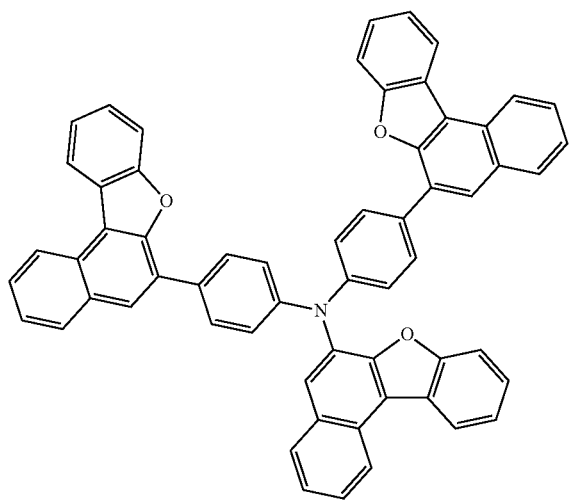
(257)
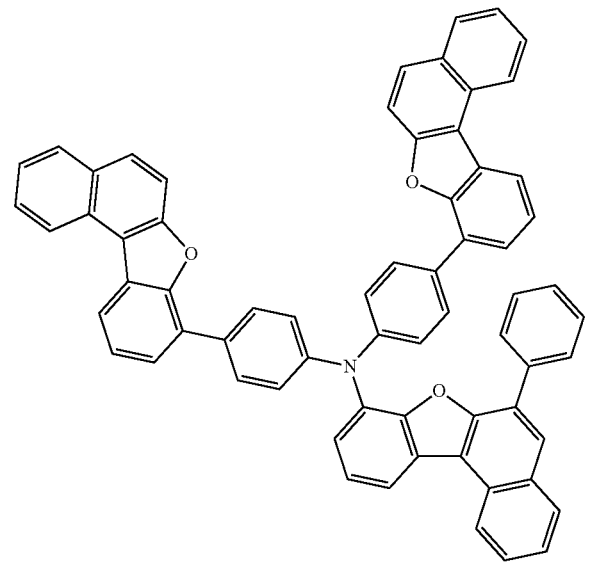
[Chemical Formula 44]
(250)
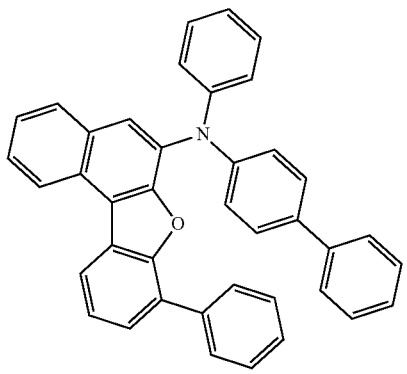
(251)
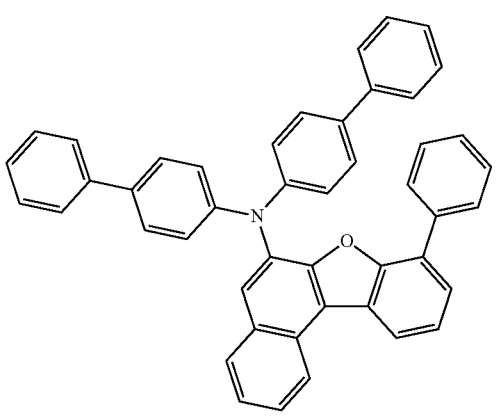

(252)
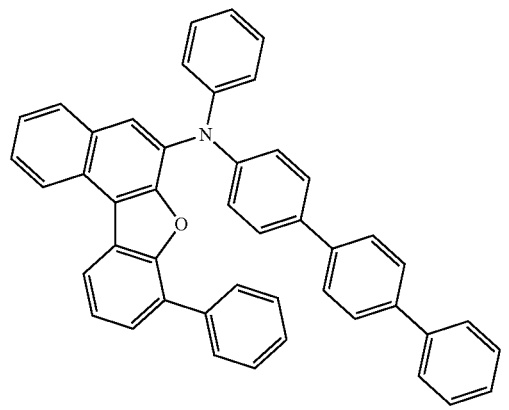
(253)
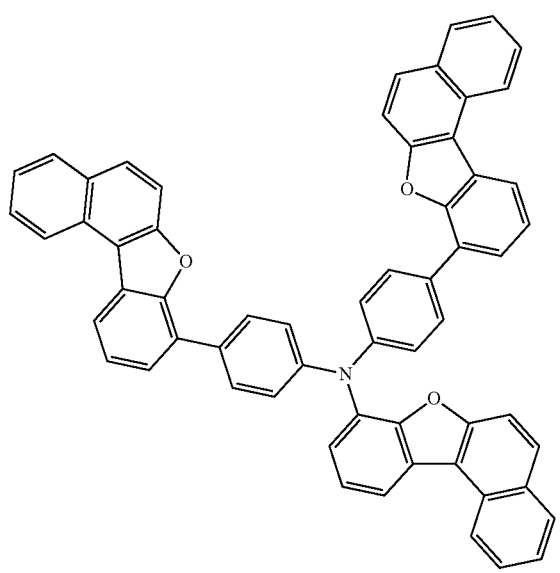
(254)
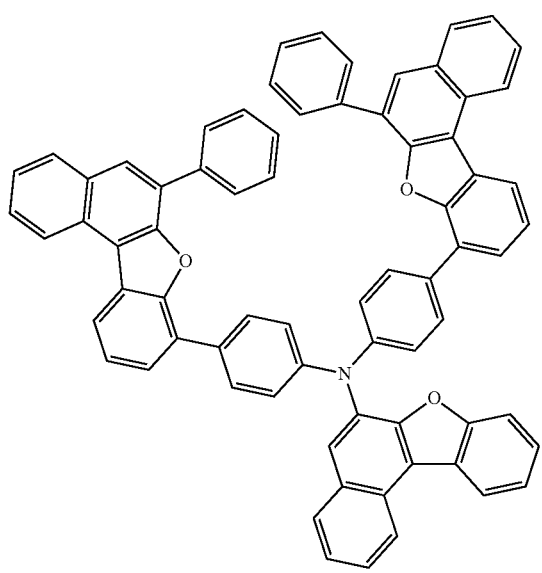
(255)
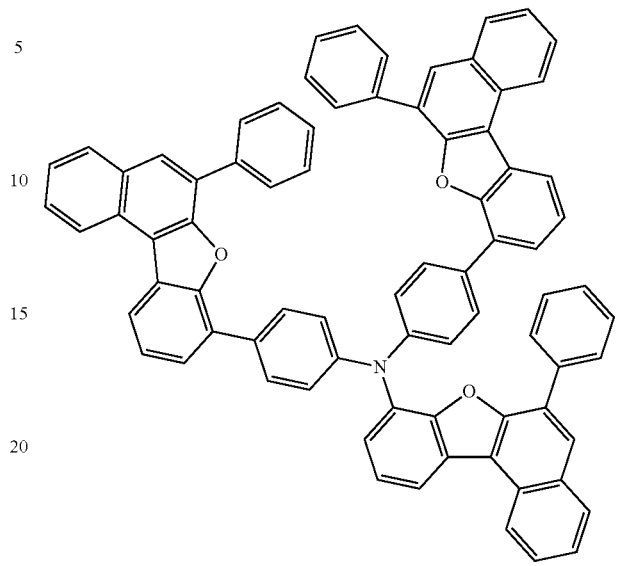
(256)
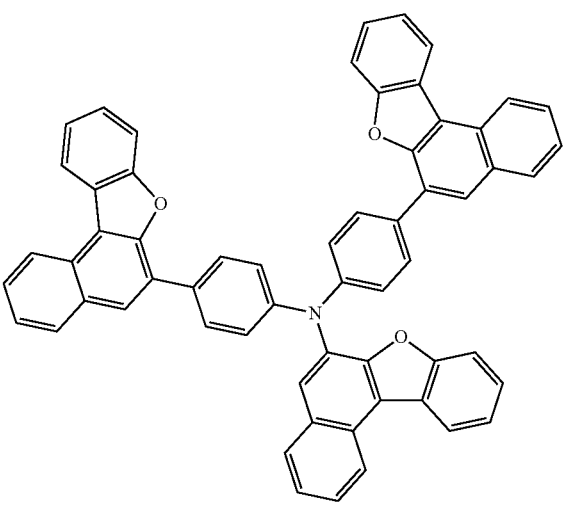

(257)
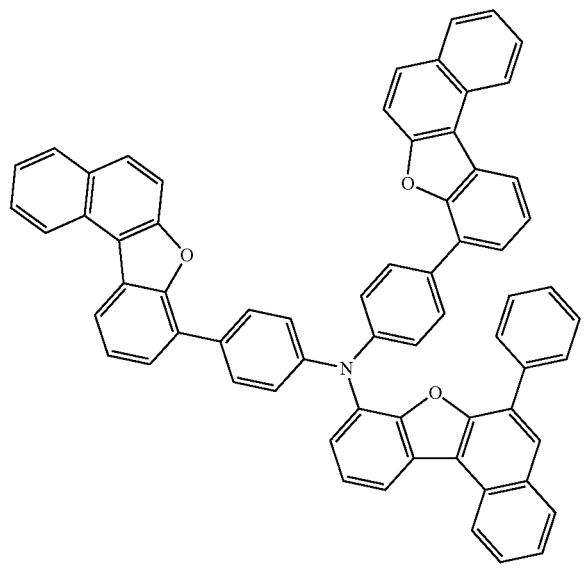
[Chemical Formula 45]
(525)
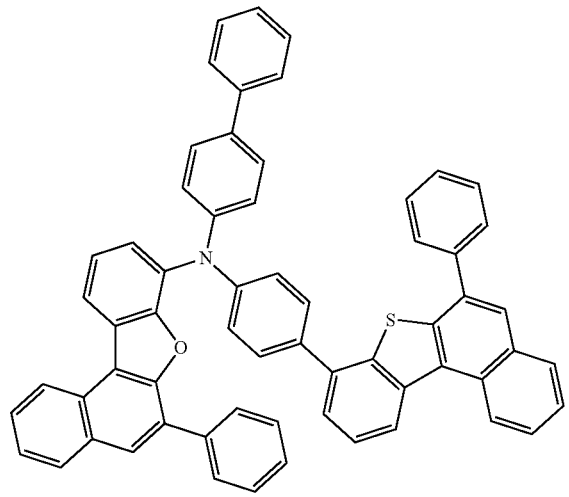
(526)
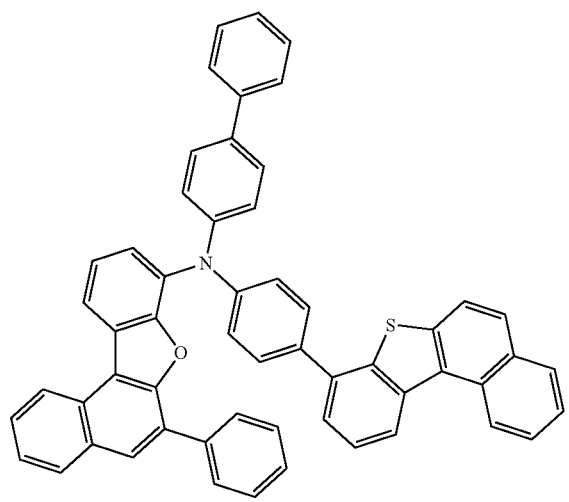
(527)
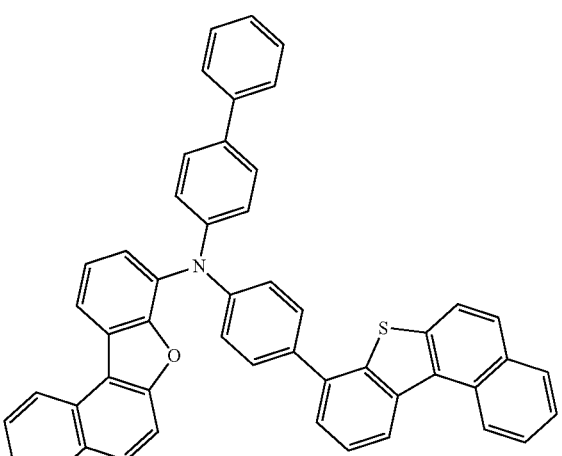
(528)
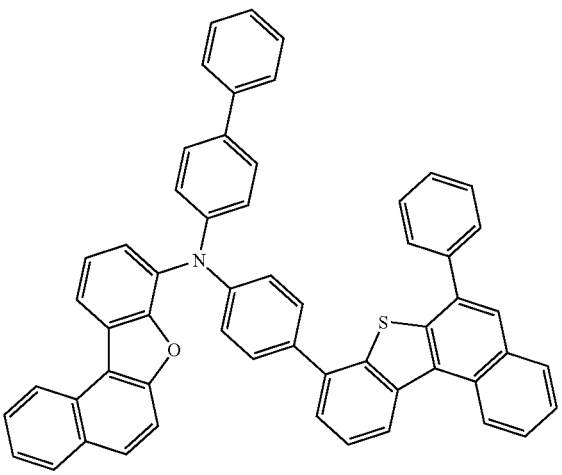
(529)
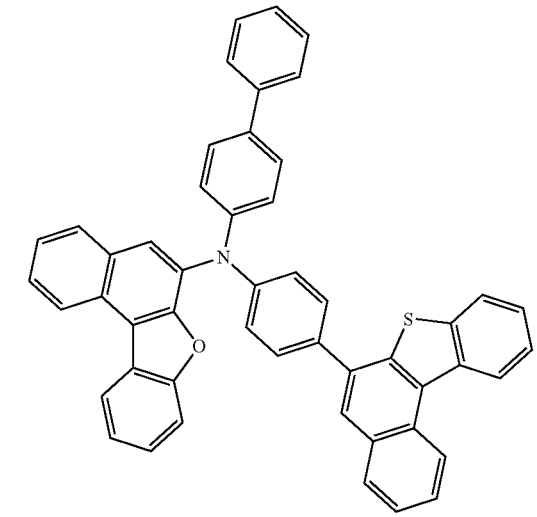

[Chemical Formula 46]
(530)
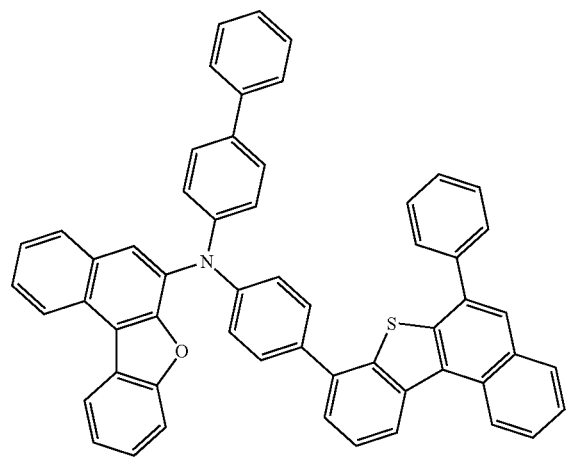
(531)
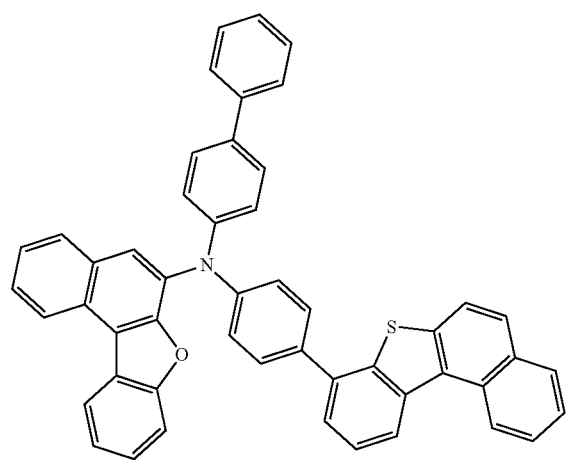
(532)
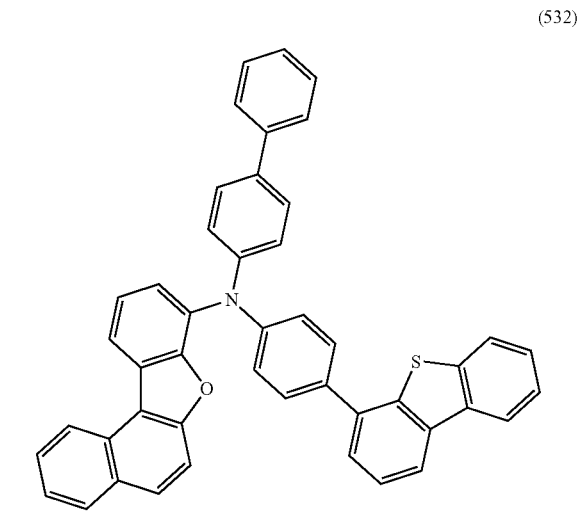
(549)
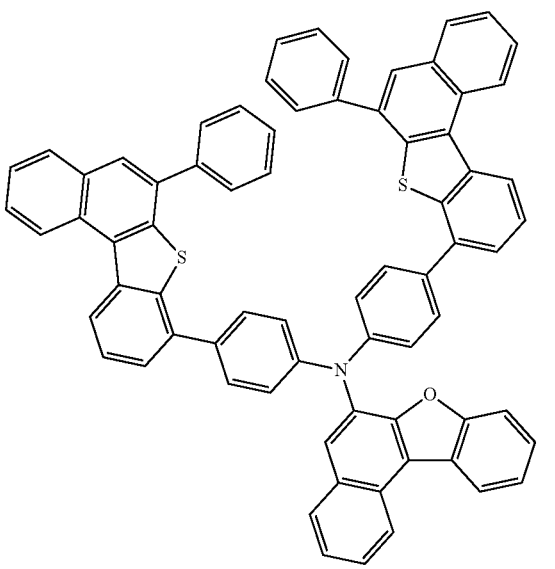
(550)
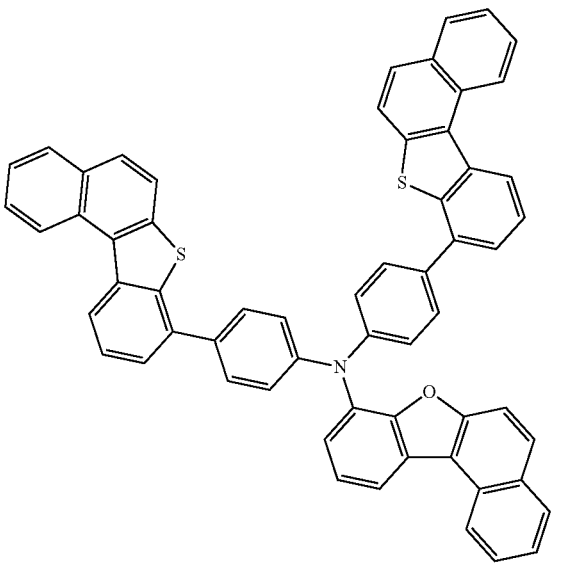

(551)
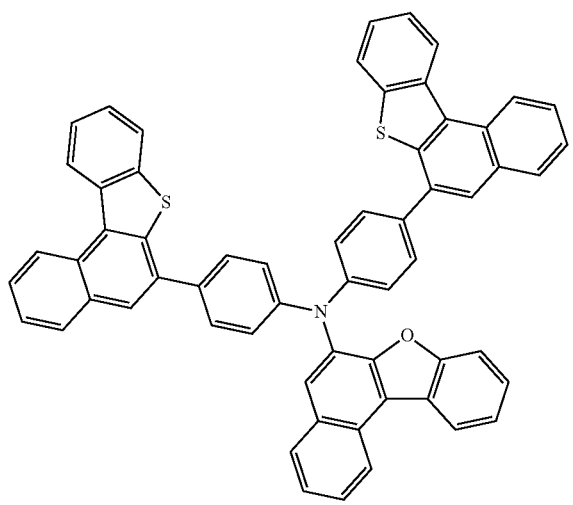
(552)
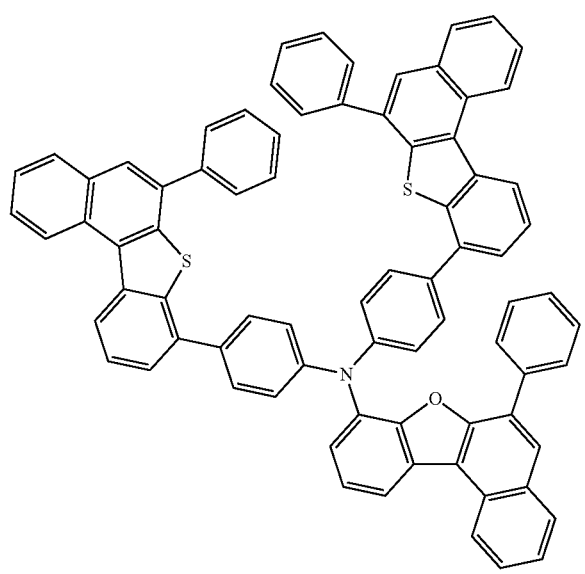
(553)
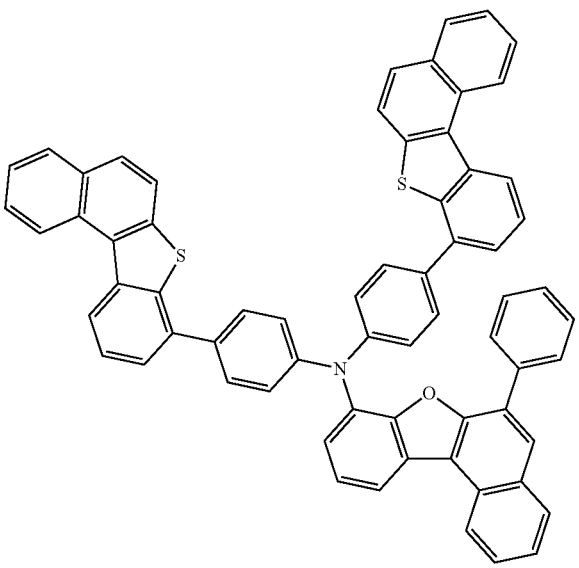
[Chemical Formula 47]
(563)
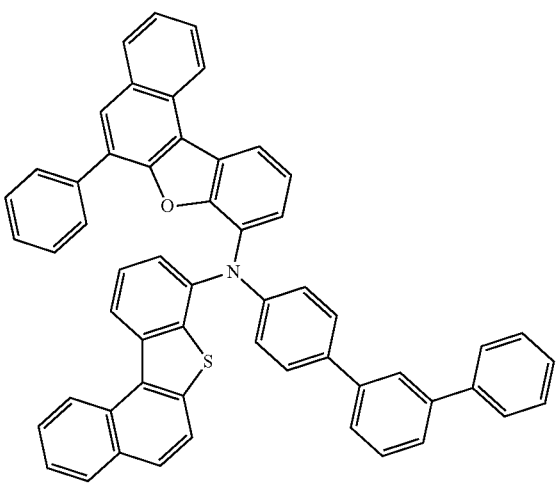
(570)
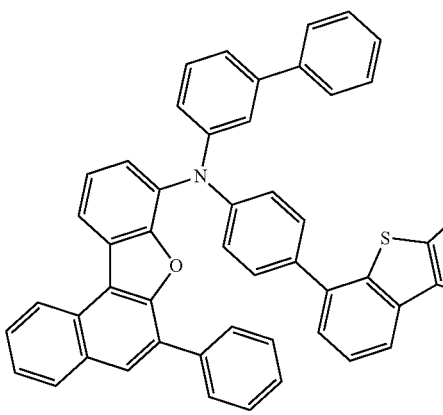

129
-continued
(595)
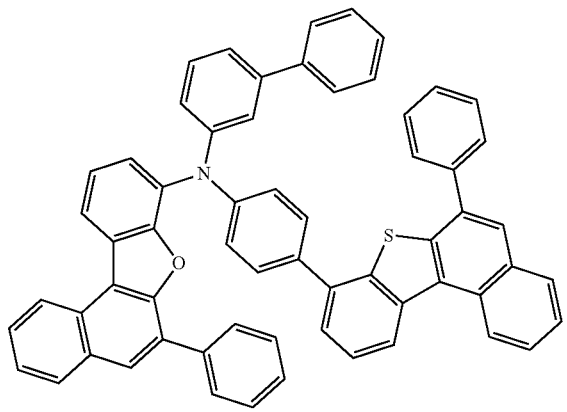
(596)
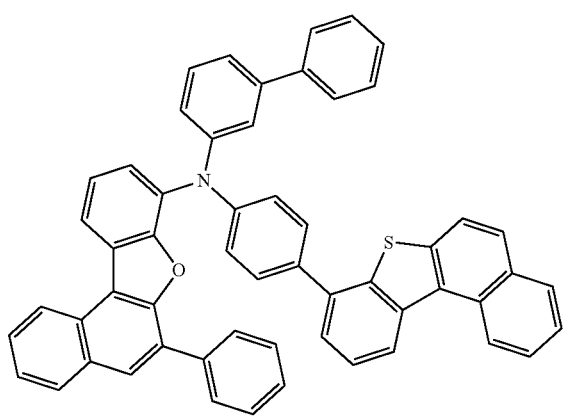
(597)
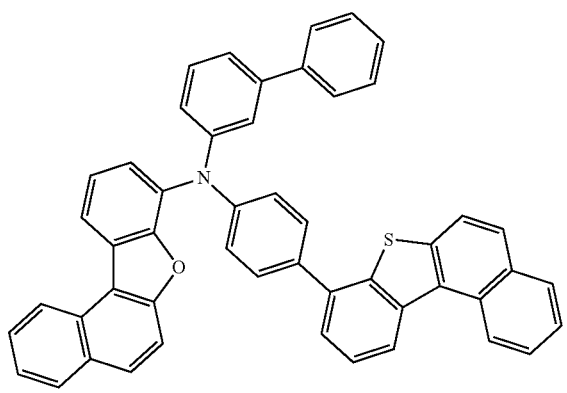
130
-continued
(598)
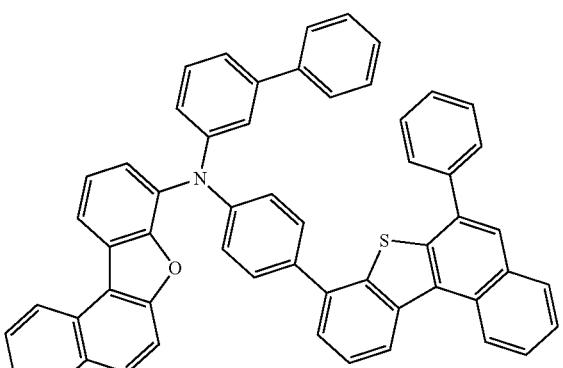
(599)
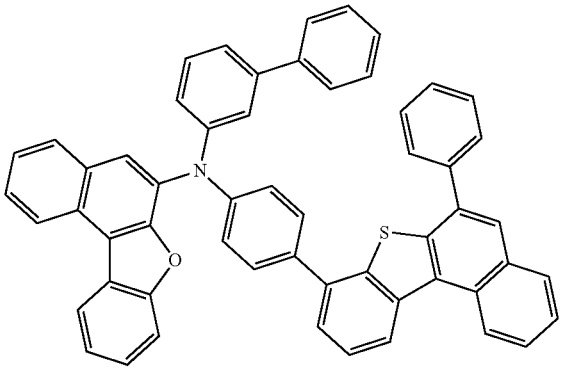
(600)
(601)
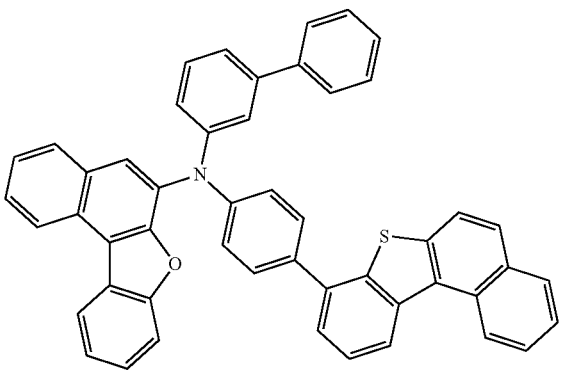

-continued (602)

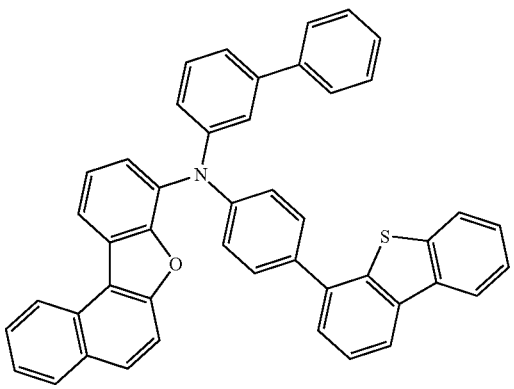

The above organic compounds can be synthesized by Synthesis Schemes (a-1), (a-2), (b-1), and (b-2) shown below.

A method for synthesizing the organic compound represented by General Formula (G1) is described. In General Formula (G1), $R^1$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. One of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms.

[Chemical Formula 48]

(G1)

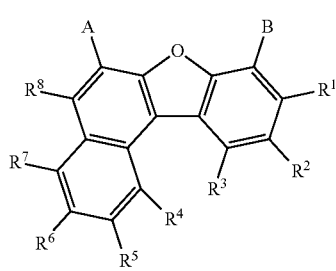

Note that in General Formula (g1), $Ar^1$ and $Ar^2$ independently represent a substituted or unsubstituted aromatic hydrocarbon group having 6 to 60 carbon atoms. In the case where $Ar^1$ and $Ar^2$ each include a substituent, the substituent includes a benzonaphthofuranyl group and a dinaphthofuranyl group.

[Chemical Formula 49]

(g1)

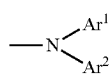

Thus, General Formula (G1) can be represented by General Formula (G1-a) or (G1-b). A variety of reactions can be applied to the method for synthesizing the organic compounds represented by General Formulae (G1-a) and (G1-b). Note that the method for synthesizing the organic compounds of one embodiment of the present invention represented by General Formulae (G1-a) and (G1-b) is not limited to the following synthesis method.

[Chemical Formula 50]

(G1-a)

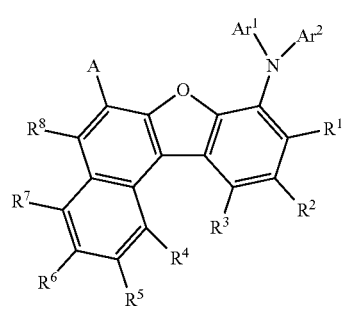

[Chemical Formula 51]

(G1-b)

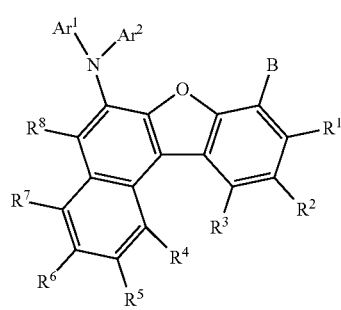

<Method for Synthesizing Organic Compound Represented by General Formula (G1-a)>

The organic compound of one embodiment of the present invention represented by General Formula (G1-a) can be synthesized by Synthesis Scheme (a-1) or (a-2) shown below.

That is, a benzonaphthofuran compound (compound 1) is coupled with diarylamine (compound 2), whereby a benzonaphthofuranylamino compound (G1-a) can be obtained. Alternatively, benzonaphthofuranylamine (compound 3) is coupled with a compound having an aryl skeleton (compound 4), whereby a benzonaphthofuranylamino compound (G1-a) can be obtained. Synthesis Schemes (a-1) and (a-2) are shown below.

[Chemical Formula 52]

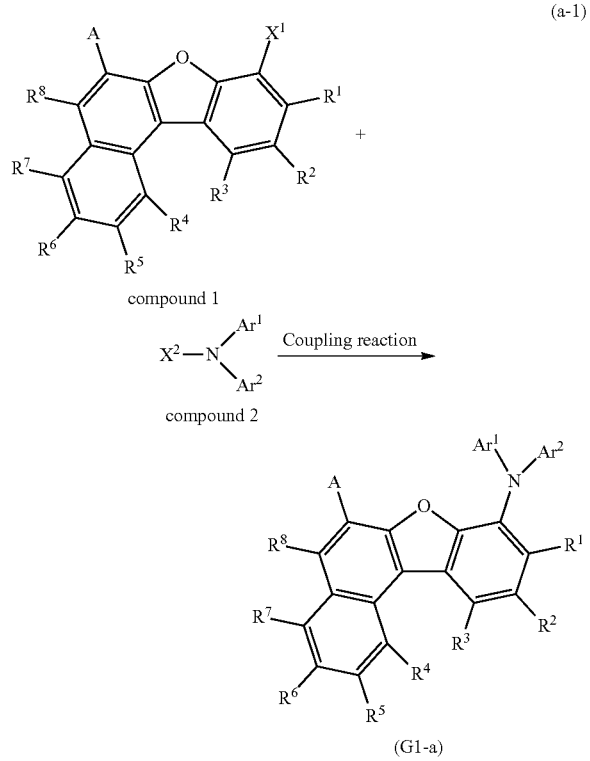

[Chemical Formula 53]

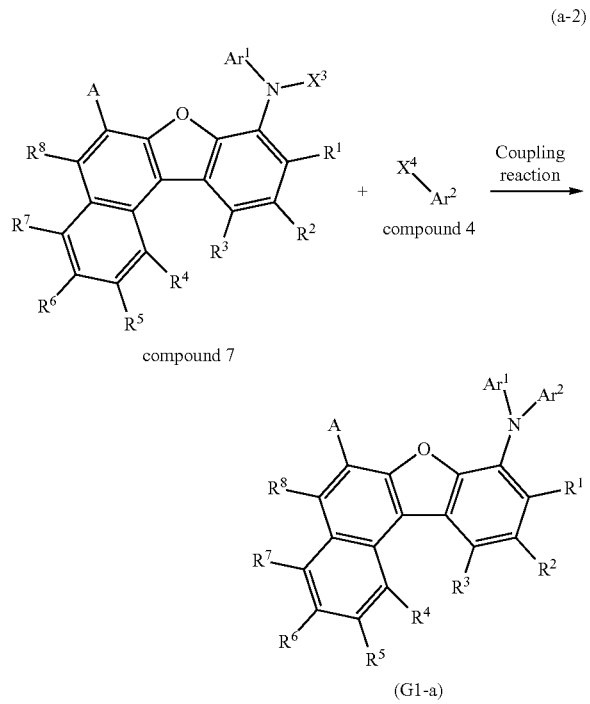

In Synthesis Schemes (a-1) and (a-2), $R^1$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. A represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms. $Ar^1$ and Ar-2 independently represent a substituted or unsubstituted aromatic hydrocarbon group having 6 to 60 carbon atoms. In the case where $Ar^1$ and $Ar^2$ each include a substituent, the substituent includes a benzonaphthofuranyl group and a dinaphthofuranyl group and does not include an amino group.

$X^1$ and $X^4$ independently represent chlorine, bromine, iodine, or a triflate group, and $X^2$ and $X^3$ independently represent hydrogen, an organotin group, or the like.

In the case where the Buchwald-Hartwig reaction using a palladium catalyst is employed in Synthesis Schemes (a-1) and (a-2), a palladium compound such as bis(dibenzylideneacetone)palladium(0), palladium(II) acetate, [1,1-bis(diphenylphosphino)ferrocene]palladium(II) dichloride, tetrakis(triphenylphosphine)palladium(0), or allylpalladium(II) chloride (dimer) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP (registered trademark)), can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. The reagents that can be used in the reaction are not limited to the above reagents.

In the case where the Ullmann reaction using copper or a copper compound is performed in Synthesis Schemes (a-1), (a-2), and (b-1), $X^1$ and $X^4$ independently represent chlorine, bromine, or iodine, and $X^2$ and $X^3$ represent hydrogen. Copper or a copper compound can be used for the reaction. Examples of the base used include an inorganic base such as potassium carbonate. Examples of the solvent that can be used for the reaction include 1,3-dimethyl-3,4,5,6-tetrahydro-2(1H)pyrimidinone (DMPU), toluene, xylene, and benzene. In the Ullmann reaction, since the objective product can be obtained in a shorter time and in a higher yield when the reaction temperature is 100° C. or higher; therefore, it is preferable to use DMPU or xylene that has a high boiling temperature. A reaction temperature of 150° C. or higher is further preferred and accordingly DMPU is more preferably used. The reagents that can be used for the reaction are not limited to the above reagents.

<Method for Synthesizing Organic Compound Represented by General Formula (G1-b)>

The organic compound of the present invention represented by General Formula (G1-b) can be synthesized by Synthesis Scheme (b-1) or (b-2) shown below.

That is, a benzonaphthofuran compound (compound 5) is coupled with diarylamine (compound 6), whereby a benzonaphthofuranylamino compound (G1-b) can be obtained. Alternatively, benzonaphthofuranylamine (compound 7) is coupled with a compound having an aryl skeleton (compound 8), whereby a benzonaphthofuranylamino compound (G1-b) can be obtained. Synthesis Schemes (b-1) and (b-2) are shown below.

[Chemical Formula 54]

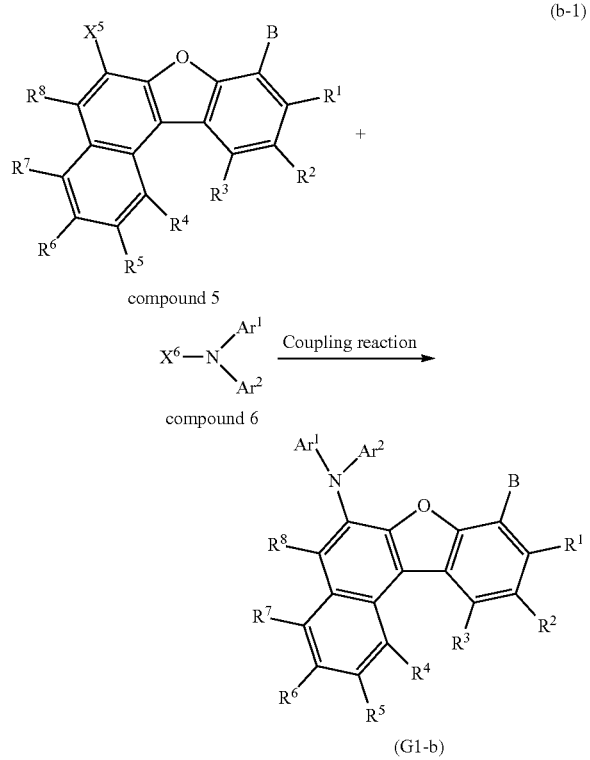

compound 5 compound 6

(G1-b)

[Chemical Formula 55]

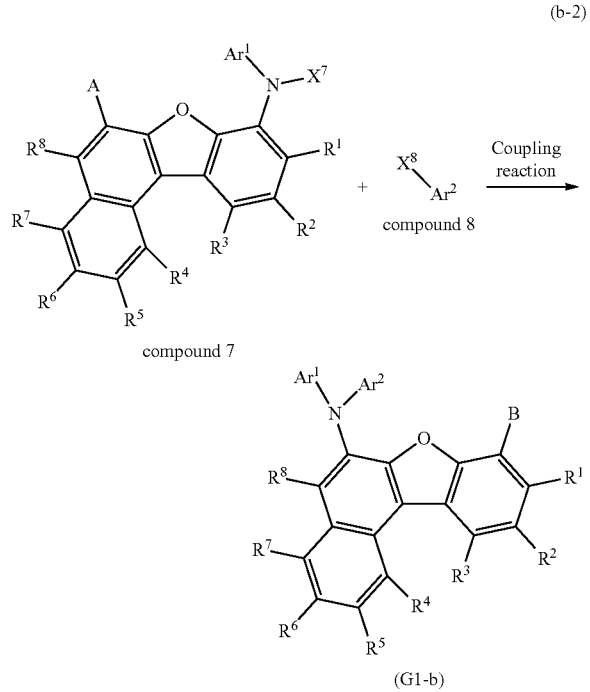

compound 7

(G1-b)

In Synthesis Schemes (b-1) and (b-2), $R^1$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms. A represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms. $Ar^1$ and $Ar^2$ independently represent a substituted or unsubstituted aromatic hydrocarbon group having 6 to 60 carbon atoms. In the case where $Ar^1$ and $Ar^2$ each include a substituent, the substituent includes a benzonaphthofuranyl group and a dinaphthofuranyl group and does not include an amino group.

$X^1$ and $X^4$ independently represent chlorine, bromine, iodine, or a triflate group, and $X^2$ and $X^3$ independently represent hydrogen, an organotin group, or the like.

In the case where the Buchwald-Hartwig reaction using a palladium catalyst is employed in Synthesis Schemes (b-1) and (b-2), a palladium compound such as bis(dibenzylideneacetone)palladium(0), palladium(II) acetate, [1,1-bis(diphenylphosphino)ferrocene]palladium(II) dichloride, tetrakis(triphenylphosphine)palladium(0), or allylpalladium(II) chloride (dimer) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP (registered trademark)), can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. The reagents that can be used in the reaction are not limited to the above reagents.

In the case where the Ullmann reaction using copper or a copper compound is performed in Synthesis Schemes (b-1) and (b-2), $X^1$ and $X^4$ independently represent chlorine, bromine, or iodine, and $X^2$ and $X^3$ represent hydrogen. Copper or a copper compound can be used for the reaction. Examples of the base used include an inorganic base such as potassium carbonate. Examples of the solvent that can be used for the reaction include 1,3-dimethyl-3,4,5,6-tetrahydro-2(1H)pyrimidinone (DMPU), toluene, xylene, and benzene. In the Ullmann reaction, since the objective product can be obtained in a shorter time and in a higher yield when the reaction temperature is 100° C. or higher; therefore, it is preferable to use DMPU or xylene that has a high boiling temperature. A reaction temperature of 150° C. or higher is further preferred and accordingly DMPU is more preferably used. The reagents that can be used for the reaction are not limited to the above reagents.

Embodiment 3

In this embodiment, a light-emitting device including the light-emitting element described in Embodiment 1 will be described.

In this embodiment, the light-emitting device manufactured using the light-emitting element described in Embodiment 1 is described with reference to FIGS. 2A and 2B. Note that FIG. 2A is a top view of the light-emitting device and FIG. 2B is a cross-sectional view taken along the lines A-B and C-D in FIG. 2A. This light-emitting device includes a driver circuit portion (source line driver circuit) 601, a pixel portion 602, and a driver circuit portion (gate line driver circuit) 603, which are to control the light emission of a light-emitting element and illustrated with dotted lines. Reference numeral 604 denotes a sealing substrate; 605, a sealing material; and 607, a space surrounded by the sealing material 605.

Reference numeral 608 denotes a wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 2B. The driver circuit portions and the pixel portion are formed over an element substrate 610; FIG. 2B shows the source line driver circuit 601, which is a driver circuit portion, and one pixel in the pixel portion 602.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, the off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and an anode 613 electrically connected to a drain of the current controlling FET 612. One embodiment of the present invention is not limited to the structure. The pixel portion 602 may include three or more FETs and a capacitor in combination.

Note that to cover an end portion of the anode 613, an insulator 614 is formed using a positive photosensitive acrylic resin film here.

In order to improve the coverage with an EL layer or the like which is formed later, the insulator 614 is formed to have a curved surface with curvature at its upper or lower end portion. For example, in the case where positive photosensitive acrylic is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a cathode 617 are formed over the anode 613. Here, as a material used for the anode 613, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance and favorable ohmic contact.

The EL layer 616 is formed by any of a variety of methods such as an evaporation method using an evaporation mask, an inkjet method, and a spin coating method. The EL layer 616 has the structure described in Embodiment 1. As another material included in the EL layer 616, a low molecular compound or a high molecular compound (including an oligomer or a dendrimer) may be used.

As a material used for the cathode 617, which is formed over the EL layer 616, a material having a low work function (e.g., Al, Mg, Li, and Ca, or an alloy or a compound thereof, such as MgAg, MgIn, or AlLi) is preferably used. In the case where light generated in the EL layer 616 is transmitted through the cathode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the cathode 617.

Note that the light-emitting element is formed with the anode 613, the EL layer 616, and the cathode 617. The light-emitting element is the light-emitting element described in Embodiment 1. In the light-emitting device of this embodiment, the pixel portion, which includes a plurality of light-emitting elements, may include both the light-emitting element described in Embodiment 1 and a light-emitting element having a different structure.

The sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, or acrylic can be used.

Although not illustrated in FIGS. 2A and 2B, a protective film may be provided over the cathode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting device manufactured using the light-emitting element described in Embodiment 1 can be obtained.

The light-emitting device in this embodiment is manufactured using the light-emitting element described in Embodiment 1 and thus can have favorable characteristics. Specifically, since the light-emitting element described in Embodiment 1 has a long lifetime, the light-emitting device can have high reliability. Since the light-emitting device using the light-emitting element described in Embodiment 1 has high emission efficiency, the light-emitting device can achieve low power consumption.

FIGS. 3A and 3B each illustrate an example of a light-emitting device in which full color display is achieved by formation of a light-emitting element exhibiting white light emission and with the use of coloring layers (color filters) and the like. FIG. 3A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, anodes 1024W, 1024R, 1024G, and 1024B of light-emitting elements, a partition 1025, an EL layer 1028, a cathode 1029 of the light-emitting elements, a sealing substrate 1031, a sealing material 1032, and the like.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. The light that does not pass through the coloring layers is white and the light that passes through any one of the coloring layers is red, green, or blue; thus, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
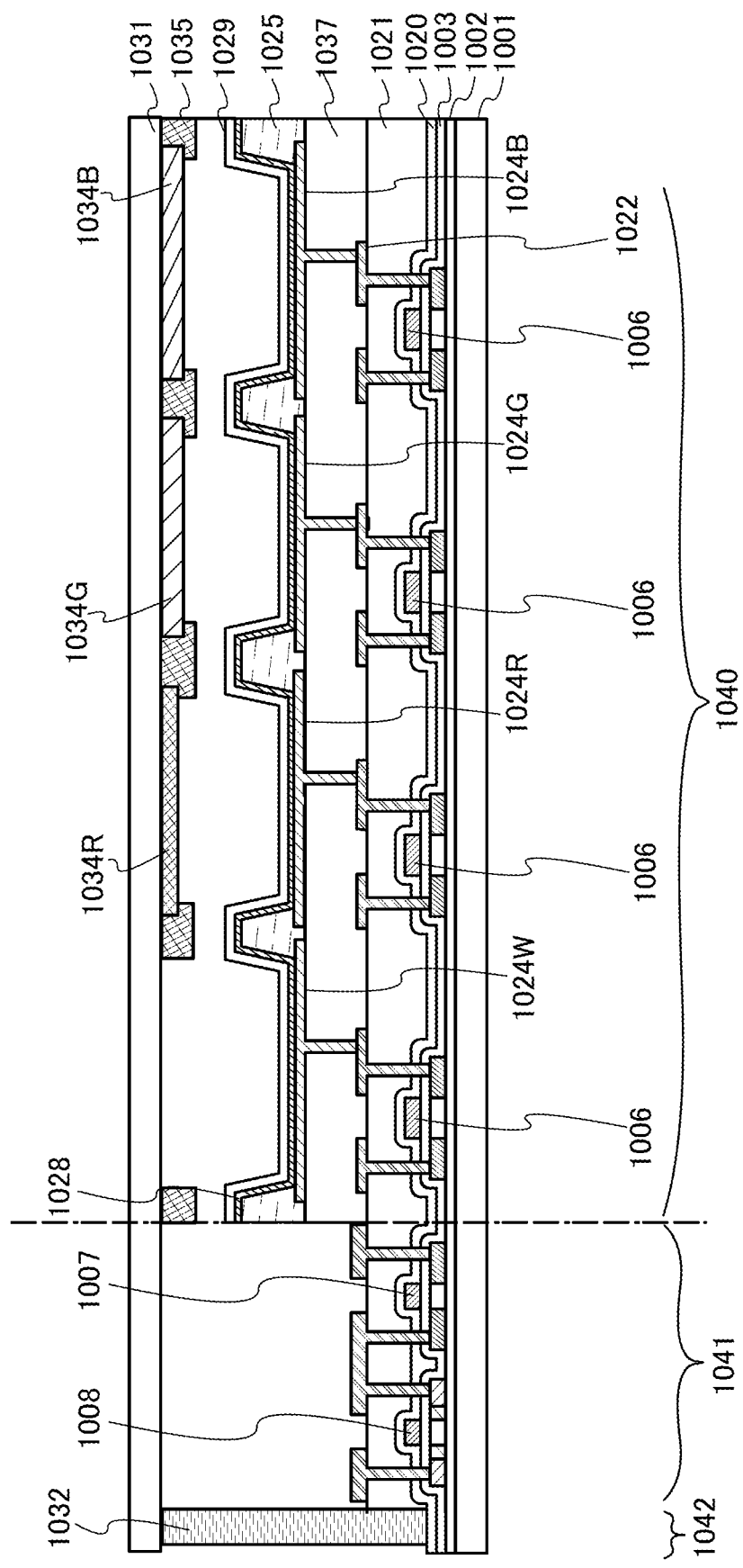
FIG. 4 is a conceptual diagram of an active matrix light-emitting device.

The above-described light-emitting device is a light-emitting device having a structure in which light is extracted from the substrate 1001 side where FETs are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate that does not transmit light can be used as the substrate 1001. The process up to the step of forming a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The anodes 1024W, 1024R, 1024G, and 1024B of the light-emitting elements each serve as an anode here, but may serve as a cathode. Furthermore, in the case of a light-emitting device having a top emission structure as illustrated in FIG. 4, the anodes are preferably reflective electrodes. The EL layer 1028 is formed to have a structure similar to the structure of the EL layer 103, which is described in Embodiment 1, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting device having a top emission structure, a microcavity structure can be favorably employed. A light-emitting element with a microcavity structure is formed with the use of a reflective electrode as the anode and a semi-transmissive and semi-reflective electrode as the cathode. The light-emitting element with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 100%, preferably 70% to 100%, and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting element, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting element described above may be combined with a plurality of EL layers; for example, a light-emitting element may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting device which displays images with subpixels of four colors, red, yellow, green, and blue, the light-emitting device can have favorable characteristics because the luminance can be increased owing to yellow light emission and each subpixel can employ a microcavity structure suitable for wavelengths of the corresponding color.

The light-emitting device in this embodiment is manufactured using the light-emitting element described in Embodiment 1 and thus can have favorable characteristics. Specifically, since the light-emitting element described in Embodiment 1 has a long lifetime, the light-emitting device can have high reliability. Since the light-emitting device using the light-emitting element described in Embodiment 1 has high emission efficiency, the light-emitting device can achieve low power consumption.

Figure 5A:
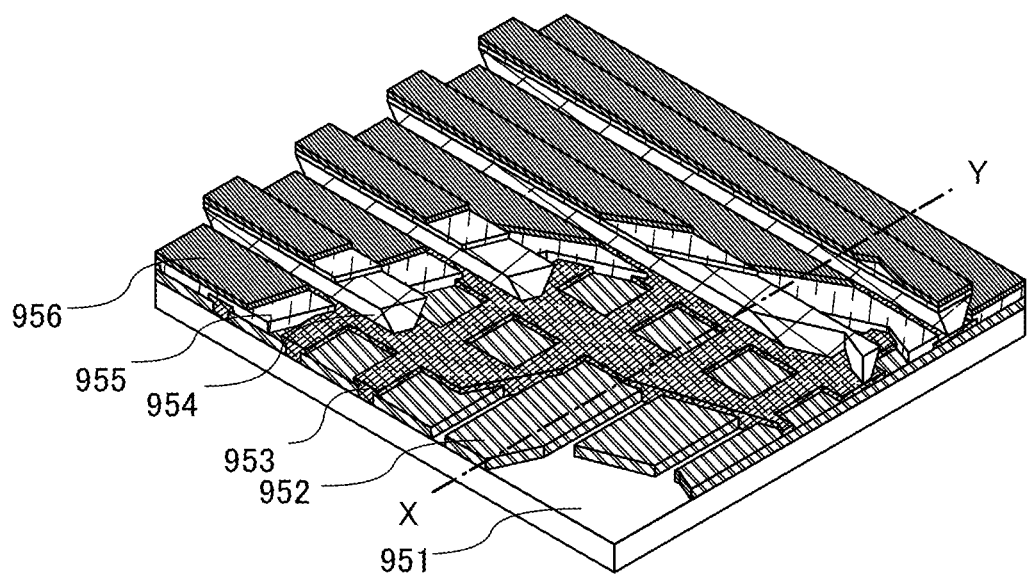
FIGS. 5A and 5B are conceptual diagrams of a passive matrix light-emitting device.
Figure 5B:
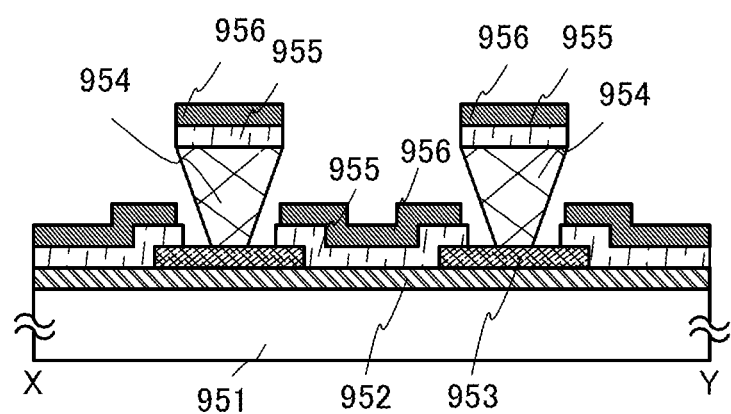

The active matrix light-emitting device is described above, whereas a passive matrix light-emitting device is described below. FIGS. 5A and 5B illustrate a passive matrix light-emitting device manufactured using the present invention. Note that FIG. 5A is a perspective view of the light-emitting device, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid that is parallel to the surface of the insulating layer 953 and is in contact with the insulating layer 953) is shorter than the upper side (a side of the trapezoid that is parallel to the surface of the insulating layer 953 and is not in contact with the insulating layer 953). The partition layer 954 thus provided can prevent defects in the light-emitting element due to static electricity or others. The passive-matrix light-emitting device also includes the light-emitting element described in Embodiment 1; thus, the light-emitting device can have high reliability or low power consumption.

Since many minute light-emitting elements arranged in a matrix in the light-emitting device described above can each be controlled, the light-emitting device can be suitably used as a display device for displaying images.

This embodiment can be freely combined with any of the other embodiments.

Embodiment 4

Figure 6A:
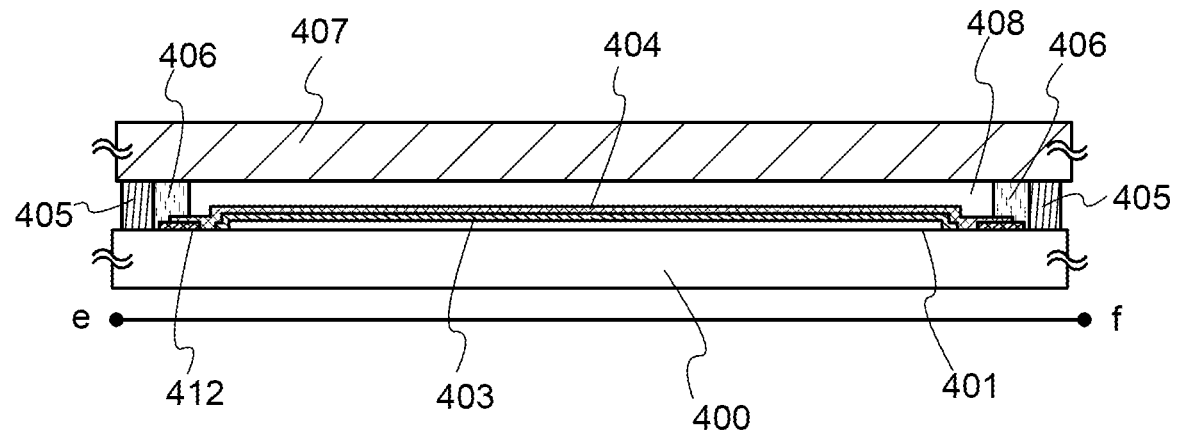
FIGS. 6A and 6B illustrate a lighting device.
Figure 6B:
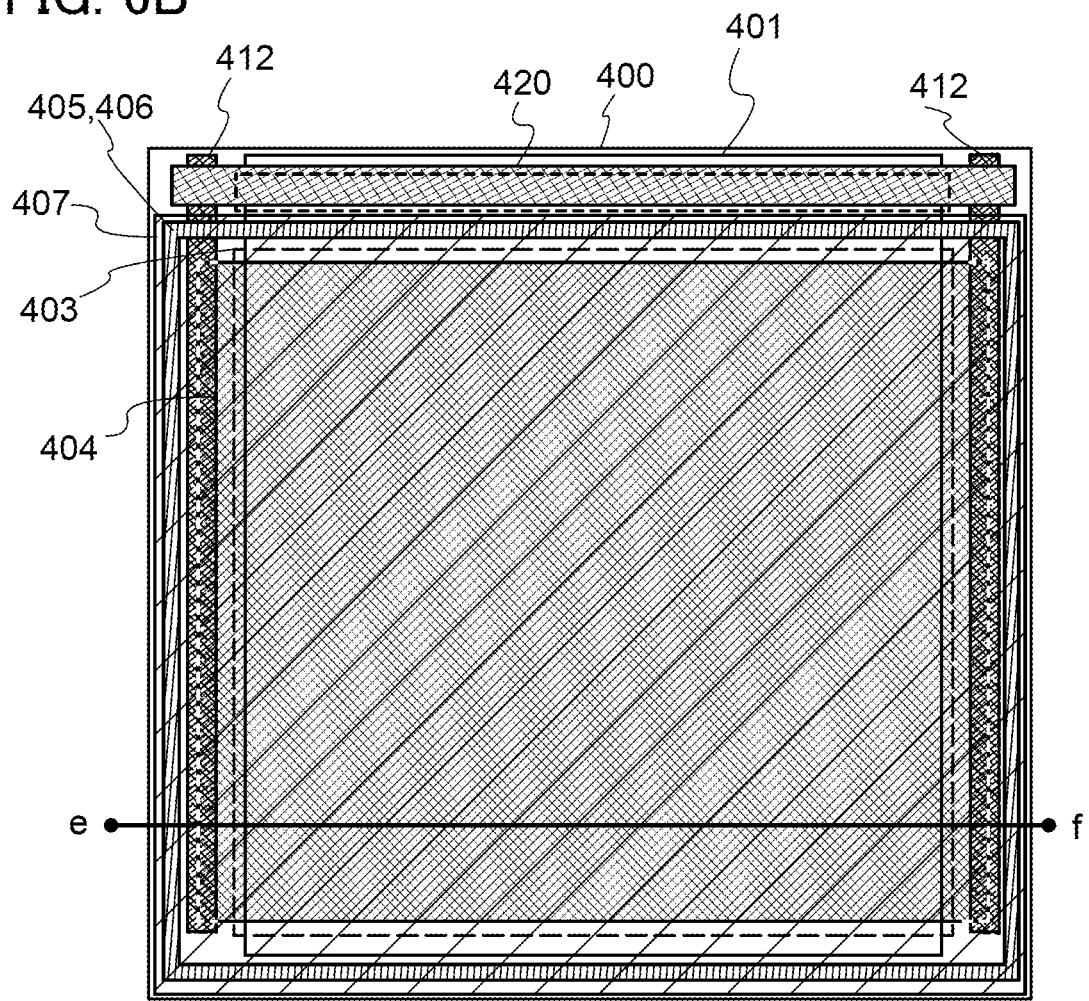

In this embodiment, an example in which the light-emitting element described in Embodiment 1 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, an anode 401 is formed over a substrate 400 which is a support and has a light-transmitting property. The anode 401 corresponds to the anode 101 in Embodiment 1. When light is extracted through the anode 401 side, the anode 401 is formed using a material having a light-transmitting property.

A pad 412 for applying voltage to a cathode 404 is provided over the substrate 400.

An EL layer 403 is formed over the anode 401. The structure of the EL layer 403 corresponds to, for example, the structure of the EL layer 103 in Embodiment 1, or the structure in which the light-emitting units 511 and 512 and the charge-generation layer 513 are combined. Refer to the descriptions for the structure.

The cathode 404 is formed to cover the EL layer 403. The cathode 404 corresponds to the cathode 102 in Embodiment 1. The cathode 404 is formed using a material having high reflectance when light is extracted through the anode 401 side. The cathode 404 is connected to the pad 412, whereby voltage is applied.

As described above, the lighting device described in this embodiment includes a light-emitting element including the anode 401, the EL layer 403, and the cathode 404. Since the light-emitting element is a light-emitting element with high emission efficiency, the lighting device in this embodiment can be a lighting device having low power consumption.

The substrate 400 provided with the light-emitting element having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the anode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting element described in Embodiment 1; thus, the light-emitting device can have high reliability. In addition, the light-emitting device can consume less power.

Embodiment 5

In this embodiment, examples of electronic devices each including the light-emitting element described in Embodiment 1 are described. The light-emitting element described in Embodiment 1 has a long lifetime and high reliability. As a result, the electronic devices described in this embodiment can each include a light-emitting portion having high reliability.

Examples of the electronic devices to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are given below.

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements described in Embodiment 1 are arranged in a matrix.

Operation of the television device can be performed with an operation switch of the housing 7101 or a separate remote controller 7110. With operation keys 7109 of the remote controller 7110, channels and volume can be controlled and images displayed on the display portion 7103 can be controlled. The remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured by arranging light-emitting elements described in Embodiment 1 in a matrix in the display portion 7203. The computer illustrated in FIG. 7B1 may have a structure illustrated in FIG. 7B2. The computer illustrated in FIG. 7B2 is provided with a second display portion 7210 instead of the keyboard 7204 and the pointing device 7206. The second display portion 7210 has a touch screen, and input can be performed by operation of images, which are displayed on the second display portion 7210, with a finger or a dedicated pen. The second display portion 7210 can also display images other than the display for input. The display portion 7203 may also have a touch screen. Connecting the two screens with a hinge can prevent troubles; for example, the screens can be prevented from being cracked or broken while the computer is being stored or carried.

FIG. 7C illustrates a portable game machine having two housings, a housing 7301 and a housing 7302, which are connected with a joint portion 7303 so that the portable game machine can be opened or folded. The housing 7301 incorporates a display portion 7304 in which the light-emitting elements described in Embodiment 1 are arranged in a matrix, and the housing 7302 incorporates a display portion 7305. In addition, the portable game machine illustrated in FIG. 7C includes a speaker portion 7306, a recording medium insertion portion 7307, an LED lamp 7308, input means (an operation key 7309, a connection terminal 7310, a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion in which the light-emitting elements described in Embodiment 1 are arranged in a matrix is used as either the display portion 7304 or the display portion 7305, or both, and the structure can include other accessories as appropriate. The portable game machine illustrated in FIG. 7C has a function of reading out a program or data stored in a recoding medium to display it on the display portion, and a function of sharing information with another portable game machine by wireless communication. Note that functions of the portable game machine illustrated in FIG. 7C are not limited to them, and the portable game machine can have various functions.

FIG. 7D illustrates an example of a portable terminal. A mobile phone 7400 is provided with a display portion 7402 incorporated in a housing 7401, operation buttons 7403, an external connection port 7404, a speaker 7405, a microphone 7406, and the like. Note that the mobile phone 7400 has the display portion 7402 in which the light-emitting elements described in Embodiment 1 are arranged in a matrix.

When the display portion 7402 of the portable terminal illustrated in FIG. 7D is touched with a finger or the like, data can be input into the portable terminal. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode is selected for the display portion 7402 so that characters displayed on a screen can be input. In this case, it is preferable to display a keyboard or number buttons on almost the entire screen of the display portion 7402.

When a sensing device including a sensor such as a gyroscope or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Furthermore, by providing a backlight or a sensing light source which emits near-infrared light in the display portion, an image of a finger vein, or a palm vein can be taken.

Note that the structure shown in this embodiment can be combined with any of the structures in Embodiments 1 to 4 as appropriate.

As described above, the application range of the light-emitting device including the light-emitting element described in Embodiment 1 is wide so that this light-emitting device can be applied to electronic devices in a variety of fields. By using the light-emitting element described in Embodiment 1, an electronic device having high reliability can be obtained.

Figure 8:
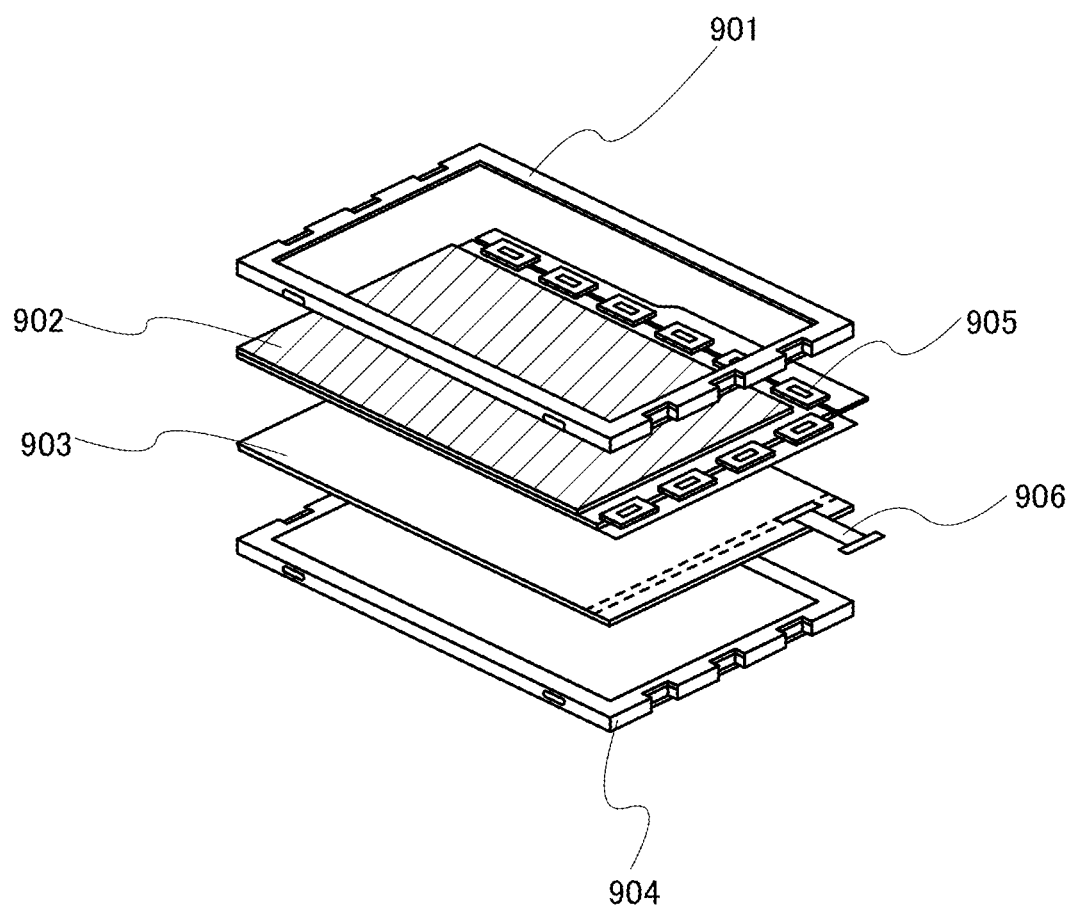
FIG. 8 illustrates a light source device.

FIG. 8 illustrates an example of a liquid crystal display device using the light-emitting element described in Embodiment 1 for a backlight. The liquid crystal display device illustrated in FIG. 8 includes a housing 901, a liquid crystal layer 902, a backlight unit 903, and a housing 904. The liquid crystal layer 902 is connected to a driver IC 905. The light-emitting element described in Embodiment 1 is used for the backlight unit 903, to which current is supplied through a terminal 906.

The light-emitting element described in Embodiment 1 is used for the backlight of the liquid crystal display device; thus, the backlight can have reduced power consumption. In addition, the use of the light-emitting element described in Embodiment 1 enables manufacture of a planar-emission lighting device and further a larger-area planar-emission lighting device; therefore, the backlight can be a larger-area backlight, and the liquid crystal display device can also be a larger-area device. Furthermore, the light-emitting device including the light-emitting element described in Embodiment 1 can be thinner than a conventional one; accordingly, the display device can also be thinner.

Figure 9:
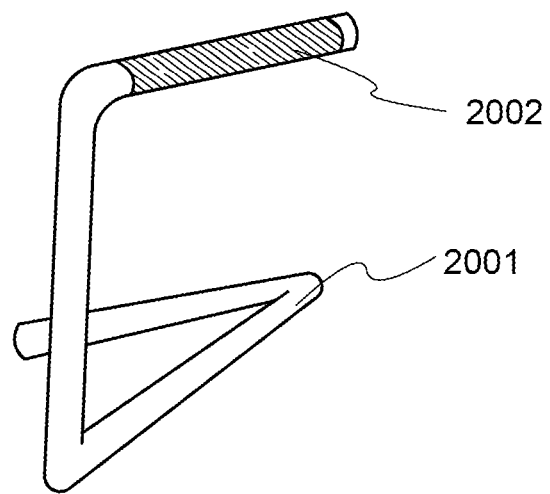
FIG. 9 illustrates a lighting device.

FIG. 9 illustrates an example in which the light-emitting element described in Embodiment 1 is used for a table lamp which is a lighting device. The table lamp illustrated in FIG. 9 includes a housing 2001 and a light source 2002, and the lighting device described in Embodiment 4 may be used for the light source 2002.

Figure 10:
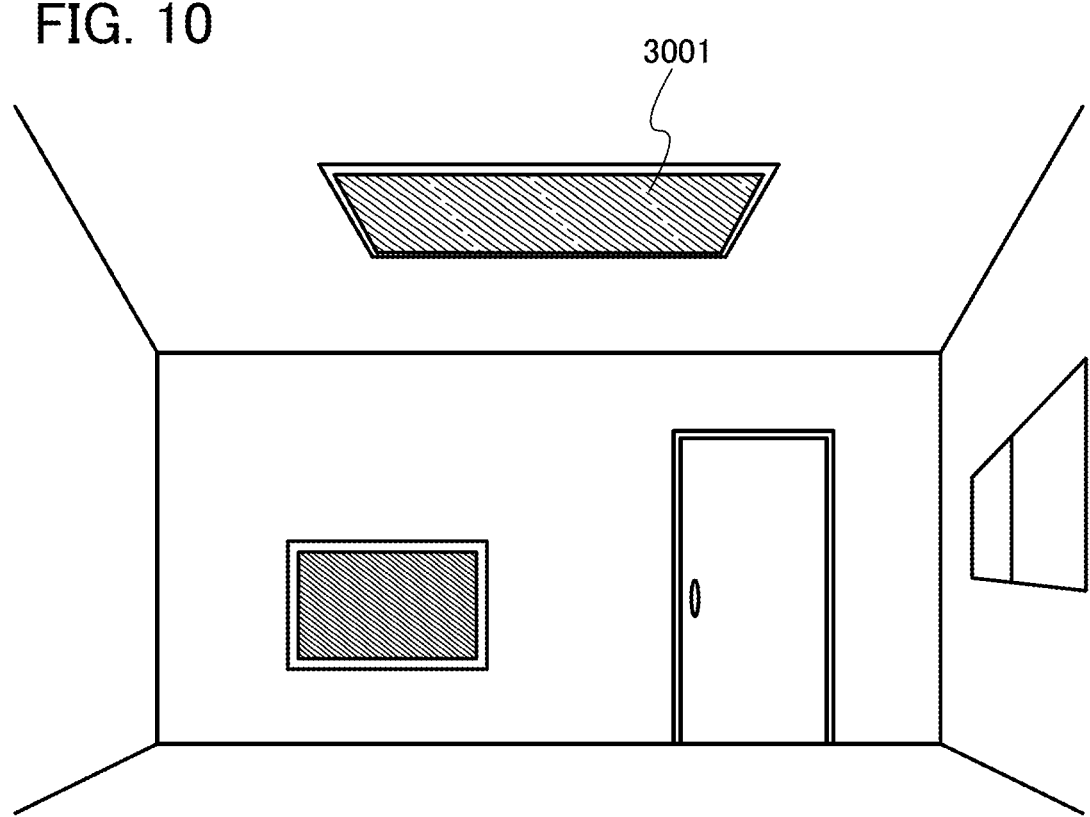
FIG. 10 illustrates a lighting device.

FIG. 10 illustrates an example in which the light-emitting element described in Embodiment 1 is used for an indoor lighting device 3001. Since the light-emitting element described in Embodiment 1 has high reliability, the lighting device can have high reliability. Furthermore, since the light-emitting element described in Embodiment 1 can have a large area, the light-emitting element can be used for a large-area lighting device. Furthermore, since the light-emitting element described in Embodiment 1 is thin, the light-emitting element can be used for a lighting device having a reduced thickness.

Figure 11:
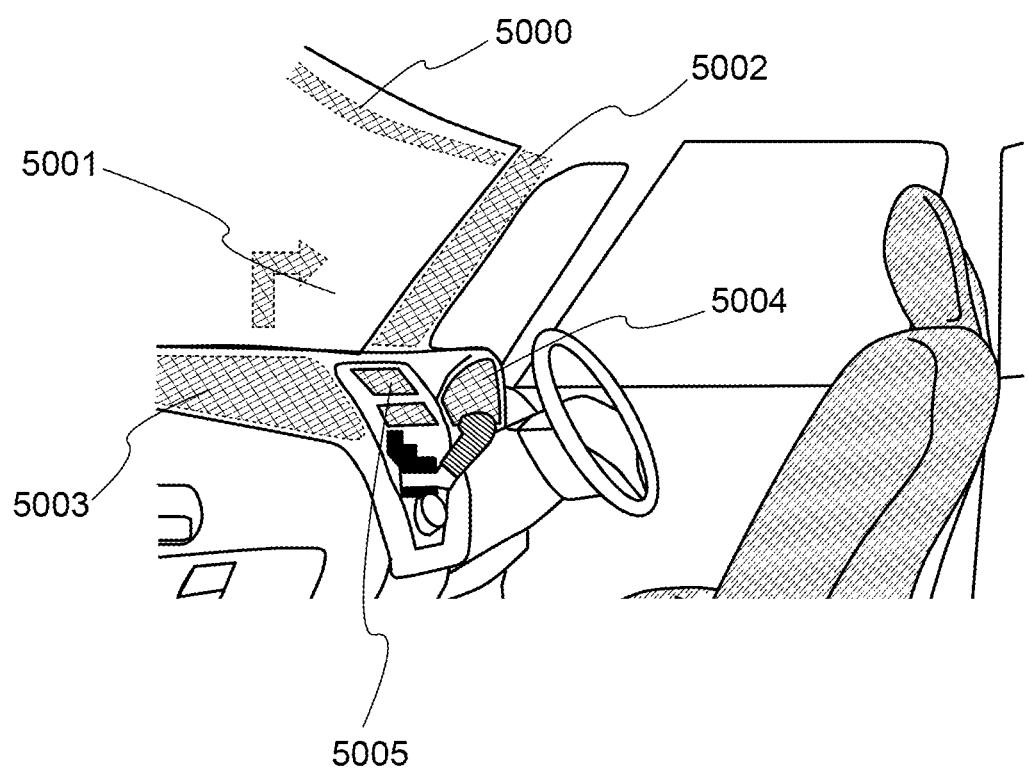
FIG. 11 illustrates in-vehicle display devices and lighting devices.

The light-emitting element described in Embodiment 1 can also be used for an automobile windshield or an automobile dashboard. FIG. 11 illustrates one mode in which the light-emitting element described in Embodiment 1 is used for an automobile windshield and an automobile dashboard. Display regions 5000 to 5005 each include the light-emitting element described in Embodiment 1.

The display region 5000 and the display region 5001 are display devices provided in the automobile windshield in which the light-emitting elements described in Embodiment 1 are incorporated. The light-emitting elements described in Embodiment 1 can be formed into what is called a see-through display device, through which the opposite side can be seen, by including an anode and a cathode formed of electrodes having a light-transmitting property. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device provided in a pillar portion in which the light-emitting element described in Embodiment 1 is incorporated. The display region 5002 can compensate for the view hindered by the pillar by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel level, a gearshift state, and air-condition setting. The content or layout of the display can be freely changed by a user as appropriate. Note that such information can also be shown by the display regions 5000 to 5003. The display regions 5000 to 5005 can also be used as lighting devices.

Figure 12A:
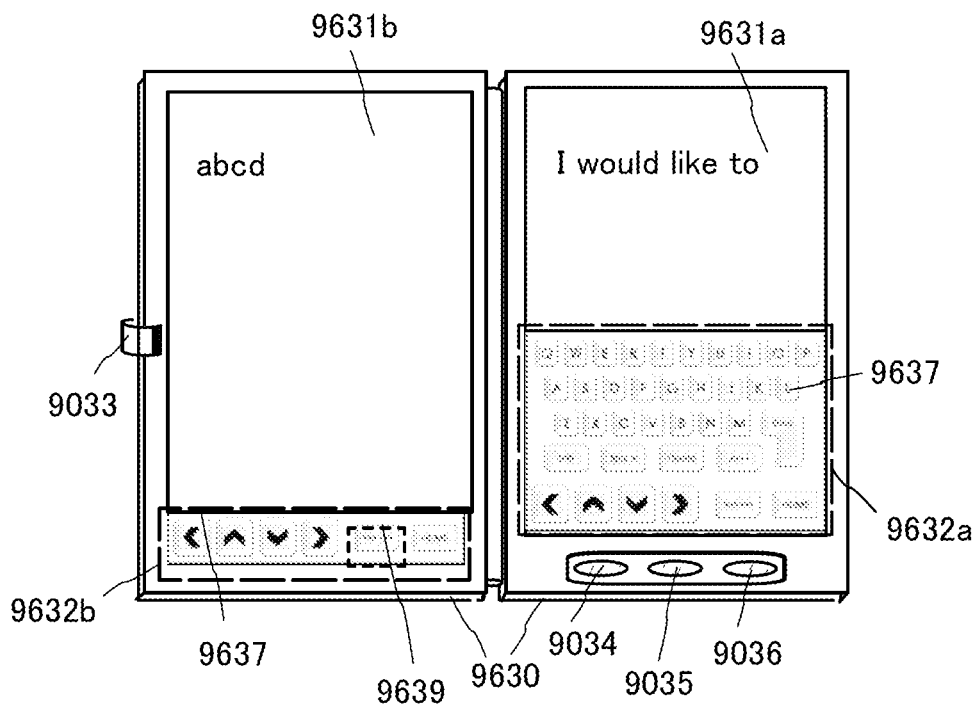
FIGS. 12A to 12C illustrate an electronic device.
Figure 12B:
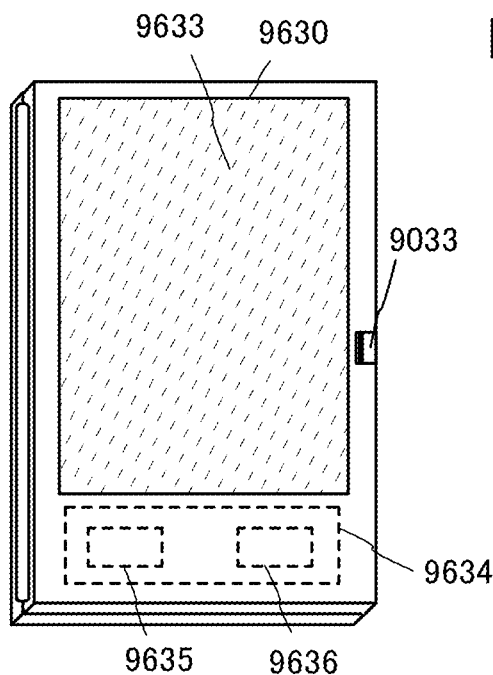

FIGS. 12A and 12B illustrate an example of a foldable tablet terminal. FIG. 12A illustrates the tablet terminal which is unfolded. The tablet terminal includes a housing 9630, a display portion 9631a, a display portion 9631b, a display mode switch 9034, a power switch 9035, a power-saving mode switch 9036, a clasp 9033, and an operation switch 9038. Note that in the tablet terminal, one or both of the display portion 9631a and the display portion 9631b is/are formed using a light-emitting device which includes the light-emitting element described in Embodiment 1.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard can be displayed on the entire region of the display portion 9631a so that the display portion 9631a is used as a touchscreen, and the display portion 9631b can be used as a display screen.

Like the display portion 9631a, part of the display portion 9631b can be a touchscreen region 9632b. When a switching button 9639 for showing/hiding a keyboard on the touchscreen is touched with a finger, a stylus, or the like, the keyboard can be displayed on the display portion 9631b.

Touch input can be performed in the touchscreen region 9632a and the touchscreen region 9632b at the same time.

The display mode switch 9034 can switch the display between portrait mode, landscape mode, and the like, and between monochrome display and color display, for example. The power-saving mode switch 9036 can control display luminance in accordance with the amount of external light in use of the tablet terminal sensed by an optical sensor incorporated in the tablet terminal. Another sensing device including a sensor such as a gyroscope or an acceleration sensor for sensing inclination may be incorporated in the tablet terminal, in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, higher definition images may be displayed on one of the display portions 9631a and 9631b.

FIG. 12B illustrates the tablet terminal which is folded. The tablet terminal in this embodiment includes the housing 9630, a solar cell 9633, a charge and discharge control circuit 9634, a battery 9635, and a DCDC converter 9636. In FIG. 12B, a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that a structure in which the solar cell 9633 is provided on one or both surfaces of the housing 9630 is preferable because the battery 9635 can be charged efficiently.

Figure 12C:
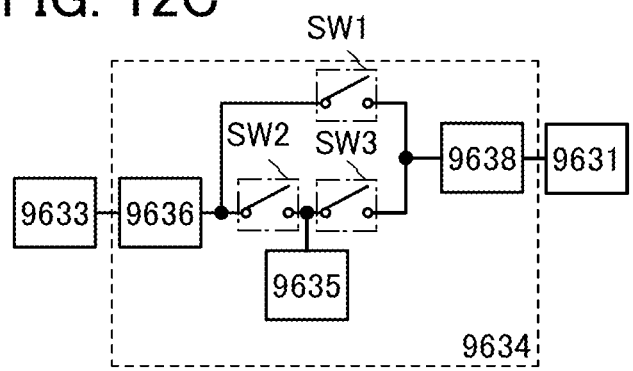

The structure and operation of the charge and discharge control circuit 9634 illustrated in FIG. 12B will be described with reference to a block diagram of FIG. 12C. FIG. 12C illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 12A to 12C as long as the display portion 9631 is included.

Figure 13A:
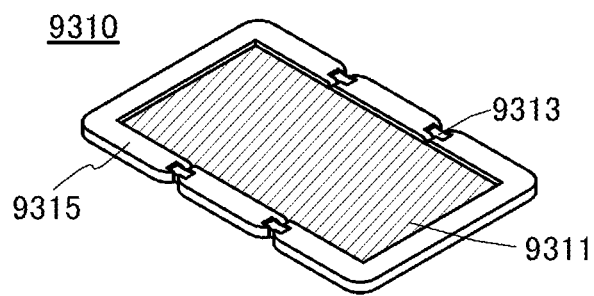
FIGS. 13A to 13C illustrate an electronic device.
Figure 13B:
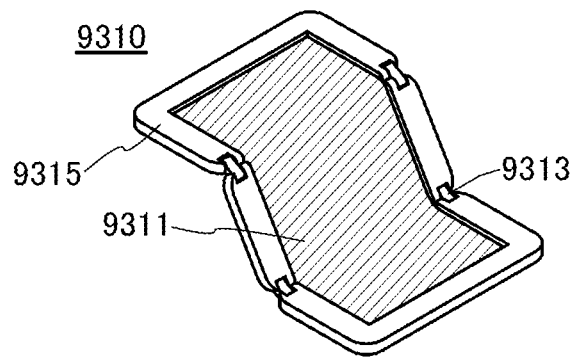
Figure 13C:
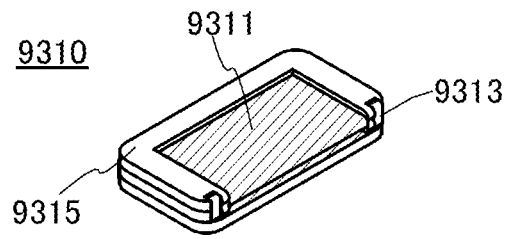

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. The display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 includes a display region that is positioned at a side surface of the portable information terminal 9310 that is folded. On the display region 9312, information icons, frequently-used applications, file shortcuts to programs, and the like can be displayed, and confirmation of information and start of application can be smoothly performed.

Note that an organic compound having a substituted or unsubstituted benzonaphthofuran skeleton and one substituted or unsubstituted amine skeleton, which is one embodiment of the present invention, can be used for an organic thin film solar cell. More specifically, the compound has a carrier-transport property and therefore can be used in a carrier-transport layer or a carrier-injection layer. In addition, a film of a mixture of the compound and an acceptor substance can be used as a charge-generation layer. Furthermore, the compound can be photoexcited and hence can be used for a power generation layer.

Example 1

Synthesis Example 1

This synthesis example specifically shows an example of synthesizing N-(4-biphenyl)-6,N-diphenylbenzo[b]naphtho[1,2-d]furan-8-amine (abbreviation: BnfABP), which is the organic compound of one embodiment of the present invention represented by Structural Formula (142) in Embodiment. The structural formula of BnfABP is as follows.

[Chemical Formula 56]

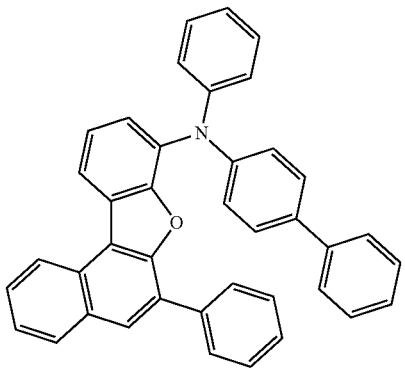

Step 1: Synthesis of 6-iodobenzo[b]naphtho[1,2-d]furan

Into a 500 mL three-neck flask was put 8.5 g (39 mmol) of benzo[b]naphtho[1,2-d]furan, and the air in the flask was replaced with nitrogen. Then, 195 mL of tetrahydrofuran (THF) was added thereto. After this solution was cooled to −75° C., 25 mL (40 mmol) of n-butyllithium (a 1.59 mol/L n-hexane solution) was dropped into this solution. After the dropping, the resulting solution was stirred at room temperature for 1 hour. After a predetermined period of time, the resulting solution was cooled to −75° C. Then, a solution in which 10 g (40 mmol) of iodine had been dissolved in 40 mL of THF was dropped into this solution. After the dropping, the resulting solution was stirred for 17 hours while the temperature of the solution was returned to room temperature. Next, an aqueous solution of sodium thiosulfate was added to the mixture, and the resulting mixture was stirred for 1 hour. Then, the organic layer of the mixture was washed with water and dried with magnesium sulfate. After the drying, the mixture was gravity-filtered to give a solution. The resulting solution was suction-filtered through Florisil (Catalog No. 066-05265 produced by Wako Pure Chemical Industries, Ltd.) and Celite (Catalog No. 537-02305 produced by Wako Pure Chemical Industries, Ltd.) to give a filtrate. The resulting filtrate was concentrated to give a solid. The resulting solid was recrystallized from toluene to give 6.0 g (18 mmol) of the target white powder in a yield of 45%. A synthesis scheme (a-1) of Step 1 is shown below.

[Chemical Formula 57]

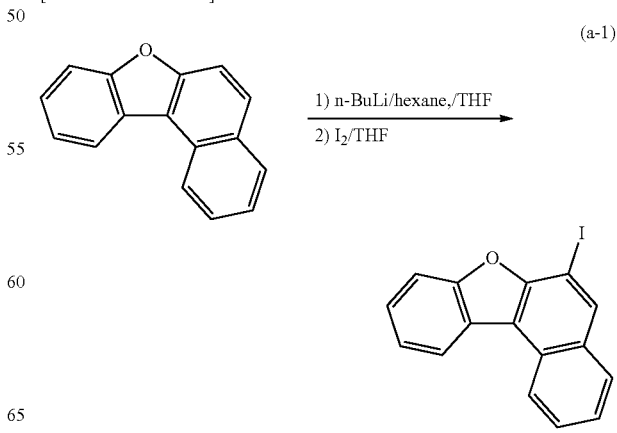

Step 2: Synthesis of 6-phenylbenzo[b]naphtho[1,2-d]furan

Into a 200 mL three-neck flask were put 6.0 g (18 mmol) of 6-iodobenzo[b]naphtho[1,2-d]furan, 2.4 g (19 mmol) of phenylboronic acid, 70 mL of toluene, 20 mL of ethanol, and 22 mL of an aqueous solution of potassium carbonate (2.0 mol/L). This mixture was degassed by being stirred while the pressure was reduced. After the degassing, the air in the flask was replaced with nitrogen, and then 480 mg (0.42 mmol) of tetrakis(triphenylphosphine)palladium(0) was added to the mixture. The resulting mixture was stirred at 90° C. under a nitrogen stream for 12 hours. After a predetermined period of time, water was added to the mixture, and an aqueous layer was subjected to extraction with toluene. The extracted solution and an organic layer were combined, and the mixture was washed with water and then dried with magnesium sulfate. The mixture was gravity-filtered to give a filtrate. The resulting filtrate was concentrated to give a solid, and the resulting solid was dissolved in toluene. The resulting solution was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give 4.9 g (17 mmol) of the target white solid in a yield of 93%. A synthesis scheme (b-1) of Step 2 is shown below.

[Chemical Formula 58]

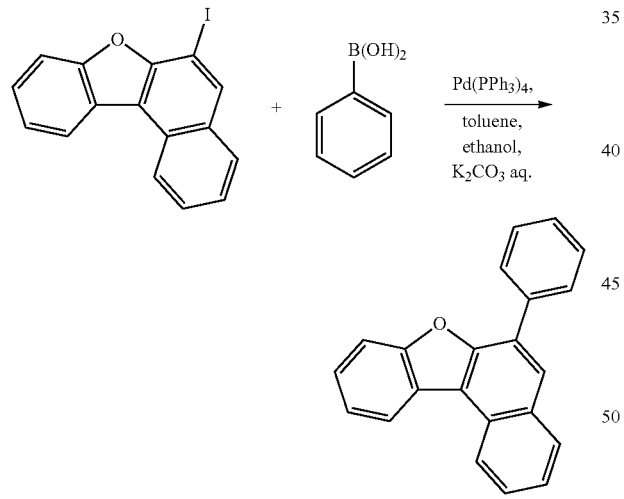

(b-1)

Step 3: Synthesis of 8-iodo-6-phenylbenzo[b]naphtho[1,2,d]furan

Into a 300 mL three-neck flask was put 4.9 g (17 mmol) of 6-phenylbenzo[b]naphtho[1,2-d]furan, and the air in the flask was replaced with nitrogen. Then, 87 mL of tetrahydrofuran (THF) was added thereto. The resulting solution was cooled to −75° C. Then, 11 mL (18 mmol) of n-butyllithium (a 1.59 mol/L n-hexane solution) was dropped into the solution. After the dropping, the resulting solution was stirred at room temperature for 1 hour. After a predetermined period of time, the resulting solution was cooled to −75° C. Then, a solution in which 4.6 g (18 mmol) of iodine had been dissolved in 18 mL of THF was dropped into the resulting solution. The resulting solution was stirred for 17 hours while the temperature of the solution was returned to room temperature. After the stirring, an aqueous solution of sodium thiosulfate was added to the mixture, and the resulting mixture was stirred for one hour. Then, an organic layer of the mixture was washed with water and dried with magnesium sulfate. The mixture was gravity-filtered to give a filtrate. The resulting filtrate was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give 3.7 g (8.8 mmol) of the target white solid in a yield of 53%. A synthesis scheme (c-1) of Step 3 is shown below.

[Chemical Formula 59]

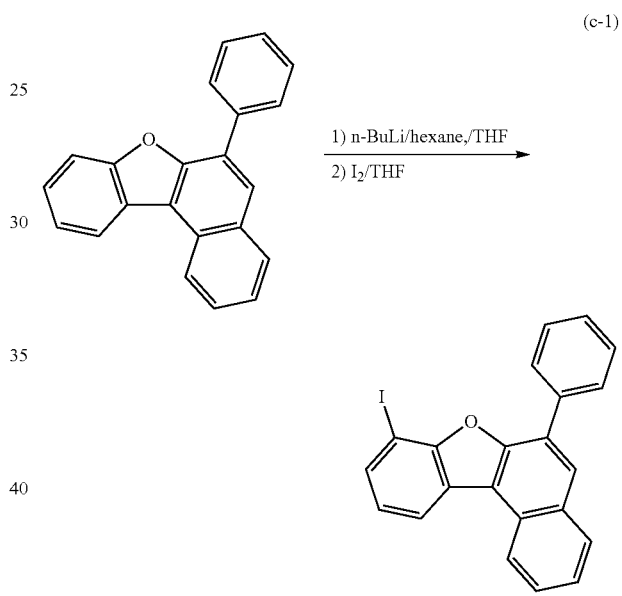

(c-1)

Step 4: Synthesis of 6,N-diphenylbenzo[b]naphtho[1,2-d]furan-8-amine

Into a 200 mL three-neck flask were added 5.0 g (12 mmol) of 8-iodo-6-phenylbenzo[b]naphtho[1,2-d]furan synthesized in Step 3 and 2.9 g (30 mmol) of sodium tert-butoxide. The air in the flask was replaced with nitrogen. After that, 60 mL of toluene and 1.4 g (13 mmol) of aniline, and 0.4 mL of tri(tert-butyl)phosphine (10 wt % hexane solution) were added. After this mixture was degassed under reduced pressure, the temperature was set at 60° C. under a nitrogen stream, 60 mg (0.1 mmol) of bis(dibenzylideneacetone)palladium(0) was added, and this mixture was stirred at 60° C. for 40 minutes. After the stirring, the obtained mixture was washed with water and a saturated aqueous solution of sodium chloride, and the organic layer was dried with magnesium sulfate. After the magnesium sulfate was removed by gravity filtration, the obtained filtrate was concentrated to give a white solid. This solid was purified by silica gel column chromatography (a developing solvent was a mixed solvent of toluene: hexane=1:2) to give 3.5 g of the target white solid in a yield of 77%. A synthesis scheme (d-1) of Step 4 is shown below.

[Chemical Formula 60]

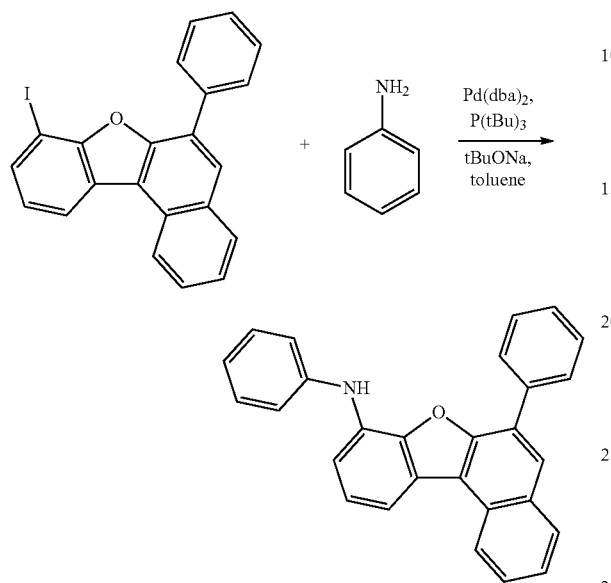

(d-1)

¹H NMR data of the obtained white solid are shown below.

¹H NMR (chloroform-d, 500 MHz): δ=6.23 (s, 1H), 7.04 (t, J=7.5 Hz, 1H), 7.24-7.26 (m, 2H), 7.34-7.41 (m, 4H), 7.47 (t, J=8.0 Hz, 1H), 7.54-7.60 (m, 3H), 7.74 (t, J=7.5 Hz, 1H), 7.95 (d, J=6.5 Hz, 2H), 7.99 (dd, J1=1.5 Hz, J2=7.0 Hz, 1H), 8.03 (s, 1H), 8.08 (d, J=8.0 Hz, 1H), 8.66 (d, J=9.0 Hz, 1H)

Step 5: Synthesis of N-4-biphenyl-6,N-diphenyl-benzo[b]naphtho[1,2-d]furan-8-amine Into a 200 mL three-neck flask were put 1.3 g (5.0 mmol) of 4-bromobiphenyl, 1.9 g (5.0 mmol) of 6,N-diphenylbenzo[b]naphtho[1,2-d]furan-8-amine synthesized in Step 4, 0.14 g (0.30 mmol) of 2-dicyclohexylphosphino-2',4',6'-triisopropylbiphenyl (abbreviation: X-Phos), and 1.5 g (15 mmol) of sodium tert-butoxide. The air in the flask was replaced with nitrogen, and then 25 mL of toluene was added. After this mixture was degassed under reduced pressure, the temperature was set at 60° C. under a nitrogen stream, 61 mg (0.10 mmol) of bis(dibenzylideneacetone)palladium(0) was added, and this mixture was stirred at 80° C. for 3 hours. After the stirring, the obtained mixture was washed with water and a saturated aqueous solution of sodium chloride, and the organic layer was dried with magnesium sulfate. After the magnesium sulfate was removed by gravity filtration, the obtained filtrate was concentrated to give a brown solid. This solid was purified by silica gel column chromatography (a developing solvent was a mixed solvent of toluene: hexane=3:7) to give 2.0 g of the target pale yellow solid in a yield of 67%. A synthesis scheme (e-1) of Step 5 is shown below.

[Chemical Formula 61]

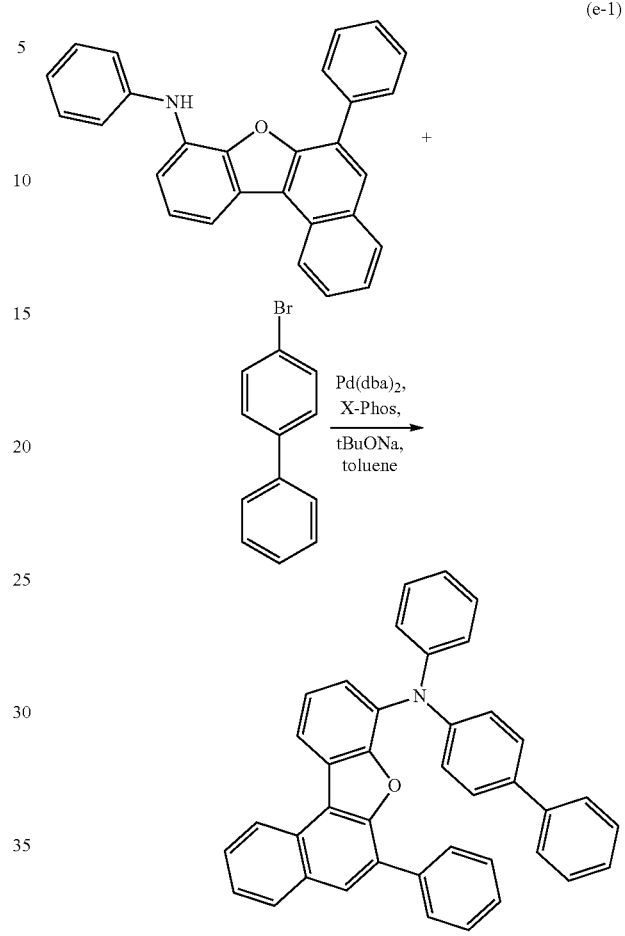

(e-1)

Figure 14A:
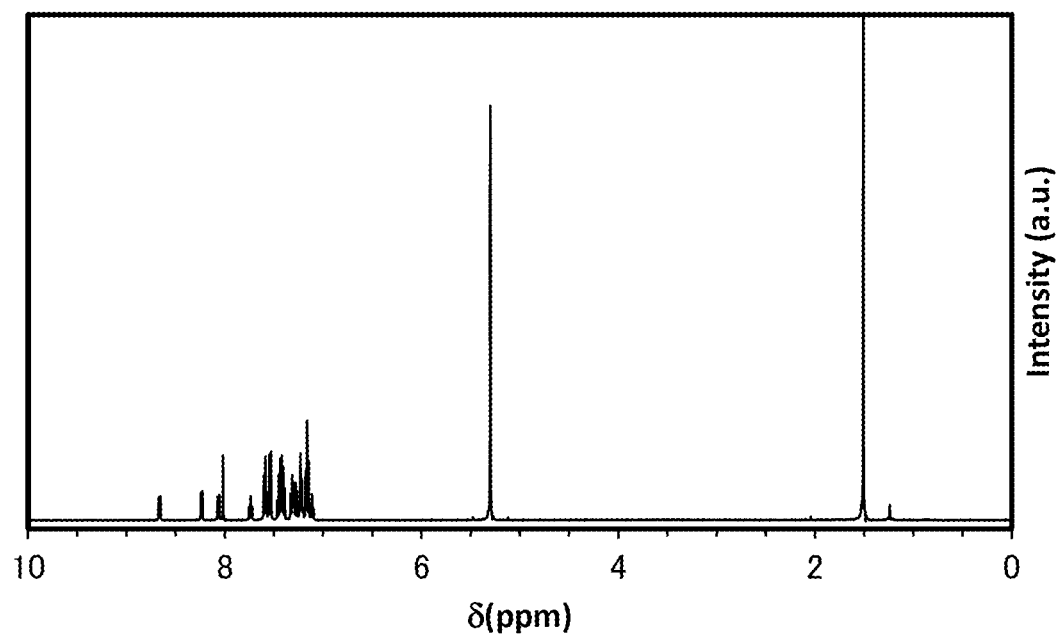
FIGS. 14A and 14B show $^1$H NMR charts of BnfABP.
Figure 14B:
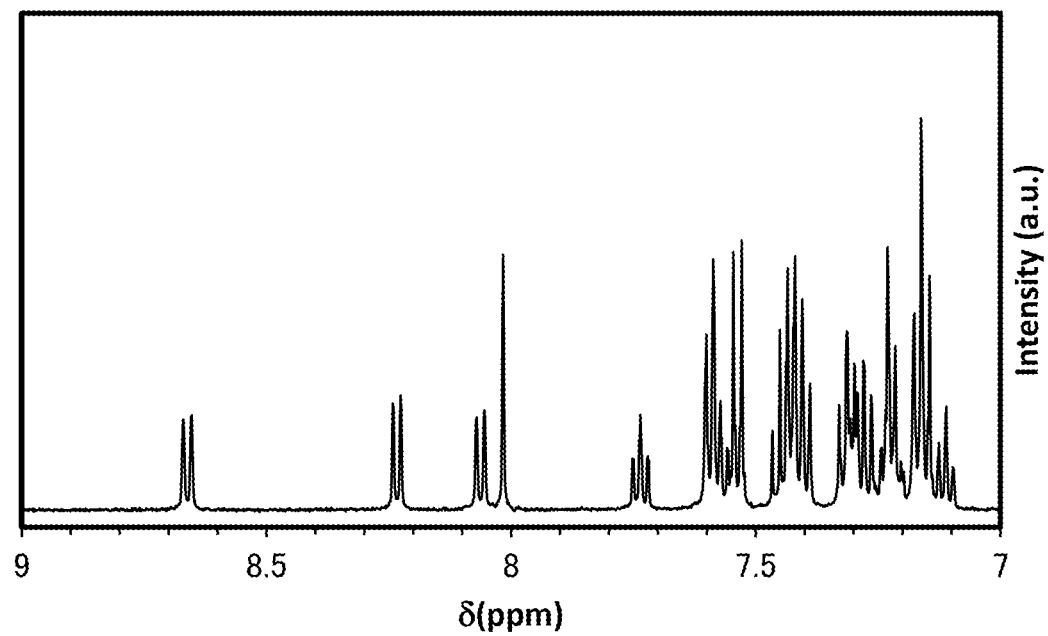

¹H NMR data of the obtained pale yellow solid are shown below. FIGS. 14A and 14B are ¹H NMR charts. Note that FIG. 14B is a chart showing an enlarged part of FIG. 14A in the range of 7.00 ppm to 9.00 ppm. These results indicate that BnfABP, which is the organic compound of one embodiment of the present invention, was obtained.

¹H NMR (dichloromethane-d2, 500 MHz): δ=7.11 (t, J=7.0 Hz, 1H), 7.16 (t, J=7.0 Hz, 4H), 7.22-7.33 (m, 7H), 7.39-7.47 (m, 5H), 7.53-7.60 (m, 5H), 7.74 (t, J=7.0 Hz, 1H), 8.02 (s, 1H), 8.06 (d, J=8.0 Hz, 1H), 8.23 (d, J=8.0 Hz, 1H), 8.66 (d, J=8.0 Hz, 1H)

By train sublimation, 1.5 g of the obtained pale yellow solid was purified. The purification by sublimation was carried out under a pressure of 3.6 Pa, with a flow rate of argon gas of 15 mL/min, at a temperature of 235° C. to 250° C., and for 16 hours. After the purification by sublimation, 1.4 g of the target pale yellow solid was obtained at a collection rate of 90%.

Figure 15:
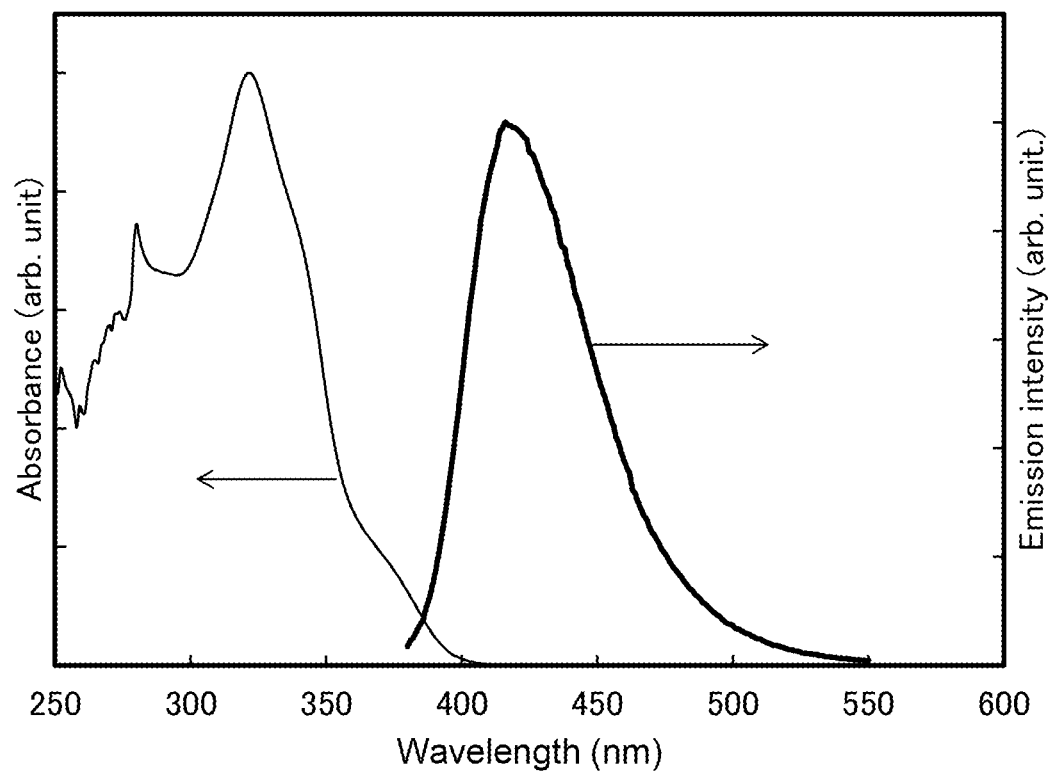
FIG. 15 shows an absorption spectrum and an emission spectrum of a solution of BnfABP.

Next, the ultraviolet-visible absorption spectrum (hereinafter, simply referred to as "absorption spectrum") and emission spectrum of a toluene solution and a solid thin film of BnfABP were measured. The solid thin film was formed over a quartz substrate by a vacuum evaporation method. The absorption spectrum of the toluene solution was measured using an ultraviolet-visible light spectrophotometer (V550 type manufactured by JASCO Corporation), the spectrum of toluene only put in a quartz cell was subtracted from the measured spectrum. The absorption spectrum of the thin film was measured using a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.). FIG. 15 shows the measurement results of the absorption and emission spectra of the obtained toluene solution and FIG. 16 shows the measurement results of the absorption and emission spectra of the obtained thin film.

From FIG. 15, the toluene solution of BnfABP has absorption peaks at around 376 nm, 340 nm, and 321 nm, and an emission peak at 417 nm (excitation wavelength: 370 nm).

Figure 16:
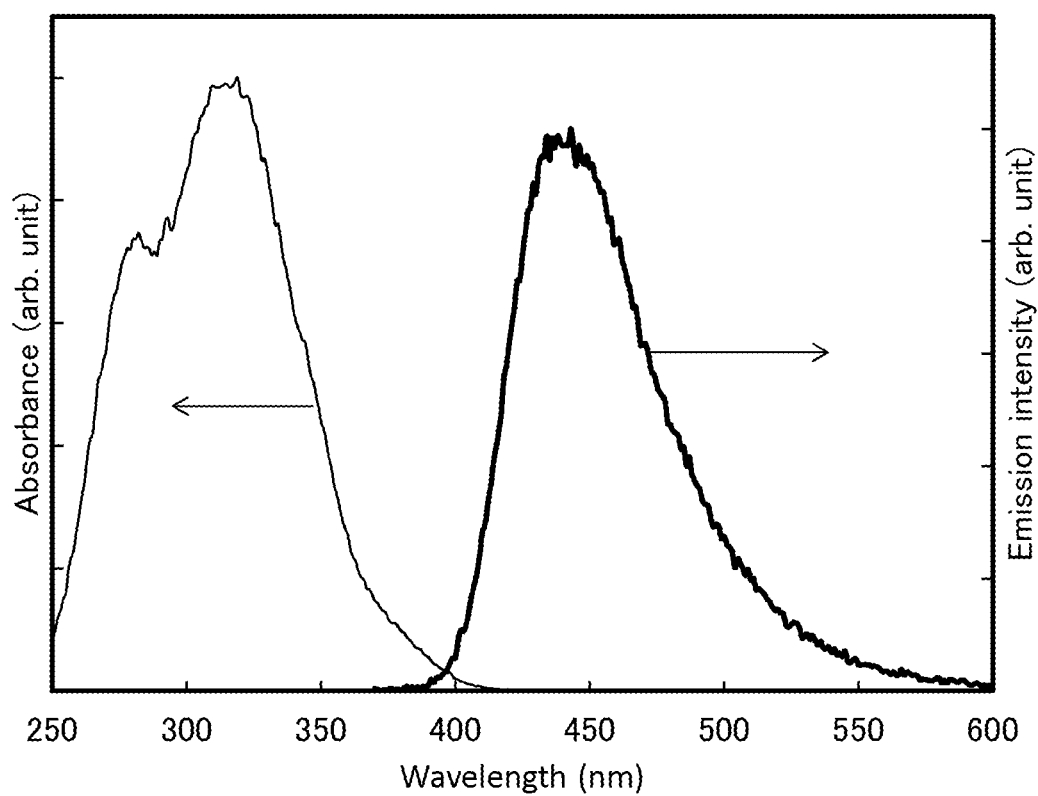
FIG. 16 shows an absorption spectrum and an emission spectrum of a thin film of BnfABP.

From FIG. 16, the thin film of BnfABP has absorption peaks at around 387 nm, 346 nm, 326 nm, 294 nm, and 262 nm, and an emission peak at 440 nm (excitation wavelength: 360 nm).

The HOMO level and the LUMO level of BnfABP were obtained through a cyclic voltammetry (CV) measurement. A calculation method is described below.

An electrochemical analyzer (ALS model 600A or 600C, manufactured by BAS Inc.) was used as a measurement apparatus. As for a solution used for the CV measurement, dehydrated dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was set to 0.1 V/sec, and an oxidation potential Ea [V] and a reduction potential Ec [V] with respect to the reference electrode were measured. The potential Ea is an intermediate potential of an oxidation-reduction wave, and Ec is an intermediate potential of a reduction-oxidation wave. Here, the potential energy of the reference electrode used in this example with respect to the vacuum level is found to be −4.94 [eV], and thus, the HOMO level and the LUMO level can be obtained from the following formula: HOMO level [eV]=−4.94−Ea and LUMO level [eV]=−4.94−Ec. Furthermore, the CV measurement was repeated 100 times, and the oxidation-reduction wave at the hundredth cycle and the oxidation-reduction wave at the first cycle were compared to examine the electric stability of the compound.

As a result, it was found that the HOMO level of BnfABP was −5.59 eV and the LUMO level thereof was −2.53 eV. After the hundredth cycle, the peak intensity of the oxidation-reduction wave maintained 83% of that of the oxidation-reduction wave at the first cycle, which indicates that BnfABP has excellent resistant to oxidation. The thermogravimetry-differential thermal analysis (TG/DTA) of BnfABP was performed. The measurement was performed using a high vacuum differential type differential thermal balance (TG-DTA2410SA, manufactured by Bruker AXS K.K.). The measurement was carried out under a nitrogen stream (flow rate: 200 mL/min) at normal pressure at a temperature rising rate of 10° C./min. From the relationship between weight and temperature (thermogravimetry), the 5% weight loss temperature of BnfABP was approximately 370° C. This indicates that BnfABP has high heat resistance. Further, differential scanning calorimetry (DSC measurement) was performed by Pyris1DSC manufactured by PerkinElmer, Inc. In the differential scanning calorimetry, after the temperature was raised from −10° C. to 300° C. at a temperature rising rate of 40° C./min, the temperature was held for a minute and then cooled to −10° C. at a temperature reduction rate of 40° C./min. This operation was repeated twice successively. It was found from the DSC measurement that the glass transition temperature of BnfABP was 97° C. and thus had high heat resistance.

Example 2

Synthesis Example 2

This synthesis example shows an example of synthesizing N,N-bis(biphenyl-4-yl)-6-phenylbenzo[b]naphtho[1,2-d]furan-8-amine (abbreviation: BBABnf), which is the organic compound of one embodiment of the present invention represented by Structural Formula (146) in Embodiment. The structural formula of BBABnf is as follows.

[Chemical Formula 62]

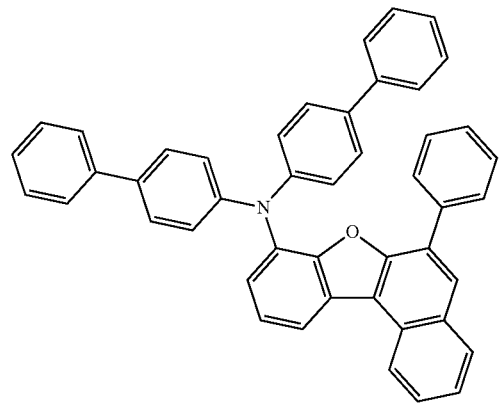

Step 1: Synthesis of 6-iodobenzo[b]naphtho[1,2-d]furan

This synthesis step is similar to Step 1 in Synthesis Example 1.

Step 2: Synthesis of 6-phenylbenzo[b]naphtho[1,2-d]furan

This synthesis step is similar to Step 2 in Synthesis Example 1.

Step 3: Synthesis of 8-iodo-6-phenylbenzo[b]naphtho[1,2,d]furan

This synthesis step is similar to Step 3 in Synthesis Example 1.

Step 4: Synthesis of (9,9-dimethyl-9H-fluorene-2,7-diyl)bis(6,N-diphenylbenzo[b]naphtho[1,2-d]furan-8-amine Into a 200 mL three-neck flask were put 2.1 g (5.0 mmol) of 8-iodo-6-phenylbenzo[b]naphtho[1,2,-d]furan obtained in Step 3 in Example 1, 1.6 g (5.0 mmol) of di(1,1'-biphenyl-4-yl)amine, 0.17 g (0.40 mmol) of 2-dicyclohexylphosphino-2',6'-dimethoxy-1,1'-biphenyl (abbreviation: S-Phos), and 0.97 g (10 mmol) of sodium tert-butoxide. The air in the flask was replaced with nitrogen, and then 25 mL of xylene was added. After this mixture was degassed under reduced pressure, the temperature was set at 80° C. under a nitrogen stream, 0.12 g (0.20 mmol) of bis(dibenzylideneacetone)palladium(0) was added, and this mixture was stirred at 80° C. for 5.5 hours and further stirred at 100° C. for 5 hours. After the stirring, the obtained mixture was washed with water and a saturated aqueous solution of sodium chloride, and the organic layer was dried with magnesium sulfate. After the magnesium sulfate was removed by gravity filtration, and the obtained filtrate was concentrated to give a brown solid. The obtained solid was dissolved in toluene and filtrated through Celite (Catalog No. 537-02305 produced by Wako Pure Chemical Industries, Ltd.) and alumina. The obtained filtrate was concentrated to give 2.0 g of the target yellow solid in a yield of 67%. A synthesis scheme (d-2) of Step 4 is shown below.

[Chemical Formula 63]

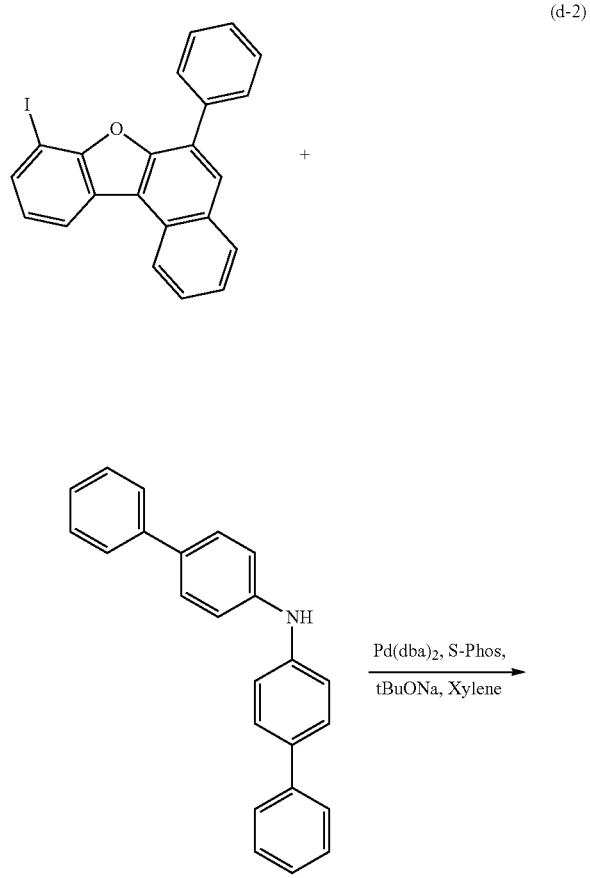

(d-2)

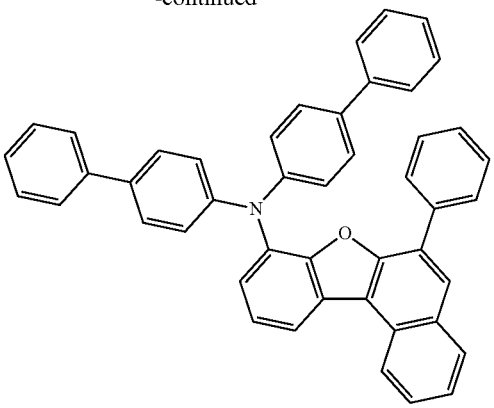

Figure 17A:
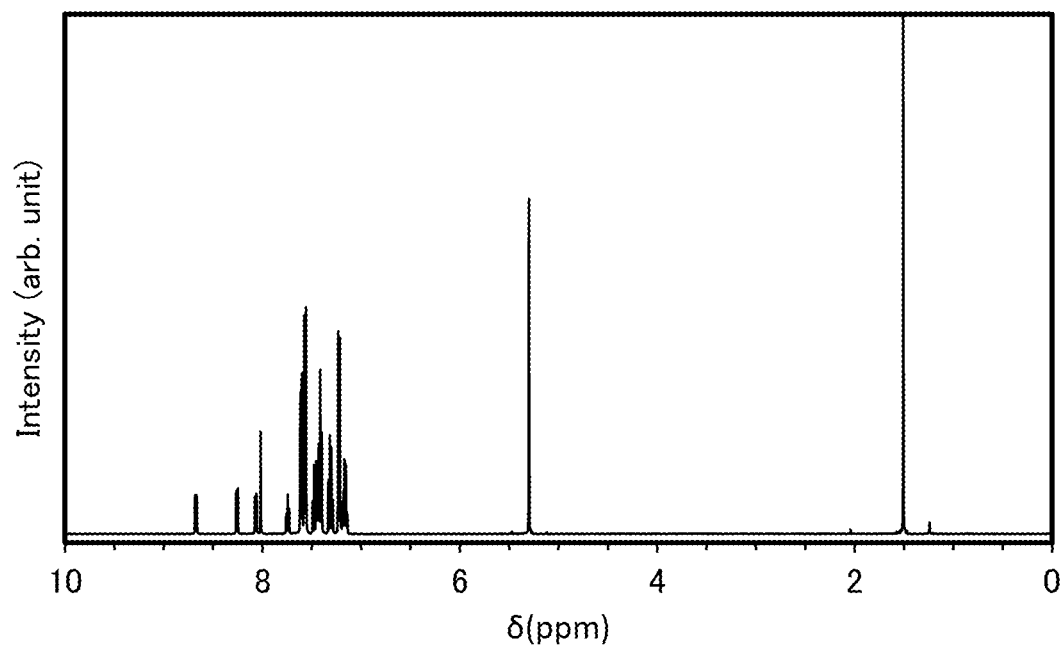
FIGS. 17A and 17B show $^1$H NMR charts of BBABnf.
Figure 17B:
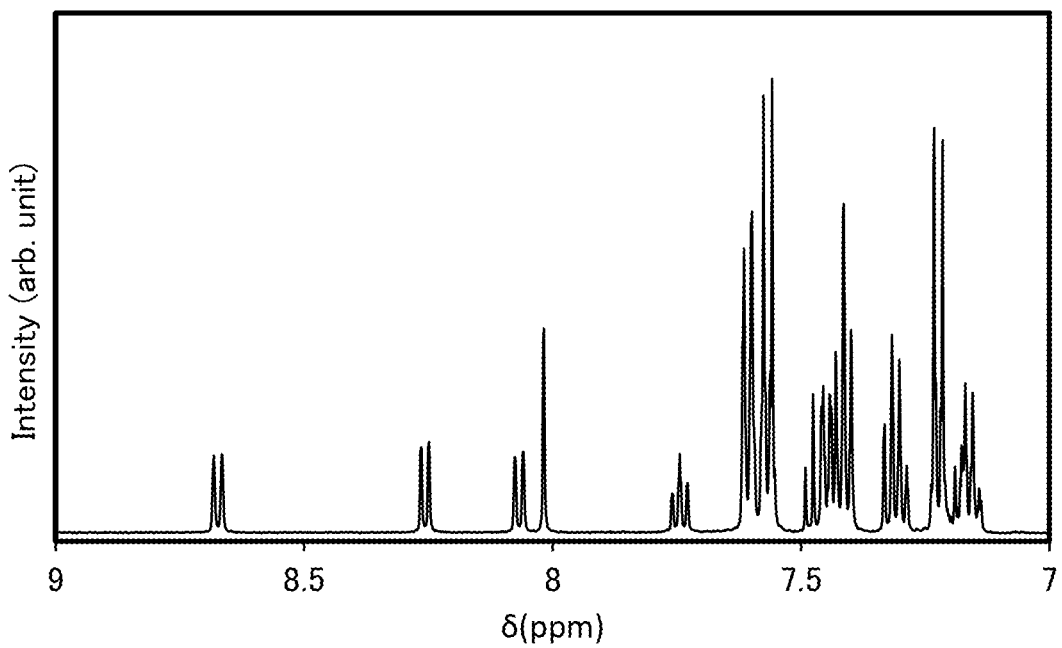

$^1$H NMR data of the obtained yellow solid are shown below. FIGS. 17A and 17B are $^1$H NMR charts. Note that FIG. 17B is a chart showing an enlarged part of FIG. 17A in the range of 7.00 ppm to 9.00 ppm. These results indicate that BBABnf, which is the organic compound of one embodiment of the present invention, was obtained.

$^1$H NMR (dichloromethane-d2, 500 MHz): δ=7.14-7.19 (m, 3H), 7.22 (d, J=8.5 Hz, 4H), 7.29-7.33 (m, 3H), 7.41 (t, J=8.0 Hz, 4H), 7.44-7.49 (m, 3H), 7.55-7.58 (m, 5H), 7.61 (d, J=8.0 Hz, 4H), 7.74 (t, J=8.0 Hz, 1H), 8.02 (s, 1H), 8.06 (d, J=8.0 Hz, 1H), 8.26 (d, 1H), 8.67 (d, J=8.0 Hz, 1H)

By train sublimation, 2.0 g of the obtained yellow solid was purified. The purification by sublimation was carried out under a pressure of 3.8 Pa, with a flow rate of argon gas of 15 mL/min, at a temperature of 270° C., and for 16 hours. After the purification by sublimation, 1.7 g of the target yellow solid was obtained at a collection rate of 81%.

Figure 18:
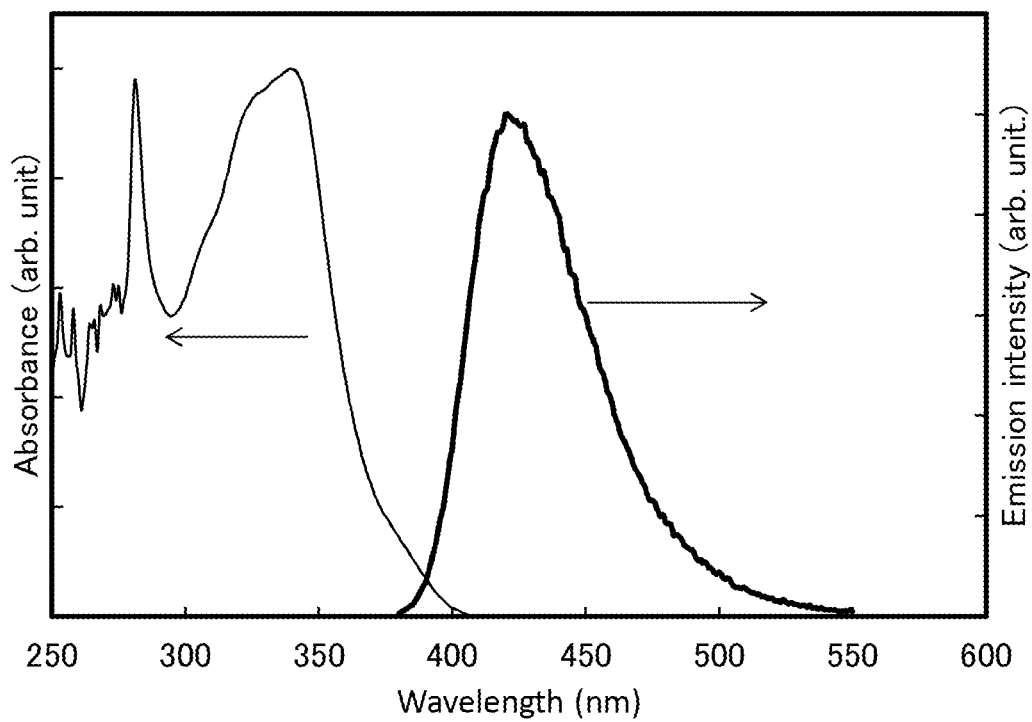
FIG. 18 shows an absorption spectrum and an emission spectrum of a solution of BBABnf.

Next, the ultraviolet-visible absorption spectrum (hereinafter, simply referred to as "absorption spectrum") and emission spectrum of a toluene solution and a solid thin film of BBABnf were measured. The measurement was performed with a device and a method similar to those for the measurement of BnfABP. FIG. 18 shows the measurement results of the absorption and emission spectra of the obtained toluene solution and FIG. 19 shows the measurement results of the absorption and emission spectra of the obtained thin film.

From FIG. 18, the toluene solution of BBABnf has an absorption peak at around 343 nm, and an emission peak at 420 nm (excitation wavelength: 340 nm).

Figure 19:
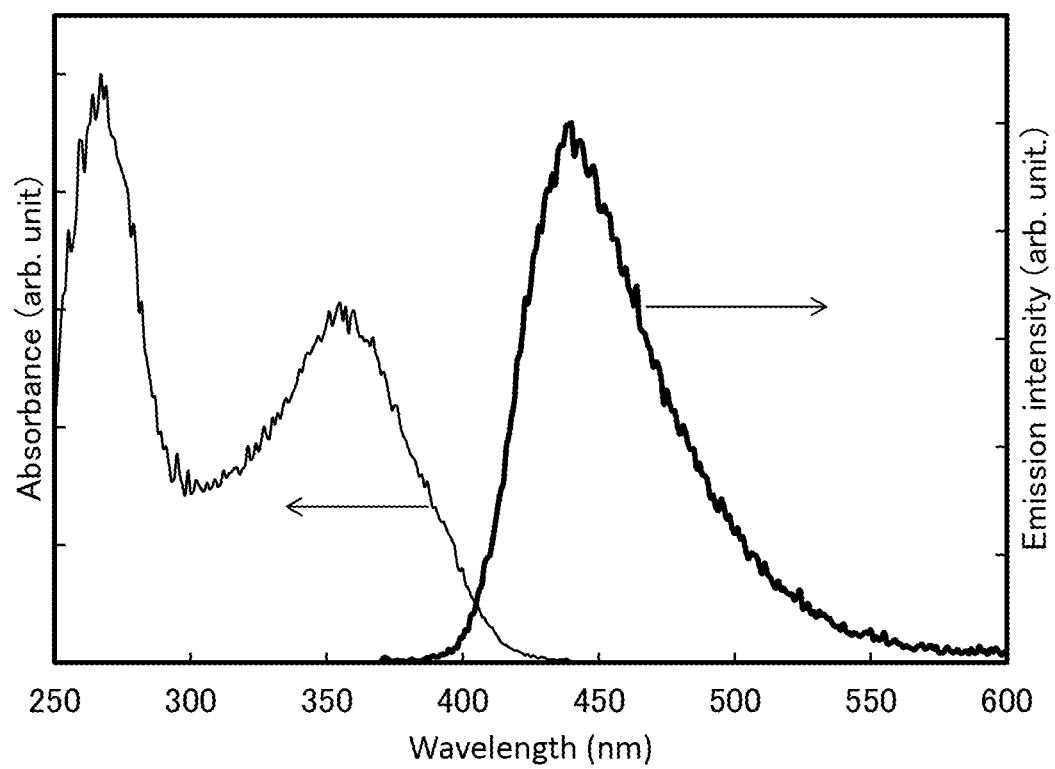
FIG. 19 shows an absorption spectrum and an emission spectrum of a thin film of BBABnf.

From FIG. 19, the thin film of BBABnf has absorption peaks at around 344 nm, 325 nm, and 257 nm, and an emission peak at 439 nm (excitation wavelength: 361 nm).

The HOMO level and the LUMO level of BBABnf were obtained through a cyclic voltammetry (CV) measurement. The calculation method is similar to that described in Example 1.

As a result, it was found that the HOMO level of BBABnf was −5.56 eV and the LUMO level thereof was −2.51 eV. After the hundredth cycle, the peak intensity of the oxidation-reduction wave maintained 90% of that of the oxidation-reduction wave at the first cycle, which indicates that BBABnf has excellent resistant to oxidation. The TG-DTA measurement and DSC measurement of BBABnf were performed in a manner similar to that for BnfABP. Note that in the DSC measurement, the temperature was raised to 330° C. From TG-DTA measurement, the 5% weight loss temperature of BBABnf was approximately 410° C. This indicates that BBABnf has high heat resistance. It was found from the DSC measurement that the glass transition temperature of BBABnf was 117° C. and thus had high heat resistance.

Example 3

In this example, a light-emitting element 1 of one embodiment of the present invention, which is described in Embodiment 1, will be described. Structural formulae of organic compounds used for the light-emitting element 1 are shown below.

[Chemical Formula 64]

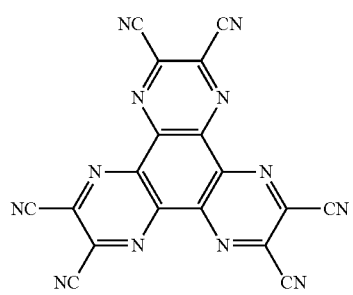

HAT-CN (i)

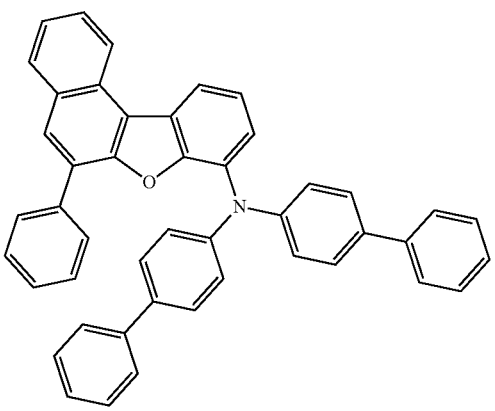

BBABnf (iii)

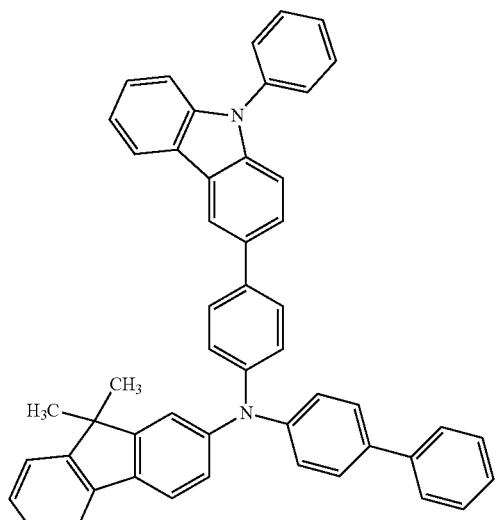

PCBBiF (ii)

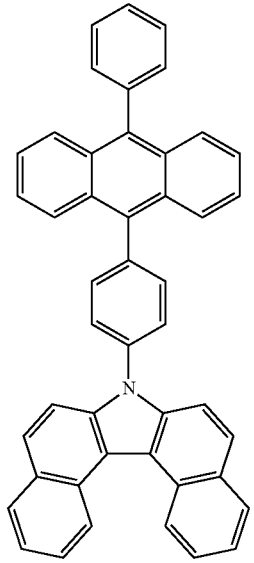

cgDBCzPA (iv)

-continued (v)

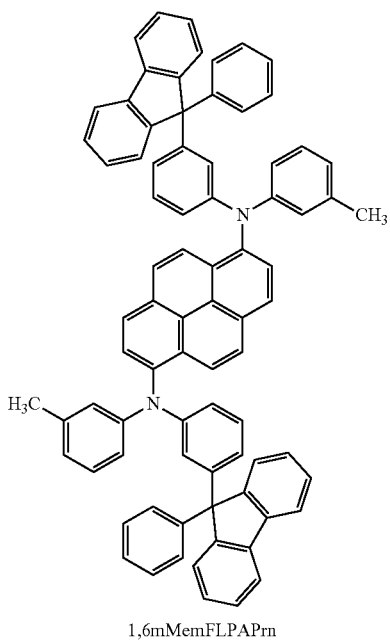

1,6mMemFLPAPrn (vi)

BPhen (Method for Fabricating Light-Emitting Element 1)

First, a film of indium tin oxide containing silicon oxide (ITSO) was formed over a glass substrate by a sputtering method, so that the anode 101 was formed. The thickness thereof was 70 nm and the electrode area was 2 mm×2 mm.

Next, as pretreatment for forming the light-emitting element over the substrate, a surface of the substrate was washed with water and baked at 200° C. for 1 hour; then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate provided with the anode 101 was fixed to a substrate holder provided in the vacuum evaporation device such that the side on which the anode 101 was formed faced downward. Then, 2,3,6,7,10,11-hexacyano-1,4,5,8,9,12-hexaazatriphenylene (abbreviation: HAT-CN) represented by Structural Formula (i) was deposited to a thickness of 5 nm over the anode 101 by an evaporation method using resistance heating, whereby the hole-injection layer 111 was formed.

Next, N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (ii) was deposited to a thickness of 25 nm by evaporation over the hole-injection layer 111, and N,N-bis(biphenyl-4-yl)-6-phenylbenzo[b]naphtho[1,2-d]furan-8-amine (abbreviation: BBABnf) represented by Structural Formula (iii) was deposited to a thickness of 5 nm by evaporation, so that the hole-transport layer 112 was formed.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iv) and N,N'-bis (3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (v) in a weight ratio of 1:0.03 (=cgDBCzPA: 1,6mMemFLPAPrn) to a thickness of 25 nm.

Then, over the light-emitting layer 113, cgDBCzPA was deposited to a thickness of 10 nm by evaporation, and bathophenanthroline (abbreviation: BPhen) represented by Structural Formula (vi) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 1 of this example was fabricated.

The element structure of the light-emitting element 1 is shown in the following table.

TABLE 1

| Hole-injection layer | Hole-transport layer | Light-emitting layer | Electron-transport layer | | Electron-injection layer |
|---|---|---|---|---|---|
| 5 nm | 25 nm | 5 nm | 25 nm | 10 nm | 15 nm | 1 nm |
| HAT-CN | PCBBiF | BBABnf | cgDBCzPA: 1,6mMemFLPAPrn (1:0.03) | cgDBCzPA | BPhen | LiF |

The light-emitting element 1 was sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting element were measured. Note that the measurements were performed at room temperature (in an atmosphere kept at 25° C.).

Figure 20:
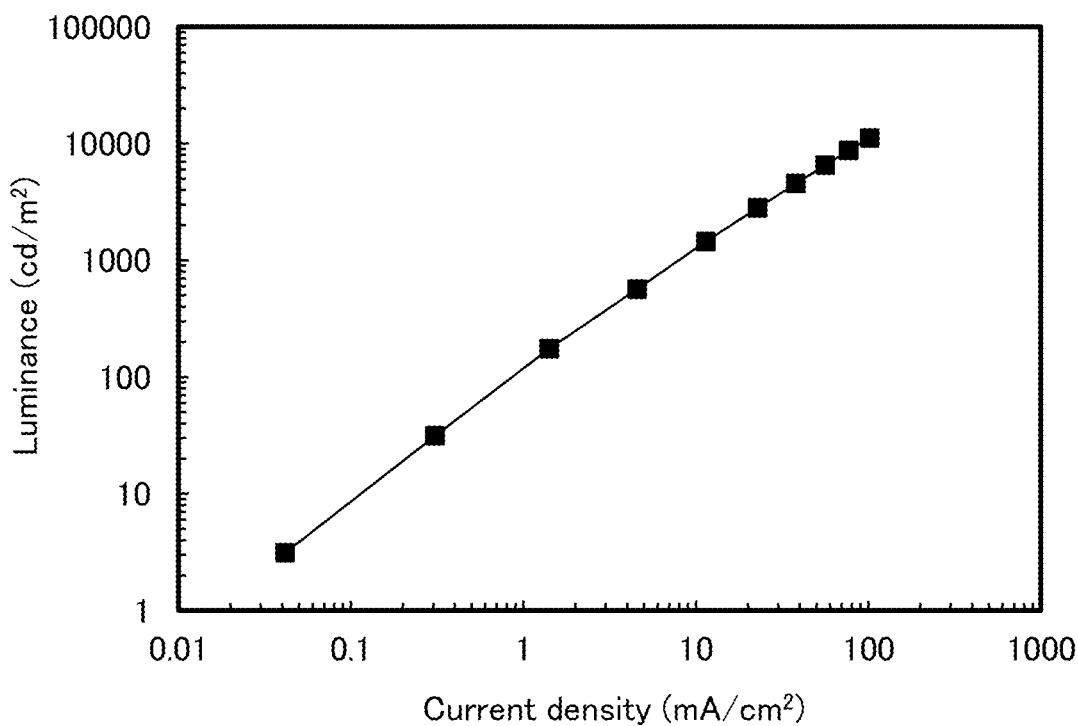
FIG. 20 shows the luminance-current density characteristics of a light-emitting element 1.
Figure 21:
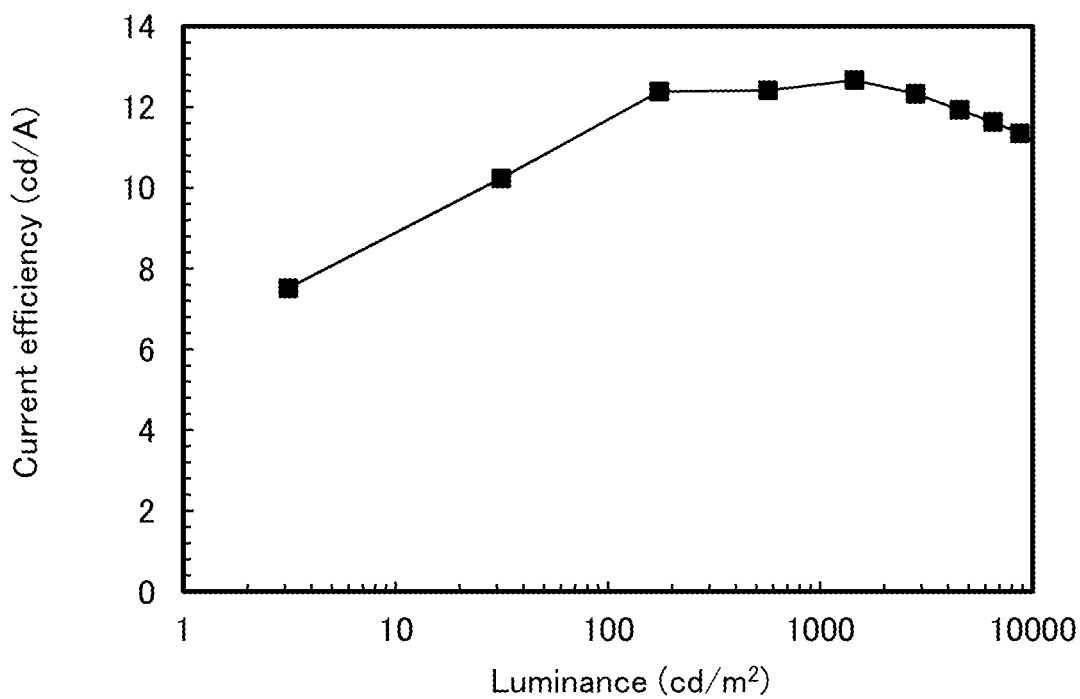
FIG. 21 shows the current efficiency-luminance characteristics of the light-emitting element 1.
Figure 22:
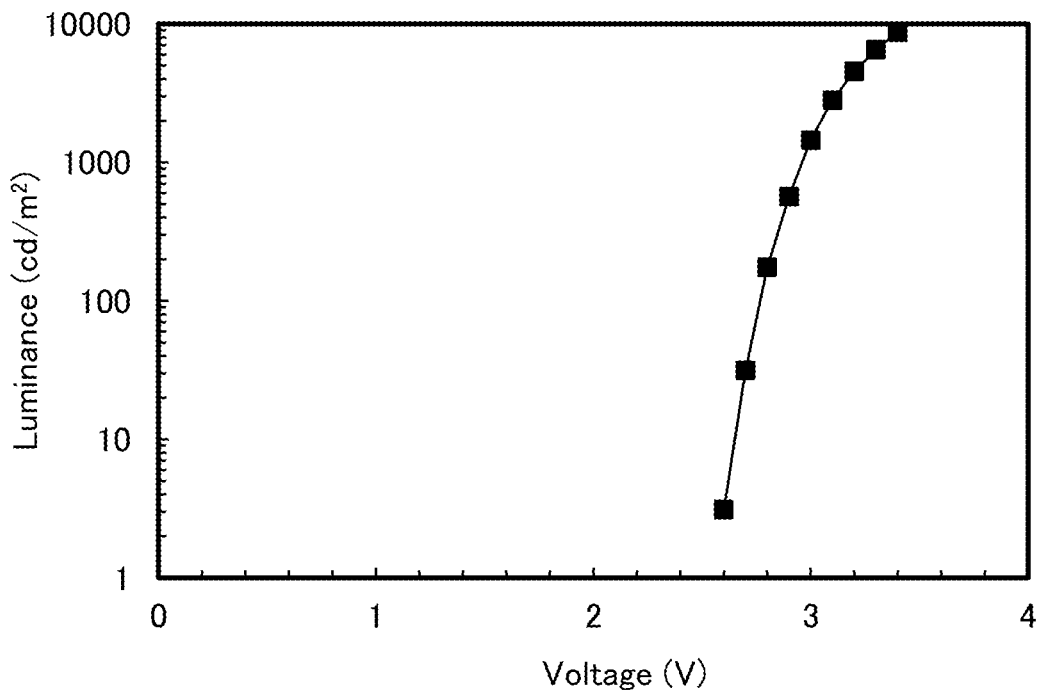
FIG. 22 shows the luminance-voltage characteristics of the light-emitting element 1.
Figure 23:
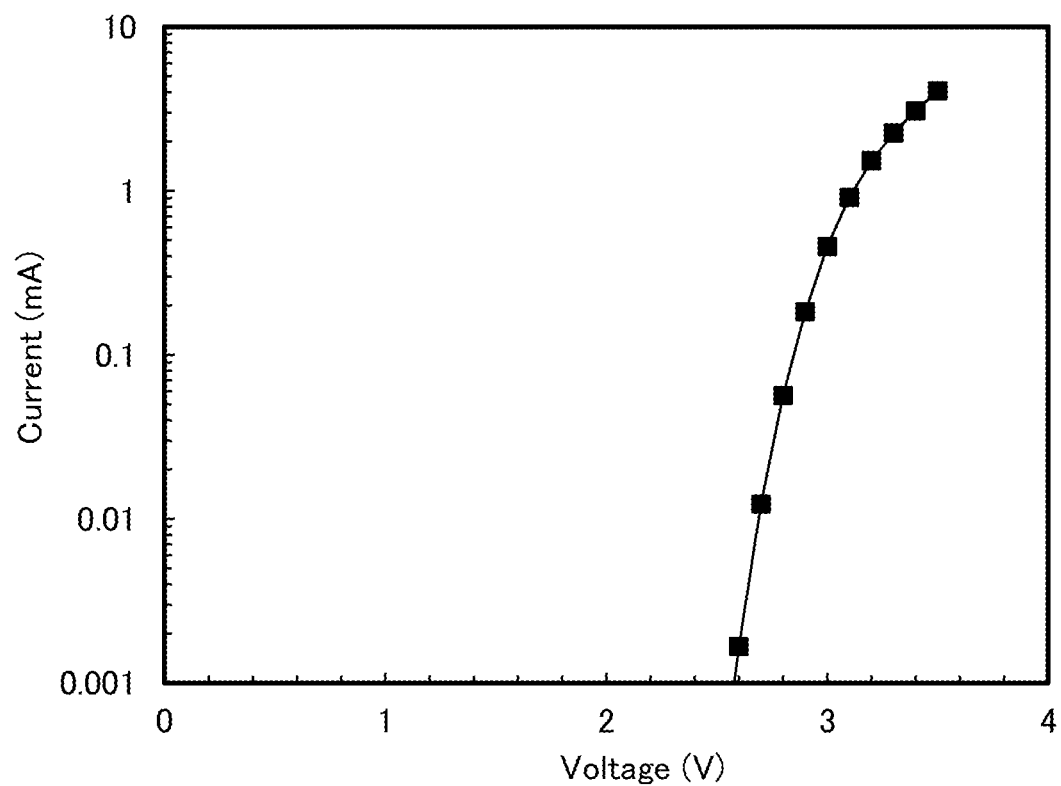
FIG. 23 shows the current-voltage characteristics of the light-emitting element 1.
Figure 24:
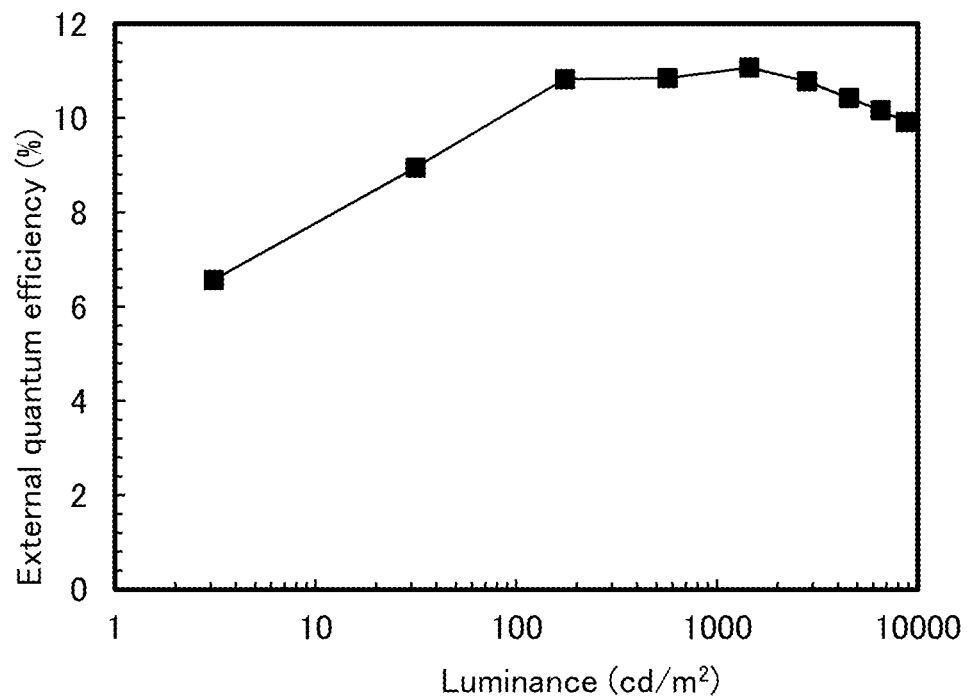
FIG. 24 shows the external quantum efficiency-luminance characteristics of the light-emitting element 1.
Figure 25:
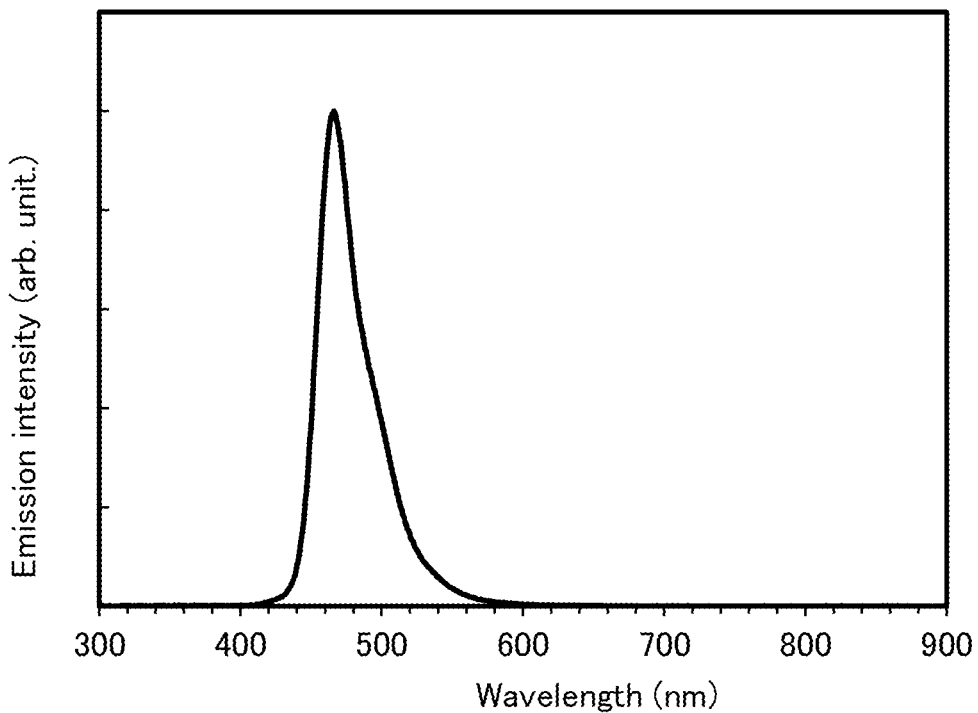
FIG. 25 shows an emission spectrum of the light-emitting element 1.

FIG. 20 shows the luminance-current density characteristics of the light-emitting element 1. FIG. 21 shows the current efficiency-luminance characteristics of the light-emitting element 1. FIG. 22 shows the luminance-voltage characteristics of the light-emitting element 1. FIG. 23 shows the current-voltage characteristics of the light-emitting element 1. FIG. 24 shows the external quantum efficiency-luminance characteristics of the light-emitting element 1. FIG. 25 shows the emission spectrum of the light-emitting element 1. Table 2 shows the main characteristics of the light-emitting element 1 at around 1000 cd/m².

TABLE 2

| Voltage (V) | Current (mA) | Current density (mA/cm²) | Chromaticity x | Chromaticity y | Current efficiency (cd/A) | External quantum efficiency (%) |
| --- | --- | --- | --- | --- | --- | --- |
| 2.9 | 0.18 | 5 | 0.14 | 0.16 | 12.4 | 10.8 |

It was found from FIGS. 20 to 25 and Table 2 that the light-emitting element 1 of one embodiment of the present invention is a blue light-emitting element with favorable efficiency and a low driving voltage.

Figure 26:
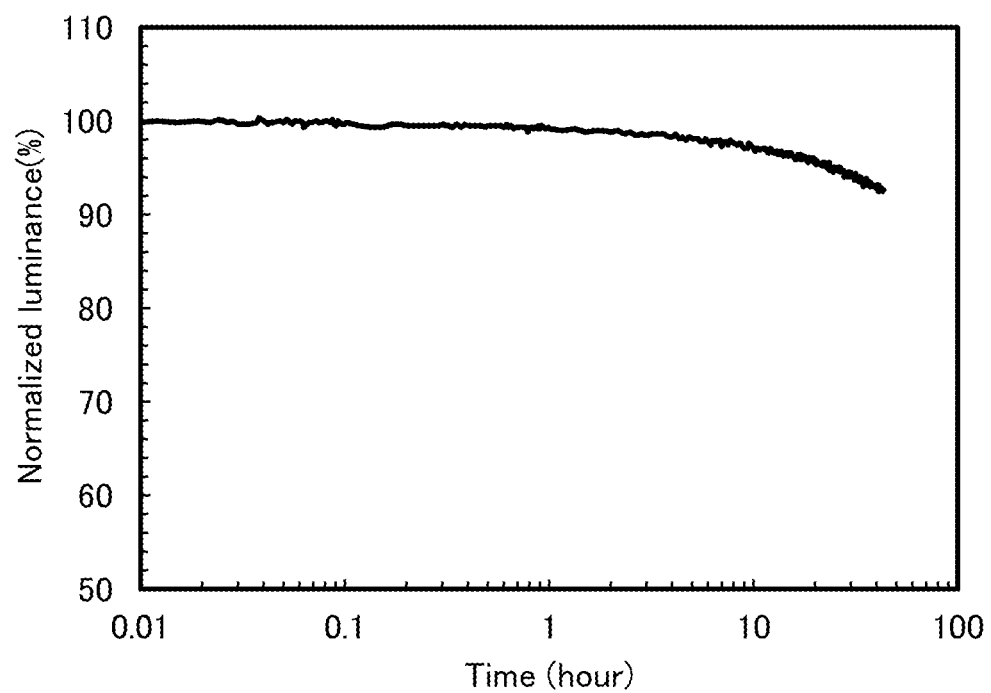
FIG. 26 shows the time dependence of normalized luminance of the light-emitting element 1.

FIG. 26 shows driving time-dependent change in luminance of the light-emitting element under the conditions where the current value was set to 2 mA and the current density was constant. As shown in FIG. 26, it was found that the light-emitting element is a long-lifetime light-emitting element with a small reduction in luminance over driving time.

Example 4

In this example, light-emitting elements 2 and 3 of one embodiment of the present invention, which are described in Embodiment 1, will be described. Structural formulae of organic compounds used for the light-emitting elements 2 and 3 are shown below.

[Chemical Formula 65]

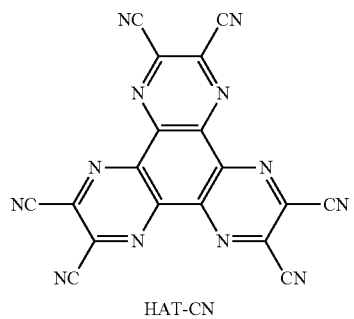

HAT-CN
(i)

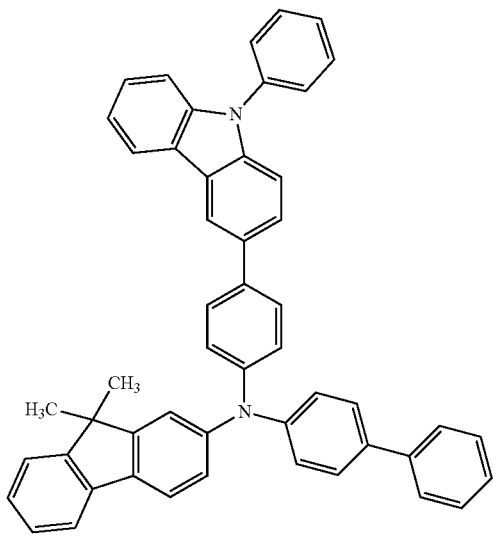

PCBBiF
(ii)

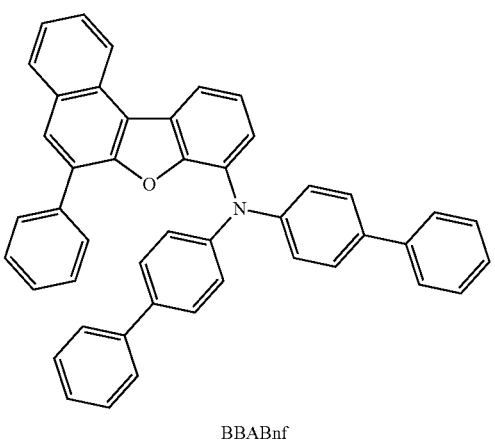

BBABnf
(iii)

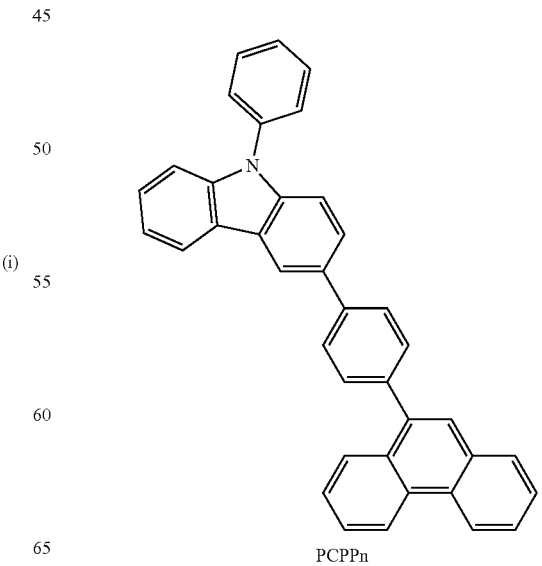

PCPPn
(vii)

(iv)

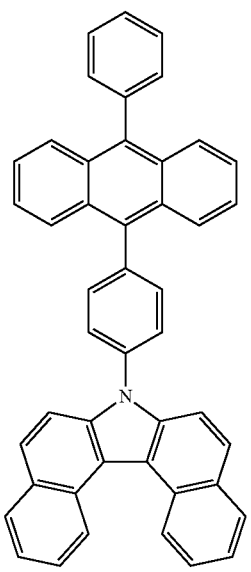

cgDBCzPA (v)

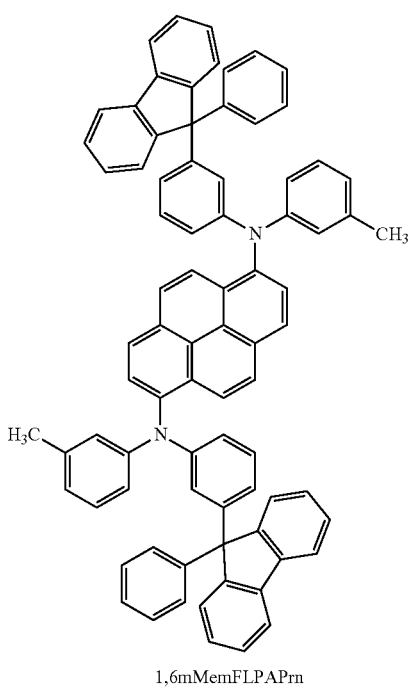

1,6mMemFLPAPrn (vi)

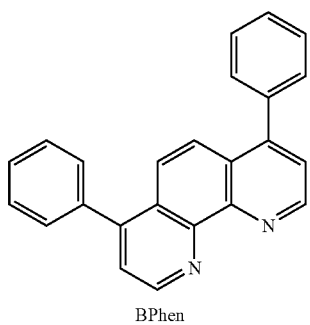

BPhen (viii)

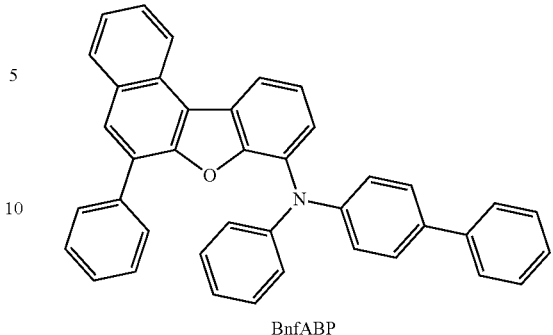

BnfABP (Method for Fabricating Light-Emitting Element 2)

First, a film of indium tin oxide containing silicon oxide (ITSO) was formed over a glass substrate by a sputtering method, so that the anode 101 was formed. The thickness thereof was 70 nm and the electrode area was 2 mm×2 mm.

Next, as pretreatment for forming the light-emitting element over the substrate, a surface of the substrate was washed with water and baked at 200° C. for 1 hour; then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate provided with the anode 101 was fixed to a substrate holder provided in the vacuum evaporation device such that the side on which the anode 101 was formed faced downward. Then, 2,3,6,7,10,11-hexacyano-1,4,5,8,9,12-hexaazatriphenylene (abbreviation: HAT-CN) represented by Structural Formula (i) was deposited to a thickness of 5 nm over the anode 101 by an evaporation method using resistance heating, whereby the hole-injection layer 111 was formed.

Next, N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (ii) was deposited to a thickness of 20 nm over the hole-injection layer 111 by evaporation, whereby the first hole-transport layer 112-1 was formed; N,N-bis(biphenyl-4-yl)-6-phenyl-benzo[b]naphtho[1,2-d]furan-8-amine (abbreviation: BBA-Bnf) represented by Structural Formula (iii) was deposited to a thickness of 5 nm over the first hole-transport layer 112-1 by evaporation, whereby the second hole-transport layer 112-2 was formed; and 3-[4-(9-phenanthryl)-phenyl]-9-phenyl-9H-carbazole (abbreviation: PCPPn) represented by Structural Formula (vii) was deposited to a thickness of 5 nm over the second hole-transport layer 112-2 by evaporation, whereby the third hole-transport layer 112-3 was formed.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iv) and N,N'-bis (3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (v) in a weight ratio of 1:0.03 (=cgDBCzPA: 1,6mMemFLPAPrn) to a thickness of 25 nm.

Then, over the light-emitting layer 113, cgDBCzPA was deposited to a thickness of 10 nm by evaporation, and bathophenanthroline (abbreviation: BPhen) represented by Structural Formula (vi) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 2 of this example was fabricated.

(Method for Fabricating Light-Emitting Element 3)

The light-emitting element 3 was formed in the same manner as the light-emitting element 2 except that the second hole-transport layer 112-2 was formed using N-(4-biphenyl)-6,N-diphenylbenzo[b]naphtho[1,2-d]furan-8-amine (abbreviation: BnfABP) instead of BBABnf.

The element structures of the light-emitting elements 2 and 3 are shown in the following table.

TABLE 3

| Hole-injection layer | Hole-transport layer | | | Light-emitting layer | Electron-transport layer | | Electron-injection layer |
|---|---|---|---|---|---|---|---|
| | 1 | 2 | 3 | | | | |
| 5 nm | 20 nm | 5 nm | 5 nm | 25 nm | 10 nm | 15 nm | 1 nm |
| HAT-CN | PCBBiF | *1 | PCPPn | cgDBCzPA: 1,6mMemFLPAPm (1:0.03) | cgDBCzPA | BPhen | LiF |

*1 Light-emitting element 2: BBABnf, Light-emitting element 3: BnfBPA

The light-emitting elements 2 and 3 were sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting elements were measured. Note that the measurements were performed at room temperature (in an atmosphere kept at 25° C.).

Figure 27:
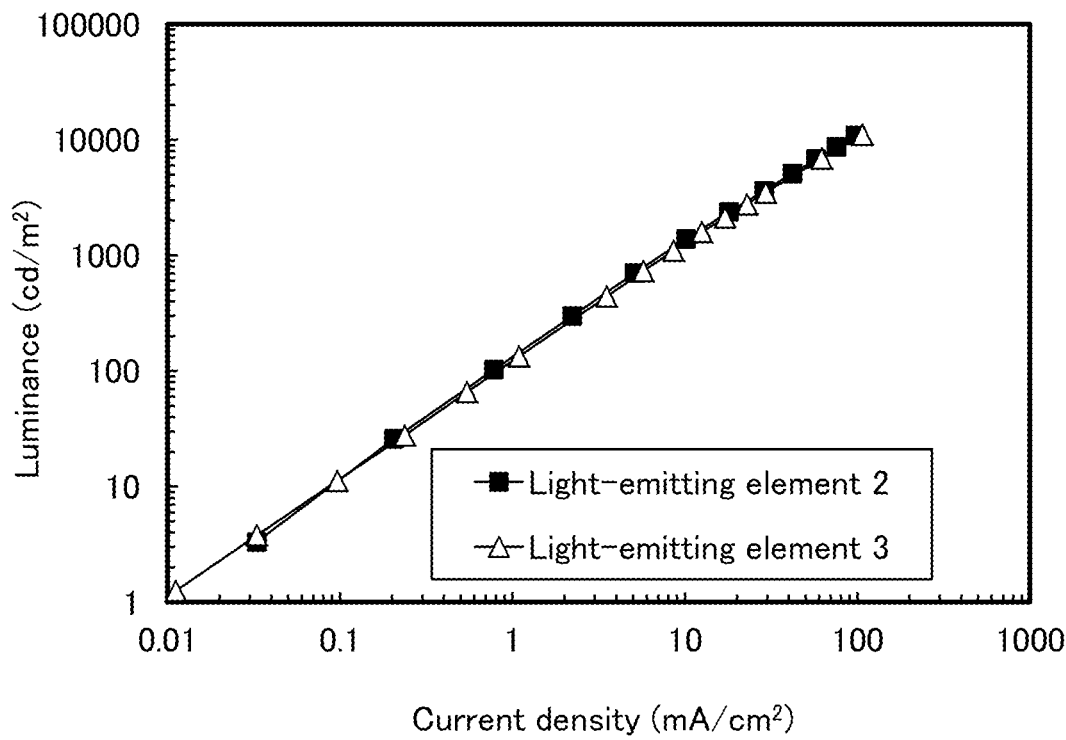
FIG. 27 shows the luminance-current density characteristics of light-emitting elements 2 and 3.
Figure 28:
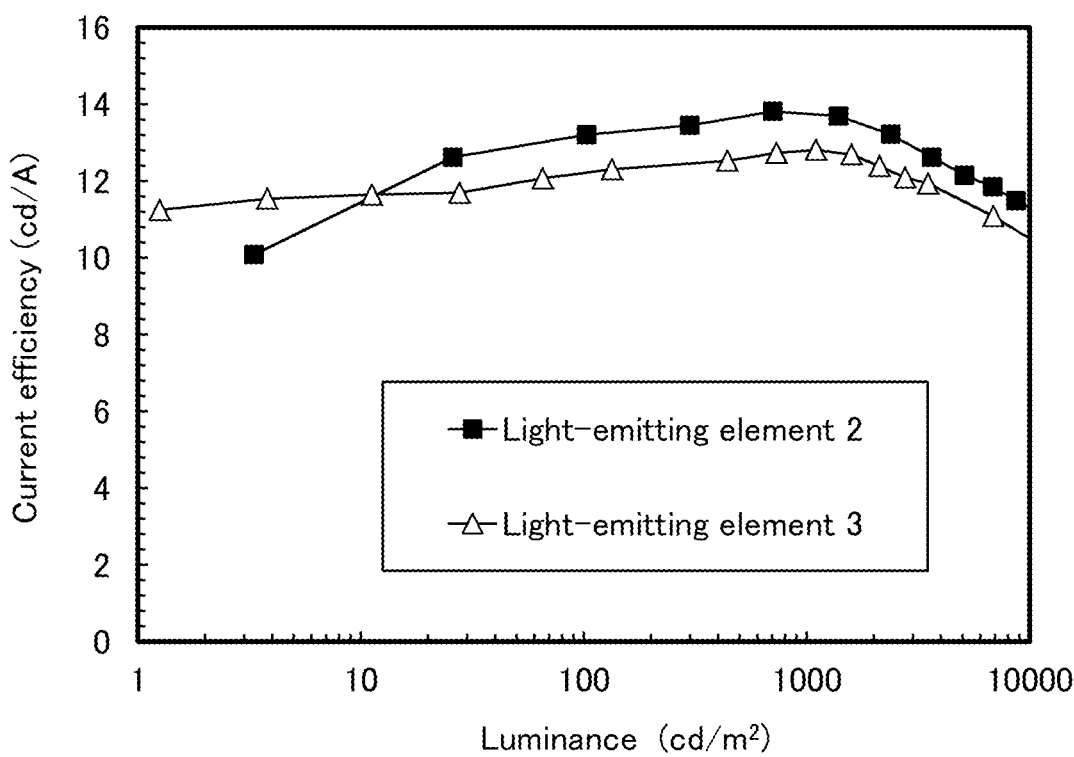
FIG. 28 shows the current efficiency-luminance characteristics of the light-emitting elements 2 and 3.
Figure 29:
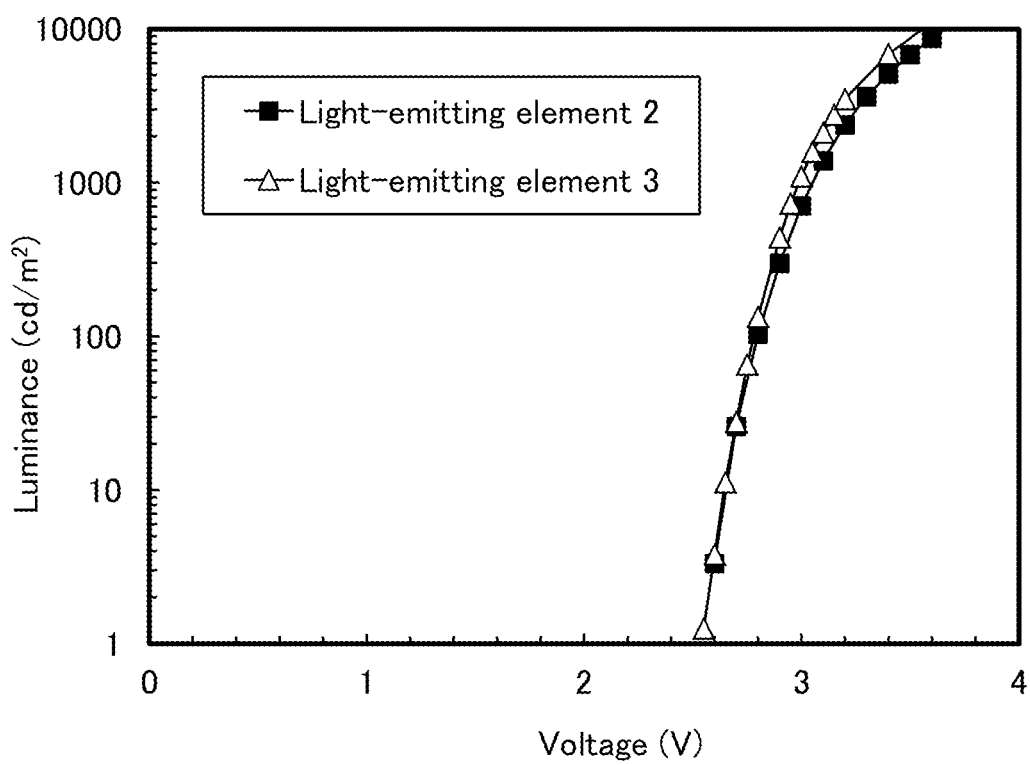
FIG. 29 shows the luminance-voltage characteristics of the light-emitting elements 2 and 3.
Figure 30:
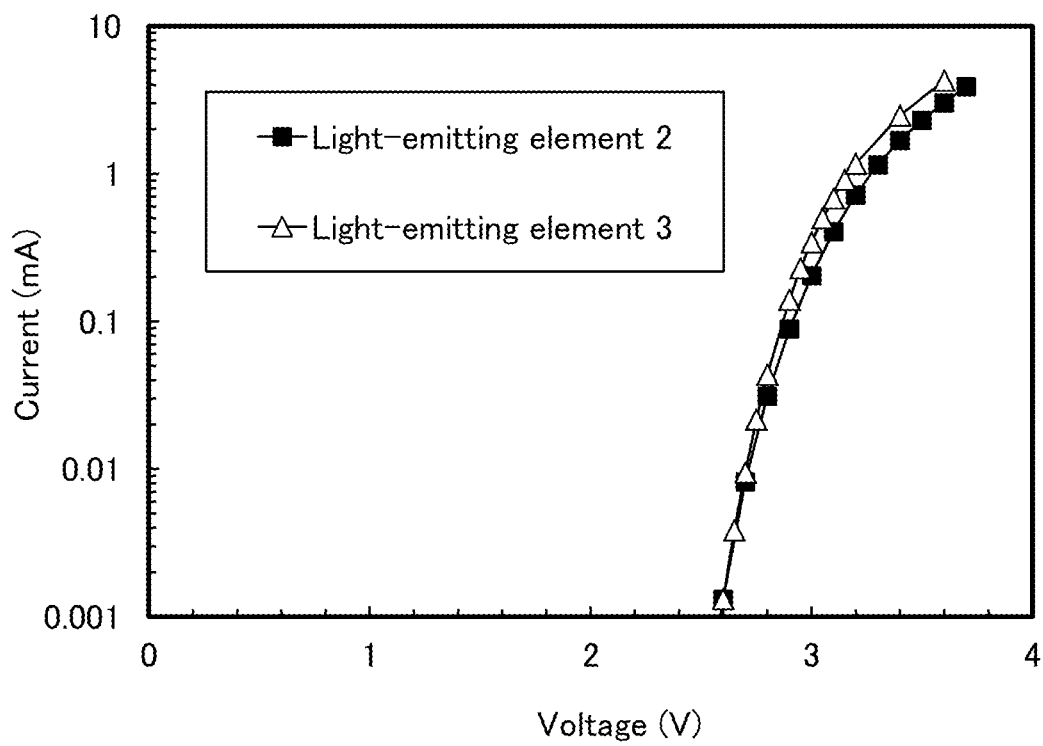
FIG. 30 shows the current-voltage characteristics of the light-emitting elements 2 and 3.
Figure 31:
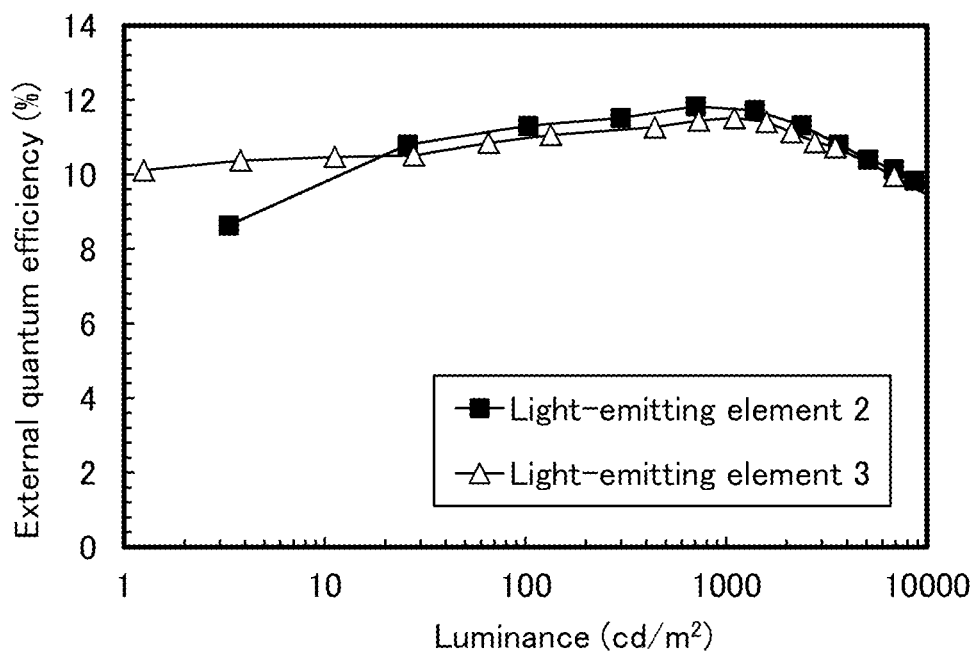
FIG. 31 shows the external quantum efficiency-luminance characteristics of the light-emitting elements 2 and 3.
Figure 32:
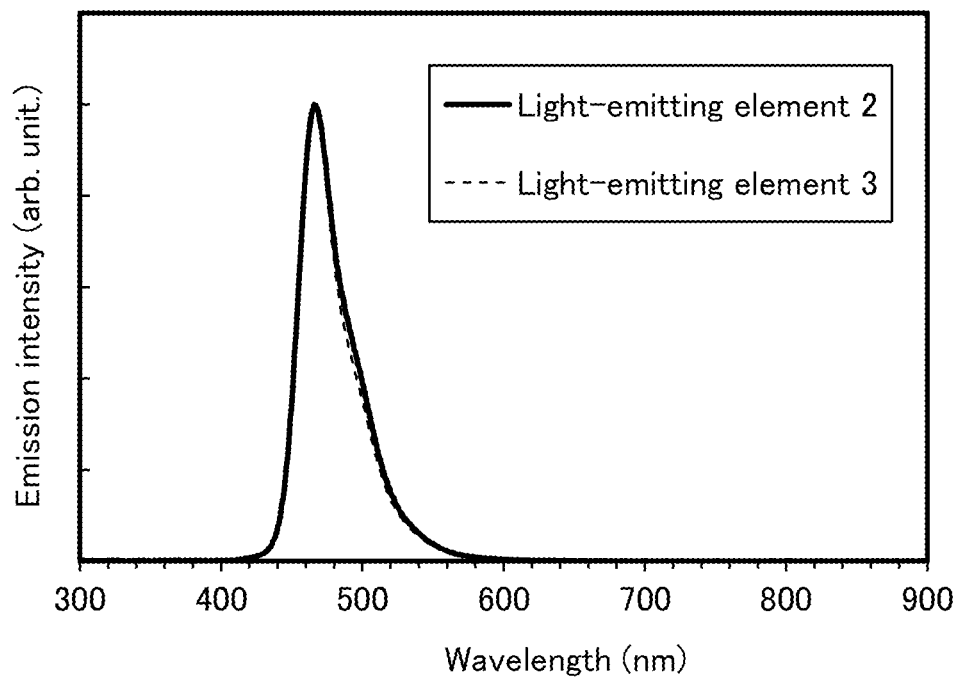
FIG. 32 shows emission spectra of the light-emitting elements 2 and 3.

FIG. 27 shows the luminance-current density characteristics of the light-emitting elements 2 and 3. FIG. 28 shows the current efficiency-luminance characteristics of the light-emitting elements 2 and 3. FIG. 29 shows the luminance-voltage characteristics of the light-emitting elements 2 and 3. FIG. 30 shows the current-voltage characteristics of the light-emitting elements 2 and 3. FIG. 31 shows the external quantum efficiency-luminance characteristics of the light-emitting elements 2 and 3. FIG. 32 shows the emission spectrum of the light-emitting elements 2 and 3. Table 4 shows the main characteristics of the light-emitting elements 2 and 3 at around 1000 cd/m$^2$.

TABLE 4

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 2 | 3.0 | 0.20 | 5 | 0.14 | 0.16 | 13.8 | 11.8 |
| Light-emitting element 3 | 3.0 | 0.34 | 9 | 0.14 | 0.15 | 12.8 | 11.5 |

It was found from FIGS. 27 to 32 and Table 4 that the light-emitting elements 2 and 3 of one embodiment of the present invention are blue light-emitting elements with favorable efficiency and a low driving voltage.

Figure 33:
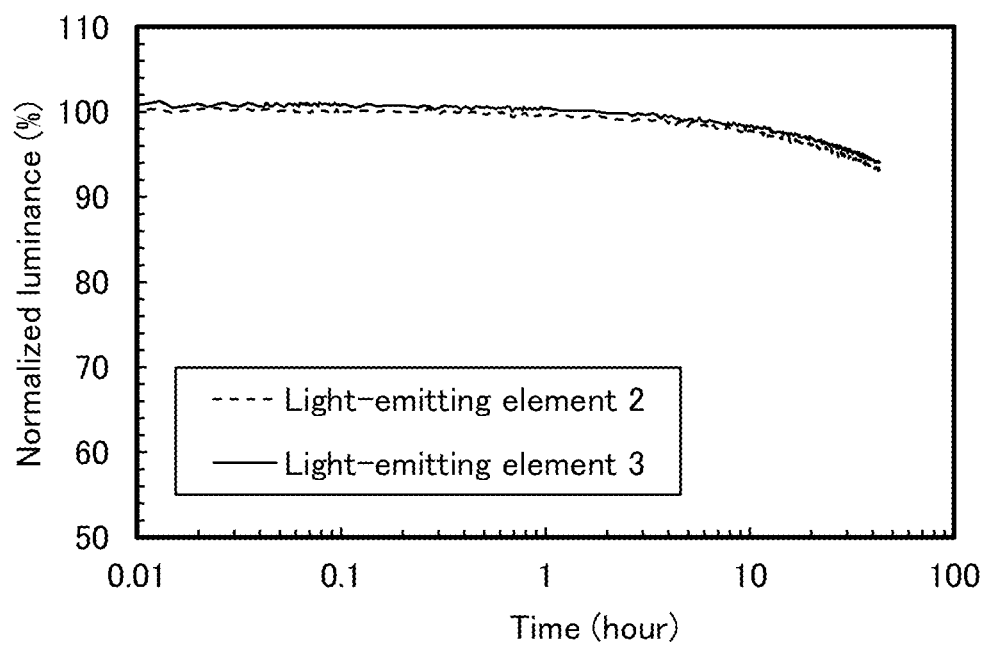
FIG. 33 shows the time dependence of normalized luminance of the light-emitting elements 2 and 3.

FIG. 33 shows driving time-dependent change in luminance of the light-emitting elements under the conditions where the current value was set to 2 mA and the current density was constant. As shown in FIG. 33, the light-emitting elements 2 and 3 maintained 94% ☐☐☐☐☐☐ of the initial luminance after 40-hour-driving and were found to be long-lifetime light-emitting elements with an extremely small reduction in luminance over driving time.

Example 5

Synthesis Example 3

This synthesis example shows an example of synthesizing N,N-bis(4-biphenyl)benzo[b]naphtho[1,2-d]furan-6-amine (abbreviation: BBABnf(6)), which is the organic compound of one embodiment of the present invention represented by Structural Formula (229) in Embodiment. The structural formula of BBABnf(6) is as follows.

[Chemical Formula 66]

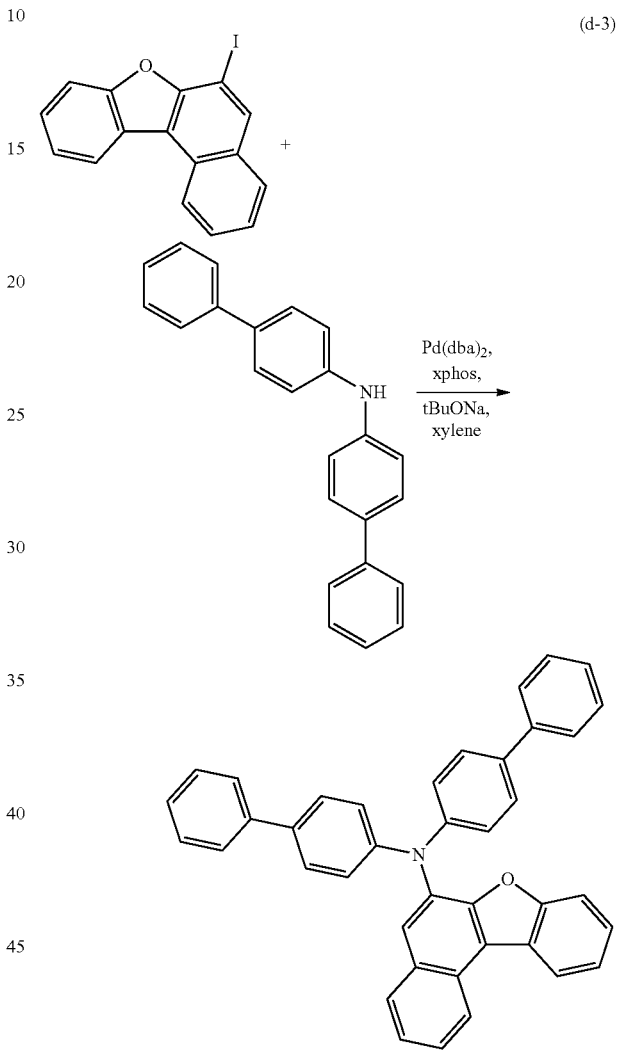

Step 1: Synthesis of 6-iodobenzo[b]naphtho[1,2-d]furan

The synthesis step of 6-iodobenzo[b]naphtho[1,2-d]furan is similar to Step 1 in Synthesis Example 1 in Example 1.

Step 2: Synthesis of BBABnf(6)

Into a 200 mL three-neck flask were put 2.7 g (8.0 mmol) of 6-iodobenzo[b]naphtho[1,2,-d]furan obtained in Step 1, 2.6 g (8.0 mmol) of bis(1,1'-biphenyl-4-yl)amine, 0.19 g (0.40 mmol) of 2-dicyclohexylphosphino-2',4',6'-triisopropylbiphenyl (abbreviation: X-Phos), and 1.5 g (15 mmol) of sodium tert-butoxide. The air in the flask was replaced with nitrogen, and then 40 mL of xylene was added. After this mixture was degassed under reduced pressure, the temperature was set at 80° C. under a nitrogen stream, 0.11 g (0.20 mmol) of bis(dibenzylideneacetone)palladium(0) was added, and this mixture was stirred at 120° C. for 3 hours and further stirred at 140° C. for 6.5 hours. After the stirring, the obtained mixture was washed with water and a saturated aqueous solution of sodium chloride, and the organic layer was dried with magnesium sulfate. After the magnesium sulfate was removed by gravity filtration, and the obtained filtrate was concentrated to give a brown solid. The obtained solid was purified by high performance liquid chromatography (mobile phase: chloroform) to give 3.4 g of the target pale yellow solid in a yield of 79%. A synthesis scheme (d-3) of Step 2 is shown below.

[Chemical Formula 67]

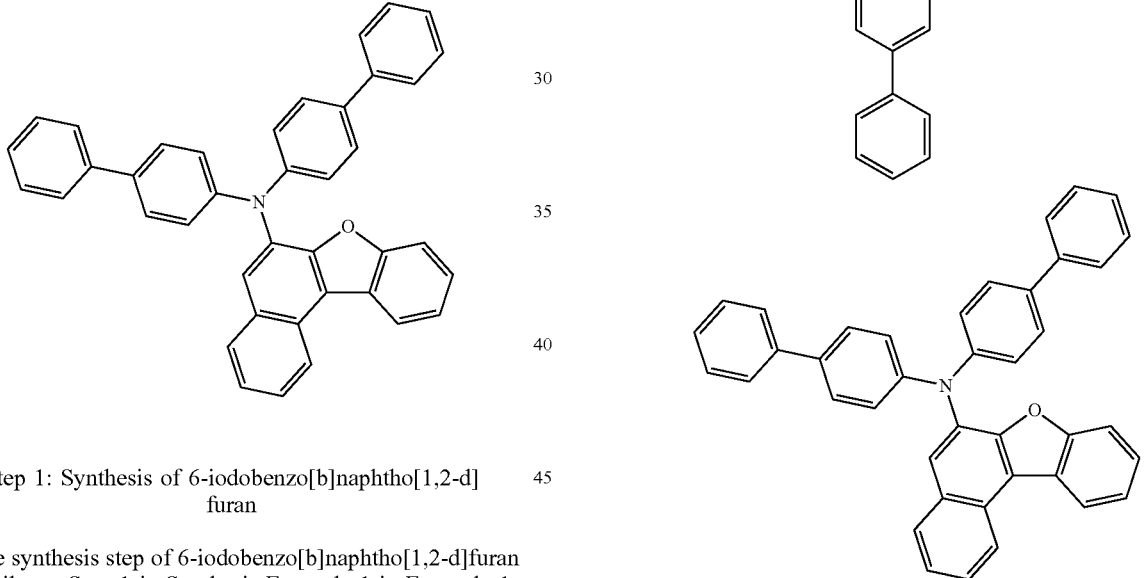

(d-3)

Figure 36A:
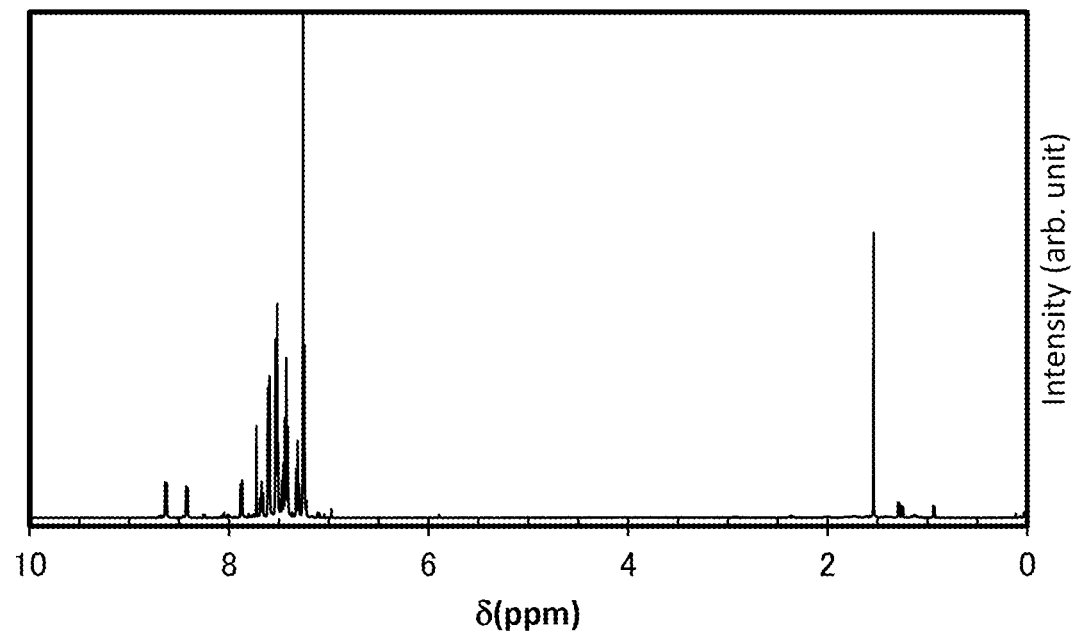
FIGS. 36A and 36B show $^1$H NMR charts of BBABnf(6).
Figure 36B:
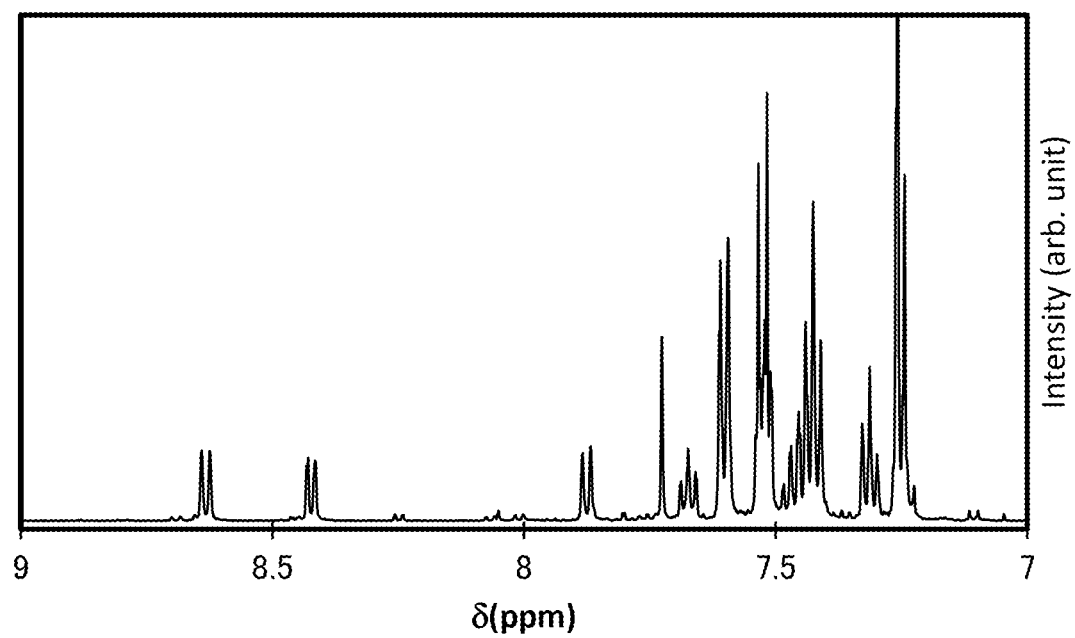

$^1$H NMR data of the obtained pale yellow solid are shown below. FIGS. 36A and 36B are $^1$H NMR charts. Note that FIG. 36B is a chart showing an enlarged part of FIG. 36A in the range of 7.00 ppm to 9.00 ppm. These results indicate that BBABnf(6), which is the organic compound of one embodiment of the present invention, was obtained in this synthesis example. $^1$H NMR (chloroform-d, 500 MHz): δ☐=7.25 (d, J=☐8.5 Hz, 4H), 7.31 (t, J=☐7.5 Hz, 2H), 7.41-7.48 (m, 6H), 7.51-7.54 (m, 6H), 7.60 (d, J=☐8.0 Hz, 4H), 7.67 (t, J=☐7.5 Hz, 1H), 7.73 (s, 1H), 7.88 (d, J=☐8.0 Hz, 1H), 8.42 (d, J=☐7.0 Hz, 1H), 6.83 (d, J=8.0 Hz, 1H)

By train sublimation, 3.4 g of the obtained pale yellow solid was purified. The purification by sublimation was carried out under a pressure of 3.8 Pa, with a flow rate of argon gas of 15 mL/min, at a temperature of 275° C., and for 15 hours. After the purification by sublimation, 3.0 g of the target yellow solid was obtained at a collection rate of 87%.

Figure 37:
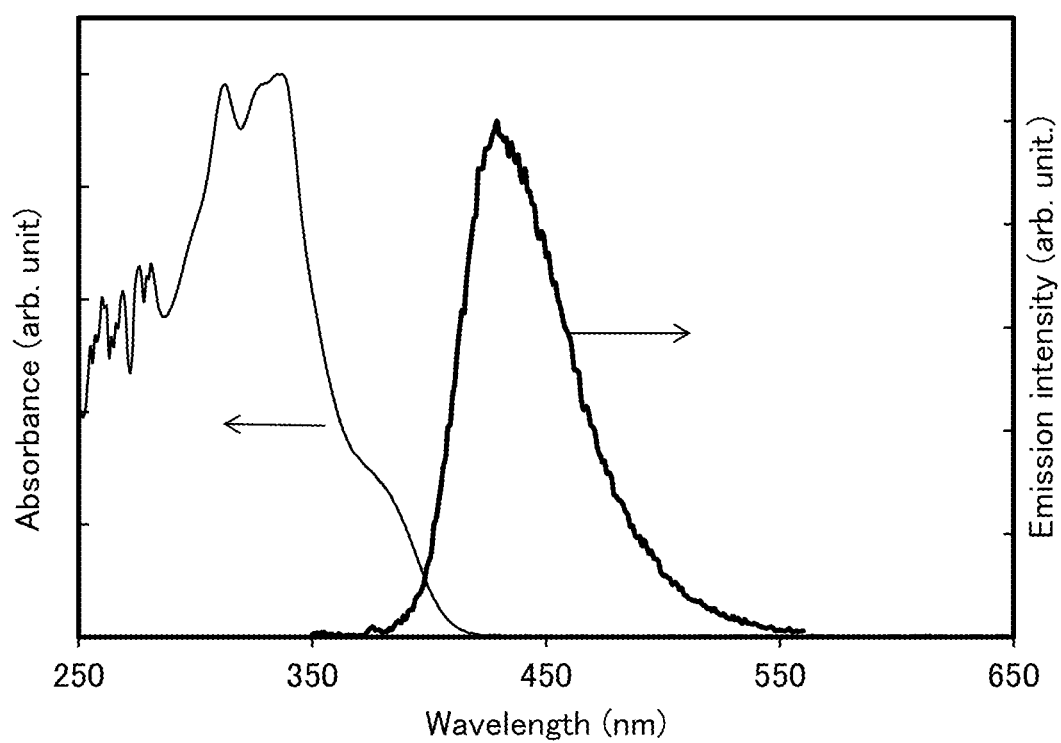
FIG. 37 shows an absorption spectrum and an emission spectrum of a solution of BBABnf(6).

Next, the ultraviolet-visible absorption spectrum (hereinafter, simply referred to as "absorption spectrum") and emission spectrum of a toluene solution and a solid thin film of BBABnf(6) were measured. The measurement was performed with a device and a method similar to those for the measurement in Example 1. FIG. 37 shows the measurement results of the absorption and emission spectra of the obtained toluene solution and FIG. 38 shows the measurement results of the absorption and emission spectra of the obtained thin film.

From FIG. 37, the toluene solution of BBABnf(6) has an absorption peak at around 382 nm, and an emission peak at 429 nm (excitation wavelength: 337 nm).

Figure 38:
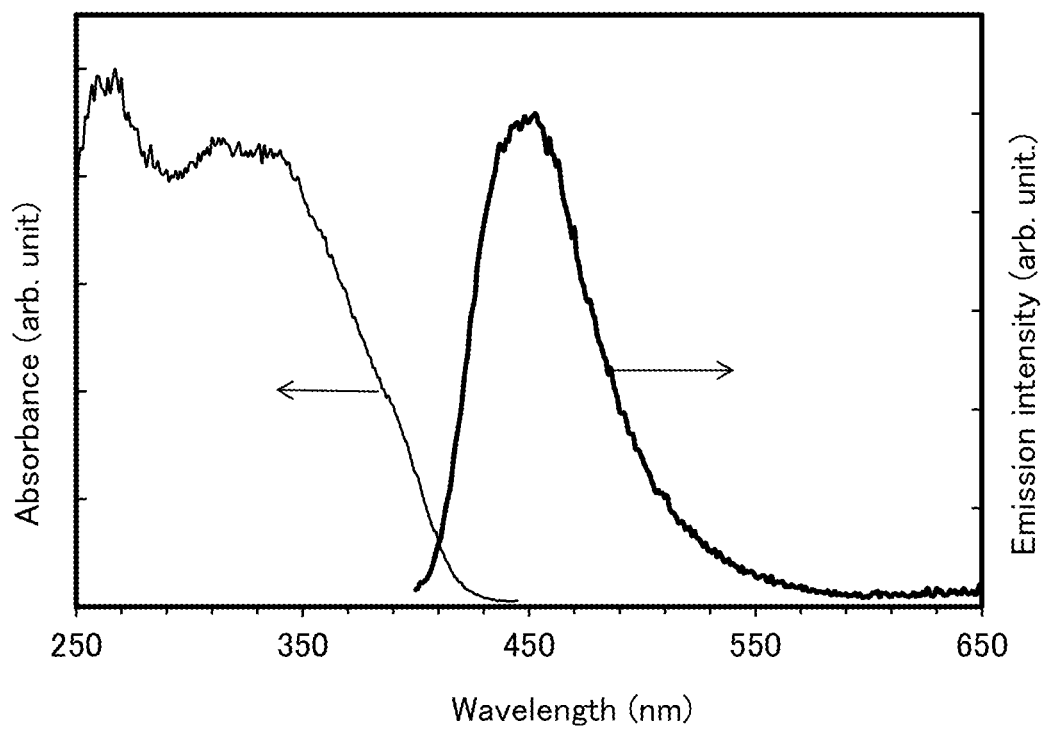
FIG. 38 shows an absorption spectrum and an emission spectrum of a thin film of BBABnf(6).

From FIG. 38, the thin film of BBABnf(6) has an absorption peak at around 390 nm, and an emission peak at 453 nm (excitation wavelength: 390 nm).

Example 6

Synthesis Example 4

This synthesis example shows an example of synthesizing N,N-bis(4-biphenyl)benzo[b]naphtho[1,2-d]furan-8-amine (abbreviation: BBABnf(8)), which is the organic compound of one embodiment of the present invention represented by Structural Formula (189) in Embodiment. The structural formula of BBABnf(8) is as follows.

[Chemical Formula 68]

Step 1: Synthesis of BBABnf(8)

Into a 200 mL three-neck flask were put 2.0 g (8.0 mmol) of 8-chlorobenzo[b]naphtho[1,2-d]furan, 2.6 g (8.0 mmol) of bis(1,1'-biphenyl-4-yl)amine, 0.19 g (0.40 mmol) of 2-dicyclohexylphosphino-2',4',6'-triisopropylbiphenyl (abbreviation: X-Phos), and 1.5 g (15 mmol) of sodium tert-butoxide. The air in the flask was replaced with nitrogen, and then 40 mL of xylene was added. After this mixture was degassed under reduced pressure, the temperature was set at 80° C. under a nitrogen stream, 0.11 g (0.20 mmol) of bis(dibenzylideneacetone)palladium(0) was added, and this mixture was stirred at 120° C. for 3 hours and further stirred at 140° C. for 6.5 hours. After the stirring, the obtained mixture was heated at 120° C. and filtered through Celite (Catalog No. 537-02305 produced by Wako Pure Chemical Industries, Ltd.), Florisil (Catalog No. 066-05265 produced by Wako Pure Chemical Industries, Ltd.), and alumina without cooling. The resulting filtrate was concentrated to give a light brown solid. The obtained solid was purified by high performance liquid chromatography (mobile phase: chloroform) to give 2.9 g of the target pale yellow solid in a yield of 68%. A synthesis scheme (d-4) of Step 1 is shown below.

[Chemical Formula 69]

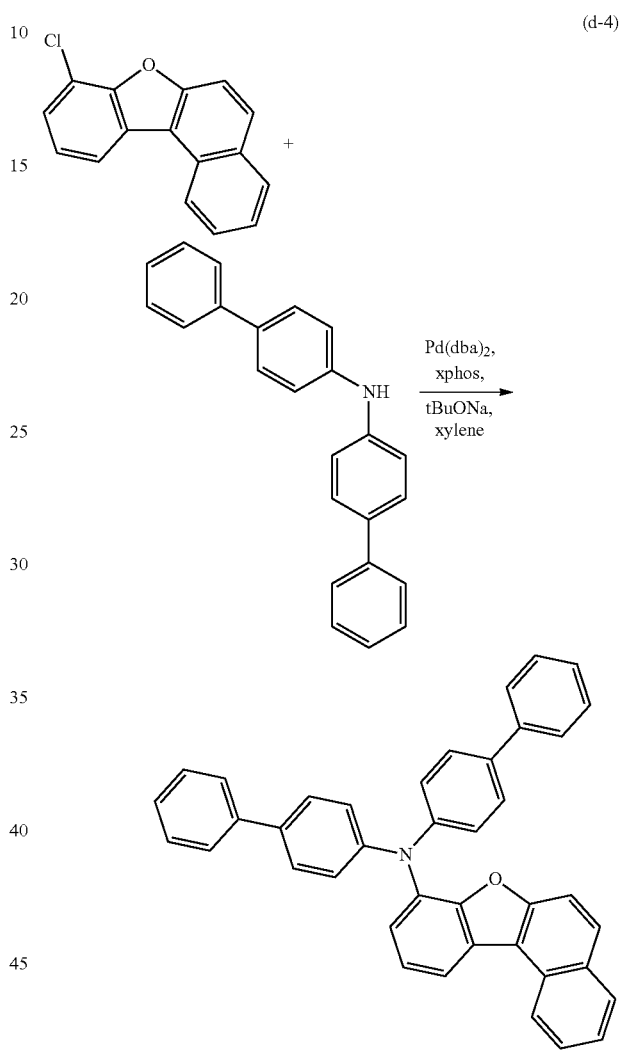

Figure 39A:
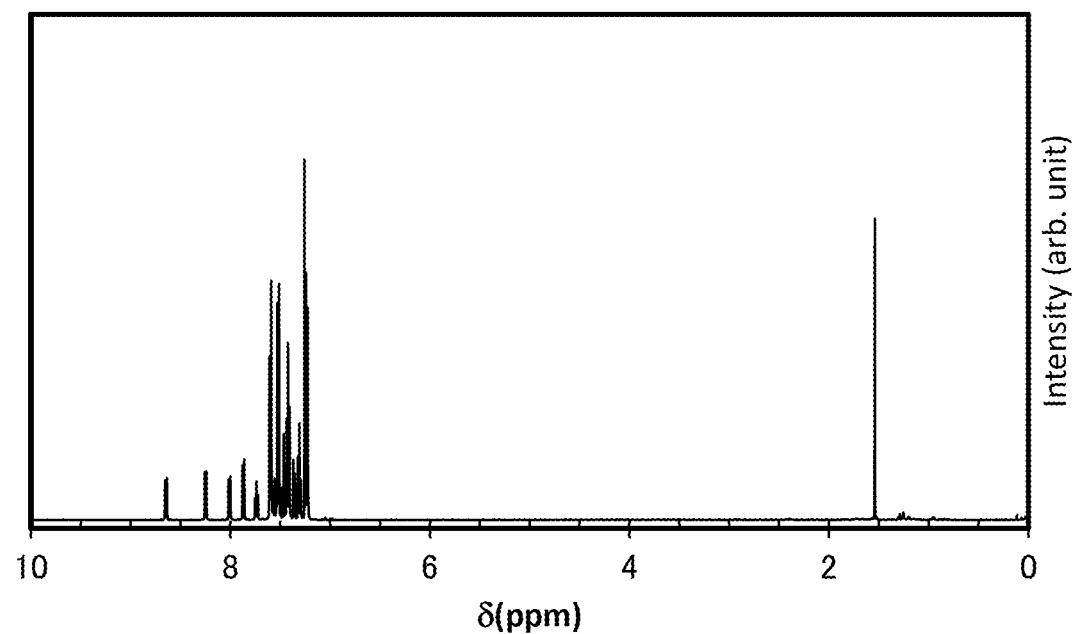
FIGS. 39A and 39B show $^1$H NMR charts of BBABnf(8).
Figure 39B:
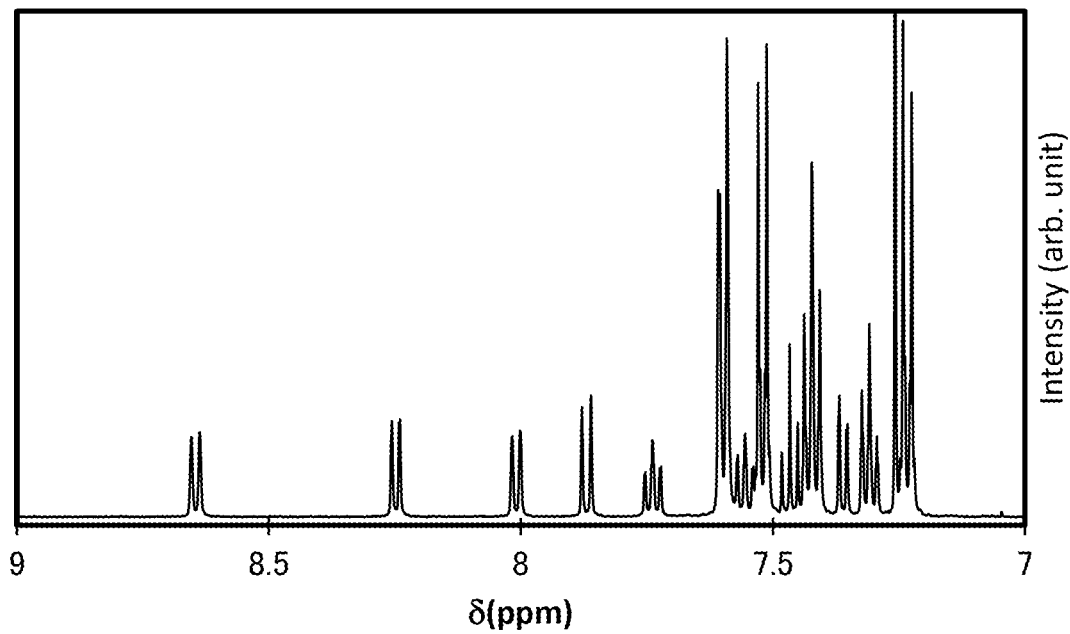

$^1$H NMR data of the obtained pale yellow solid are shown below. FIGS. 39A and 39B are $^1$H NMR charts. Note that FIG. 39B is a chart showing an enlarged part of FIG. 39A in the range of 7.00 ppm to 9.00 ppm. These results indicate that BBABnf(8), which is the organic compound of one embodiment of the present invention, was obtained.

$^1$H NMR (chloroform-d, 500 MHz): δ=7.23 (d, J=8.5 Hz, 4H), 7.31 (t, J=7.5 Hz, 2H), 7.36 (d, J=8.0 Hz, 1H), 7.42 (t, J=8.0 Hz, 4H), 7.47 (d, J=8.0 Hz, 1H), 7.52 (d, J=9.0 Hz, 4H), 7.56 (t, J=7.5 Hz, 1H), 7.59-7.61 (m, 5H), 7.74 (t, J=8.5 Hz, 1H), 7.87 (d, J=8.0 Hz, 1H), 8.01 (d, J=8.0 Hz, 1H), 8.25 (d, J=8.0 Hz, 1H), 8.65 (d, J=8.0 Hz, 1H)

By train sublimation, 3.9 g of the obtained pale yellow solid was purified. The purification by sublimation was carried out under a pressure of 3.8 Pa, with a flow rate of argon gas of 15 mL/min, at a temperature of 275° C., and for 15 hours. After the purification by sublimation, 2.1 g of the target yellow solid was obtained at a collection rate of 72%.

Figure 40:
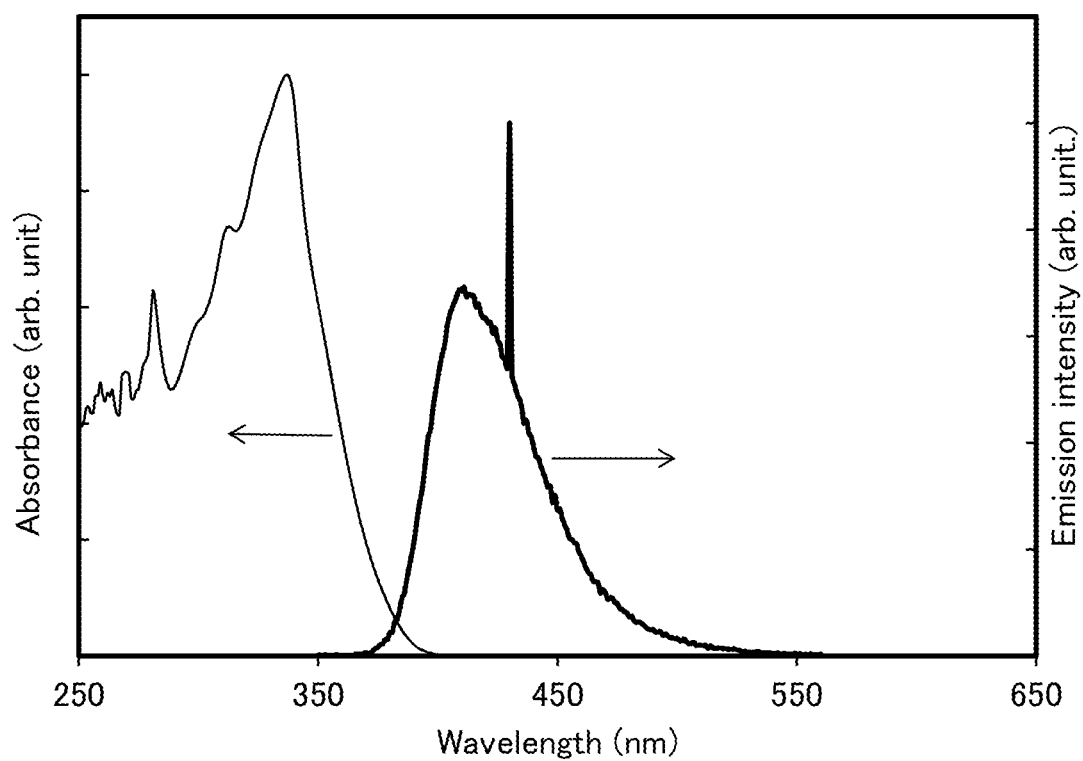
FIG. 40 shows an absorption spectrum and an emission spectrum of a solution of BBABnf(8).

Next, the ultraviolet-visible absorption spectrum (hereinafter, simply referred to as "absorption spectrum") and emission spectrum of a toluene solution and a solid thin film of BBABnf(8) were measured. The measurement was performed with a device and a method similar to those for the measurement in Example 1. FIG. 40 shows the measurement results of the absorption and emission spectra of the obtained toluene solution and FIG. 41 shows the measurement results of the absorption and emission spectra of the obtained thin film.

From FIG. 40, the toluene solution of BBABnf(8) has an absorption peak at around 337 nm, and an emission peak at 410 nm (excitation wavelength: 337 nm).

Figure 41:
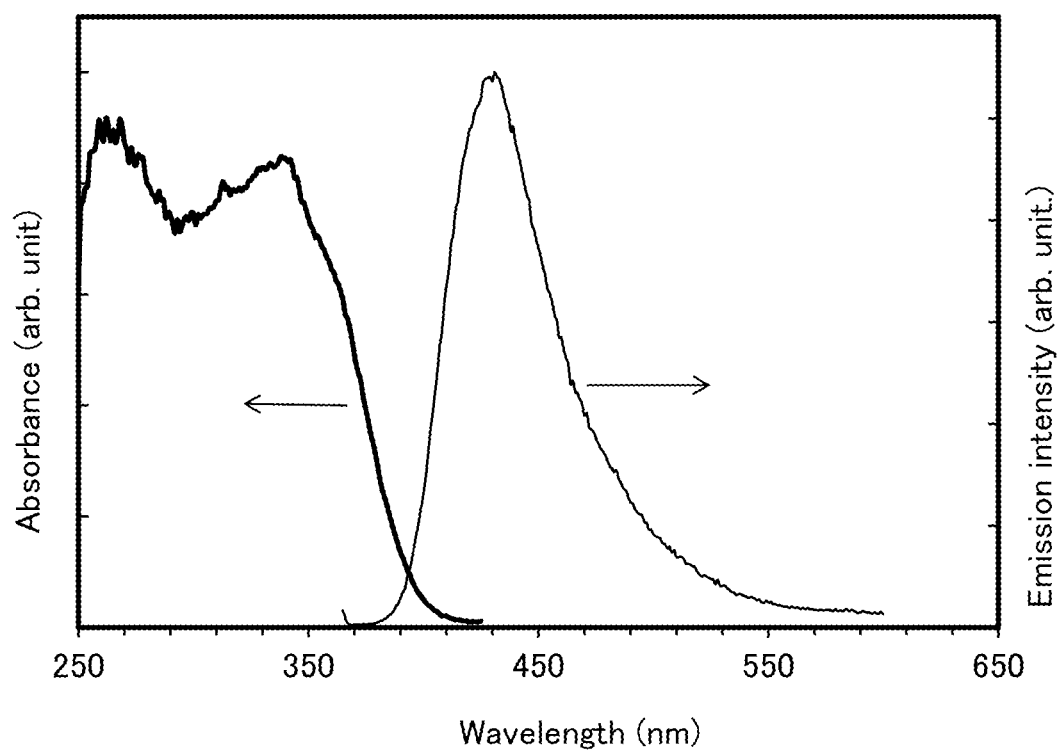
FIG. 41 shows an absorption spectrum and an emission spectrum of a thin film of BBABnf(8).

From FIG. 41, the thin film of BBABnf(8) has an absorption peak at around 370 nm, and an emission peak at 431 nm (excitation wavelength: 358 nm).

Example 7

In this example, light-emitting elements 4 and 5 of one embodiment of the present invention, which are described in Embodiment 1, will be described. Structural formulae of organic compounds used for the light-emitting elements 4 and 5 are shown below.

[Chemical Formula 70]

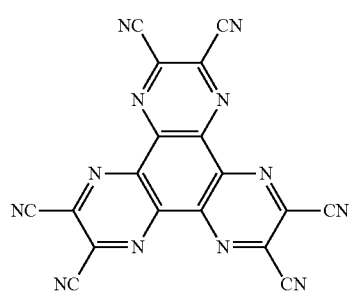

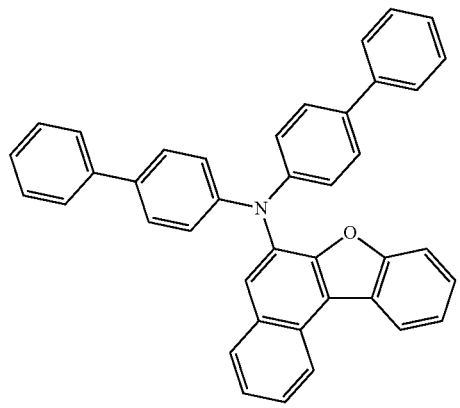

-continued (vi)
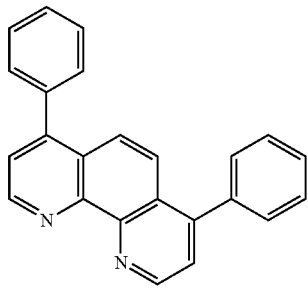
BPhen (iv)
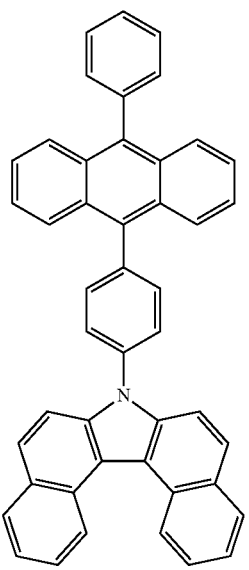
cgDBCzPA (v)
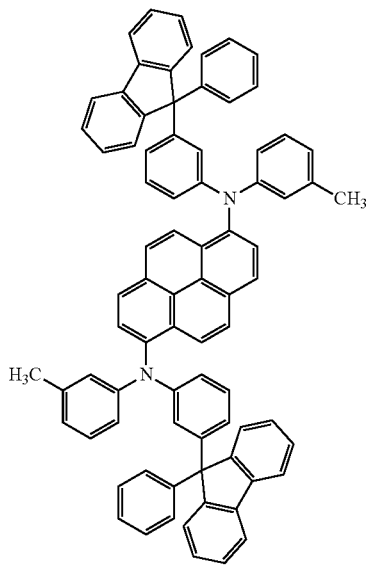
1,6mMemFLPAPrn (Method for Fabricating Light-Emitting Element 4)

First, a film of indium tin oxide containing silicon oxide (ITSO) was formed over a glass substrate by a sputtering method, so that the anode 101 was formed. The thickness thereof was 70 nm and the electrode area was 2 mm×2 mm.

Next, as pretreatment for forming the light-emitting element over the substrate, a surface of the substrate was washed with water and baked at 200° C. for 1 hour; then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate provided with the anode 101 was fixed to a substrate holder provided in the vacuum evaporation device such that the side on which the anode 101 was formed faced downward. Then, 2,3,6,7,10,11-hexacyano-1,4,5,8,9,12-hexaazatriphenylene (abbreviation: HAT-CN) represented by Structural Formula (i) was deposited to a thickness of 5 nm over the anode 101 by an evaporation method using resistance heating, whereby the hole-injection layer 111 was formed.

Next, 4,4'-bis[N-(1-naphthyl)-N-phenylamino]biphenyl (abbreviation: NPB) represented by Structural Formula (ix) was deposited to a thickness of 10 nm over the hole-injection layer 111 by evaporation, whereby the first hole-transport layer 112-1 was formed; N,N-di(4-biphenyl)benzo[b]naphtho[1,2-d]furan-6-amine (abbreviation: BBABnf(6)), which is the organic compound of one embodiment of the present invention represented by Structural Formula (229), was deposited to a thickness of 10 nm over the first hole-transport layer 112-1 by evaporation, whereby the second hole-transport layer 112-2 was formed; and 3,6-bis[4-(2-naphthyl)phenyl]-9-phenyl-9H-carbazole (abbreviation: βNP2PC)) represented by Structural Formula (x) was deposited to a thickness of 10 nm over the second hole-transport layer 112-2 by evaporation, whereby the third hole-transport layer 112-3 was formed.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iv) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (v) in a weight ratio of 1:0.03 (=cgDBCzPA: 1,6mMemFLPAPrn) to a thickness of 25 nm.

Then, over the light-emitting layer 113, cgDBCzPA was deposited to a thickness of 10 nm by evaporation, and bathophenanthroline (abbreviation: BPhen) represented by Structural Formula (vi) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 4 of this example was fabricated.

(Method for Fabricating Light-Emitting Element 5)

The light-emitting element 5 was formed in the same manner as the light-emitting element 4 except that the second hole-transport layer 112-2 was formed using N,N-di(4-biphenyl)benzo[b]naphtho[1,2-d]furan-8-amine (abbreviation: BBABnf(8)) instead of BBABnf(6).

The element structures of the light-emitting elements 4 and 5 are shown in the following table.

TABLE 5

| Hole-injection layer | Hole-transport layer | | | Light-emitting layer | Electron-transport layer | | Electron-injection layer |
|---|---|---|---|---|---|---|---|
| | 1 | 2 | 3 | | | | |
| 5 nm | 10 nm | 10 nm | 10 nm | 25 nm | 10 nm | 15 nm | 1 nm |
| HAT-CN | NPB | *2 | βNP2PC | cgDBCzPA: 1,6mMemFLPAPm (1:0.03) | cgDBCzPA | BPhen | LiF |

*2 Light-emitting element 4: BBABnf(6), Light-emitting element 5: BBABnf(8)

The light-emitting elements 4 and 5 were sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting elements were measured. Note that the measurements were performed at room temperature (in an atmosphere kept at 25° C.).

Figure 42:
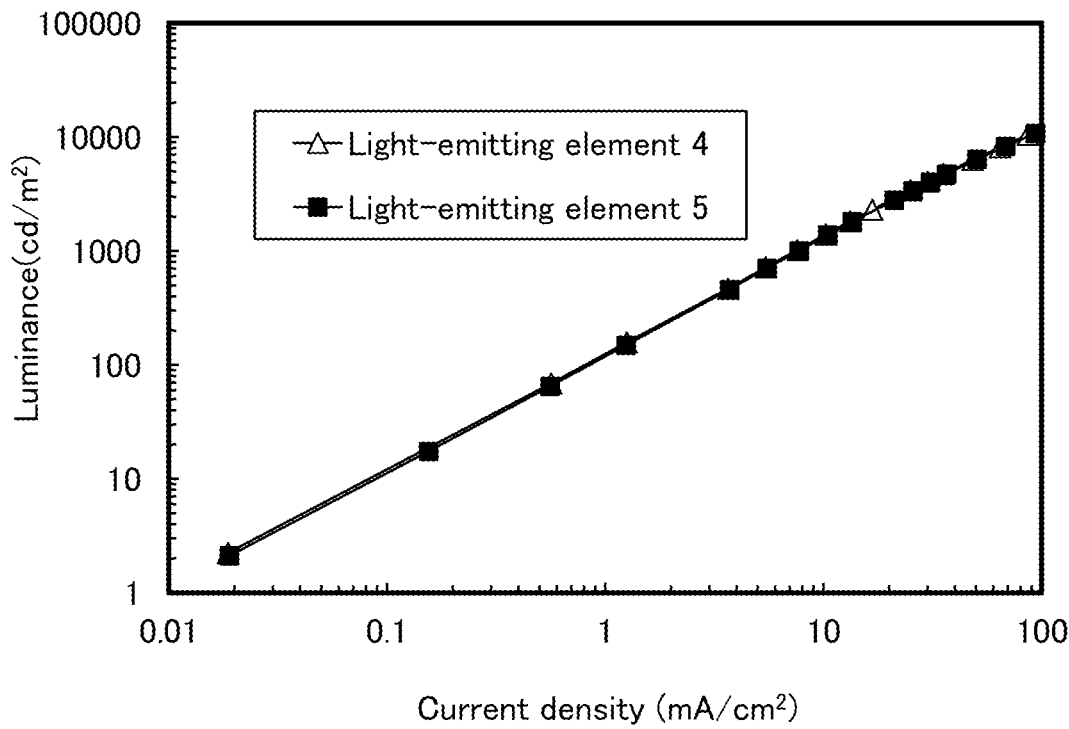
FIG. 42 shows the luminance-current density characteristics of light-emitting elements 4 and 5.
Figure 43:
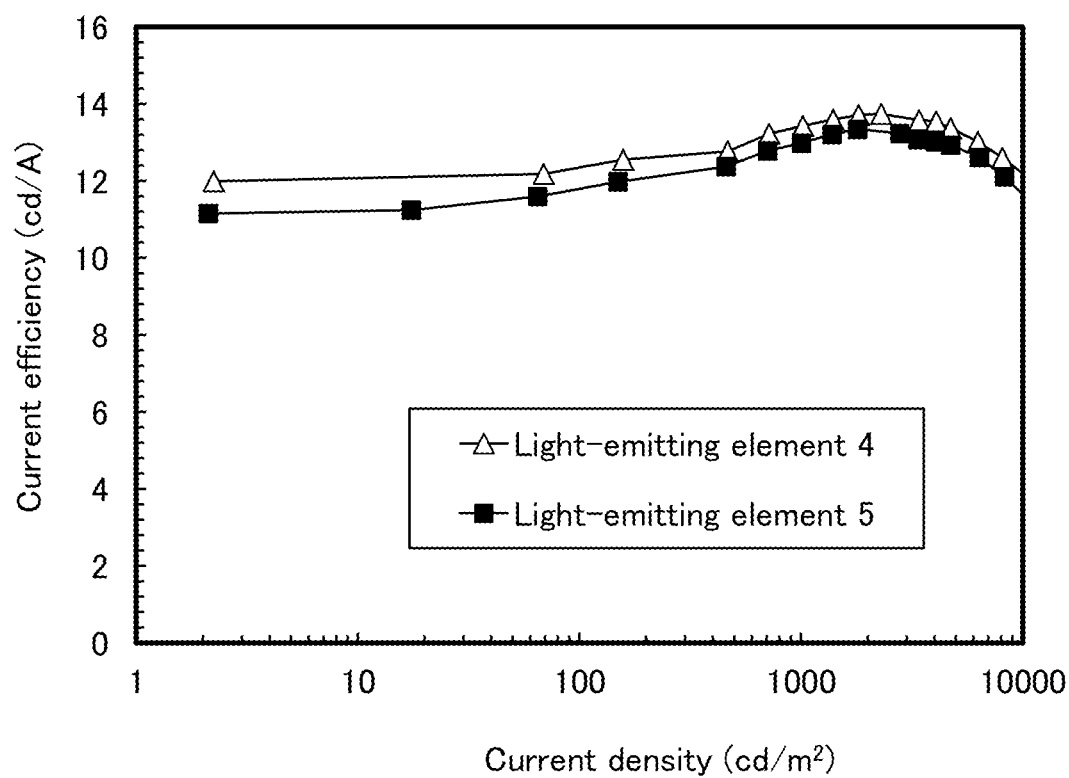
FIG. 43 shows the current efficiency-luminance characteristics of the light-emitting elements 4 and 5.
Figure 44:
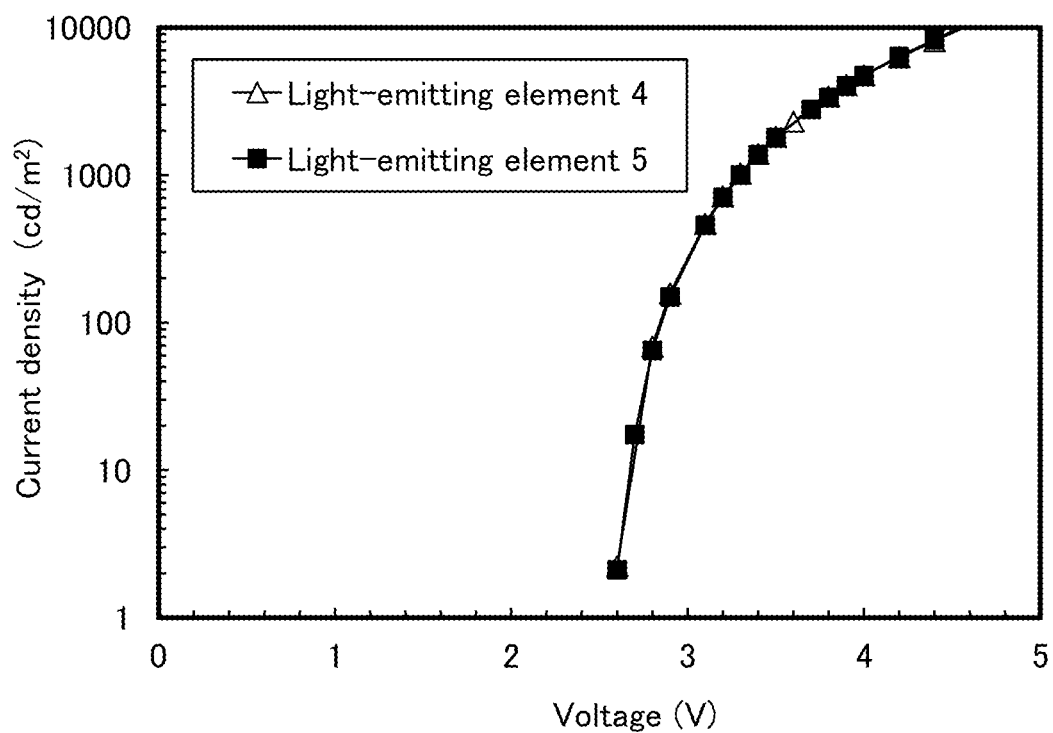
FIG. 44 shows the luminance-voltage characteristics of the light-emitting elements 4 and 5.
Figure 45:
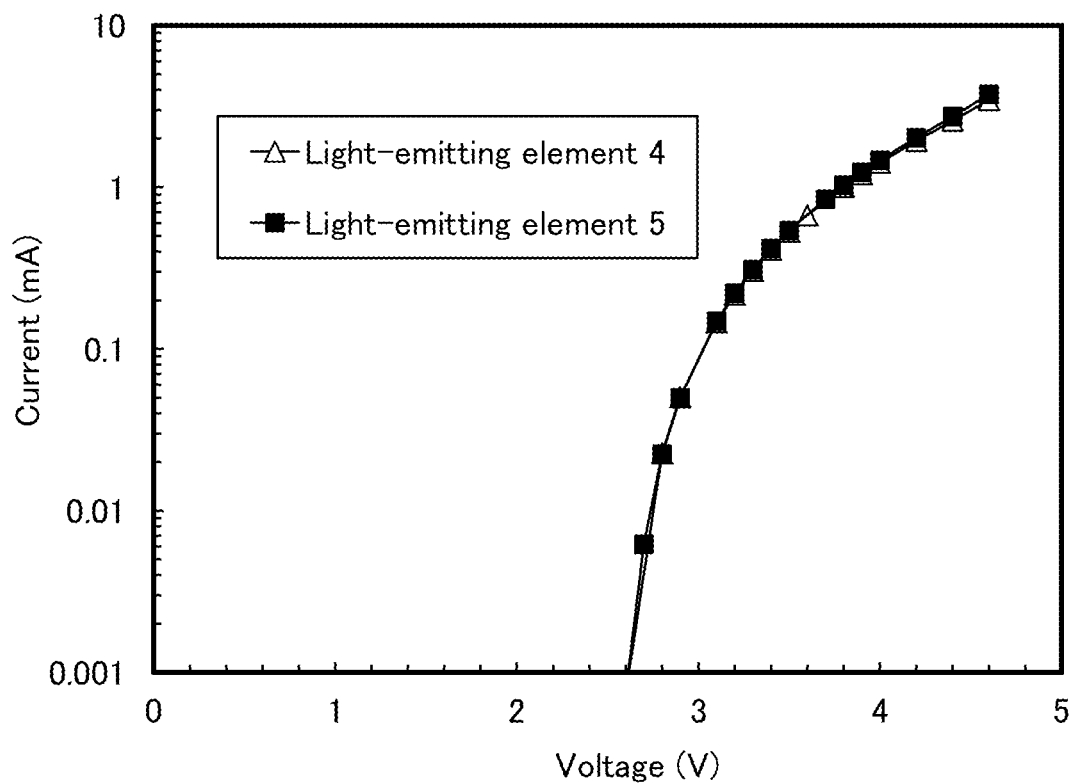
FIG. 45 shows the current-voltage characteristics of the light-emitting elements 4 and 5.
Figure 46:
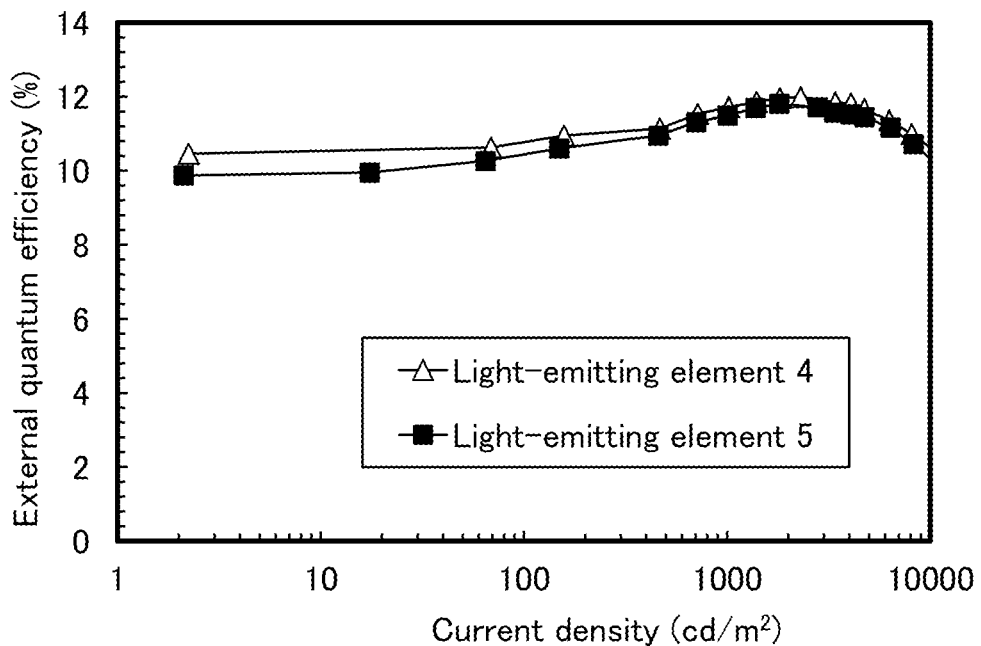
FIG. 46 shows the external quantum efficiency-luminance characteristics of the light-emitting elements 4 and 5.
Figure 47:
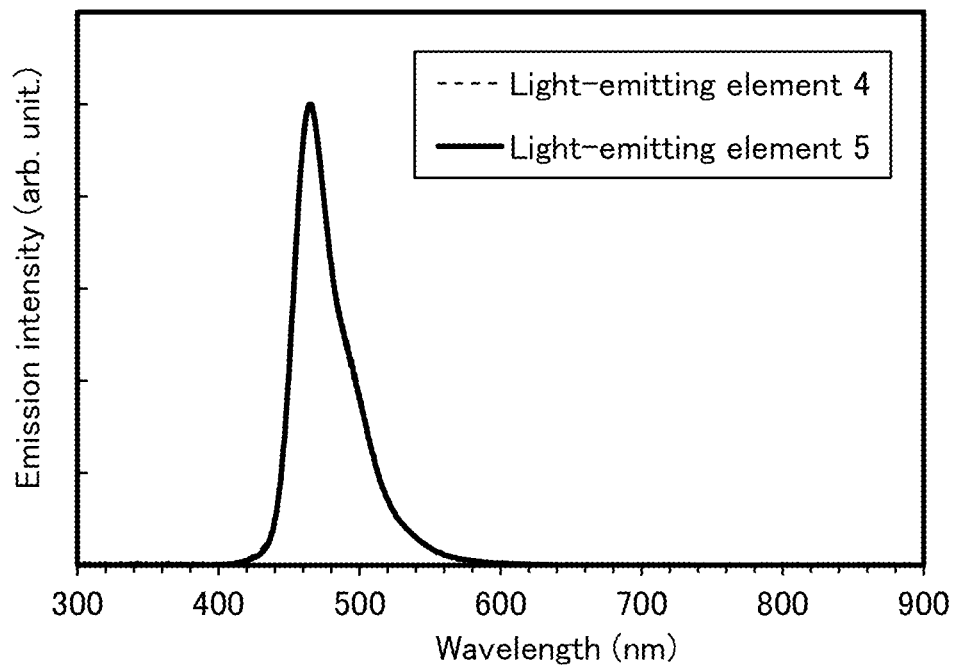
FIG. 47 shows emission spectra of the light-emitting elements 4 and 5.

FIG. 42 shows the luminance-current density characteristics of the light-emitting elements 4 and 5. FIG. 43 shows the current efficiency-luminance characteristics of the light-emitting elements 4 and 5. FIG. 44 shows the luminance-voltage characteristics of the light-emitting elements 4 and 5. FIG. 45 shows the current-voltage characteristics of the light-emitting elements 4 and 5. FIG. 46 shows the external quantum efficiency-luminance characteristics of the light-emitting elements 4 and 5. FIG. 47 shows the emission spectrum of the light-emitting elements 4 and 5. Table 6 shows the main characteristics of the light-emitting elements 4 and 5 at around 1000 cd/m².

TABLE 6

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting element 4 | 3.30 | 0.30 | 7.60 | 0.14 | 0.17 | 13.4 | 11.7 |
| Light-emitting element 5 | 3.30 | 0.31 | 7.74 | 0.14 | 0.15 | 13.0 | 11.5 |

It was found from FIGS. 42 to 46 and Table 6 that the light-emitting elements 4 and 5 of one embodiment of the present invention are blue light-emitting elements with favorable efficiency and a low driving voltage.

Figure 48:
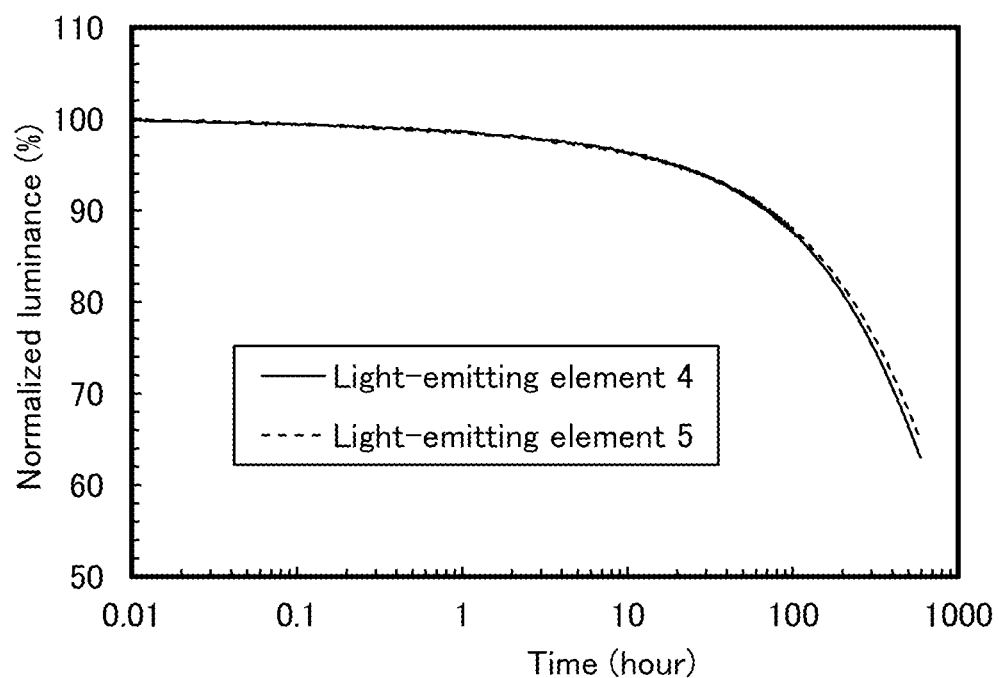
FIG. 48 shows the time dependence of normalized luminance of the light-emitting elements 4 and 5.

FIG. 48 shows driving time-dependent change in luminance of the light-emitting elements under the conditions where the current value was set to 2 mA and the current density was constant. As shown in FIG. 48, the light-emitting elements 4 and 5 maintained 85% ☐☐☐☐☐☐ of the initial luminance after 100-hour-driving and were found to be long-lifetime light-emitting elements with an extremely small reduction in luminance over driving time.

Example 8

In this example, light-emitting elements 6 and 7 of one embodiment of the present invention, which are described in Embodiment 1, will be described. Structural formulae of organic compounds used for the light-emitting elements 6 and 7 are shown below.

[Chemical Formula 71]

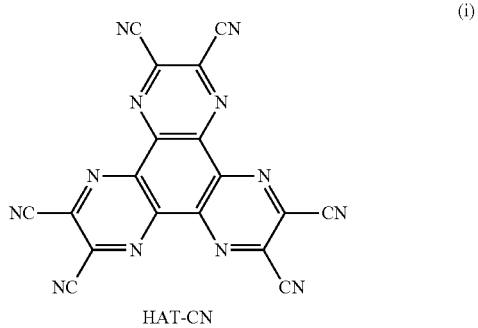

(i) HAT-CN

-continued

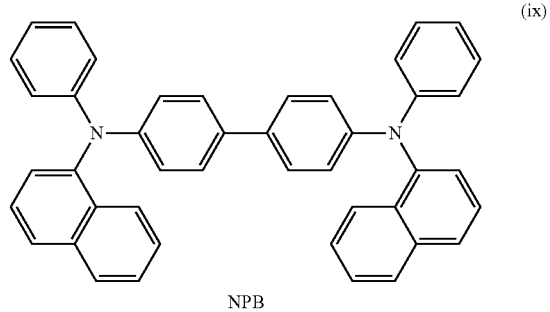

(ix) NPB

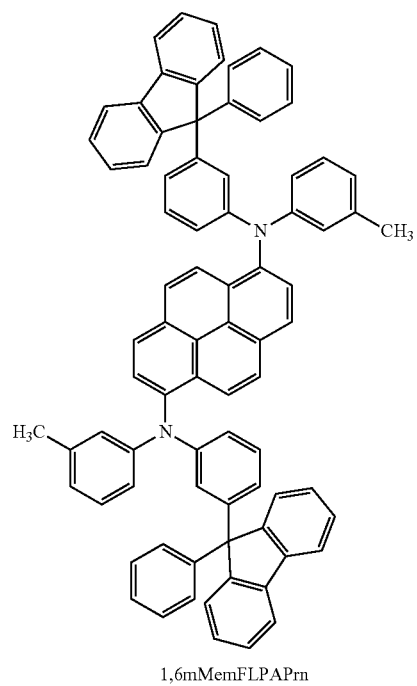

1,6mMemFLPAPrn

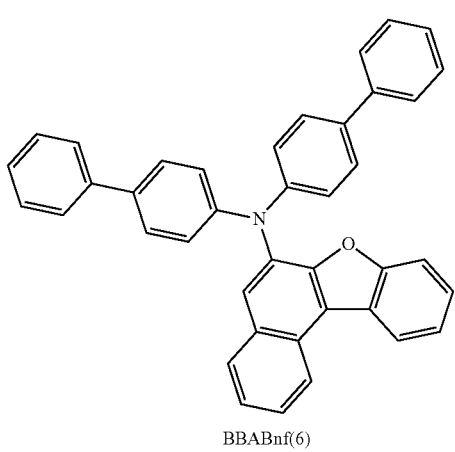

BBABnf(6)

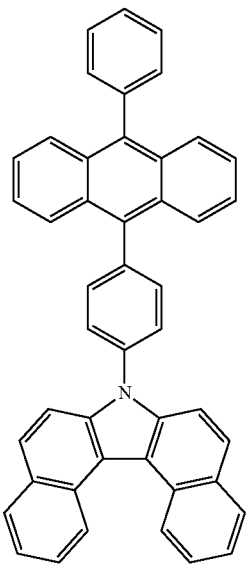

cgDBCzPA

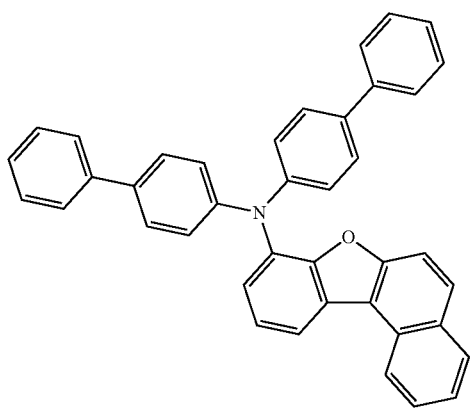

BBABnf(8)

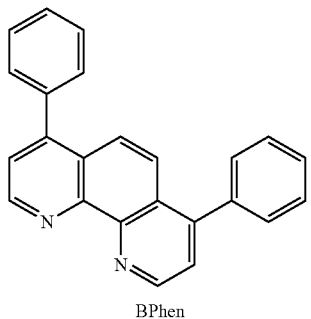

BPhen (Method for Fabricating Light-Emitting Element 6)

First, a film of indium tin oxide containing silicon oxide (ITSO) was formed over a glass substrate by a sputtering method, so that the anode 101 was formed. The thickness thereof was 70 nm and the electrode area was 2 mm×2 mm.

Next, as pretreatment for forming the light-emitting element over the substrate, a surface of the substrate was washed with water and baked at 200° C. for 1 hour; then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate provided with the anode 101 was fixed to a substrate holder provided in the vacuum evaporation device such that the side on which the anode 101 was formed faced downward. Then, 2,3,6,7,10,11-hexacyano-1,4,5,8,9,12-hexaazatriphenylene (abbreviation: HAT-CN) represented by Structural Formula (i) was deposited to a thickness of 5 nm over the anode 101 by an evaporation method using resistance heating, whereby the hole-injection layer 111 was formed.

Next, 4,4'-bis[N-(1-naphthyl)-N-phenylamino]biphenyl (abbreviation: NPB) represented by Structural Formula (ix) was deposited to a thickness of 20 nm over the hole-injection layer 111 by evaporation, whereby the first hole-transport layer 112-1 was formed; and N,N-di(4-biphenyl)benzo[b]naphtho[1,2-d]furan-6-amine (abbreviation: BBABnf(6)), which is the organic compound of one embodiment of the present invention represented by Structural Formula (229), was deposited to a thickness of 10 nm over the first hole-transport layer 112-1 by evaporation, whereby the second hole-transport layer 112-2 was formed.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iv) and N,N'-bis (3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (v) in a weight ratio of 1:0.03 (=cgDBCzPA: 1,6mMemFLPAPrn) to a thickness of 25 nm.

Then, over the light-emitting layer 113, cgDBCzPA was deposited to a thickness of 10 nm by evaporation, and bathophenanthroline (abbreviation: BPhen) represented by Structural Formula (vi) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 6 of this example was fabricated.

(Method for Fabricating Light-Emitting Element 7)

The light-emitting element 7 was formed in the same manner as the light-emitting element 6 except that the second hole-transport layer 112-2 was formed using N,N-di(4-biphenyl)benzo[b]naphtho[1,2-d]furan-8-amine (abbreviation: BBABnf(8)) instead of BBABnf(6).

The element structures of the light-emitting elements 6 and 7 are shown in the following table.

TABLE 7

| Hole-injection layer | Hole-transport layer | | Light-emitting layer | Electron-transport layer | | Electron-injection layer |
|---|---|---|---|---|---|---|
| 5 nm | 20 nm | 10 nm | 25 nm | 10 nm | 15 nm | 1 nm |
| HAT-CN | NPB | *3 | cgDBCzPA: 1,6mMemFLPAPrn (1:0.03) | cgDBCzPA | BPhen | LiF |

*3 Light-emitting element 6: BBABnf(6), Light-emitting element 7: BBABnf(8).

The light-emitting elements 6 and 7 were sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting elements were measured. Note that the measurements were performed at room temperature (in an atmosphere kept at 25° C.).

Figure 49:
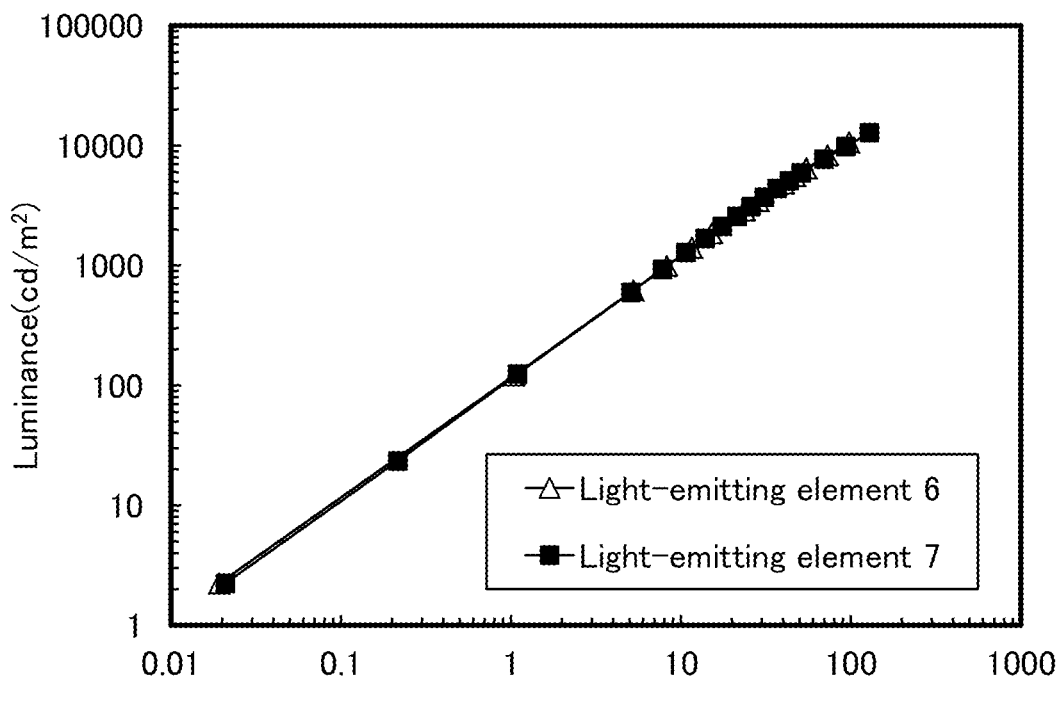
FIG. 49 shows the luminance-current density characteristics of light-emitting elements 6 and 7.
Figure 50:
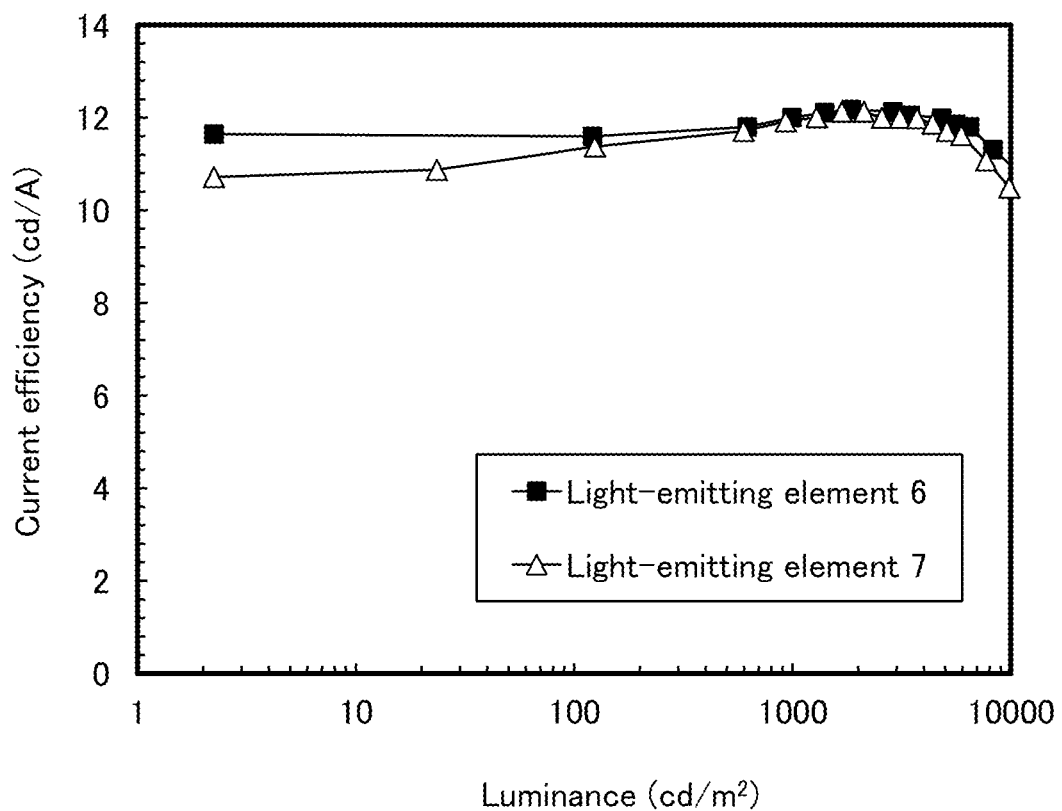
FIG. 50 shows the current efficiency-luminance characteristics of the light-emitting elements 6 and 7.
Figure 51:
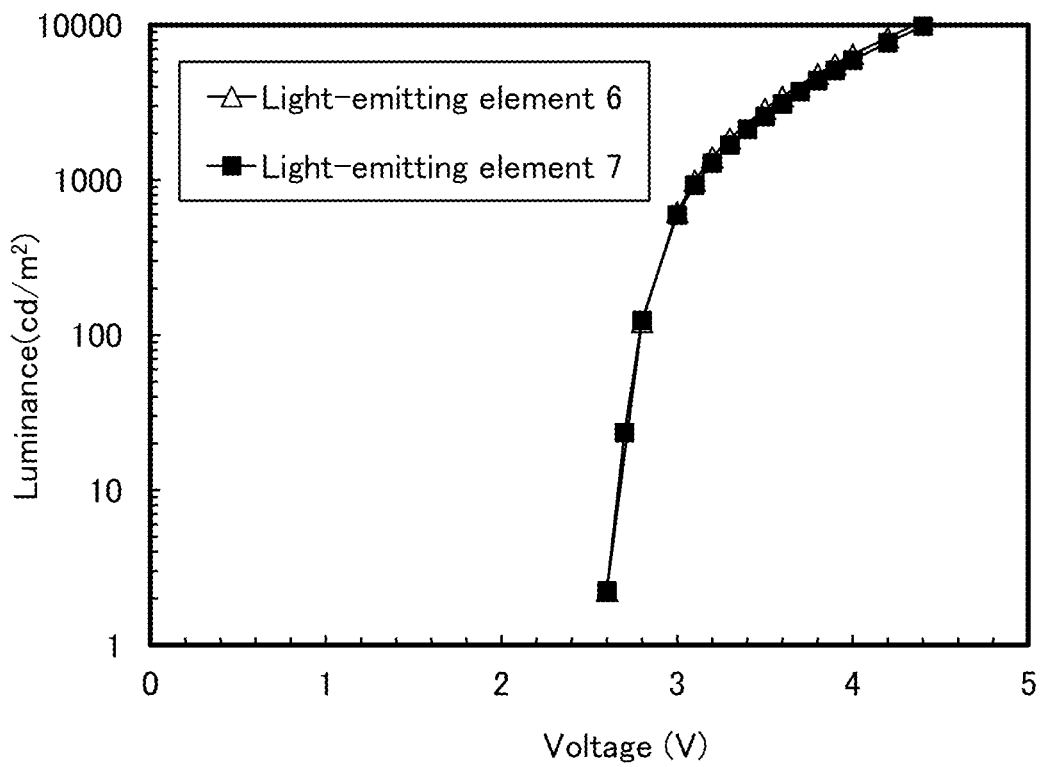
FIG. 51 shows the luminance-voltage characteristics of the light-emitting elements 6 and 7.
Figure 52:
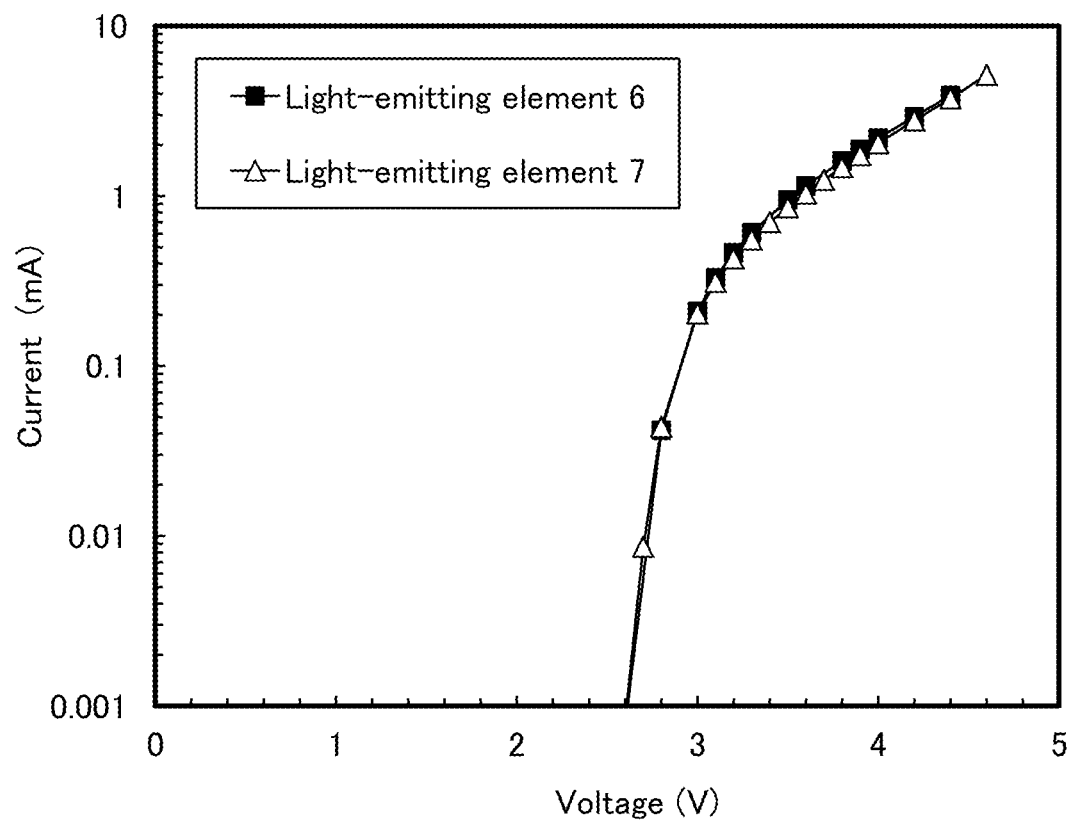
FIG. 52 shows the current-voltage characteristics of the light-emitting elements 6 and 7.
Figure 53:
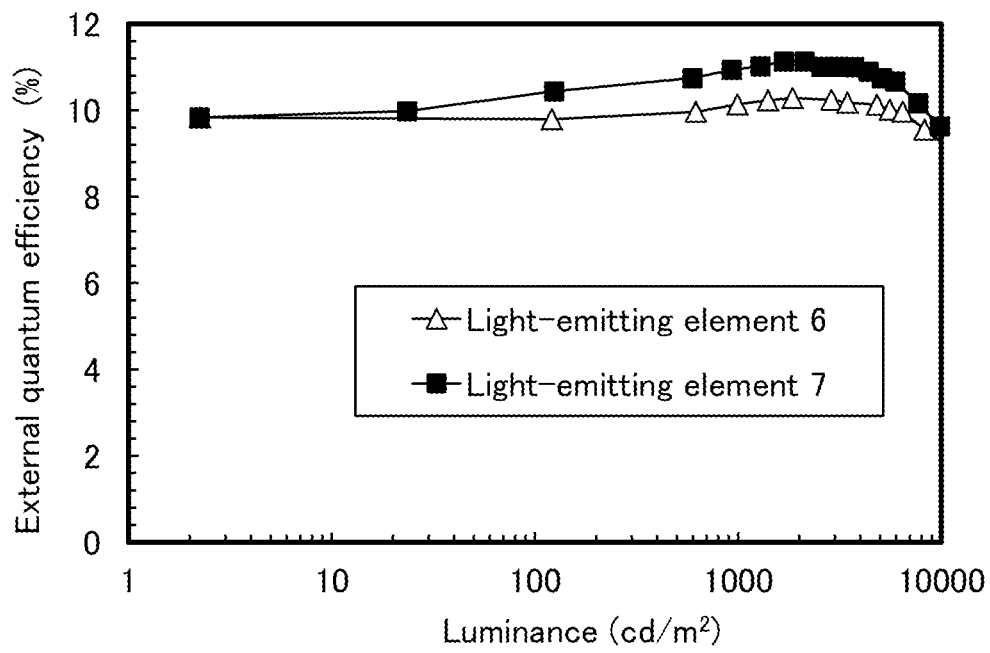
FIG. 53 shows the external quantum efficiency-luminance characteristics of the light-emitting elements 6 and 7.
Figure 54:
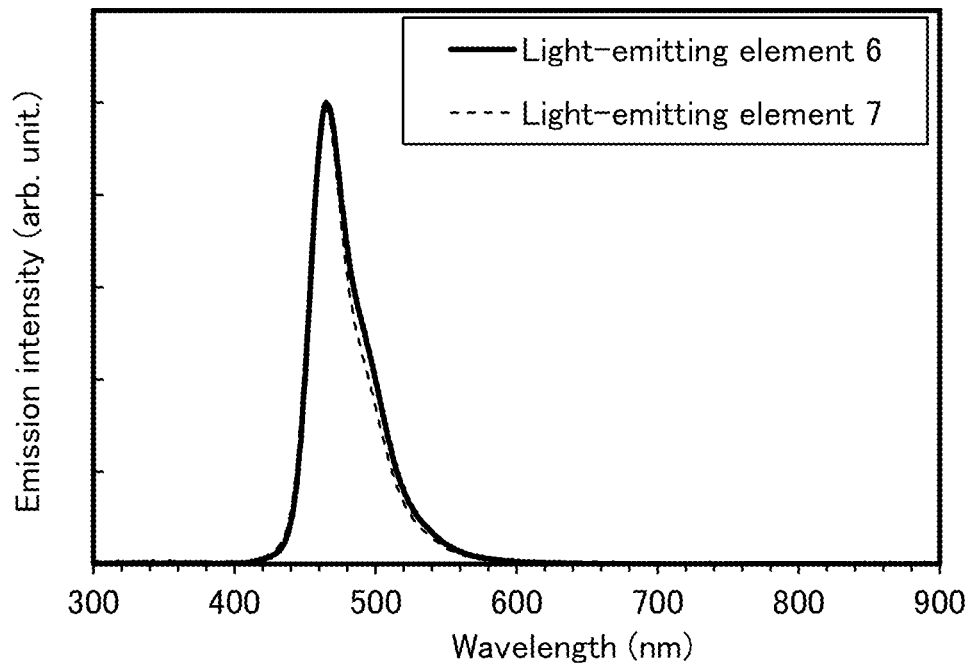
FIG. 54 shows emission spectra of the light-emitting elements 6 and 7.

FIG. 49 shows the luminance-current density characteristics of the light-emitting elements 6 and 7. FIG. 50 shows the current efficiency-luminance characteristics of the light-emitting elements 6 and 7. FIG. 51 shows the luminance-voltage characteristics of the light-emitting elements 6 and 7. FIG. 52 shows the current-voltage characteristics of the light-emitting elements 6 and 7. FIG. 53 shows the external quantum efficiency-luminance characteristics of the light-emitting elements 6 and 7. FIG. 54 shows the emission spectrum of the light-emitting elements 6 and 7. Table 8 shows the main characteristics of the light-emitting elements 6 and 7 at around 1000 cd/m$^2$.

TABLE 8

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 6 | 3.10 | 0.33 | 8.27 | 0.14 | 0.16 | 12.0 | 10.1 |
| Light-emitting element 7 | 3.10 | 0.31 | 7.80 | 0.14 | 0.15 | 11.9 | 10.9 |

It was found from FIGS. 49 to 54 and Table 8 that the light-emitting elements 6 and 7 of one embodiment of the present invention are blue light-emitting elements with favorable efficiency and a low driving voltage.

Example 9

In this example, a light-emitting element 8 of one embodiment of the present invention, which is described in Embodiment 1, will be described. Structural formulae of organic compounds used for the light-emitting element 8 are shown below.

[Chemical Formula 72]

(xi)

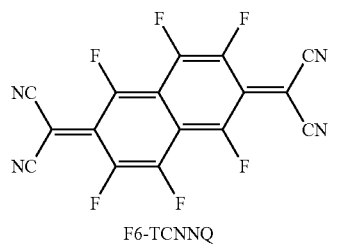

F6-TCNNQ

-continued (vii)

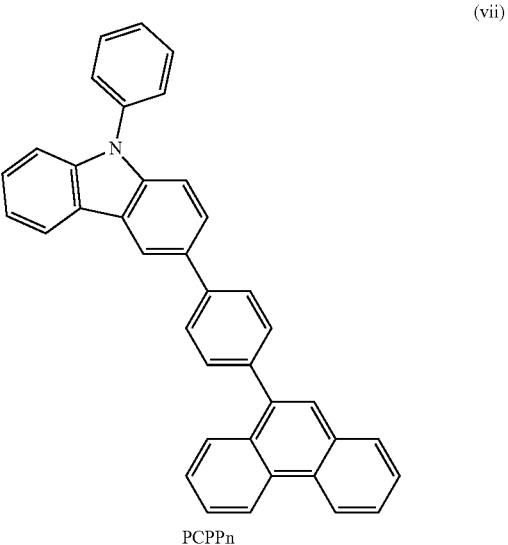

PCPPn (146)

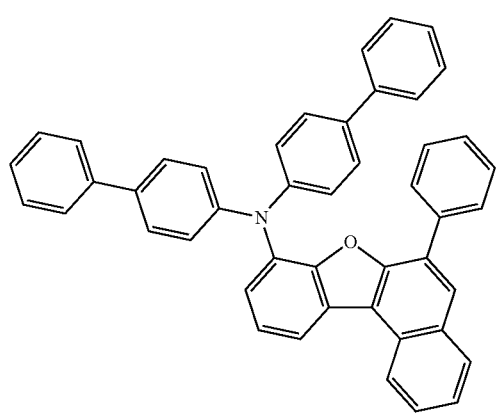

BBABnf (iv)

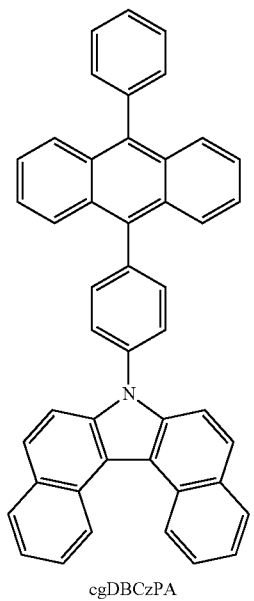

cgDBCzPA

-continued (v)

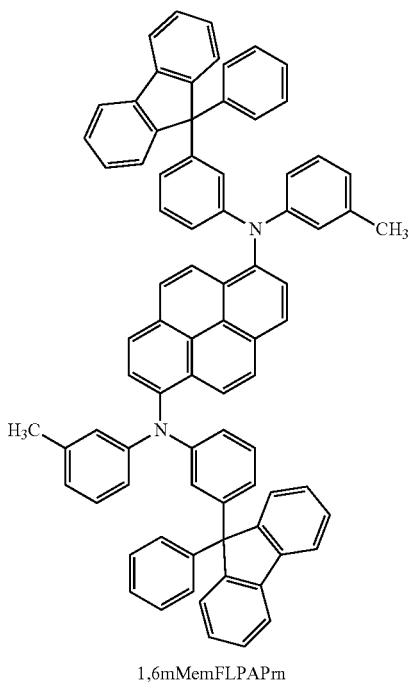

1,6mMemFLPAPrn (xii)

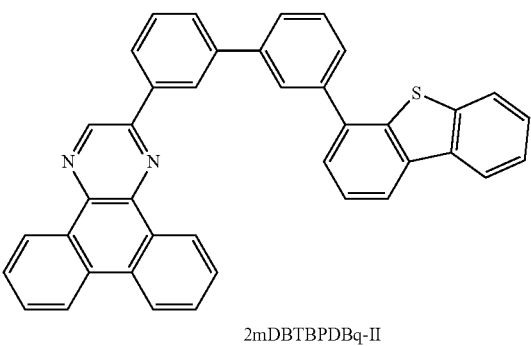

2mDBTBPDBq-II (xiii)

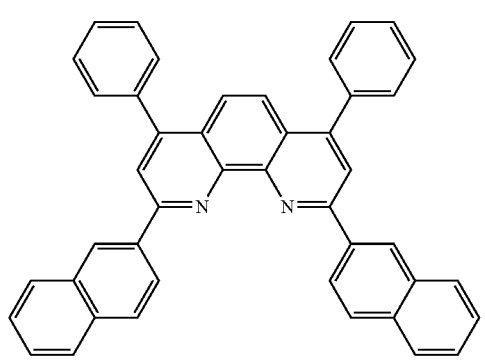

NBPhen (Method for Fabricating Light-Emitting Element 8)

First, a film of indium tin oxide containing silicon oxide (ITSO) was formed over a glass substrate by a sputtering method, so that the anode 101 was formed. The thickness thereof was 70 nm and the electrode area was 2 mm×2 mm.

Next, as pretreatment for forming the light-emitting element over the substrate, a surface of the substrate was washed with water and baked at 200° C. for 1 hour; then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Next, the substrate provided with the anode 101 was fixed to a substrate holder provided in the vacuum evaporation device such that the side on which the anode 101 was formed faced downward. Then, N,N-bis(biphenyl-4-yl)-6-phenyl-benzo[b]naphtho[1,2-d]furan-8-amine (abbreviation: BBA-Bnf), which is the organic compound of one embodiment of the present invention represented by Structural Formula (146), and 1,3,4,5,7,8-hexafluorotetracyano-naphthoquinodimethane (abbreviation: F6-TCNNQ), which is represented by Structural Formula (xi), were deposited to a thickness of 10 nm over the anode 101 by co-evaporation in a weight ratio of 2:1 (=BBABnf: F6-TCNNQ), whereby the hole-injection layer 111 was formed.

Next, BBABnf was deposited to a thickness of 10 nm over the hole-injection layer 111 by evaporation, whereby the first hole-transport layer 112-1 was formed; and 3-[4-(9-phenanthryl)-phenyl]-9-phenyl-9H-carbazole (abbreviation: PCPPn) represented by Structural Formula (vii) was deposited to a thickness of 20 nm over the first hole-transport layer 112-1 by evaporation, whereby the second hole-transport layer 112-2 was formed.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (iv) and N,N'-bis (3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (v) in a weight ratio of 1:0.03 (=cgDBCzPA: 1,6mMemFLPAPrn) to a thickness of 25 nm.

Then, over the light-emitting layer 113, 2-[3'-(dibenzothiophen-4-yl)biphenyl-3-yl]dibenzo[f,h]quinoxaline (abbreviation: 2mDBTBPDBq-II), which is represented by Structural Formula (xii), was deposited to a thickness of 10 nm by evaporation, and 2,9-bis(naphthalen-2-yl)-4,7-diphenyl-1,10-phenanthroline (abbreviation: NBPhen) represented by Structural Formula (xiii) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, the light-emitting element 8 of this example was fabricated.

The element structure of the light-emitting element 8 is shown in the following table.

TABLE 9

| Hole-injection layer | Hole-transport layer | | Light-emitting layer | Electron-transport layer | | Electron-injection layer |
|---|---|---|---|---|---|---|
| 10 nm | 10 nm | 20 nm | 25 nm | 10 nm | 15 nm | 1 nm |
| BBABnf: F6-TCNNQ (1:0.5) | BBABnf | PCPPn | cgDBCzPA: 1,6mMemFLPAPrn (1:0.03) | 2mDBTBPDBq-II | NBPhen | LiF |

The light-emitting element 8 was sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting element were measured. Note that the measurements were performed at room temperature (in an atmosphere kept at 25° C.).

Figure 55:
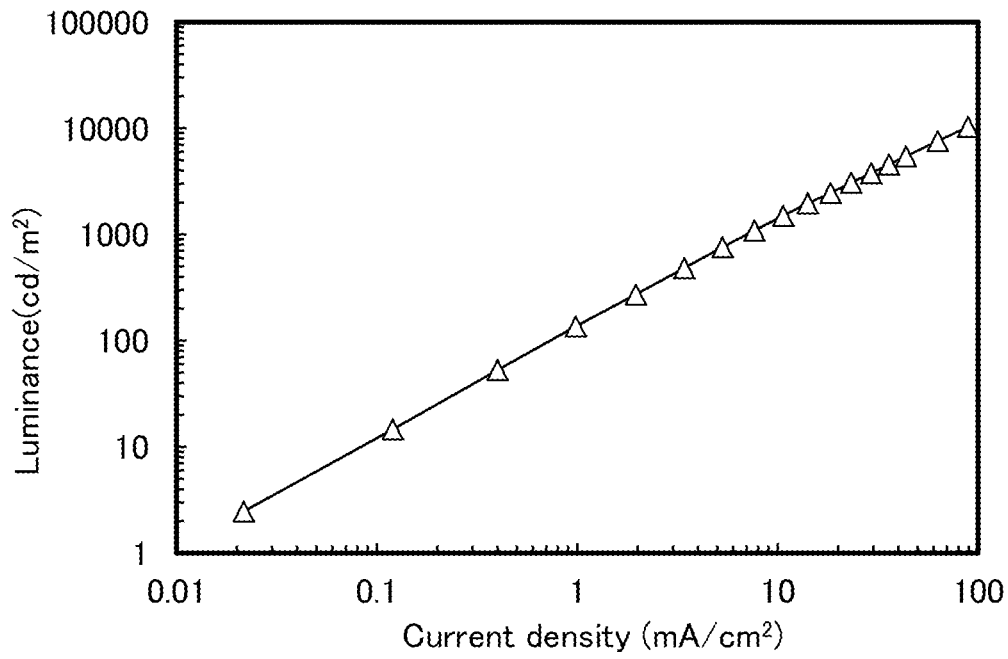
FIG. 55 shows the luminance-current density characteristics of a light-emitting element 8.
Figure 56:
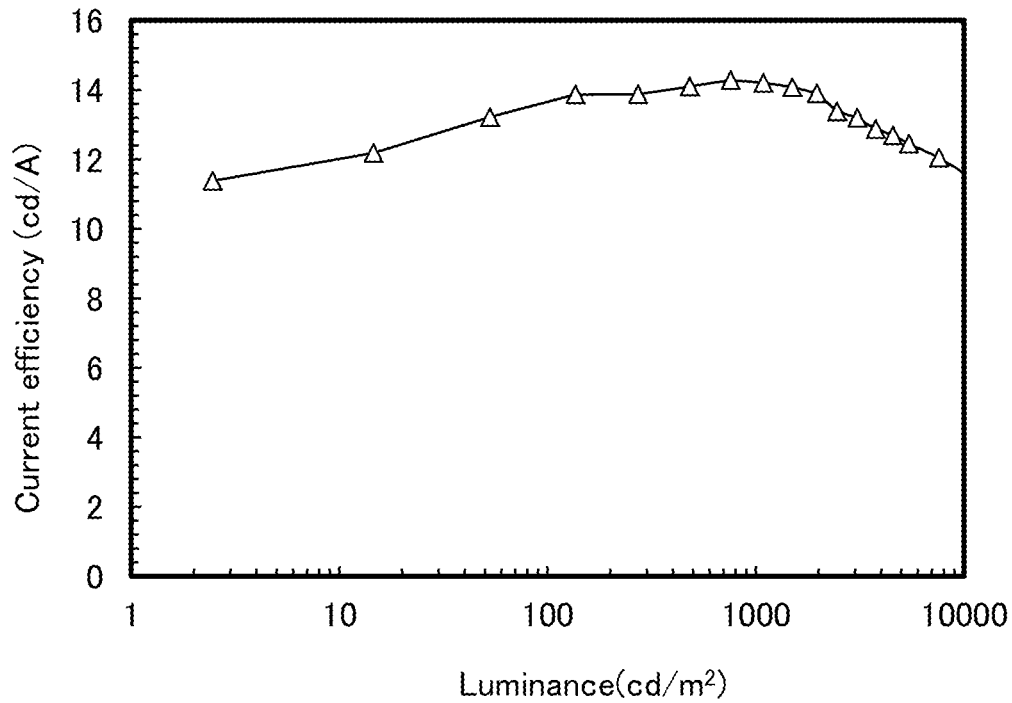
FIG. 56 shows the current efficiency-luminance characteristics of the light-emitting element 8.
Figure 57:
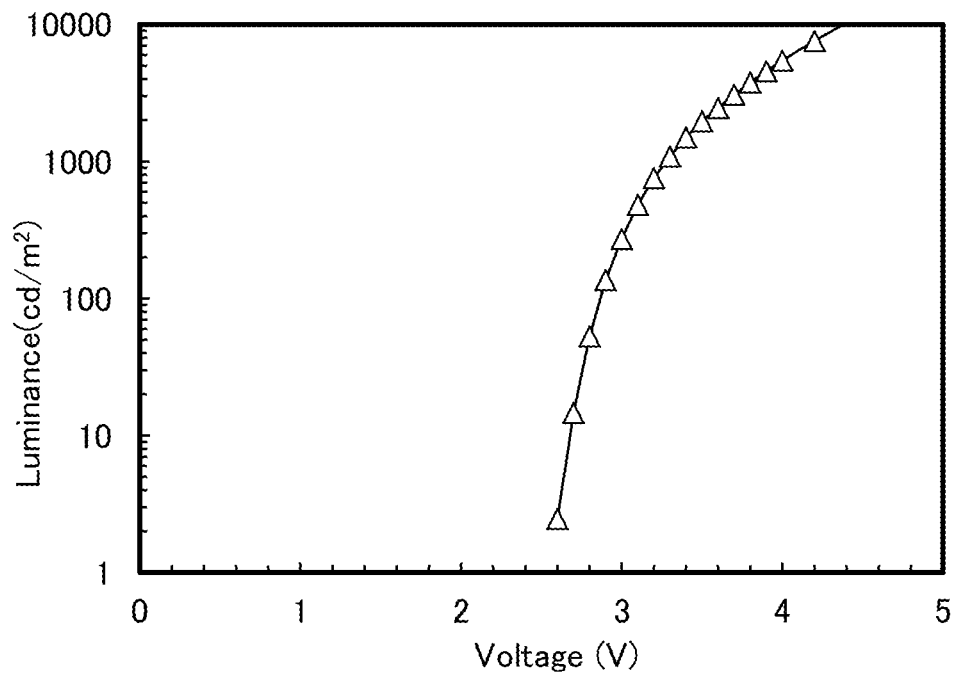
FIG. 57 shows the luminance-voltage characteristics of the light-emitting element 8.
Figure 58:
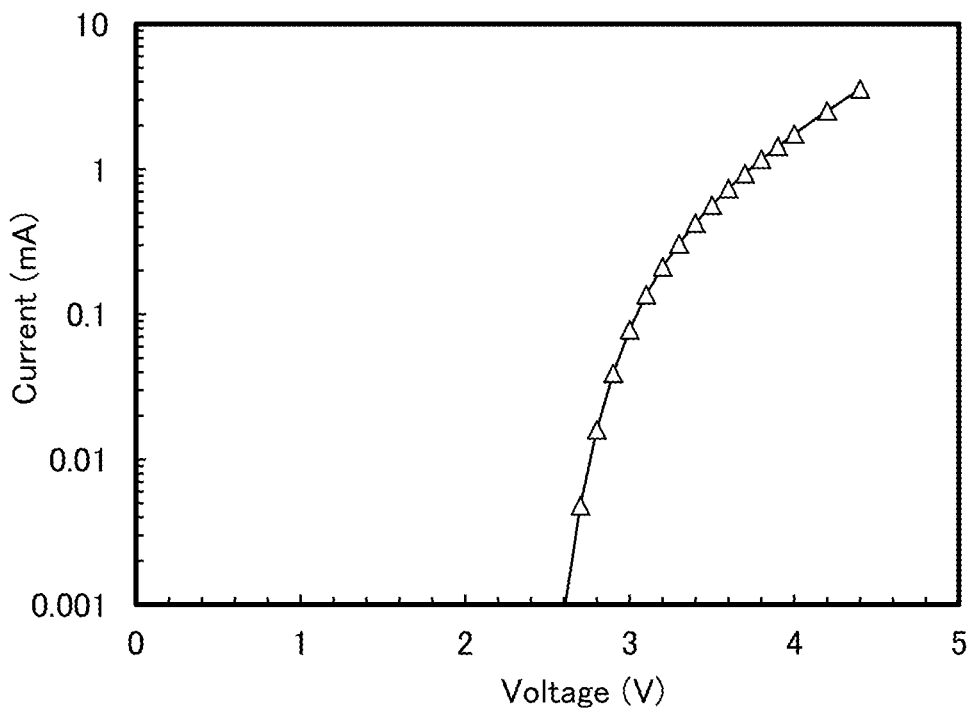
FIG. 58 shows the current-voltage characteristics of the light-emitting element 8.
Figure 59:
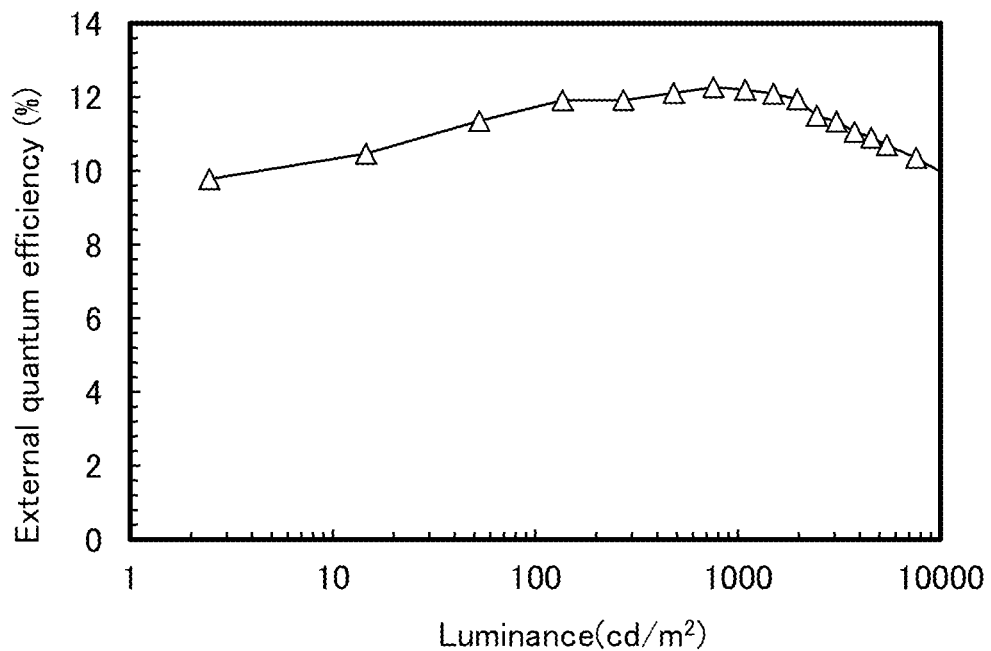
FIG. 59 shows the external quantum efficiency-luminance characteristics of the light-emitting element 8.
Figure 60:
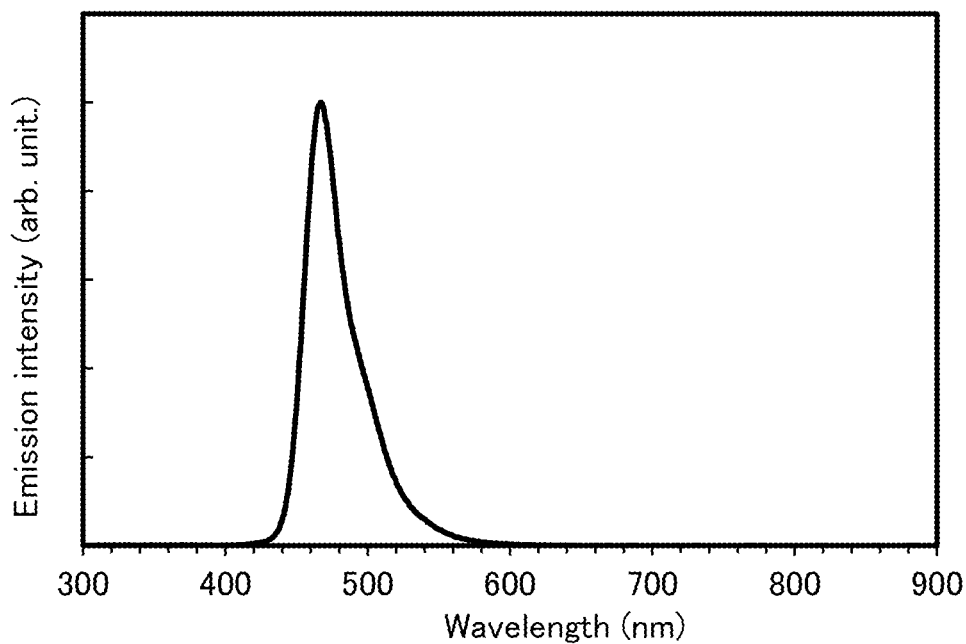
FIG. 60 shows an emission spectrum of the light-emitting element 8.

FIG. 55 shows the luminance-current density characteristics of the light-emitting element 8. FIG. 56 shows the current efficiency-luminance characteristics of the light-emitting element 8. FIG. 57 shows the luminance-voltage characteristics of the light-emitting element 8. FIG. 58 shows the current-voltage characteristics of the light-emitting element 8. FIG. 59 shows the external quantum efficiency-luminance characteristics of the light-emitting element 8. FIG. 60 shows the emission spectrum of the light-emitting element 8. Table 10 shows the main characteristics of the light-emitting element 8 at around 1000 cd/m$^2$.

TABLE 10

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 8 | 3.30 | 0.31 | 7.65 | 0.14 | 0.16 | 14.2 | 12.2 |

It was found from FIGS. 55 to 60 and Table 10 that the light-emitting element 8 of one embodiment of the present invention is a blue light-emitting element with favorable efficiency and a low driving voltage.

Figure 61:
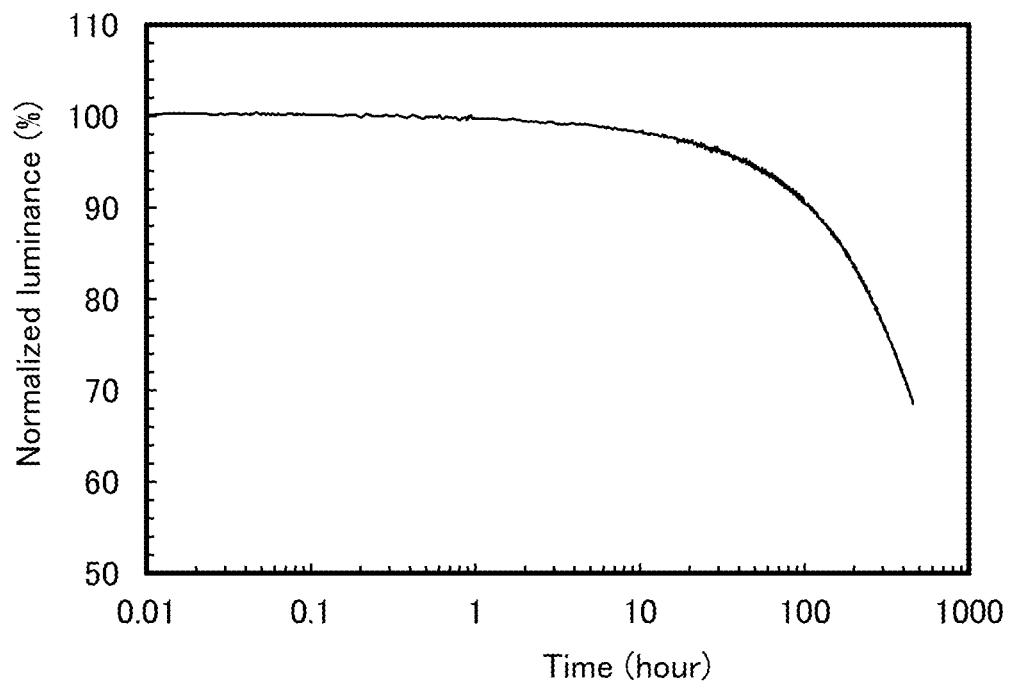
FIG. 61 shows the time dependence of normalized luminance of the light-emitting element 8.

FIG. 61 shows driving time-dependent change in luminance of the light-emitting element under the conditions where the current value was set to 2 mA and the current density was constant. As shown in FIG. 61, the light-emitting element 8 maintained 90% ☐☐☐☐☐☐ of the initial luminance after 100-hour-driving and were found to be long-lifetime light-emitting element with an extremely small reduction in luminance over driving time.

This application is based on Japanese Patent Application serial No. 2016-016262 filed with Japan Patent Office on Jan. 29, 2016, the entire contents of which are hereby incorporated by reference.

EXPLANATION OF REFERENCE

101: anode 102: cathode 103: EL layer 111: hole-injection layer 112: hole-transport layer 112-1: first hole-transport layer 112-2: second hole-transport layer 112-3: third hole-transport layer 113: light-emitting layer 114: electron-transport layer 115: electron-injection layer 116: charge-generation layer 117: p-type layer 118: electron-relay layer 119: electron-injection buffer layer 400: substrate 401: anode 403: EL layer 404: cathode 405: sealing material 406: sealing material 407: sealing substrate 412: pad 420: IC chip 501: anode 502: cathode 511: first light-emitting unit 512: second light-emitting unit 513: charge-generation layer 601: driver circuit portion (source line driver circuit) 602: pixel portion 603: driver circuit portion (gate line driver circuit) 604: sealing substrate 605: sealing material 607: space 608: wiring 609: FPC (flexible printed circuit) 610: element substrate 611: switching FET 612: current controlling FET 613: anode 614: insulator 616: EL layer 617: cathode 618: light-emitting element 730: insulating film 770: planarization insulating film 772: conductive film 782: light-emitting element 783: droplet discharge apparatus 784: droplet 785: layer 786: EL layer 788: conductive film 901: housing 902: liquid crystal layer 903: backlight unit 904: housing 905: driver IC 906: terminal 951: substrate 952: electrode 953: insulating layer 954: partition layer 955: EL layer 956: electrode 1001: substrate 1002: base insulating film 1003: gate insulating film 1006: gate electrode 1007: gate electrode 1008: gate electrode 1020: first interlayer insulating film 1021: second interlayer insulating film 1022: electrode 1024W: anode 1024R: anode 1024G: anode 1024B: anode 1025: partition 1028: EL layer 1029: cathode 1031: sealing substrate 1032: sealing material 1033: transparent base material 1034R: red coloring layer 1034G: green coloring layer 1034B: blue coloring layer 1035: black matrix 1036: overcoat layer 1037: third interlayer insulating film 1040: pixel portion 1041: driver circuit portion 1042: peripheral portion 1400: droplet discharge apparatus 1402: substrate 1403: droplet discharge means 1404: imaging means 1405: head 1406: dotted line 1407: control means 1408: storage medium 1409: image processing means 1410: computer 1411: marker 1412: head 1413: material supply source 1414: material supply source 1415: material supply source 1416: head 2001: housing 2002: light source 3001: lighting device 5000: display region 5001: display region 5002: display region 5003: display region 5004: display region 5005: display region 7101: housing 7103: display portion 7105: stand 7107: display portion 7109: operation key 7110: remote controller 7201: main body 7202: housing 7203:

display portion 7204: keyboard 7205: external connection port 7206: pointing device 7210: second display portion 7301: housing 7302: housing 7303: joint portion 7304: display portion 7305: display portion 7306: speaker portion 7307: recording medium insertion portion 7308: LED lamp 7309: operation key 7310: connection terminal 7311: sensor 7401: housing 7402: display portion 7403: operation button 7404: external connection port 7405: speaker 7406: microphone 7400: mobile phone 9033: clasp 9034: switch 9035: power switch 9036: switch 9038: operation switch 9310: portable information terminal 9311: display panel 9312: display region 9313: hinge 9315: housing 9630: housing 9631: display portion 9631a: display portion 9631b: display portion 9632a: touchscreen region 9632b: touchscreen region 9633: solar cell 9634: charge and discharge control circuit 9635: battery 9636: DCDC converter 9637: operation kay 9638: converter 9639: button

The invention claimed is:

1. An organic compound represented by General Formula (G1),

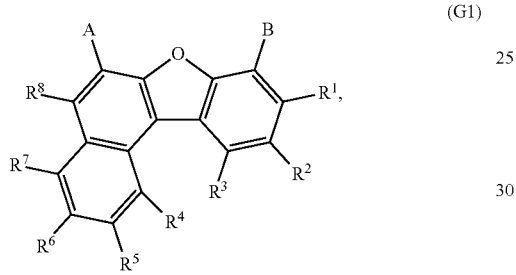

(G1)

wherein $R^1$ and $R^3$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein $R^2$ represents hydrogen, and wherein one of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms,

(g1)

wherein $Ar^1$ and $Ar^2$ independently represent any one of a substituted or unsubstituted aromatic hydrocarbon group having 6 to 60 carbon atoms and a group represented by General Formula (g2), and in $Ar^1$ and $Ar^2$, a substituent of the substituted aromatic hydrocarbon group having 6 to 60 carbon atoms is any of a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituent represented by Formulae (1-41) to (1-135),

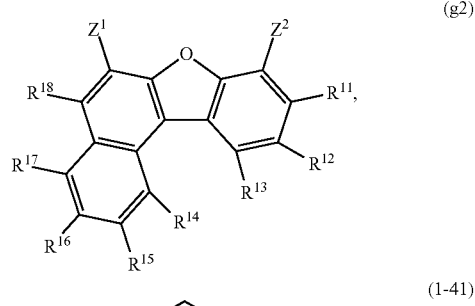

(g2)

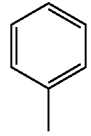

(1-41)

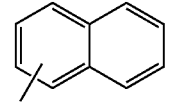

(1-42)

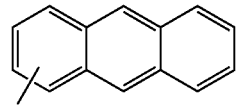

(1-43)

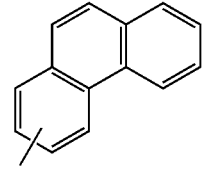

(1-44)

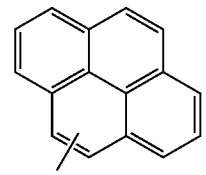

(1-45)

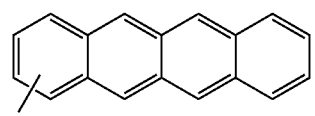

(1-46)

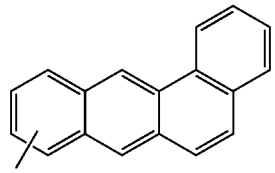

(1-47)

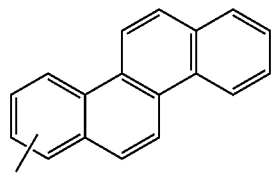

(1-48)

(1-49)
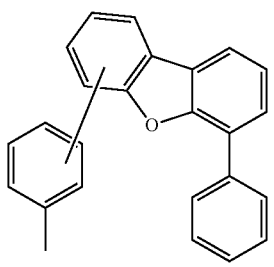
(1-50)
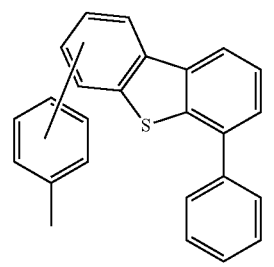
(1-51)
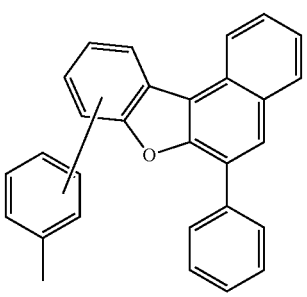
(1-52)
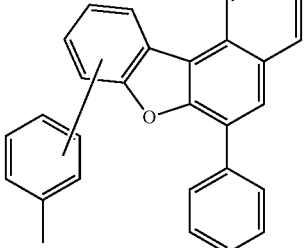
(1-53)
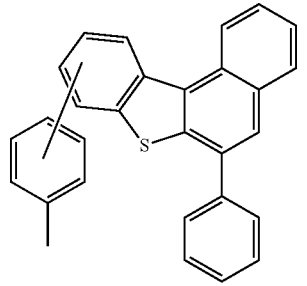
(1-54)
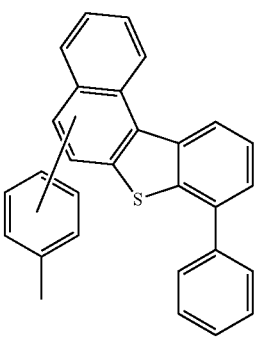
(1-55)
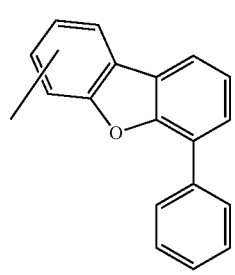
(1-56)
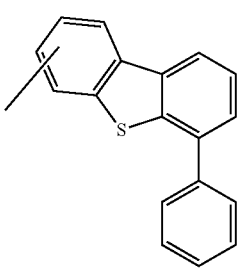
(I-57)
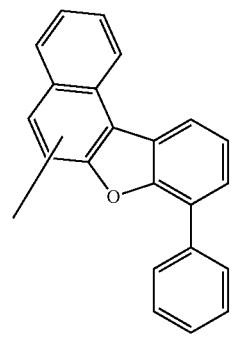
(1-58)
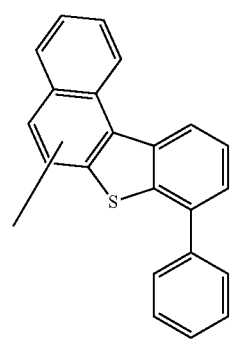

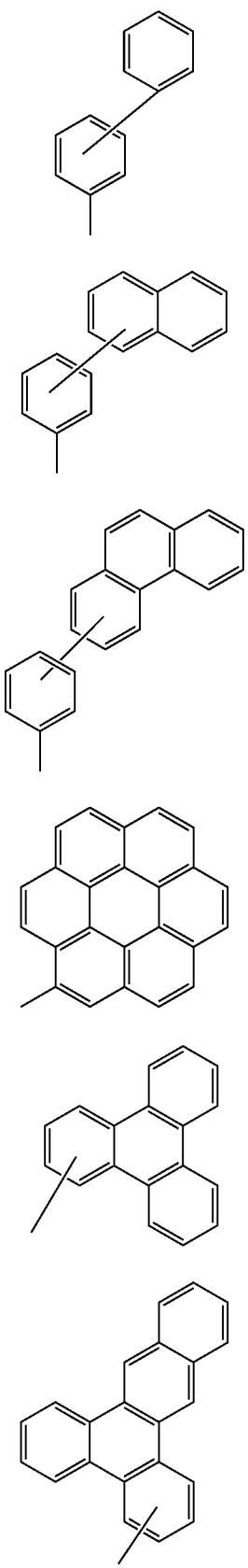
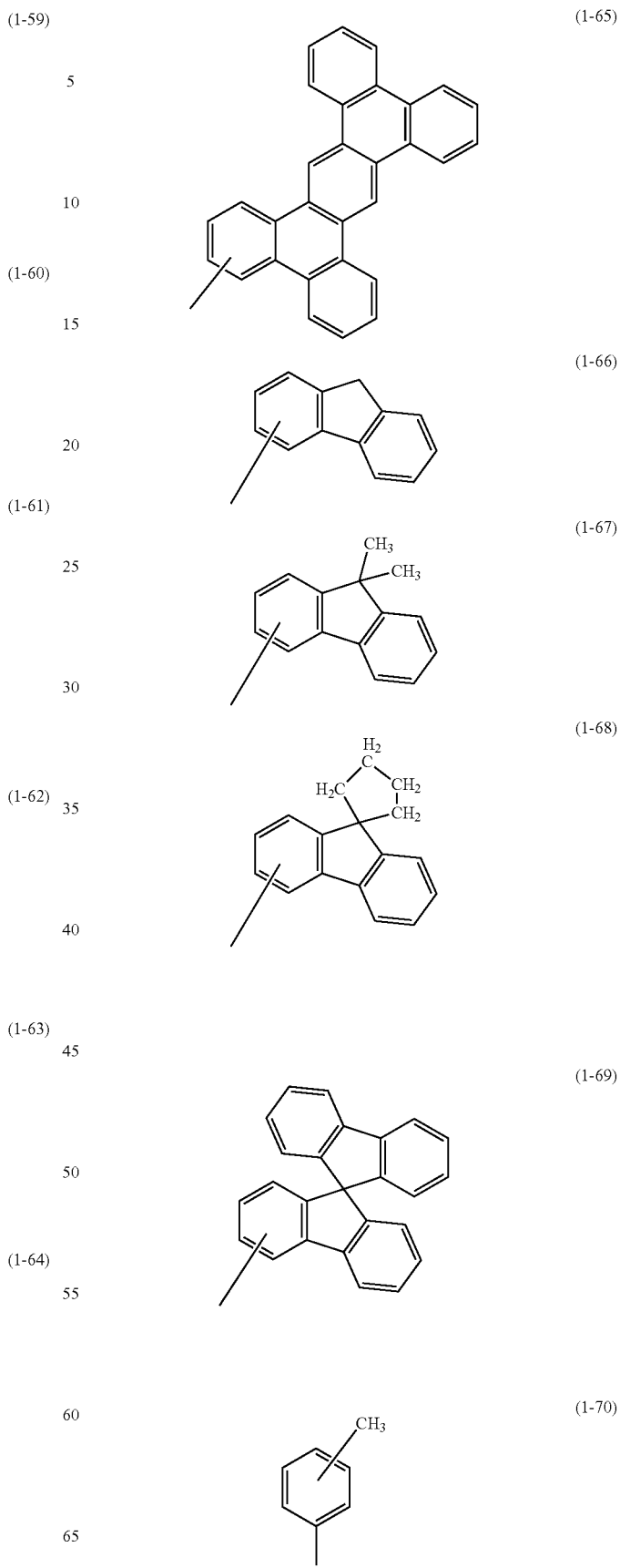

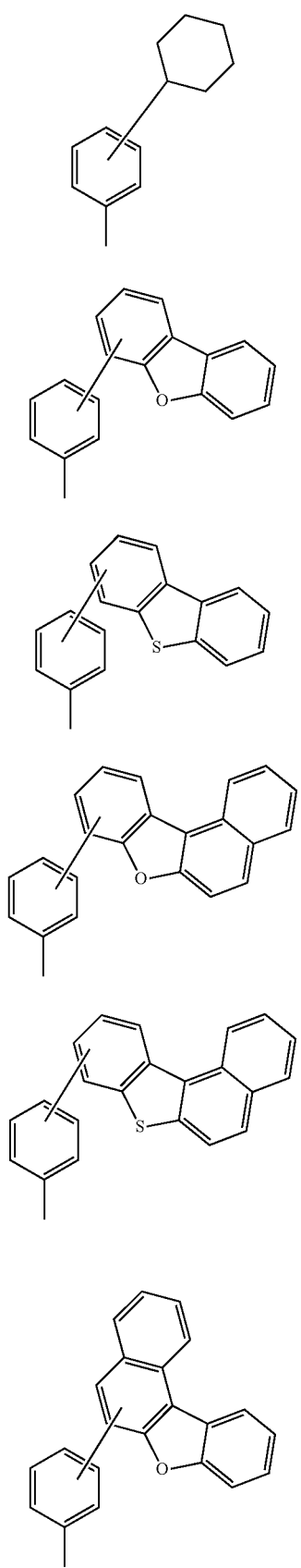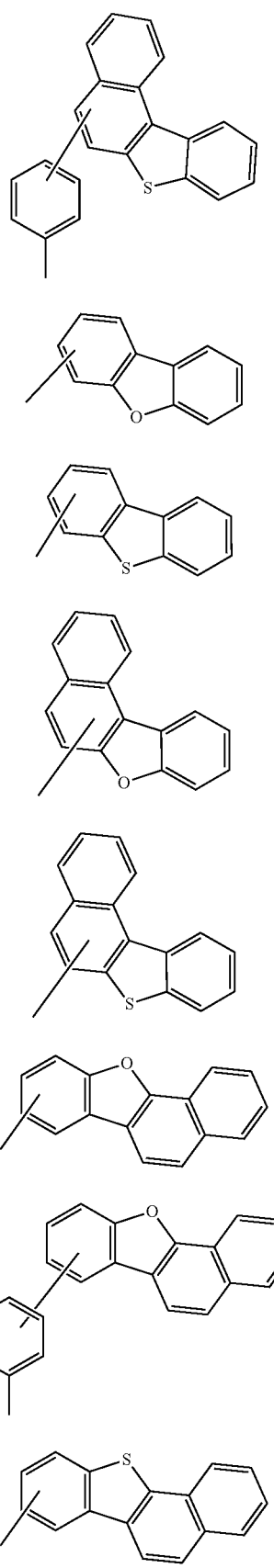

(1-85)
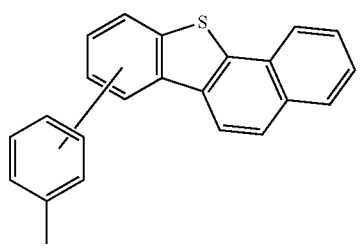
(1-86)
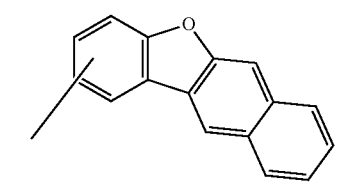
(1-87)
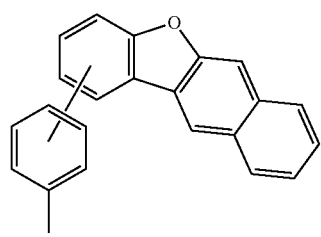
(1-88)
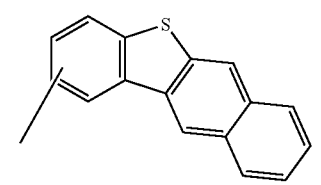
(1-89)
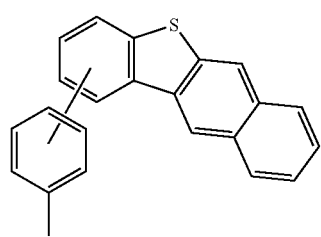
(1-90)
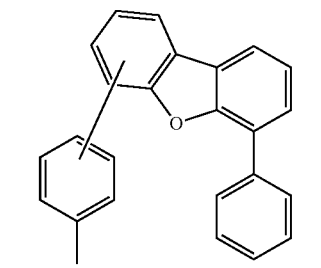
(1-91)
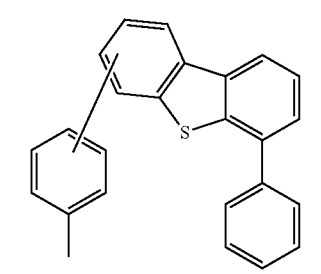
(1-92)
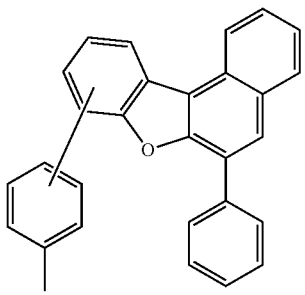
(1-93)
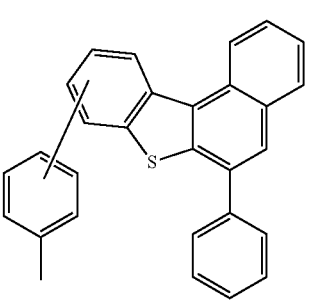
(1-94)
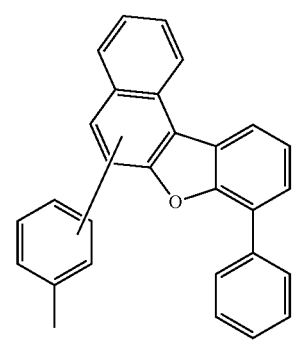
(I-95)
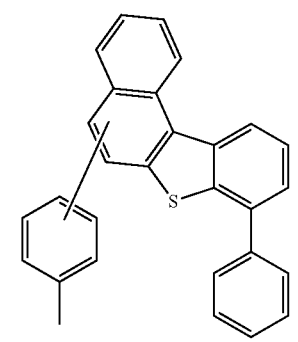
(1-96)
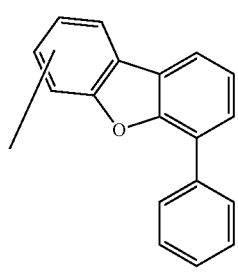

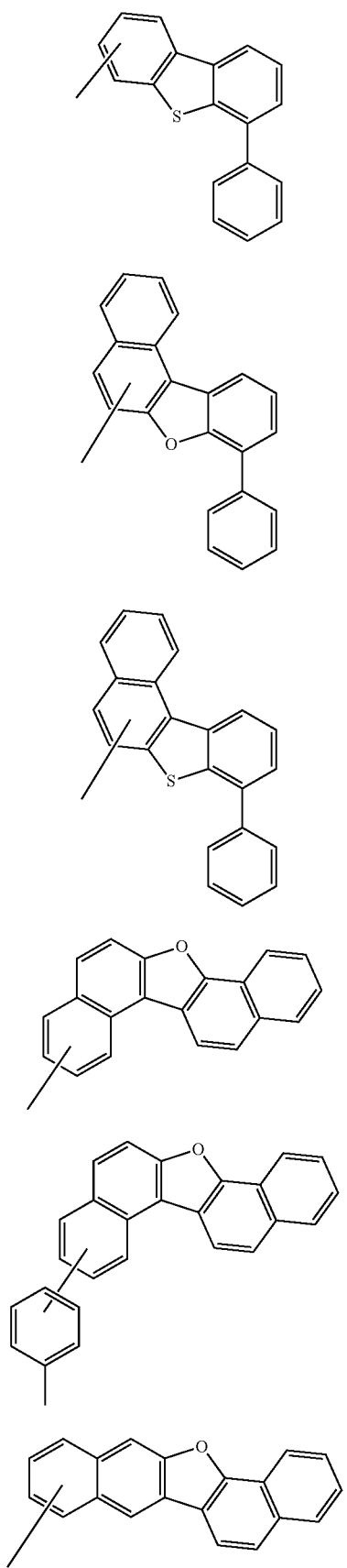
(1-97)
(1-98)
(1-99)
(1-100)
(1-101)
(1-102)
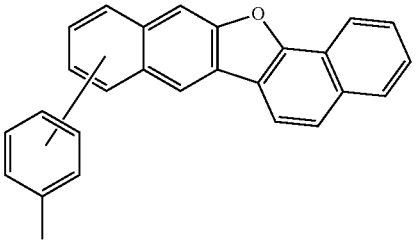
(1-103)
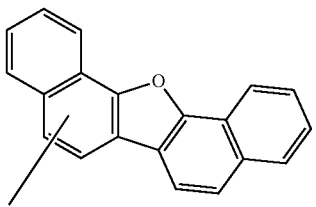
(1-104)
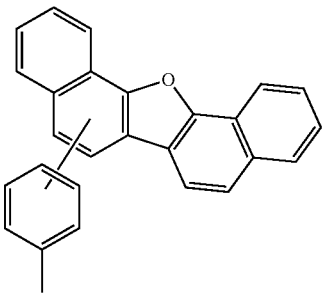
(1-105)
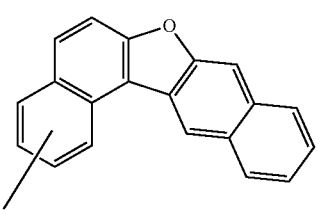
(1-106)
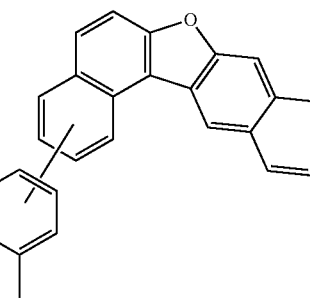
(1-107)
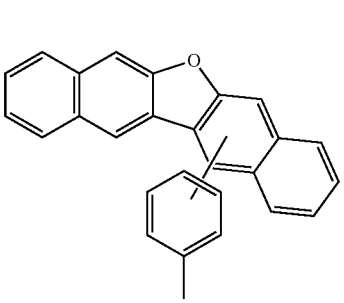
(1-108)

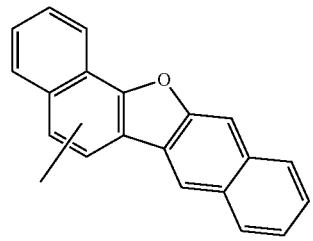
(1-109)
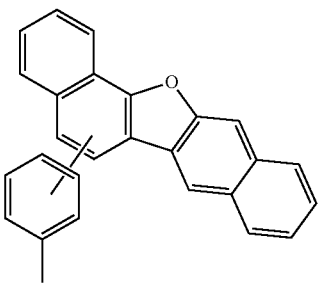
(1-110)
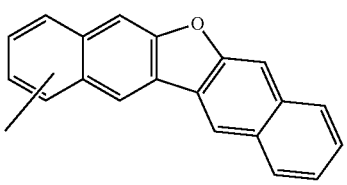
(1-111)
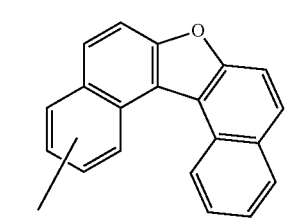
(1-112)
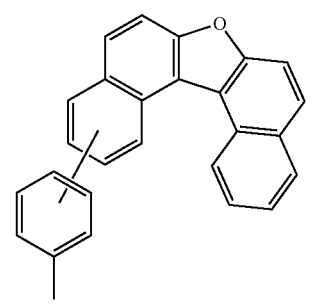
(1-113)
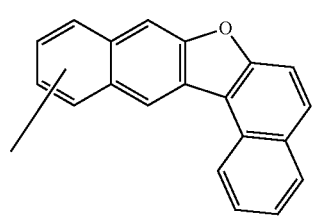
(1-114)
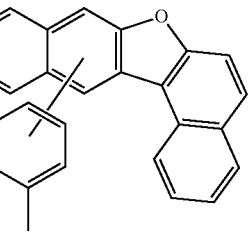
(1-115)
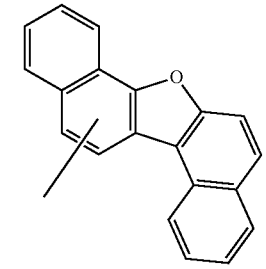
(1-116)
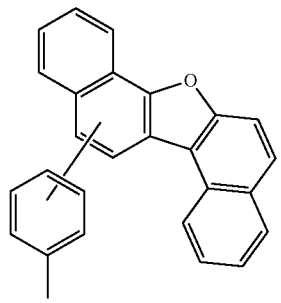
(1-117)
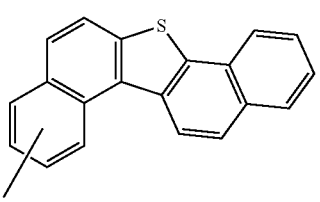
(1-118)
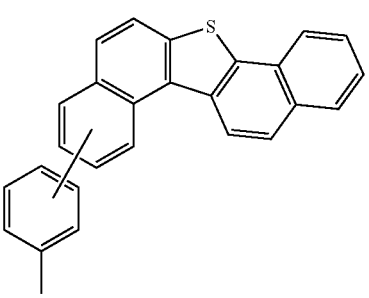
(1-119)
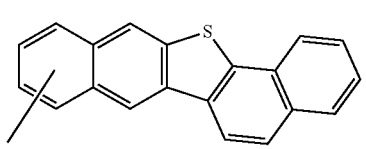
(1-120)

(1-121)
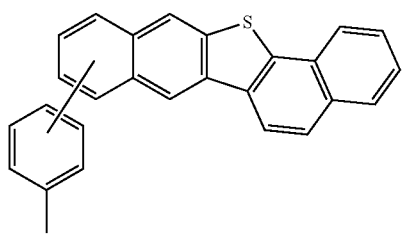
(1-122)
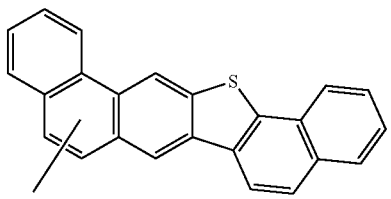
(1-123)
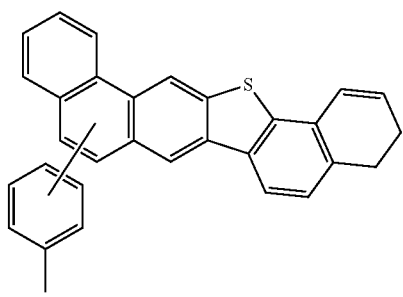
(1-124)
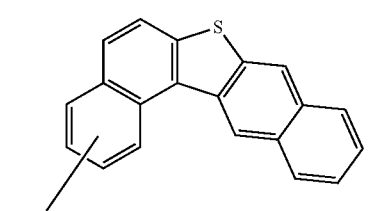
(1-125)
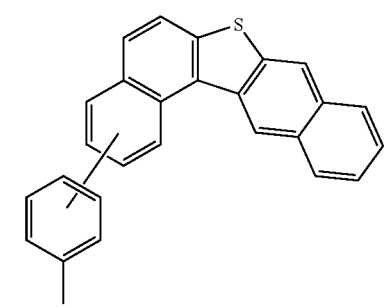
(1-126)
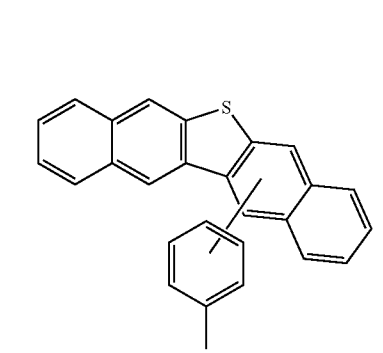
(1-127)
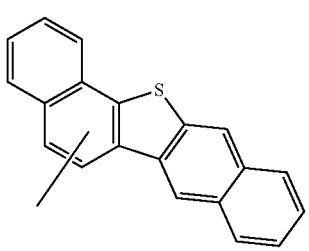
(1-128)
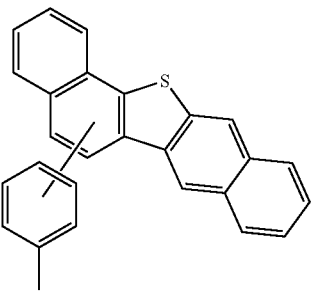
(1-129)
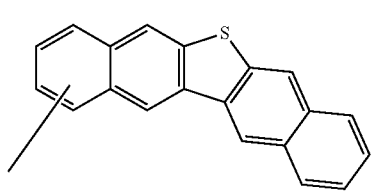
(1-130)
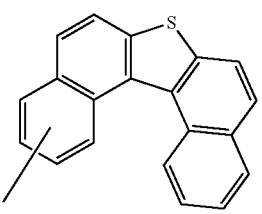
(1-131)
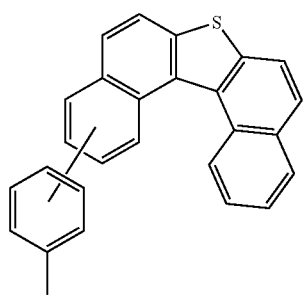
(1-132)
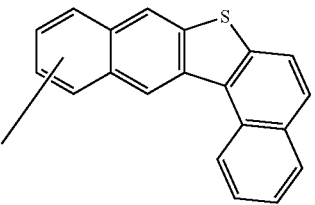

(1-133)

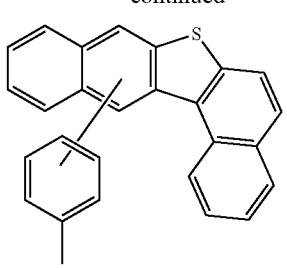

(1-134)

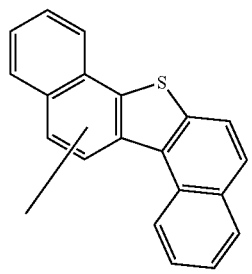

(1-135)

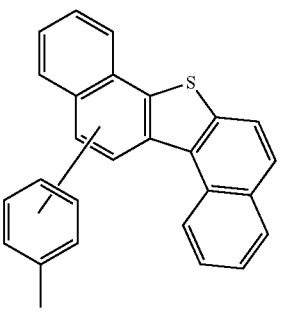

wherein $R^{11}$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein one of $Z^1$ and $Z^2$ is bonded to a nitrogen atom in General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms, and wherein at least one of $Ar^1$ and $Ar^2$ represents a group represented by General Formula (g2).

2. The organic compound according to claim 1, wherein General Formula (g1) is represented by General Formula (g3),

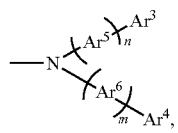

(g3)

wherein $Ar^3$ and $Ar^4$ independently represent any one of a substituted or unsubstituted aromatic hydrocarbon group, a substituted or unsubstituted benzonaphthofuranyl group, and a substituted or unsubstituted dinaphthofuranyl group, wherein $Ar^5$ and $Ar^6$ independently represent a substituted or unsubstituted aromatic hydrocarbon group, n and m independently represent 0 or 1, and wherein a sum of carbon atoms of $Ar^3$ and $Ar^5$ is less than or equal to 60, and a sum of carbon atoms of $Ar^4$ and $Ar^6$ is less than or equal to 60.

3. The organic compound according to claim 2, wherein one of $Ar^3$ and $Ar^4$ independently represents any one of a substituted or unsubstituted phenyl group, a substituted or unsubstituted naphthyl group, a substituted or unsubstituted anthracenyl group, and a substituted or unsubstituted pyrenyl group.

4. The organic compound according to claim 2, wherein $Ar^5$ and $Ar^6$ independently represent any one of a substituted or unsubstituted phenylene group, a substituted or unsubstituted naphthylene group, a substituted or unsubstituted anthracenylene group, and a substituted or unsubstituted pyrenylene group.

5. The organic compound according to claim 2, wherein one of $Ar^3$ and $Ar^4$ represents a phenyl group.

6. The organic compound according to claim 2, wherein $Ar^5$ and $Ar^6$ represent a phenylene group.

7. The organic compound according to claim 2, wherein one of n and m represents 1, and the other represents 0.

8. An organic compound represented by General Formula (G1),

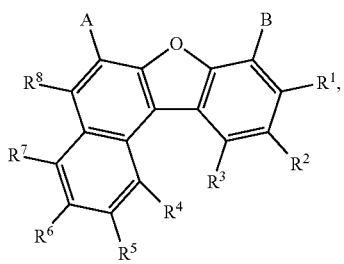

(G1)

wherein $R^1$ and $R^3$ to $R^8$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein $R^2$ represents hydrogen, and wherein one of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms,

(g1)

wherein Ar¹ and Ar² independently represent any one of an unsubstituted aromatic hydrocarbon group having 6 to 60 carbon atoms and a group represented by General Formula (g2), and in the case Ar¹ and Ar² have a substituent, the substituent excludes a dinaphthothiophenyl group and a fluorenyl group,

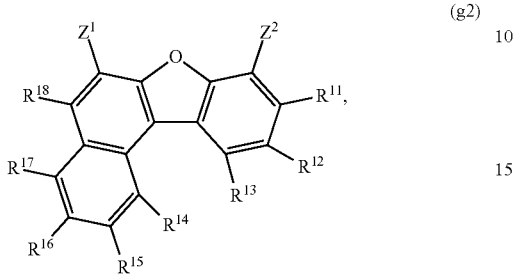

(g2)

wherein R¹¹ to R¹⁸ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein one of Z¹ and Z² is bonded to a nitrogen atom in General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms, and wherein at least one of Ar¹ and Ar² represents a group represented by General Formula (g2).

9. The organic compound according to claim 8,
wherein General Formula (g1) is represented by General Formula (g3),

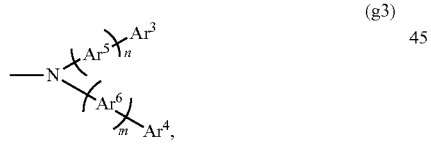

(g3)

wherein Ar³ and Ar⁴ independently represent any one of a substituted or unsubstituted aromatic hydrocarbon group, a substituted or unsubstituted benzonaphthofuranyl group, and a substituted or unsubstituted dinaphthofuranyl group, wherein Ar⁵ and Ar⁶ independently represent a substituted or unsubstituted aromatic hydrocarbon group, n and m independently represent 0 or 1, and wherein a sum of carbon atoms of Ar³ and Ar⁵ is less than or equal to 60, and a sum of carbon atoms of Ar⁴ and Ar⁶ is less than or equal to 60.

10. The organic compound according to claim 9,
wherein one of Ar³ and Ar⁴ independently represents any one of a substituted or unsubstituted phenyl group, a substituted or unsubstituted naphthyl group, a substituted or unsubstituted anthracenyl group, and a substituted or unsubstituted pyrenyl group.

11. The organic compound according to claim 9,
wherein Ar⁵ and Ar⁶ independently represent any one of a substituted or unsubstituted phenylene group, a substituted or unsubstituted naphthylene group, a substituted or unsubstituted anthracenylene group, and a substituted or unsubstituted pyrenylene group.

12. The organic compound according to claim 9,
wherein one of Ar³ and Ar⁴ represents a phenyl group.

13. The organic compound according to claim 9,
wherein Ar⁵ and Ar⁶ represent a phenylene group.

14. The organic compound according to claim 9,
wherein one of n and m represents 1, and the other represents 0.

15. An organic compound represented by General Formula (G1),

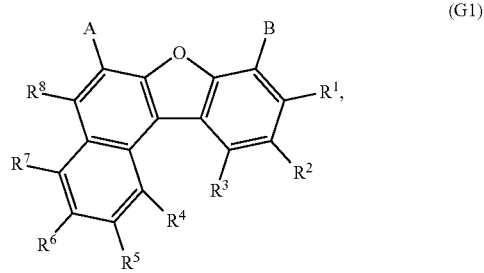

(G1)

wherein R¹ and R³ to R⁸ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein R² represents hydrogen, and wherein one of A and B represents a group represented by General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms,

(g1)

wherein Ar¹ and Ar² independently represent any one of a substituted or unsubstituted aromatic hydrocarbon group having 6 to 60 carbon atoms and a group represented by General Formula (g2), and in the case Ar¹ and Ar² have a substituent, the substituent excludes a dinaphthothiophenyl group and a fluorenyl group,

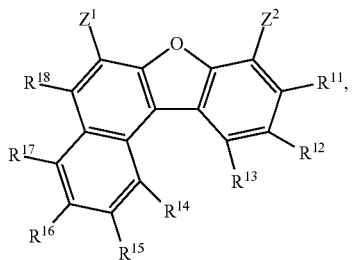

(g2)

wherein R¹¹ to R¹⁸ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, wherein one of Z¹ and Z² is bonded to a nitrogen atom in General Formula (g1) and the other represents any one of hydrogen, a cyclic hydrocarbon group having 3 to 6 carbon atoms, an alkoxy group having 1 to 6 carbon atoms, a cyano group, halogen, a haloalkyl group having 1 to 6 carbon atoms, a hydrocarbon group having 1 to 6 carbon atoms, and a substituted or unsubstituted aromatic hydrocarbon group having 6 to 60 carbon atoms, and wherein at least one of Ar¹ and Ar² represents a group represented by General Formula (g2).

16. The organic compound according to claim 15, wherein General Formula (g1) is represented by General Formula (g3),

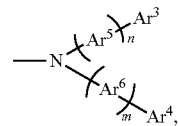

(g3)

wherein Ar³ and Ar⁴ independently represent any one of a substituted or unsubstituted aromatic hydrocarbon group, a substituted or unsubstituted benzonaphtofuranyl group, and a substituted or unsubstituted dinaphthofuranyl group, wherein Ar⁵ and Ar⁶ independently represent a substituted or unsubstituted aromatic hydrocarbon group, n and m independently represent 0 or 1, and wherein a sum of carbon atoms of Ar³ and Ar⁵ is less than or equal to 60, and a sum of carbon atoms of Ar⁴ and Ar⁶ is less than or equal to 60.

17. The organic compound according to claim 16, wherein one of Ar³ and Ar⁴ independently represents any one of a substituted or unsubstituted phenyl group, a substituted or unsubstituted naphthyl group, a substituted or unsubstituted anthracenyl group, and a substituted or unsubstituted pyrenyl group.

18. The organic compound according to claim 16, wherein Ar⁵ and Ar⁶ independently represent any one of a substituted or unsubstituted phenylene group, a substituted or unsubstituted napthylene group, a substituted or unsubstituted anthracenylene group, and a substituted or unsubstituted pyrenylene group.

19. The organic compound according to claim 16, wherein one of Ar³ and Ar⁴ represents a phenyl group.

20. The organic compound according to claim 16, wherein Ar⁵ and Ar⁶ represent a phenylene group.

21. The organic compound according to claim 16, wherein one of n and m represents 1, and the other represents 0.

* * * * *